United States Patent
Shepherd et al.

(10) Patent No.: US 7,585,885 B2
(45) Date of Patent: Sep. 8, 2009

(54) PYRROLIDINE DERIVATIVES USEFUL AS BACE INHIBITORS

(75) Inventors: Timothy Alan Shepherd, Indianapolis, IN (US); Isabel Rojo Garcia, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/599,129

(22) PCT Filed: Apr. 8, 2005

(86) PCT No.: PCT/US2005/012191

§ 371 (c)(1), (2), (4) Date: Sep. 20, 2006

(87) PCT Pub. No.: WO2005/108358

PCT Pub. Date: Nov. 17, 2005

(65) Prior Publication Data

US 2007/0213331 A1  Sep. 13, 2007

Related U.S. Application Data

(60) Provisional application No. 60/564,538, filed on Apr. 22, 2004.

(51) Int. Cl.
*A01N 43/36* (2006.01)
(52) U.S. Cl. .................................. 514/408; 548/579
(58) Field of Classification Search ................ 514/408; 548/579
See application file for complete search history.

(56) References Cited

FOREIGN PATENT DOCUMENTS

| WO | WO 89/03842 | 5/1989 |
|---|---|---|
| WO | WO2004/024081 | 3/2004 |
| WO | WO 2004/043916 | 5/2004 |
| WO | WO 2005/014540 | 2/2005 |
| WO | WO 2005/016876 | * 2/2005 |
| WO | WO2005/016876 A | 2/2005 |
| WO | WO 2005/108391 | 11/2005 |
| WO | WO 2006/034093 | 3/2006 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
McCarty, et al. J. Med. Chem. 13(5), 1970, pp. 814-819.*

* cited by examiner

*Primary Examiner*—James O Wilson
*Assistant Examiner*—Douglas M Willis
(74) *Attorney, Agent, or Firm*—Elizabeth A. Dingess-Hammond; Robert D. Titus

(57) ABSTRACT

The present invention provides BACE inhibitors of Formula I:

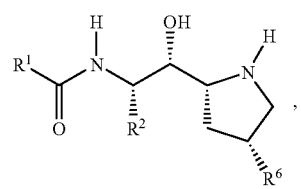

methods for their use and preparation, and intermediates for their preparation.

3 Claims, No Drawings

PYRROLIDINE DERIVATIVES USEFUL AS BACE INHIBITORS

This application is a United States national phase entry, pursuant to 35 U.S.C. 371, of PCT/US2005/012191, filed Apr. 8, 2005, which claims the benefit of U.S. provisional patent application Ser. No. 60/564,538, filed Apr. 22, 2004.

BACKGROUND OF THE INVENTION

Alzheimer's disease, characterized by cognitive and behavioral deterioration in its latter stages, has emerged as a significant social and financial concern. With a prevalence approaching 5.5% in the population above the age of 60, the cost for care of Alzheimer's disease patients has been estimated to be in excess of $100 billion annually. Although cholinesterase inhibitors are somewhat effective in reducing the symptoms of Alzheimer's disease, particularly when the disease is in its early phases, they are not at all effective in slowing or stopping the progression of the disease.

Neurofibrillary tangles and neuritic plaques are generally found in the brain regions associated with memory and cognition of those afflicted with Alzheimer's disease. These plaques are also found in the brains of individuals with Down's syndrome, Hereditary Cerebral Hemorrhage of the Dutch-Type, and other neurodegenerative disorders. The neuritic plaques are comprised primarily of amyloid β (Aβ) peptide, a neurotoxic and highly aggregatory peptide segment of amyloid precursor protein (APP). Aβ peptide is formed by the proteolytic cleavage of APP by β-secretase (BACE) followed by at least one subsequent C-terminal cleavage by γ-secretase. As such, inhibition of BACE is an attractive target for the treatment or prevention of Alzheimer's disease as well as other diseases characterized pathologically by amyloid plaques.

BACE is a member of the pepsin sub-family of mammalian aspartyl proteases and, like its substrate APP, is a type I transmembrane protein. BACE has been disclosed in the literature and is referred to also as "β-site APP-cleaving enzyme", "membrane aspartic protease of the pepsin family", "Asp-2", "β-secretase", "membrane-bound aspartic protease" and "Memapsin 2" (See: Ghosh, et al., *Current Medicinal Chemistry*, 9(11), 1135-1144 (2002)). Two isoforms of BACE have been identified in humans, designated BACE1 and BACE2. It is believed that the BACE1 inhibitory activity is most important to inhibition of amyloid β (Aβ) peptide (Roggo, *Current Topics in Medicinal Chemistry*, 2, 359-370 (2002)). Currently described BACE inhibitors are peptidomimetic transition state analogs, typically containing a hydroxyethyl moiety. Although many of these compounds are potent inhibitors of BACE, their high molecular weights and low membrane permeability make them poor drug candidates. (See: Park and Lee, *Journal of the American Chemical Society*, 125(52), 16416-16422 (2003)). Additional compounds described as BACE inhibitors are disclosed in WO 03/040096, WO 04/024081, WO 04/0039034, and WO 04/043916. Additional BACE inhibitors are necessary to provide treatments for A-β peptide mediated disorders such as Alzheimer's disease. The present invention provides new inhibitors of BACE.

BRIEF SUMMARY OF THE INVENTION

The present invention provides compounds of Formula I:

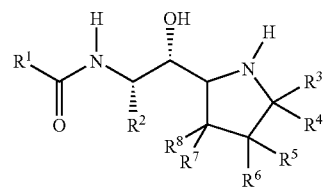

I where:

$R^1$ is $(C_3-C_7$ cycloalkyl$)_{0-1}(C_1-C_6$ alkyl), $(C_3-C_7$ cycloalkyl$)_{0-1}(C_2-C_6$ alkenyl), $(C_3-C_7$ cycloalkyl$)_{0-1}(C_2-C_6$ alkynyl) or $C_3-C_7$ cycloalkyl, each optionally substituted with up to three groups independently selected from halo, hydroxy, thiol, cyano, trifluoromethyl, trifluoromethoxy, $C_1-C_6$ alkoxy, $C_3-C_7$ cycloalkoxy, oxo, and $NR^9R^{10}$, hydrogen, biphenyl substituted with halo,

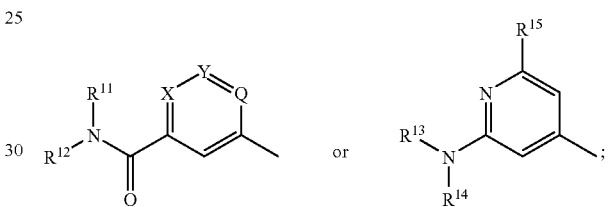

X is CH, N, or $N^+$—$O^-$;
Y is $CR^{16}$, N, or $N^+$—$O^-$;
Q is $CR^{17}$, N, or $N^+$—$O^-$;
$R^2$ is $C_1-C_3$ alkyl, benzyl optionally monosubstituted in the phenyl ring with a substituent selected from the group consisting of halo, $C_1-C_6$ alkoxy optionally substituted in the alkyl chain with $C_3-C_7$ cycloalkyl, and $C_1-C_6$ alkylthio optionally substituted in the alkyl chain with $C_3-C_7$ cycloalkyl, or benzyl optionally disubstituted in the phenyl ring with a first substituent independently selected from halo and a second substituent independently selected from halo, $C_1-C_6$ alkoxy optionally substituted in the alkyl chain with $C_3-C_7$ cycloalkyl, and $C_1-C_6$ alkylthio optionally substituted in the alkyl chain with $C_3-C_7$ cycloalkyl;
$R^3$ is hydrogen or $C_1-C_6$ alkyl;
$R^4$ is hydrogen, $C_1-C_6$ alkyl, or phenyl;
$R^3$ and $R^4$ taken together with the carbon to which they are attached form a $C_3-C_6$ cycloalkyl ring;
$R^5$ is hydrogen, fluoro, trifluoromethyl, $R^{32}$, or phenyl optionally monosubstituted with $C_1-C_6$ alkyl or $C_1-C_6$ alkoxy;
$R^6$ is fluoro, hydroxy, p-toluenesulfonyloxy, $R^{34}$, —$CH_2C(O)R^{35}$, or —$OC(O)NHR^{36}$; or $R^5$ and $R^6$ taken together form =$CHC(O)(C_1-C_4$ alkoxy);
$R^7$ is hydrogen or fluoro; or $R^6$ and $R^7$ taken together form a bond;
$R^8$ is hydrogen or fluoro;
$R^9$ is hydrogen, $C_1-C_6$ alkyl, or phenyl;
$R^{10}$ is hydrogen, $C_1-C_6$ alkyl, phenyl, —$C(O)(C_1-C_6$ alkyl), or —$SO_2(C_1-C_6$ alkyl);
$R^{11}$ and $R^{12}$ are independently selected from the group consisting of methyl, ethyl, and propyl;
$R^{13}$ is hydrogen or $C_1-C_6$ alkyl;

$R^{14}$ is $C_3$-$C_5$ cycloalkyl, $C_1$-$C_6$ alkyl, or —$CH_2R^{18}$;

$R^{15}$ is —$CF_2R^{19}$, —$OR^{20}$, —$CH_2C(O)CH_3$, —$S(O)_{1-2}R^{21}$, —$NR^{22}SO_2R^{23}$, ($C_1$-$C_3$ alkoxy)-carbonyl, phenyl optionally substituted with halo, 1,3-dioxolan-2-yl, 1,3-dioxan-2-yl, 1,1-dioxo-2,3,4,5-tetrahydroisothiazol-2-yl, or tetrazol-5-yl optionally substituted with $C_1$-$C_3$ alkyl;

$R^{16}$ is hydrogen, chloro, isobutyl, $CH_2R^{24}$; $CF_2R^{25}$, 1,1,1-trifluoro-2-hydroxyeth-2-yl, $C_2$-$C_4$ alkenyl optionally substituted with one or two fluorine atoms, $OR^{26}$, $C(O)R^{27}$, N(methyl)(methylsulfonyl), N(methyl)(acetyl), pyrrolidin-2-on-1-yl, methylsulfonyl, N,N-dimethylaminosulfonyl, phenyl optionally substituted with one or two substituents selected from the group consisting of hydroxymethyl, methoxy, fluoro, and methylsulfonyl, 1,3-dioxolan-2-yl, 1,3-dithiolan-2-yl, 1,3-oxathiolan-2-yl, 1,3-dioxan-2-yl, 1,3-dithian-2-yl, pyridinyl, thiazolyl, oxazolyl, or 1,2,4-oxadiazolyl optionally substituted with methyl;

$R^{17}$ is hydrogen or fluoro;

$R^{18}$ is ethynyl or cyclopropyl;

$R^{19}$ is hydrogen or methyl;

$R^{20}$ is difluoromethyl or methanesulfonyl;

$R^{21}$ is $C_1$-$C_4$ alkyl, $C_3$-$C_6$ cycloalkyl, phenyl, or —$NR^{30}R^{31}$;

$R^{22}$ is hydrogen, $C_1$-$C_3$ alkyl optionally substituted with up to 3 fluorine atoms, or $C_3$-$C_6$ cycloalkyl;

$R^{23}$ is $C_1$-$C_3$ alkyl or $C_3$-$C_6$ cycloalkyl;

$R^{24}$ is fluoro, hydroxy, or $C_1$-$C_3$ alkoxy;

$R^{25}$ is hydrogen, phenyl, or furyl;

$R^{26}$ is $C_1$-$C_3$ alkyl optionally substituted with one or two fluorine atoms;

$R^{27}$ is $C_1$-$C_3$ alkyl, $C_3$-$C_5$ cycloalkyl, $C_2$-$C_3$ alkenyl, $C_1$-$C_3$ alkoxy, $NR^{28}R^{29}$, pyrrolidin-1-yl optionally substituted with methyl or one or two fluorine atoms, piperidin-1-yl, phenyl, pyridinyl, or furyl;

$R^{28}$ is hydrogen or methyl;

$R^{29}$ is methyl, ethyl, or propyl;

$R^{30}$ is hydrogen or methyl;

$R^{31}$ is methyl; or $R^{30}$ and $R^{31}$ taken together with the nitrogen atom to which they are attached form a pyrrolidine or piperidine ring;

$R^{32}$ is $C_1$-$C_{10}$ alkyl optionally substituted with 1-6 fluorine atoms, oxo, or one or two hydroxy groups, $C_2$-$C_6$ alkenyl, or —$(CH_2)_{0-3}$—$R^{33}$;

$R^{33}$ is $C_3$-$C_7$ cycloalkyl or phenyl each optionally substituted with one or two substitutents independently selected from the group consisting of halo, $C_1$-$C_6$ alkyl, $C_1$-$C_6$ alkoxy, hydroxy, trifluoromethyl, and trifluoromethoxy, or $R^{33}$ is adamantyl;

$R^{34}$ is hydrogen, $R^{32}$, or —$(CH_2)_{0-2}$—$OR^{32}$;

$R^{35}$ is hydroxy, $C_1$-$C_6$ alkoxy, or $NR^{37}R^{38}$ where $R^{37}$ and $R^{38}$ are independently hydrogen or $C_1$-$C_6$ alkyl, or $R^{37}$ and $R^{38}$, taken together with the nitrogen to which they are attached, form a piperidine ring optionally substituted with $C_1$-$C_6$ alkyl, a homopiperidine ring, a morpholine ring, or a pyrrolidine ring optionally substituted with ($C_1$-$C_6$ alkoxy) methyl;

$R^{36}$ is $C_1$-$C_6$ alkyl or adamantyl;

or a pharmaceutically acceptable salt thereof; provided that: a) no more than one of X, Y, and Q may be N or $N^+$—$O^-$; and b) when X is CH, Y is $CR^{16}$, and Q is $CR^{17}$, then one of $R^{16}$ and $R^{17}$ is other than hydrogen.

The present invention also provides a method of treating Alzheimer's disease in a mammal comprising administering to a mammal in need of such treatment an effective amount of a compound of Formula I.

The present invention further provides a method of preventing the progression of mild cognitive impairment to Alzheimer's disease in a mammal comprising administering to a mammal in need of such treatment an effective amount of a compound of Formula I.

The present invention also provides a method of inhibiting BACE in a mammal comprising administering to a mammal in need of such treatment an effective amount of a compound of Formula I.

The present invention also provides a method for inhibiting β-secretase mediated cleavage of amyloid precursor protein comprising administering to a mammal in need of such treatment an effective amount of a compound of Formula I.

The present invention further provides a method for the inhibition of production of A-β peptide comprising administering to a mammal in need of such treatment an effective amount of a compound of Formula I.

The present invention also provides a pharmaceutical formulation comprising a compound of Formula I, in combination with a pharmaceutically acceptable carrier, diluent, or excipient.

Furthermore, this invention provides the use of a compound of Formula I for the manufacture of a medicament for the treatment of Alzheimer's disease. This invention also provides the use of a compound of Formula I for the manufacture of a medicament for the prevention of the progression of mild cognitive impairment to Alzheimer's disease. The invention also provides the use of a compound of Formula I for the manufacture of a medicament for the inhibition of BACE. The present invention also provides the use of a compound of Formula I for the manufacture of a medicament for the inhibition of β-secretase mediated cleavage of amyloid precursor protein. The invention further provides the use of a compound of Formula I for the manufacture of a medicament for the inhibition of production of A-β peptide.

Additionally, this invention provides a pharmaceutical formulation adapted for the treatment of Alzheimer's disease. Furthermore, this invention provides a pharmaceutical formulation adapted for the prevention of the progression of mild cognitive impairment to Alzheimer's disease. This invention also provides a pharmaceutical formulation adapted for the inhibition of BACE.

Furthermore the present invention provides a pharmaceutical formulation adapted for the inhibition of β-secretase mediated cleavage of amyloid precursor protein. The present invention also provides a pharmaceutical formulation adapted for the treatment of conditions resulting from excessive production and/or reduced clearance of A-β peptide comprising a compound of Formula I or a pharmaceutically acceptable salt thereof in combination with one or more pharmaceutically acceptable excipients, carriers, or diluents.

This invention also provides intermediates of Formula II:

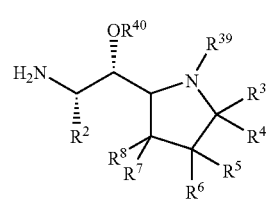

II $R^2$ is $C_1$-$C_3$ alkyl, benzyl optionally monosubstituted in the phenyl ring with a substituent selected from the group consisting of halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl, or benzyl optionally disubstituted in the phenyl ring with a first substituent independently selected from halo and a second substituent independently selected from halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl;

$R^3$ is hydrogen or $C_1$-$C_6$ alkyl;

$R^4$ is hydrogen, $C_1$-$C_6$ alkyl, or phenyl;

$R^3$ and $R^4$ taken together with the carbon to which they are attached form a $C_3$-$C_6$ cycloalkyl ring;

$R^5$ is hydrogen, fluoro, trifluoromethyl, $R^{32}$, or phenyl optionally monosubstituted with $C_1$-$C_6$ alkyl or $C_1$-$C_6$ alkoxy;

$R^6$ is fluoro, hydroxy, p-toluenesulfonyloxy, $R^{34}$, —$CH_2C(O)R^{35}$, or —$OC(O)NHR^{36}$; or $R^5$ and $R^6$ taken together form =$CHC(O)(C_1$-$C_4$ alkoxy);

$R^7$ is hydrogen or fluoro;

$R^8$ is hydrogen or fluoro;

$R^{32}$ is $C_1$-$C_{10}$ alkyl optionally substituted with 1-6 fluorine atoms, oxo, or one or two hydroxy groups, $C_2$-$C_6$ alkenyl, or —$(CH_2)_{0-3}$—$R^{33}$;

$R^{33}$ is $C_3$-$C_7$ cycloalkyl or phenyl each optionally substituted with one or two substitutents independently selected from the group consisting of halo, $C_1$-$C_6$ alkyl, $C_1$-$C_6$ alkoxy, hydroxy, trifluoromethyl, and trifluoromethoxy, or $R^{33}$ is adamantyl;

$R^{34}$ is hydrogen, $R^{32}$, or —$CH_2)_{0-2}$—$OR^{32}$;

$R^{35}$ is hydroxy, $C_1$-$C_6$ alkoxy, or $NR^{37}R^{38}$ where $R^{37}$ and $R^{38}$ are independently hydrogen or $C_1$-$C_6$ alkyl, or $R^{37}$ and $R^{38}$, taken together with the nitrogen to which they are attached, form a piperidine ring optionally substituted with $C_1$-$C_6$ alkyl, a homopiperidine ring, a morpholine ring, or a pyrrolidine ring optionally substituted with ($C_1$-$C_6$ alkoxy)methyl;

$R^{36}$ is $C_1$-$C_6$ alkyl or adamantyl;

$R^{39}$ is hydrogen or a nitrogen protecting group;

$R^{40}$ is hydrogen or an oxygen protecting group; or an acid addition salt thereof; provided that $R^3$ and $R^4$ must both be other than hydrogen when $R^2$ is benzyl and $R^5$, $R^6$, $R^7$, and $R^8$ are all hydrogen.

This invention further provides intermediates of Formula III:

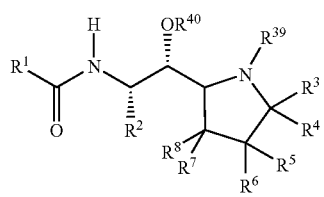

where:

$R^1$ is ($C_3$-$C_7$ cycloalkyl)$_{0-1}$($C_1$-$C_6$ alkyl), ($C_3$-$C_7$ cycloalkyl)$_{0-1}$($C_2$-$C_6$ alkenyl), ($C_3$-$C_7$ cycloalkyl)$_{0-1}$($C_2$-$C_6$ alkynyl) or $C_3$-$C_7$ cycloalkyl, each optionally substituted with up to three groups independently selected from halo, hydroxy, thiol, cyano, trifluoromethyl, trifluoromethoxy, $C_1$-$C_6$ alkoxy, $C_3$-$C_7$ cycloalkoxy, oxo, and $NR^9R^{10}$, hydrogen, biphenyl substituted with halo,

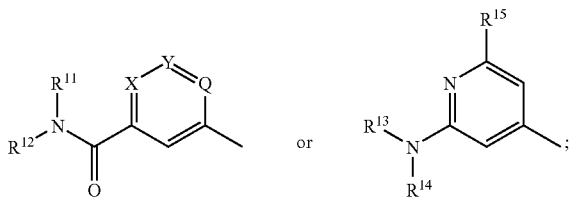

X is CH, N, or $N^+$—$O^-$;
Y is $CR^{16}$, N, or $N^+$—$O^-$;
Q is $CR^{17}$, N, or $N^+$—$O^-$;

$R^2$ is $C_1$-$C_3$ alkyl, benzyl optionally monosubstituted in the phenyl ring with a substituent selected from the group consisting of halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl, or benzyl optionally disubstituted in the phenyl ring with a first substituent independently selected from halo and a second substituent independently selected from halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl;

$R^3$ is hydrogen or $C_1$-$C_6$ alkyl;

$R^4$ is hydrogen, $C_1$-$C_6$ alkyl, or phenyl;

$R^3$ and $R^4$ taken together with the carbon to which they are attached form a $C_3$-$C_6$ cycloalkyl ring;

$R^5$ is hydrogen, fluoro, trifluoromethyl, $R^{32}$, or phenyl optionally mono substituted with $C_1$-$C_6$ alkyl or $C_1$-$C_6$ alkoxy;

$R^6$ is fluoro, hydroxy, p-toluenesulfonyloxy, $R^{34}$, —$CH_2C(O)R^{35}$, or —$OC(O)NHR^{36}$; or $R^5$ and $R^6$ taken together form =$CHC(O)(C_1$-$C_4$ alkoxy);

$R^7$ is hydrogen or fluoro; or $R^6$ and $R^7$ taken together form a bond;

$R^8$ is hydrogen or fluoro;

$R^9$ is hydrogen, $C_1$-$C_6$ alkyl, or phenyl;

$R^{10}$ is hydrogen, $C_1$-$C_6$ alkyl, phenyl, —$C(O)(C_1$-$C_6$ alkyl), or —$SO_2(C_1$-$C_6$ alkyl);

$R^{11}$ and $R^{12}$ are independently selected from the group consisting of methyl, ethyl, and propyl;

$R^{13}$ is hydrogen or $C_1$-$C_6$ alkyl;

$R^{14}$ is $C_3$-$C_5$ cycloalkyl, $C_1$-$C_6$ alkyl, or —$CH_2R^{18}$;

$R^{15}$ is —$CF_2R^{19}$, —$OR^{20}$, —$CH_2C(O)CH_3$, —$S(O)_{1-2}R^{21}$, —$NR^{22}SO_2R^{23}$, ($C_1$-$C_3$ alkoxy)-carbonyl, phenyl optionally substituted with halo, 1,3-dioxolan-2-yl, 1,3-dioxan-2-yl, 1,1-dioxo-2,3,4,5-tetrahydroisothiazol-2-yl, or tetrazol-5-yl optionally substituted with $C_1$-$C_3$ alkyl;

$R^{16}$ is hydrogen, chloro, isobutyl, $CH_2R^{24}$; $CF_2R^{25}$, 1,1,1-trifluoro-2-hydroxyeth-2-yl, $C_2$-$C_4$ alkenyl optionally substituted with one or two fluorine atoms, $OR^{26}$, $C(O)R^{27}$, N(methyl)(methylsulfonyl), N(methyl)(acetyl), pyrrolidin-2-on-1-yl, methylsulfonyl, N,N-dimethylaminosulfonyl, phenyl optionally substituted with one or two substituents selected from the group consisting of hydroxymethyl, methoxy, fluoro, and methylsulfonyl, 1,3-dioxolan-2-yl, 1,3-dithiolan-2-yl, 1,3-oxathiolan-2-yl, 1,3-dioxan-2-yl, 1,3-dithian-2-yl, pyridinyl, thiazolyl, oxazolyl, or 1,2,4-oxadiazolyl optionally substituted with methyl;

$R^{17}$ is hydrogen or fluoro;

$R^{18}$ is ethynyl or cyclopropyl;

$R^{19}$ is hydrogen or methyl;

$R^{20}$ is difluoromethyl or methanesulfonyl;

$R^{21}$ is $C_1$-$C_4$ alkyl, $C_3$-$C_6$ cycloalkyl, phenyl, or —$NR^{30}R^{31}$;

$R^{22}$ is hydrogen, $C_1$-$C_3$ alkyl optionally substituted with up to 3 fluorine atoms, or $C_3$-$C_6$ cycloalkyl;

$R^{23}$ is $C_1$-$C_3$ alkyl or $C_3$-$C_6$ cycloalkyl;

$R^{24}$ is fluoro, hydroxy, or $C_1$-$C_3$ alkoxy;

$R^{25}$ is hydrogen, phenyl, or furyl;

$R^{26}$ is $C_1$-$C_3$ alkyl optionally substituted with one or two fluorine atoms;

$R^{27}$ is $C_1$-$C_3$ alkyl, $C_3$-$C_5$ cycloalkyl, $C_2$-$C_3$ alkenyl, $C_1$-$C_3$ alkoxy, $NR^{28}R^{29}$, pyrrolidin-1-yl optionally substituted with methyl or one or two fluorine atoms, piperidin-1-yl, phenyl, pyridinyl, or furyl;

$R^{28}$ is hydrogen or methyl;

$R^{29}$ is methyl, ethyl, or propyl;

$R^{30}$ is hydrogen or methyl;

$R^{31}$ is methyl; or $R^{30}$ and $R^{31}$ taken together with the nitrogen atom to which they are attached form a pyrrolidine or piperidine ring;

$R^{32}$ is $C_1$-$C_{10}$ alkyl optionally substituted with 1-6 fluorine atoms, oxo, or one or two hydroxy groups, $C_2$-$C_6$ alkenyl, or —$(CH_2)_{0-3}$—$R^{33}$;

$R^{33}$ is $C_3$-$C_7$ cycloalkyl or phenyl each optionally substituted with one or two substituents independently selected from the group consisting of halo, $C_1$-$C_6$ alkyl, $C_1$-$C_6$ alkoxy, hydroxy, trifluoromethyl, and trifluoromethoxy, or $R^{33}$ is adamantyl;

$R^{34}$ is hydrogen, $R^{32}$, or —$(CH_2)_{0-2}$—$OR^{32}$;

$R^{35}$ is hydroxy, $C_1$-$C_6$ alkoxy, or $NR^{37}R^{38}$ where $R^{37}$ and $R^{38}$ are independently hydrogen or $C_1$-$C_6$ alkyl, or $R^{37}$ and $R^{38}$, taken together with the nitrogen to which they are attached, form a piperidine ring optionally substituted with $C_1$-$C_6$ alkyl, a homopiperidine ring, a morpholine ring, or a pyrrolidine ring optionally substituted with ($C_1$-$C_6$ alkoxy)methyl;

$R^{36}$ is $C_1$-$C_6$ alkyl or adamantyl;

$R^{39}$ is hydrogen or a nitrogen protecting group;

$R^{40}$ is hydrogen or an oxygen protecting group;

or an acid addition salt thereof; provided that: a) no more than one of X, Y, and Q may be N or $N^+$—$O^-$; b) when X is CH, Y is $CR^{16}$, and Q is $CR^{17}$, then one of $R^{16}$ and $R^{17}$ is other than hydrogen; and c) at least one of $R^{39}$ and $R^{40}$ is other than hydrogen.

The present invention also provides intermediates of Formula IV:

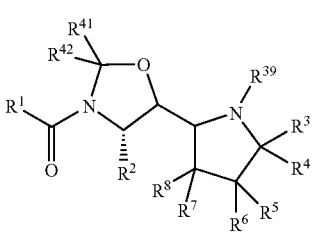

IV where:

$R^1$ is ($C_3$-$C_7$ cycloalkyl)$_{0-1}$($C_1$-$C_6$ alkyl), ($C_3$-$C_7$ cycloalkyl)$_{0-1}$($C_2$-$C_6$ alkenyl), ($C_3$-$C_7$ cycloalkyl)$_{0-1}$($C_2$-$C_6$ alkynyl) or $C_3$-$C_7$ cycloalkyl, each optionally substituted with up to three groups independently selected from halo, hydroxy, thiol, cyano, trifluoromethyl, trifluoromethoxy, $C_1$-$C_6$ alkoxy, $C_3$-$C_7$ cycloalkoxy, oxo, and $NR^9R^{10}$, hydrogen, biphenyl substituted with halo,

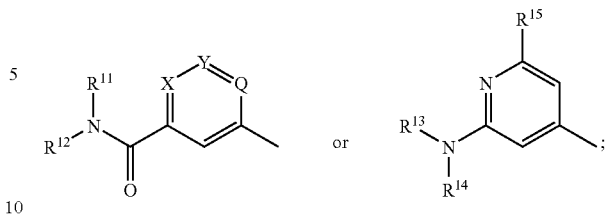

X is CH, N, or $N^+$—$O^-$;

Y is $CR^{16}$, N, or $N^+$—$O^-$;

Q is $CR^{17}$, N, or $N^+$—$O^-$;

$R^2$ is $C_1$-$C_3$ alkyl, benzyl optionally monosubstituted in the phenyl ring with a substituent selected from the group consisting of halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl, or benzyl optionally disubstituted in the phenyl ring with a first substituent independently selected from halo and a second substituent independently selected from halo, $C_1$-$C_6$ alkoxy optionally substituted in the alkyl chain with $C_3$-$C_7$ cycloalkyl, and $C_1$-$C_6$ alkylthio optionally substituted in the alkyl chain with $C_3$-$C_7$ cycloalkyl;

$R^3$ is hydrogen or $C_1$-$C_6$ alkyl;

$R^4$ is hydrogen, $C_1$-$C_6$ alkyl, or phenyl;

$R^3$ and $R^4$ taken together with the carbon to which they are attached form a $C_3$-$C_6$ cycloalkyl ring;

$R^5$ is hydrogen, fluoro, trifluoromethyl, $R^{32}$, or phenyl optionally monosubstituted with $C_1$-$C_6$ alkyl or $C_1$-$C_6$ alkoxy;

$R^6$ is fluoro, hydroxy, p-toluenesulfonyloxy, $R^{34}$, —$CH_2C(O)R^{35}$, or —$OC(O)NHR^{36}$; or $R^5$ and $R^6$ taken together form =$CHC(O)(C_1$-$C_4$ alkoxy) or oxo;

$R^7$ is hydrogen or fluoro; or $R^6$ and $R^7$ taken together form a bond;

$R^8$ is hydrogen or fluoro;

$R^9$ is hydrogen, $C_1$-$C_6$ alkyl, or phenyl;

$R^{10}$ is hydrogen, $C_1$-$C_6$ alkyl, phenyl, -C(O)($C_1$-$C_6$ alkyl), or —$SO_2(C_1$-$C_6$ alkyl);

$R^{11}$ and $R^{12}$ are independently selected from the group consisting of methyl, ethyl, and propyl;

$R^{13}$ is hydrogen or $C_1$-$C_6$ alkyl;

$R^{14}$ is $C_3$-$C_5$ cycloalkyl, $C_1$-$C_6$ alkyl, or —$CH_2R^{18}$;

$R^{15}$ is —$CF_2R^{19}$, —$OR^{20}$, —$CH_2C(O)CH_3$, —$S(O)_{1-2}R^{21}$, —$NR^{22}SO_2R^{23}$, ($C_1$-$C_3$ alkoxy)-carbonyl, phenyl optionally substituted with halo, 1,3-dioxolan-2-yl, 1,3-dioxan-2-yl, 1,1-dioxo-2,3,4,5-tetrahydroisothiazol-2-yl, or tetrazol-5-yl optionally substituted with $C_1$-$C_3$ alkyl;

$R^{16}$ is hydrogen, chloro, isobutyl, $CH_2R^{24}$; $CF_2R^{25}$, 1,1,1-trifluoro-2-hydroxyeth-2-yl, $C_2$-$C_4$ alkenyl optionally substituted with one or two fluorine atoms, $OR^{26}$, $C(O)R^{27}$, N(methyl)(methylsulfonyl), N(methyl)(acetyl), pyrrolidin-2-on-1-yl, methylsulfonyl, N,N-dimethylaminosulfonyl, phenyl optionally substituted with one or two substituents selected from the group consisting of hydroxymethyl, methoxy, fluoro, and methylsulfonyl, 1,3-dioxolan-2-yl, 1,3-dithiolan-2-yl, 1,3-oxathiolan-2-yl, 1,3-dioxan-2-yl, 1,3-dithian-2-yl, pyridinyl, thiazolyl, oxazolyl, or 1,2,4-oxadiazolyl optionally substituted with methyl;

$R^{17}$ is hydrogen or fluoro;

$R^{18}$ is ethynyl or cyclopropyl;

$R^{19}$ is hydrogen or methyl;

$R^{20}$ is difluoromethyl or methanesulfonyl;

$R^{21}$ is $C_1$-$C_4$ alkyl, $C_3$-$C_6$ cycloalkyl, phenyl, or —$NR^{30}R^{31}$;

$R^{22}$ is hydrogen, $C_1$-$C_3$ alkyl optionally substituted with up to 3 fluorine atoms, or $C_3$-$C_6$ cycloalkyl;

$R^{23}$ is $C_1$-$C_3$ alkyl or $C_3$-$C_6$ cycloalkyl;

$R^{24}$ is fluoro, hydroxy, or $C_1$-$C_3$ alkoxy;

$R^{25}$ is hydrogen, phenyl, or furyl;

$R^{26}$ is $C_1$-$C_3$ alkyl optionally substituted with one or two fluorine atoms;

$R^{27}$ is $C_1$-$C_3$ alkyl, $C_3$-$C_5$ cycloalkyl, $C_2$-$C_3$ alkenyl, $C_1$-$C_3$ alkoxy, $NR^{28}R^{29}$, pyrrolidin-1-yl optionally substituted with methyl or one or two fluorine atoms, piperidin-1-yl, phenyl, pyridinyl, or furyl;

$R^{28}$ is hydrogen or methyl;

$R^{29}$ is methyl, ethyl, or propyl;

$R^{30}$ is hydrogen or methyl;

$R^{31}$ is methyl; or $R^{30}$ and $R^{31}$ taken together with the nitrogen atom to which they are attached form a pyrrolidine or piperidine ring;

$R^{32}$ is $C_1$-$C_{10}$ alkyl optionally substituted with 1-6 fluorine atoms, oxo, or 1 or 2 hydroxy groups, $C_2$-$C_6$ alkenyl, or —$(CH_2)_{0-3}$—$R^{33}$;

$R^{33}$ is $C_3$-$C_7$ cycloalkyl or phenyl each optionally substituted with one or two substitutents independently selected from the group consisting of halo, $C_1$-$C_6$ alkyl, $C_1$-$C_6$ alkoxy, hydroxy, trifluoromethyl, and trifluoromethoxy, or $R^{33}$ is adamantyl;

$R^{34}$ is hydrogen, $R^{32}$, or —$(CH_2)_{0-2}$—$OR^{32}$;

$R^{35}$ is hydroxy, $C_1$-$C_6$ alkoxy, or $NR^{37}R^{38}$ where $R^{37}$ and $R^{38}$ are independently hydrogen or $C_1$-$C_6$ alkyl, or $R^{37}$ and $R^{38}$, taken together with the nitrogen to which they are attached, form a piperidine ring optionally substituted with $C_1$-$C_6$ alkyl, a homopiperidine ring, a morpholine ring, or a pyrrolidine ring optionally substituted with ($C_1$-$C_6$ alkoxy) methyl;

$R^{36}$ is $C_1$-$C_6$ alkyl or adamantyl;

$R^{39}$ is hydrogen or a nitrogen protecting group;

$R^{41}$ and $R^{42}$ are independently selected from methyl, ethyl, and propyl;

or an acid addition salt thereof; provided that no more than one of X, Y, and Q may be N or $N^+$—$O^-$.

DETAILED DESCRIPTION OF THE INVENTION

The general chemical terms used in the formulae above have their usual meanings. For example, the term "$C_1$-$C_3$ alkyl" includes methyl, ethyl, propyl, and isopropyl, and the terms "$C_1$-$C_6$ alkyl" and "$C_1$-$C_{10}$ alkyl" include methyl, ethyl, propyl, isopropyl, butyl, isobutyl, sec-butyl, tert-butyl, pentyl, neopentyl, and hexyl moieties.

The term "$C_3$-$C_5$ cycloalkyl" includes cyclopropyl, cyclobutyl, and cyclopentyl moieties, the term "$C_3$-$C_6$ cycloalkyl" includes cyclopropyl, cyclobutyl, cyclopentyl, and cyclohexyl, likewise, the term "$C_3$-$C_7$ cycloalkyl" includes cyclopropyl, cyclobutyl, cyclopentyl, cyclohexyl, and cycloheptyl moieties.

The term "$C_2$-$C_3$ alkenyl" includes ethenyl, prop-1-en-3-yl, prop-1-en-2-yl, and the like. The terms "$C_2$-$C_6$ alkenyl" and "$C_2$-$C_{10}$ alkenyl" include ethenyl, prop-1-en-3-yl, prop-1-en-2-yl, 2-methylprop-1-en-1-yl, and the like.

The terms "$C_2$-$C_6$ alkynyl" and "$C_2$-$C_{10}$ alkynyl" include ethynyl, prop-1-yn-3-yl, prop-1-yn-1-yl, 4-methylpent-2-yn-1-yl, and the like.

"Halo" includes fluoro, chloro, bromo, and iodo.

The terms "$C_1$-$C_3$ alkoxy" and "$C_1$-$C_6$ alkoxy" are a $C_1$-$C_3$ alkyl group or a $C_1$-$C_6$ alkyl group, respectively, bonded to an oxygen atom and include methoxy, ethoxy, isopropoxy, tert-butoxy, and the like. Similarly, the terms "$C_3$-$C_5$ cycloalkoxy" and "$C_3$-$C_7$ cycloalkoxy" are a $C_3$-$C_5$ cycloalkyl group or a $C_3$-$C_7$ cycloalkyl group, respectively, bonded through an oxygen atom and include cyclopropoxy, cyclobutoxy, cyclopentoxy, and the like.

The term "($C_3$-$C_7$ cycloalkyl)$_{0-1}$($C_1$-$C_6$ alkyl)" is taken to mean a $C_1$-$C_6$ alkyl moiety optionally substituted with one $C_3$-$C_7$ cycloalkyl moiety at any available carbon atom in the $C_1$-$C_6$ alkyl moiety. Similarly, "($C_3$-$C_7$ cycloalkyl)$_{0-1}$($C_2$-$C_6$ alkenyl)" and "($C_3$-$C_7$ cycloalkyl)$_{0-1}$($C_2$-$C_6$ alkynyl)" are taken to mean a $C_2$-$C_6$ alkenyl or $C_2$-$C_6$ alkynyl moiety optionally substituted at any available carbon atom in the $C_2$-$C_6$ alkenyl or $C_2$-$C_6$ alkynyl moiety.

The term "$C_1$-$C_6$ alkoxy optionally substituted in the alkyl chain with $C_3$-$C_7$ alkyl" is taken to mean a $C_1$-$C_6$ alkoxy moiety optionally substituted with one $C_3$-$C_7$ cycloalkyl moiety at any available carbon atom in the $C_1$-$C_6$ alkoxy moiety. Similarly, the term "$C_1$-$C_6$ alkylthio optionally substituted in the alkyl chain with $C_3$-$C_7$ alkyl" is taken to mean a $C_1$-$C_6$ alkylthio moiety optionally substituted with one $C_3$-$C_7$ cycloalkyl moiety at any available carbon atom in the $C_1$-$C_6$ alkylthio moiety.

The term "nitrogen protecting group" is taken to mean a moiety that is stable to projected reaction conditions and yet may be selectively removed by reagents and reaction conditions compatible with the regenerated amine. Such groups are well known by the skilled artisan and are described in the literature. (See, for example: Greene and Wuts, *Protective Groups in Organic Synthesis*, Third Edition, Chapter 7, John Wiley and Sons Inc., (1999)). Nitrogen protecting groups contemplated include:

a) suitable carbamates, such as:
1) $C_1$-$C_7$ alkyl carbamates including methyl, ethyl, tert-butyl, tert-amyl, diisopropylmethyl carbamates, and the like;
2) substituted ethyl carbamates, such as 2,2,2-trichloroethyl, 2-trimethylsilylethyl, 2-phenylethyl, 1,1-dimethyl-2-haloethyl, 1,1-dimethyl-2,2-dibromoethyl, 1,1-dimethyl-2,2,2-trichloro-ethyl, 2-(pyridin-2-yl) ethyl, 2-(pyridin-4-yl)ethyl, 2-methylthioethyl, 2-methylsulfonylethyl, 2-(p-toluenesulfonyl)ethyl, 2-phosphonioethyl, 1,1-dimethyl-2-cyanoethyl, 2-iodoethyl carbamates, and the like;
3) 1-adamantyl carbamate;
4) vinyl carbamate;
5) allyl carbamate;
6) 1-isopropylallyl carbamate;
7) cinnamyl carbamates, such as cinnamyl carbamate, 4-nitrocinnamyl, and the like;
8) 8-quinolinyl carbamate;
9) N-hydroxypiperidinyl carbamate;
10) $C_1$-$C_4$ alkyldithio carbamates;
11) Benzyl carbamates, such as benzyl, 4-methoxybenzyl, 4-nitrobenzyl, 4-halobenzyl, 4-cyanobenzyl, 4-decyloxybenzyl, 2,4-dichlorobenzyl, 3,5-dimethoxybenzyl, 2-nitrobenzyl, 3,4-dimethoxy-6-nitrobenzyl, phenyl (2-nitrophenyl)methyl, 4-methylsulfinylbenzyl, 9-anthrylmethyl, diphenylmethyl, 3-chloro-4-($C_2$-$C_6$ acyloxy)benzyl, 4-(dihydroxyboryl)benzyl carbamates, and the like;
12) 2-(1,3-dithianyl)methyl carbamate;
13) aryl carbamates, such as phenyl, nicotinyl, 4-(methylthio)phenyl, 2,4-di(methylthio)phenyl, 3-nitrophenyl carbamates, and the like;
14) 2-triphenylphosphonioisopropyl carbamate;
15) 5-benzisoxazolylmethyl carbamate;
16) 2-(trifluoromethyl)-6-chromonylmethyl carbamate;
17) S-benzyl thiocarbamate; and 18) C$_3$-C$_7$ cycloalkyl carbamates, such as cyclobutyl, cyclopentyl, 1-methylcyclohexyl, cyclopropylmethyl carbamates, and the like;

b) suitable ureas, such as:
1) phenothiazinyl-(10)-carbonyl;
2) N'-(p-toluenesulfonylaminocarbonyl); and
3) N'-phenylaminothiocarbonyl;

c) suitable formyl and acyl groups, such as:
1) formyl; and
2) acetyl groups, such as acetyl, chloroacetyl, trichloroacetyl, trifluoroacetyl, 4-chlorobutanoyl, phenylacetyl, 3-phenylpropanoyl, N-benzoylphenylalanyl, 2-nitrophenylacetyl, 2-nitrophenoxyacetyl, acetoacetyl, and the like;

d) suitable aroyl groups, such as:
1) picolinoyl;
2) 3-pyridinylcarbonyl;
3) benzoyl;
4) 4-phenylbenzoyl;
5) 2-nitrobenzoyl; and
6) 2-nitrocinnamoyl, and the like;

e) suitable cyclic imide groups, such as:
1) N-phthalimide;
2) N-dithiasuccinimide;
3) N-2,3-diphenylmaleimide; and
4) N-2,5-dimethylpyrrole, and the like;

f) allyl;
g) 3-acetoxypropyl;
h) suitable benzylic groups, such as benzyl, 2-methylbenzyl, α-methylbenzyl, and the like;
i) triphenylmethyl; and
j) suitable imine moieties, such as:
1) 1,1-dimethylthiomethyleneimine;
2) benzylidene imine; and
3) diphenylmethyleneimine, and the like.

The term "oxygen protecting group" is taken to mean a moiety that is stable to projected reaction conditions and yet may be selectively removed by reagents and reaction conditions compatible with the regenerated alcohol. Such groups are well known by the skilled artisan and are described in the literature. (See, for example: Greene and Wuts, *Protective Groups in Organic Synthesis*, Third Edition, Chapter 7, John Wiley and Sons Inc., (1999)). Oxygen protecting groups contemplated include:

a) methyl and substituted methyl groups such as methoxymethyl, methylthio-methyl, (phenyldimethylsilyl)methoxymethyl, benzyloxymethyl, p-methoxy-benzyloxymethyl, p-nitrobenzyloxy-methyl, o-nitrobenzyloxymethyl, (4-methoxyphenoxy)methyl, guiaiacolmethyl, tert-butoxymethyl, 4-pentenyloxymethyl, siloxymethyl, 2-methoxyethoxymethyl, 2,2,2-trichloroeth-oxymethyl, bis(2-chloroethoxy)methyl, 2-(trimethylsilyl)ethoxymethyl, 2-quinolinylmethyl, 1-pyrenylmethyl, diphenylmethyl, triphenylmethyl, and the like;

b) tetrahydropyranyl and substituted tetrahydropyranyl groups such as 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl-S,S-dioxide, and the like;

c) tetrahydrofuranyl and substituted tetrahydrofuranyl groups such as tetrahydrothiofuranyl and the like;

d) ethyl and substituted ethyl groups such as 1-ethoxyethyl, 1-(2-chloroethoxy)-ethyl, 1-[(2-trimethylsilyl)ethoxy]ethyl, 1-methyl-1-methoxy-ethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tert-butyl, and the like;

e) allyl;
f) propargyl;
g) substituted phenyl groups such as p-chlorophenyl, p-nitrophenyl, 2,4-dinitrophenyl, 2,3,5,6-tetrafluoro-4-(trifluoromethyl)phenyl, and the like;

h) benzyl and substituted benzyl groups such as p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2,6-difluorobenzyl, p-acylaminobenzyl, p-azidobenzyl, 4-azido-3-chlorobenzyl, 2-trifluoromethylbenzyl, p-(methylsulfinyl)benzyl, and the like;

i) silyl groups such as trimethylsilyl, triethylsilyl, triisopropylsilyl, dimethylisopropylsilyl, diethylisopropylsilyl, dimethylthexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenyl silyl, tert-butoxydiphenylsilyl, and the like;

j) formyl and benzoylformyl groups;
k) acetyl and substituted acetyl groups such as chloroacetyl, dichloroacetyl, trichloroacetyl, trifluoroacetyl, methoxyacetyl, triphenylmethoxyacetyl, phenoxyacetyl, p-chlorophenoxyacetyl, phenylacetyl, chlorodiphenylacetyl and the like;

l) pivaloyl;
m) crotonyl;
n) benzoyl and substituted benzoyl groups such as p-phenylbenzoyl, 2-chlorobenzoyl, 4-bromobenzoyl, 2,4,6-trimethylbenzoyl;

o) methoxycarbonyl and substituted methoxycarbonyl groups such as methoxymethoxycarbonyl, 9-flurenylmethoxycarbonyl, and the like;

p) ethoxycarbonyl and substituted ethoxycarbonyl groups such as 2,2,2-trichloroethoxycarbonyl, 1,1-dimethyl-2,2,2-trichloroethoxycarbonyl, 2-(trimethylsilyl)ethoxycarbonyl, 2-dansylethoxycarbonyl, 2-(4-nitrophenyl)-ethoxycarbonyl, 2-(2,4-dinitrophenyl)ethoxycarbonyl, 2-cyano-1-phenylethoxycarbonyl, and the like;

q) isobutoxycarbonyl;
r) vinyloxycarbonyl;
s) allyloxycarbonyl;
t) substituted phenoxycarbonyl groups such as p-nitrophenoxycarbonyl, 2-iodophenoxycarbonyl, 2-chlorophenoxycarbonyl, 4-bromophenoxycarbonyl, 4-nitrophenoxycarbonyl, o-(dibromomethyl)phenoxycarbonyl, and the like;

u) benzyloxycarbonyl and substituted benzyloxycarbonyl groups such as p-methoxybenzyloxycarbonyl, 3,4-dimethoxybenzyloxycarbonyl, o-nitrobenzyloxycarbonyl, p-nitrobenzyloxycarbonyl, and the like; and v) sulfonyl groups such as methanesulfonyl, benzylsulfonyl, p-toluenesulfonyl, 2-[(4-nitrophenyl)ethyl]sulfonyl, and the like.

The term "inhibition of production of A-β peptide" is taken to mean decreasing of excessive in vivo levels of A-β peptide in a mammal to normal or sub-normal levels.

The term "effective amount of a compound of Formula I" is taken to mean the dose or doses of a compound of Formula I required to inhibit BACE sufficiently to decrease in vivo levels of A-β peptide in a mammal to normal or sub-normal levels.

The term "treatment" includes treating one or more disease symptoms present in a patient as well as slowing, arresting, or reversing the progression of the disease.

The term "BACE" includes both BACE1 and BACE2.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.,* 58, 397-405 (2001); Petersen, et al., *Arch. Neurol.,* 56, 303-308 (1999)). The term "prevention of the progression of mild cognitive impairment to Alzheimer's disease" includes slowing, arresting, or reversing the progression of mild cognitive impairment to Alzheimer's disease in a patient.

The skilled artisan will appreciate that compounds of Formulae I, II, and III are comprised of a 1-amino-2-hydroxyethyl core that contains two chiral centers:

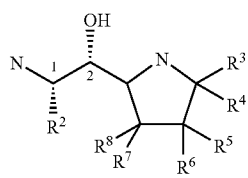

(i)

Although the present invention contemplates all individual enantiomers or diastereomers, as well as mixtures of the enantiomers and diastereomers of said compounds including racemates, compounds with the absolute configuration at atoms labeled 1 and 2 as illustrated in figure (i) are preferred compounds of Formulae I, II, and III. The skilled artisan will also appreciate that the compounds of Formula IV comprise an oxazolidinyl ring that contains chiral centers corresponding to the atoms labeled 1 and 2 in FIG. (1). Although all individual enantiomers or diastereomers, as well as mixtures of the enantiomers and diastereomers of compounds of Formula IV including racemates are contemplated by the present invention, the compounds of Formula IV with the absolute configuration at atoms labeled 1 and 2 in FIG. (1) are preferred compounds of Formula IV. The skilled artisan will also appreciate that the point of attachment of the pyrrolidine ring to the 1-amino-2-hydroxyethyl core introduces a third chiral center into the compounds of the present invention. Although the present invention contemplates all individual enantiomers or diastereomers, as well as mixtures of the enantiomers and diastereomers of said compounds including racemates, it is preferred that compounds of the invention exist with the absolute configuration illustrated in figure (ii).

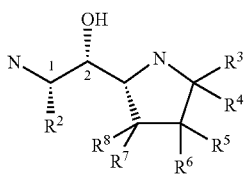

(ii)

Additionally, the skilled artisan will appreciate that additional chiral centers may be created in the compounds of the invention by the selection of certain variables. The present invention contemplates all individual enantiomers or diastereomers, as well as mixtures of the enantiomers and diastereomers of said compounds including racemates. The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers and diastereomers of compounds of the invention are a preferred embodiment of the invention.

It will be understood by the skilled reader that some or all of the compounds of Formulae I, II, III, and IV are capable of forming salts. In all cases, the acid addition or pharmaceutically acceptable salts of all of the compounds are included in the names of them. The compounds of the present invention are amines, and accordingly react with any of a number of inorganic and organic acids to form pharmaceutically acceptable acid addition salts. Preferred pharmaceutically acceptable salts are those formed with hydrochloric acid and trifluoroacetic acid.

Although all of the compounds of Formula I are useful inhibitors of BACE, certain classes of compounds are preferred. The following paragraphs describe such preferred classes:

a) $R^1$ is hydrogen;
b) $R^1$ is $C_1$-$C_6$ alkyl;
c) $R^1$ is $C_1$-$C_4$ alkyl;
d) $R^1$ is $C_1$-$C_2$ alkyl;
e) $R^1$ is methyl optionally substituted with chloro or fluoro;
f) $R^1$ is methyl;
g) $R^1$ is

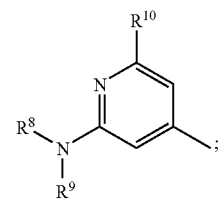

h) $R^2$ is benzyl optionally mono- or difluorinated in the phenyl ring;
i) $R^2$ is benzyl;
j) $R^2$ is 3-fluorobenzyl;
k) $R^2$ is 3,5-difluorobenzyl;
l) The compound of Formula I is a free base;
m) The compound of Formula I is a pharmaceutically acceptable salt;
n) The compound of Formula I is the hydrochloride salt.

Preferred embodiments of the invention include all combinations of paragraphs a)-n). Other preferred compounds of Formula I are those where $R^1$ is $(C_3\text{-}C_7 \text{ cycloalkyl})_{0-1}(C_1\text{-}C_6$ alkyl), $(C_3\text{-}C_7$ cycloalkyl$)_{0-1}(C_2\text{-}C_6$ alkenyl), $(C_3\text{-}C_7$ cycloalkyl$)_{0-1}(C_2\text{-}C_6$ alkynyl) or $C_3\text{-}C_7$ cycloalkyl, each optionally substituted with up to three groups independently selected from halo, hydroxy, thiol, cyano, trifluoromethyl, trifluoromethoxy, $C_1\text{-}C_7$ alkoxy, $C_3\text{-}C_7$ cycloalkoxy, oxo, and $NR^4R^5$, biphenyl optionally substituted with halo, hydrogen, or

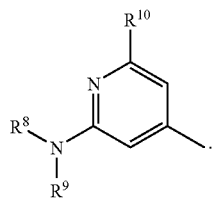

Especially preferred compounds of Formula I are those where $R^1$ is $C_1$-$C_6$ alkyl and $R^2$ is benzyl, 3-fluorobenzyl, or 3,5-difluorobenzyl. Most preferred compounds of Formula I are those where $R^1$ is methyl and $R^2$ is benzyl, 3-fluorobenzyl, or 3,5-difluorobenzyl.

A preferred subgenus of compounds of Formula I are compounds of Formula I(a):

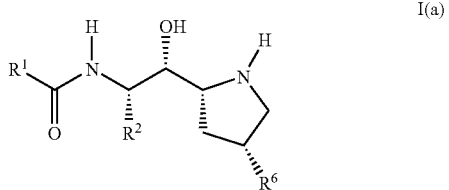

or a pharmaceutically acceptable salt thereof where $R^1$, $R^2$, and $R^6$ are as previously defined. Other preferred compounds of Formula I(a) are those where $R^1$ is $(C_3$-$C_7$ cycloalkyl$)_{0-1}$ $(C_1$-$C_6$ alkyl), $(C_3$-$C_7$ cycloalkyl$)_{0-1}(C_2$-$C_6$ alkenyl), $(C_3$-$C_7$ cycloalkyl$)_{0-1}(C_2$-$C_6$ alkynyl) or $C_3$-$C_7$ cycloalkyl, each optionally substituted with up to three groups independently selected from halo, hydroxy, thiol, cyano, trifluoromethyl, trifluoromethoxy, $C_1$-$C_7$ alkoxy, $C_3$-$C_7$ cycloalkoxy, oxo, and $NR^4R^5$, biphenyl optionally substituted with halo, hydrogen, or

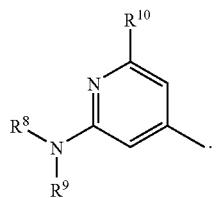

Compounds of Formula I(a) where $R^6$ is either —$(CH_2)_{0-2}$ $OR^{32}$ or —$CH_2C(O)R^{35}$ where $R^{32}$ and $R^{35}$ are as previously defined are preferred. Compounds of Formula I(a) where $R^1$ is $C_1$-$C_6$ alkyl, $R^2$ is benzyl, 3-fluorobenzyl, or 3,5-difluorobenzyl, and $R^{37}$ is —$CH_2C(O)NR^{37}R^{38}$ where $R^{37}$ and $R^{38}$ are as previously defined are most preferred.

Although all of the compounds of Formula II are useful intermediates for the preparation of BACE inhibitors, certain of the compounds are preferred:
o) $R^2$ is benzyl optionally mono- or difluorinated in the phenyl ring;
p) $R^2$ is benzyl;
q) $R^2$ is 3-fluorobenzyl;
r) $R^2$ is 3,5-difluorobenzyl;
s) $R^{39}$ is a carbamate protecting group;
t) $R^{39}$ is tert-butoxycarbonyl;
u) $R^{39}$ is α-methylbenzyl;
v) $R^{40}$ is benzyl;
w) $R^{40}$ is 2-methylbenzyl;
x) $R^{40}$ is hydrogen;
y) $R^{40}$ is hydrogen and $R^{39}$ is tert-butoxycarbonyl or α-methylbenzyl;
z) $R^{40}$ is hydrogen and $R^{39}$ is tert-butoxycarbonyl;
aa) The compound of Formula II is a free base;
bb) The compound of Formula II is an acid addition salt.

Preferred embodiments of compounds of Formula II include all combinations of paragraphs o)-bb).

Although all of the compounds of Formula III are useful intermediates for the preparation of BACE inhibitors, certain of the compounds are preferred:
cc) $R^1$ is hydrogen;
dd) $R^1$ is $C_1$-$C_6$ alkyl;
ee) $R^1$ is $C_1$-$C_4$ alkyl;
ff) $R^1$ is $C_1$-$C_2$ alkyl;
gg) $R^1$ is methyl optionally substituted with chloro or fluoro;
hh) $R^1$ is methyl;
ii) $R^1$ is

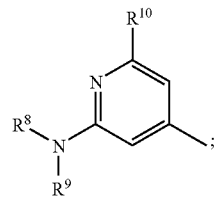

jj) $R^2$ is benzyl optionally mono- or difluorinated in the phenyl ring;
kk) $R^2$ is benzyl;
ll) $R^2$ is 3-fluorobenzyl;
mm) $R^2$ is 3,5-difluorobenzyl;
nn) $R^{39}$ is a carbamate protecting group;
oo) $R^{39}$ is tert-butoxycarbonyl;
pp) $R^{39}$ is benzyl;
qq) $R^{39}$ is α-methylbenzyl;
rr) $R^{40}$ is hydrogen;
ss) The compound of Formula III is a free base;
tt) The compound of Formula III is an acid addition salt.

Preferred embodiments of compounds of Formula III include all combinations of paragraphs cc)-tt). Especially preferred compounds of Formula III are those where $R^1$ is $C_1$-$C_6$ alkyl, $R^2$ is benzyl, 3-fluorobenzyl, or 3,5-difluorobenzyl, $R^{40}$ is hydrogen and $R^{39}$ is tert-butoxycarbonyl or α-methylbenzyl. Most preferred compounds of Formula III are those where $R^1$ is methyl, $R^2$ is benzyl, 3-fluorobenzyl, or 3,5-difluorobenzyl, $R^{40}$ is hydrogen and $R^{39}$ is tert-butoxycarbonyl or α-methylbenzyl.

Although all of the compounds of Formula IV are useful intermediates for the preparation of BACE inhibitors, certain of the compounds are preferred:
uu) $R^1$ is hydrogen;
vv) $R^1$ is $C_1$-$C_6$ alkyl;
ww) $R^1$ is $C_1$-$C_4$ alkyl;
xx) $R^1$ is $C_1$-$C_2$ alkyl;
yy) $R^1$ is methyl optionally substituted with chloro or fluoro;
zz) $R^1$ is methyl;
aaa) $R^1$ is

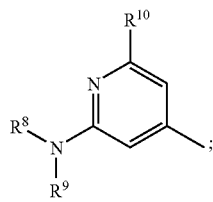

bbb) $R^2$ is benzyl optionally mono- or difluorinated in the phenyl ring;
ccc) $R^2$ is benzyl;
ddd) $R^2$ is 3-fluorobenzyl;
eee) $R^2$ is 3,5-difluorobenzyl;
fff) $R^{41}$ and $R^{42}$ are both methyl;
ggg) $R^{39}$ is tert-butoxycarbonyl;
hhh) $R^{39}$ is benzyl;
iii) $R^{39}$ is α-methylbenzyl;
jjj) The compound of Formula IV is a free base;
kkk) The compound of Formula IV is an acid addition salt.

Preferred embodiments of compounds of Formula IV include all combinations of paragraphs uu)-kkk). Especially preferred compounds of Formula IV are those where $R^1$ is $C_1$-$C_6$ alkyl, $R^2$ is benzyl, 3-fluorobenzyl, or 3,5-difluorobenzyl, and $R^{39}$ is tert-butoxycarbonyl or α-methylbenzyl. Most preferred compounds of Formula IV are those where $R^1$ is methyl, $R^2$ is benzyl, 3-fluorobenzyl, or 3,5-difluorobenzyl, and $R^{39}$ is tert-butoxycarbonyl or α-methylbenzyl.

The compounds of Formula I are inhibitors of BACE. It is preferred the compound of Formula I selectively inhibits BACE1 relative to BACE2. Thus, the present invention also provides a method of inhibiting BACE in a mammal that comprises administering to a mammal in need of said treatment a BACE-inhibiting amount of a compound of Formula I. It is preferred that the mammal to be treated by the administration of the compounds of Formula I is human.

As inhibitors of BACE, the compounds of the present invention are useful for suppressing the production of A-β peptide, and therefore for the treatment of disorders resulting from excessive A-β peptide levels due to over-production and/or reduced clearance of A-β peptide. A further embodiment of the present invention is the use of a compound of Formula I for the manufacture of a medicament for treating a disease or condition capable of being improved or prevented by inhibition of BACE. The compounds of Formula I are therefore believed to be useful in treating or preventing Alzheimer's disease, mild cognitive impairment, Down's Syndrome, Hereditary Cerebral Hemorrhage with Amyloidosis of the Dutch-Type, cerebral amyloid angiopathy, other degenerative dementias such as: dementias of mixed vascular and degenerative origin, dementia associated with Parkinson's disease, dementia associated with progressive supranuclear palsy, dementia associated cortical basal degeneration, and diffuse Lewy body type of Alzheimer's disease.

The compounds of the present invention may be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. Some stereochemical centers have been specified and certain substituents have been eliminated in the following schemes for the sake of clarity and are not intended to limit the teaching of the schemes in any way. Furthermore, individual isomers, enantiomers, or diastereomers may be separated at any convenient point in the synthesis of compounds of Formula I.

The compounds of Formula I may be prepared as described in Scheme I where variables $R^1$, $R^2$, $R^3$, $R^4$, $R^5$, $R^6$, $R^7$, $R^8$, $R^{39}$, and $R^{40}$ are as previously defined:

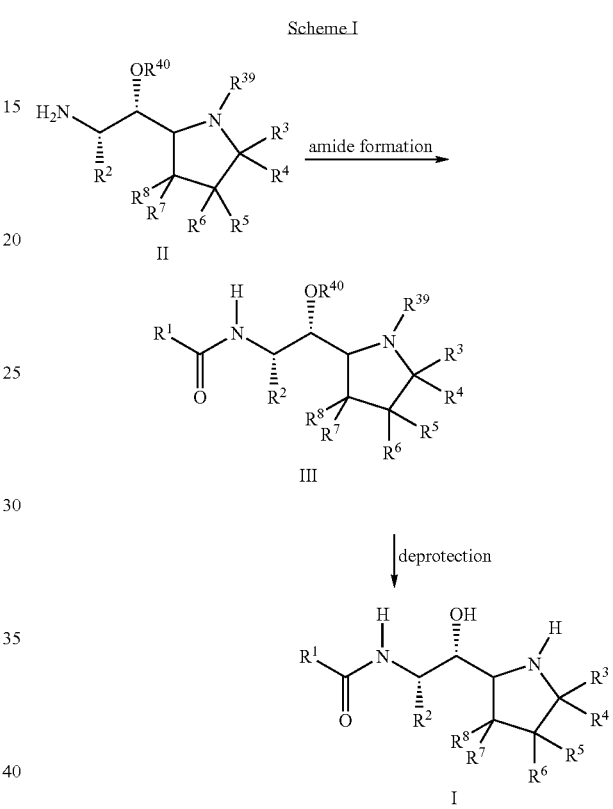

The amine of Formula II is reacted under standard amide forming conditions well known to the skilled artisan to provide compounds of Formula III (for example, see WO 03/040096 and WO 04/024081). An appropriate carboxylic acid of Formula $R^1$—COOH or an equivalent thereof, such as the sodium or, preferably, potassium carboxylate salt is reacted with a peptide coupling agent such as dicyclohexylcarbodiimide (DCC), 1-(3-dimethylaminopropyl)-3-ethylcarbodiimide hydrochloride (EDCl), or n-propylphosphonic anhydride, and an appropriate amine such as N-methylmorpholine or triethylamine, in a suitable solvent such as dichloromethane, dimethylformamide (DMF) or tetrahydrofuran (THF) to provide the compound of Formula III. If necessary or required, an additive such as 4-(dimethylamino)pyridine and/or 1-hydroxybenzotriazole or equivalents thereof may be added to the reaction mixture to facilitate the reaction. Alternatively, other carboxylic acid equivalents, including acylating agents, such as an appropriate acylimidazole, or a mixed anhydride, such as formic acetic anhydride, or an appropriate acid halide may be reacted directly with the amine of Formula II to provide the desired amide. The requisite carboxylic acids, carboxylic acid salts, acylating agents, and mixed anhydrides are either commercially available or may be prepared from commercially available materials by methods well known to the skilled artisan. (For example, See: *Comprehensive Organic Transformations*, Larock, Wiley-VCH Publishers, Inc., New York, (1999); *Advanced Organic Chemistry*, March, Wiley Interscience, New York, Third Edition, (1985))

The conditions for deprotection of compounds of Formula III to provide compounds of Formula I depend on the nature of variables $R^{39}$ and $R^{40}$. The deprotection conditions are those well known to the skilled artisan and are described in the literature. (For example, see: Greene and Wuts, *Protective Groups in Organic Synthesis*, Third Edition, Chapters 2 and 7, John Wiley and Sons Inc., (1999)). Again, depending upon the nature of variables $R^{39}$ and $R^{40}$, they may both be removed in a single reaction, for example by treatment with acid or under hydrogenation conditions, or may be removed sequentially as necessary or desired. The skilled artisan will appreciate that where $R^{40}$ is hydrogen, only nitrogen deprotection is necessary to provide compounds of Formula I. Additionally, where $R^{39}$ and $R^{40}$ are both hydrogen, the skilled artisan will appreciate that no deprotection step is necessary. Further, if salts of compounds of the invention are desired, an appropriate free base of Formula I is simply reacted with an appropriate pharmaceutically acceptable acid in a suitable solvent under standard conditions to provide a pharmaceutically acceptable salt of a compound of Formula I. The skilled artisan will appreciate that, depending on the nature of variables $R^{39}$ and $R^{40}$, the deprotection and salt forming steps may occur simultaneously to provide a pharmaceutically acceptable salt of a compound of Formula I in a single step.

Intermediates of Formula II may be prepared as described in the following scheme where $R^2$, $R^3$, $R^4$, $R^5$, $R^6$, $R^7$, $R^8$, and $R^{39'}$ are as previously defined.

The N,N-diprotected aminoaldehyde (iii) is reacted with the anion of appropriately substituted cyclic amine (iv) at low temperature in a suitable solvent, for example tetrahydrofuran, to provide the N,N-diprotected aminoethanol (v). The amine moiety is deprotected under standard conditions (For example, see: Greene and Wuts, *Protective Groups in Organic Synthesis*, Third Edition, Chapter 7, John Wiley and Sons Inc., (1999)) to provide the desired aminoethanol II(a). Alternatively, aldehyde (vi) is reacted with the anion of an appropriately substituted nitroalkane (vii) to provide the corresponding nitroethane (viii). The nitroethane is reduced to provide the desired aminoethanol II(a). The requisite anions are prepared by treating the appropriately substituted pyrrolidine or appropriately substituted nitroethane with a suitable base at low temperature. The requisite appropriately substituted pyrrolidines, appropriately substituted nitroethanes, and appropriately substituted aldehydes are either commercially available or may be prepared from commercially available starting materials. (For example, see: *Comprehensive Organic Transformations*, Larock, Wiley-VCH Publishers, Inc., New York, (1999); *Advanced Organic Chemistry*, March, Wiley Interscience, New York, Third Edition, (1985))

A further alternative to Scheme II is to react the anion of an appropriately substituted pyrrole with an N,N-diprotected aminoaldehyde (iii). The pyrrole moiety in the resulting N,N-diprotected aminoethanol must then be hydrogenated in an additional step to provide certain of the desired aminoethanols (v).

The compounds of Formula II may also be prepared as described in Scheme III where variable $R^2$, $R^3$, $R^4$, $R^5$, $R^6$, $R^7$, $R^8$, $R^{39}$, and $R^{39'}$ are as previously defined and variable $R^{40'}$ is an oxygen protecting group.

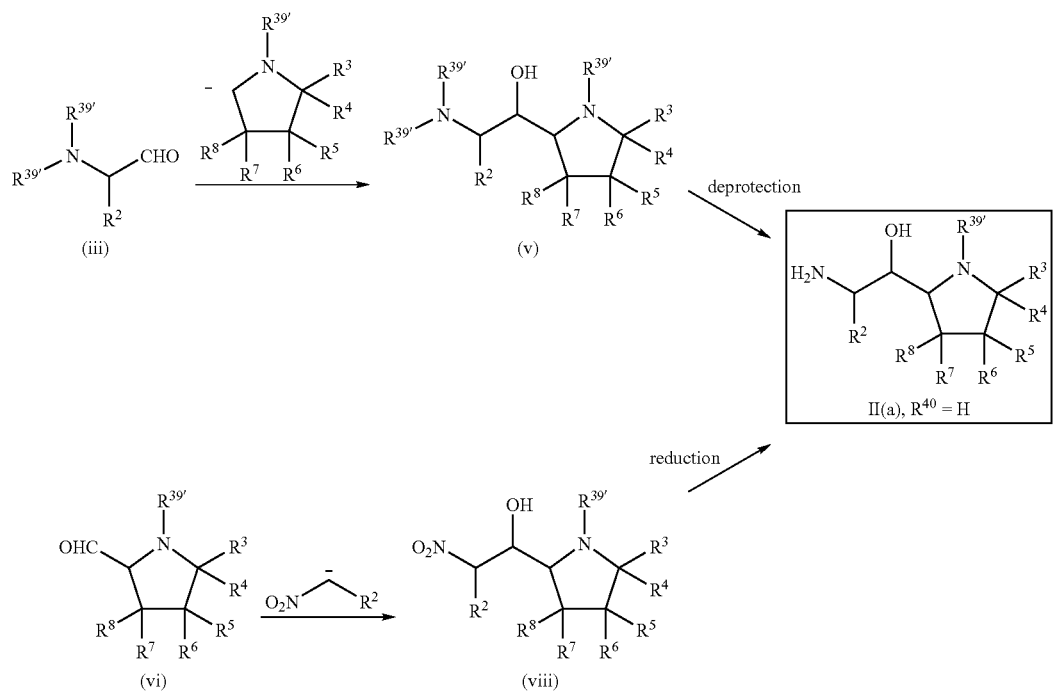

Scheme II

Scheme III

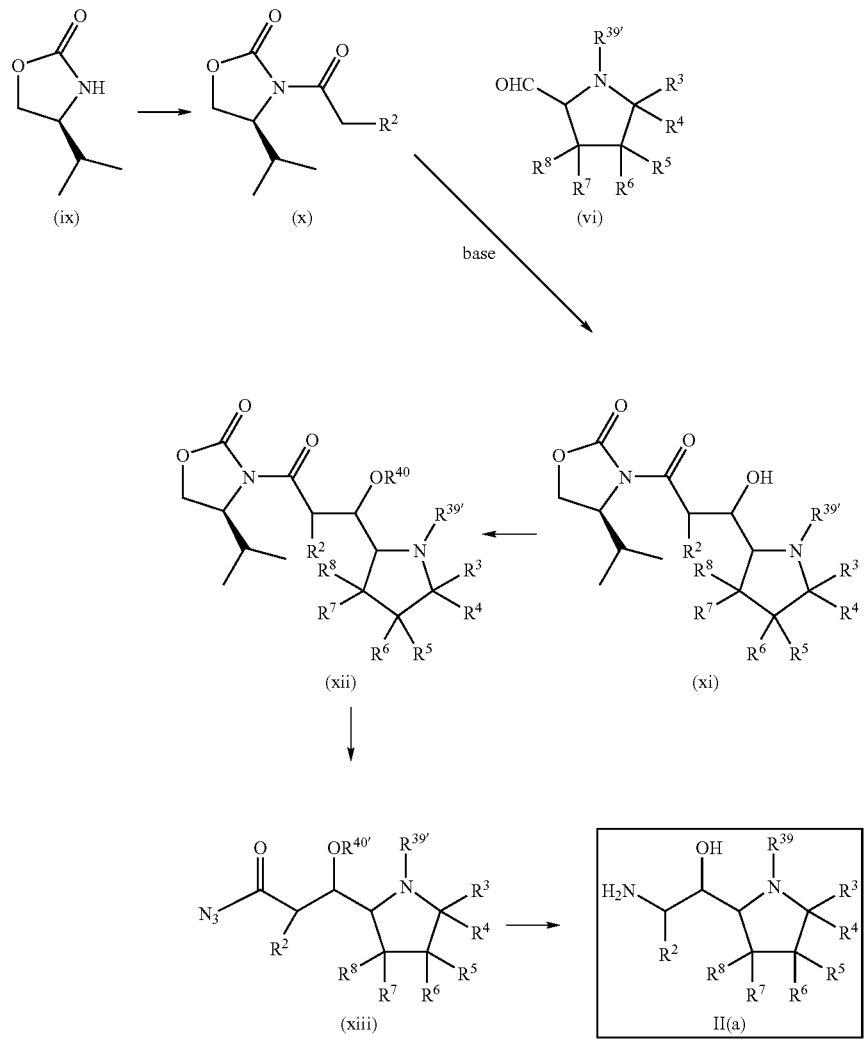

4-(S)-Isopropyloxazolidin-2-one (ix) is deprotonated with a suitable base, such as n-butyllithium in tetrahydrofuran, and then acylated with an appropriately substituted carboxylic acid derivative, such as an acid halide or acid anhydride, to provide the substituted acetamide (x). This acetamide is deprotonated by reaction with a suitable base, such as N,N-diisopropylethylamine and reacted with aldehyde (vi) to provide the corresponding alcohol (xi). This alcohol is protected with an oxygen protecting group, preferably tert-butyldimethylsilyl, to provide the oxazolidin-2-one intermediate (xii). This intermediate is then reacted with basic hydrogen peroxide followed by treatment with a source of azide, such as diphenylphosphoryl azide, to provide the azidocarbonyl intermediate (xiii). Treatment of the azidocarbonyl with benzyl alcohol followed by catalytic hydrogenation provides the desired amine (IIa).

Additional intermediates useful for the preparation of compounds of Formula I may be prepared as illustrated in the following scheme where $R^1$, $R^2$, $R^{39}$, $R^{41}$, and $R^{42}$ are as previously defined.

Scheme IV

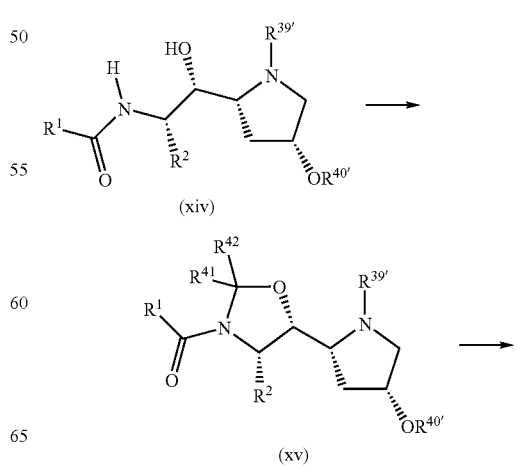

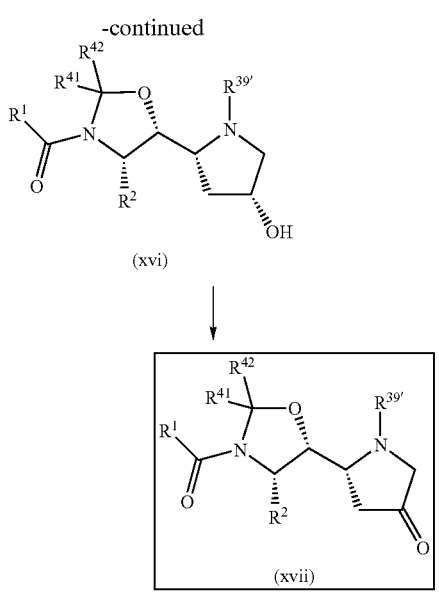

The protected pyrrolidin-2-yl compound (xiv) is treated with a suitable enol ether, for example 2-methoxypropene, in the presence of a suitable acid catalyst, such as pyridine/p-toluenesulfonic acid, to provide the bicyclic derivative (xv). The hydroxy group on the pyrrolidine ring is deprotected and the resulting alcohol (xvi) is oxidized under standard conditions, for example under Swern conditions (*Journal of Organic Chemistry*, 43, 2480-2482 (1978)) to provide the pyrrolidin-4-one intermediate (xvii), which represents a further embodiment of the present invention. This ketone may now be reacted under a variety of conditions well known to the skilled artisan to introduce the desired substituents at the 4-position of the pyrrolidine ring. (For example, see: *Comprehensive Organic Transformations*, Larock, Wiley-VCH Publishers, Inc., New York, (1989); *Advanced Organic Chemistry*, March, Wiley Interscience, New York, Third Edition, (1985)) Specifically, the ketone may be reacted under Wittig-type conditions to provide alkenes that may be reduced under standard catalytic hydrogenation conditions to provide the corresponding alkyl moieties (See: *Journal of Organic Chemistry* 68(10), 3923-3931 (2003)). The ketone may also be reacted with a variety of amines under standard reductive amination conditions to provide the desired amine functionality. Additionally, the ketone may be reacted under a variety of Grignard conditions to introduce alkyl and aryl moieties. The resulting teriary alcohols may be further substituted or reduced under standard conditions. These advanced derivatives are then deprotected under standard conditions to provide the compounds of Formula I. The intermediates of formulae (xiv), (xv), and (xvi) represent further embodiments of the present invention.

Additional intermediates useful for the preparation of additional compounds of Formula I may be prepared as illustrated in the following scheme where $R^3$, $R^4$, $R^5$, $R^6$, and $R^{39'}$ are as previously defined.

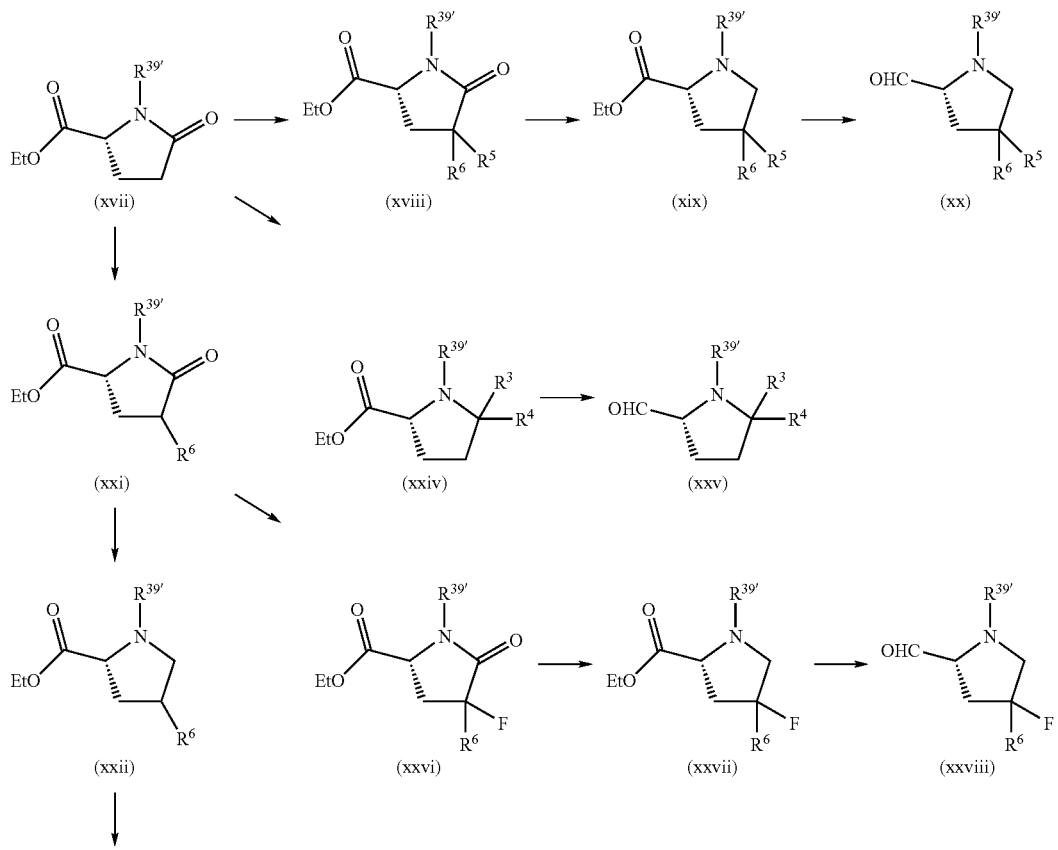

Scheme V

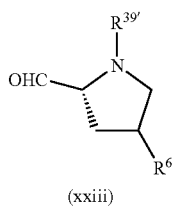

(xxiii)

An appropriately substituted ester of 2-pyrrolidone-5-carboxylic acid (xvii) may be treated with a suitable base, such as potassium hexamethyldisilazane, and the resulting anion reacted with an appropriate electrophilic agent, such as an alkyl halide, to provide either a mono- (xxi) or disubstituted (xviii) derivative. Alternatively, different substituents may be introduced to the carbon adjacent to the carbonyl by sequentially forming an anion and quenching with different electrophilic agents as exemplified by the fluorinated derivative (xxvi). The lactam in each of these derivatives is then reduced under standard conditions, the ester reduced to the corresponding alcohol, and this alcohol oxidized to provide the desired aldehydes (xx), (xxiii) and (xxviii). Additionally, instead of being reduced, the lactam carbonyl may be reacted with a variety of reagents to provide substitution at the 5-position of the pyrrolidine ring (xiv). Transformation of the ester into the corresponding aldehyde through a reduction/oxidation sequence provides additional aldehydes (xxv). These aldehydes may then be reacted as previously described in Schemes I and II to provide additional compounds of Formula I. The skilled artisan will appreciate that additional substituted aldehydes useful for the preparation of compounds of Formula I may be prepared from the structures illustrated above. (For example, see: *Comprehensive Organic Transformations*, Larock, Wiley-VCH Publishers, Inc., New York, (1999); *Advanced Organic Chemistry*, March, Wiley Interscience, New York, Third Edition, (1985)) Intermediates (xx), (xxiii), (xxv), and (xxviii) represent further embodiments of the present invention.

Preparation 1

2-(R)-[2-(S)-Amino-3-(3,5-difluorophenyl)-1-(S)-hydroxypropyl]-pyrrolidine-1-carboxylic acid tert-butyl ester

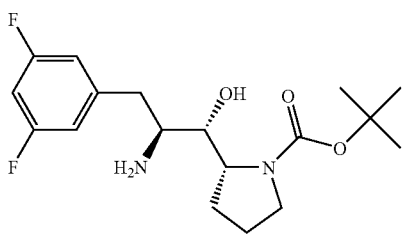

2-[2-(S)-[Bis-(2-methylbenzyl)-amino]-3-(3,5-difluorophenyl)-1-(S)-hydroxypropyl]-pyrrole-1-carboxylic acid tert-butyl ester Add n-butyllithium (3.30 mL, 8.25 mmol, 2.5 M in hexanes) to a solution of 2,2,6,6-tetramethylpiperidine (1.40 mL, 8.18 mmol) in tetrahydrofuran (THF) (30 mL) at −78° C. over 2 min. Stir 5 min, then warm to −10° C. and stir 5 min, then cool to −78° C. Add N-tert-butoxycarbonylpyrrole (1.37 mL, 8.25 mmol) in THF (1.6 mL) over 3 min. Stir 30 min and add 2-(S)-[bis-(2-methylbenzyl)-amino]-3-(3,5-difluorophenyl)-propionaldehyde (2.96 g, 7.44 mmol) in THF (15 mL) over 5 min. Stir 60 min at −78° C., warm to 0° C. and stir 60 min. Cool −78° C. and quench with saturated aqueous ammonium chloride solution. Extract with ethyl acetate, dry (magnesium sulfate), concentrate and purify (silica gel chromatography, eluting with hexanes and dichloromethane) to give the title compound as a foam (0.416 g, 10%).

MS (ES): m/z=561.2 [M+H].

2-(R)-[2-(S)-[Bis-(2-methylbenzyl)-amino]-3-(3,5-difluorophenyl)-1-(S)-hydroxypropyl]-pyrrolidine-1-carboxylic acid tert-butyl ester Add 2-[2-(S)-[bis-(2-methylbenzyl)-amino]-3-(3,5-difluorophenyl)-1-(S)-hydroxypropyl]-pyrrole-1-carboxylic acid tert-butyl ester (0.415 g, 0.74 mmol), 10% platinum on carbon (0.087 g) and methanol (15 mL) and hydrogenate at one atmosphere hydrogen gas for 1-8 h. Add filter agent and filter, concentrate and purify (silica gel chromatography, eluting with hexanes and ethyl acetate) to give the title compound as a white foam (0.116 g, 28%).

MS (ES): m/z=564.3 [M+H].

2-(R)-[2-(S)-Amino-3-(3,5-difluorophenyl)-1-(S)-hydroxypropyl]-pyrrolidine-1-carboxylic acid tert-butyl ester Add 2-(R)-[2-(S)-[bis-(2-methylbenzyl)-amino]-3-(3,5-difluorophenyl)-1-(S)-hydroxypropyl]-pyrrolidine-1-carboxylic acid tert-butyl ester (0.116 g, 0.205 mmol), 20% palladium on carbon (0.069 g) and methanol (3 mL) and hydrogenate at one atmosphere hydrogen gas for 18 h. Add filter agent and filter and concentrate to give the title compound as a residue (0.069 g, 94%).

MS (ES): m/z=357.3 [M+H].

Preparation 2

2-(R)-(2-(S)-Amino-1-(S)-hydroxy-3-phenylpropyl)-pyrrolidine-1-carboxylic acid tert-butyl ester 2-(S)-Dibenzylamino-3-phenyl-propionaldehyde Dissolve 2-(S)-dibenzylamino-3-phenylpropan-1-ol (5.00 g, 15.08 mmol) in dimethylsulfoxide (DMSO) (15 mL) and cool in an ice bath. Add triethylamine (8.4 mL, 60.0 mmol) followed by sulfur trioxide-pyridine complex (4.80 g, 30.2 mmol). Stir 30 min then slowly add water (15 mL). Dilute with ethyl acetate and wash with 5% aqueous citric acid (3×), saturated aqueous sodium chloride, dry (magnesium sulfate) and concentrate to give the title compound as a light yellow residue.

MS (ES): m/z=330.2 [M+H].

2-(R)-(2-(S)-Dibenzylamino-1-(S)-hydroxy-3-phenylpropyl)-pyrrolidine-1-carboxylic acid tert-butyl ester Add sec-butyllithium (1.29 mL, 1.8 mmol) dropwise to a solution of (−)-sparteine (0.44 mL, 1.36 mmol) in diethyl ether (10 mL) over 3 min at −78° C. Add N-Boc-pyrrolidine (0.245 mL, 1.4 mmol) in diethyl ether (2 mL) dropwise over 10 min. Stir 2 h, add 2-(S)-dibenzylamino-3-phenylpropionaldehyde (0.69 g, 2.1 mmol) in diethyl ether (1.8 mL) over 5 min and stir 20 min. Add acetic acid (0.16 mL) and warm to room temperature. Add saturated aqueous sodium chloride (20 mL), separate layers, dry (magnesium sulfate), concentrate and purify (silica gel chromatography, eluting with hexanes and ethyl acetate) to give the title compound as a foam (0.421 g, 60%).

MS (ES): m/z=501.3 [M+H].

2-(R)-(2-(S)-Amino-1-(S)-hydroxy-3-phenylpropyl)-pyrrolidine-1-carboxylic acid tert-butyl ester Dissolve 2-(R)-(2-(S)-dibenzylamino-1-(S)-hydroxy-3-phenylpropyl)-pyrrolidine-1-carboxylic acid tert-butyl ester (0.75 g, 1.49 mmol) in methanol (20 mL). Add 20% palladium hydroxide on carbon (0.33 g) and stir 1 h under one atmosphere of hydrogen gas. Filter through filter agent and concentrate to give the title compound as a white foam (0.45 g, 93%).

MS (ES): m/z=321.2 [M+H].

The compound of Preparation 3 may be prepared essentially as described in Preparation 2 except 2-(S)-dibenzylaminopropan-1-ol is used.

| Prep | Compound | MS [M + H] |
|---|---|---|
| 3 | 2-(R)-[(2-(S)-Amino-1-(S)-hydroxypropyl)]-pyrrolidine-1-carboxylic acid tert-butyl ester | 321.2 |

Preparation 4

2-(R)-(2-(S)-Amino-1-(S)-hydroxy-3-phenylpropyl)-4-(S)-fluoropyrrolidine-1-carboxylic acid tert-butyl ester

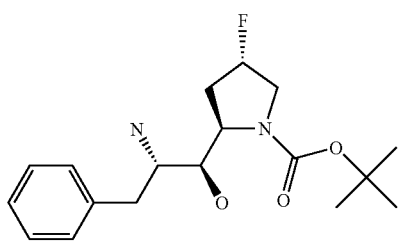

4-(R)-Hydroxypyrrolidine-2-(R)-carboxylic acid methyl ester hydrochloride

Add thionyl chloride (5.5 mL, 75.8 mmol) to an ice-cold suspension of 4-(R)-hydroxypyrrolidine-2-(R)-carboxylic acid (4.97 g, 31.9 mmol) in methanol (60 mL). Stir 10 min, then warm to room temperature and stir 3.5 h. Concentrate, add methanol, and concentrate again. Dissolve in absolute ethanol (25 mL) and precipitate with diethyl ether (50 mL) and filter. Dry cake under vacuum to give the title compound as a white solid (4.77 g, 82%).

MS (ES): m/z=146.1 [M+H].

4-(R)-Hydroxypyrrolidine-N1,2-(R)-dicarboxylic acid 1-tert-butyl ester 2-methyl ester Add di-tert-butyl dicarbonate (10.4 g, 47.7 mmol) in 1,4-dioxane (10 mL) to a solution of 4-(R)-hydroxypyrrolidine-2-(R)-carboxylic acid methyl ester hydrochloride (6.66 g, 36.7 mmol) in 1,4-dioxane (80 mL). Cool in an ice bath and add N,N-diisopropylethylamine (11 mL, 62.4 mmol), then remove ice bath and stir 1 h at room temperature. Concentrate and dissolve in ethyl acetate and wash with aqueous citric acid solution (2×100 mL), water, saturated aqueous sodium bicarbonate, saturated aqueous sodium chloride, dry (magnesium sulfate), filter and concentrate to give the title compound as a white solid (7.1 g, 79%). MS (ES): m/z=246.1 [M+H].

4-(S)-Fluoropyrrolidine-N1,2-(R)-dicarboxylic acid 1-tert-butyl ester 2-methyl ester Add (diethylamino)sulfur trifluoride (3.9 mL, 29.8 mmol) to a −78° C. cooled solution of 4-(R)-hydroxypyrrolidine-N1,2-(R)-dicarboxylic acid 1-tert-butyl ester 2-methyl ester (3.81 g, 15.54 mmol) in dichloromethane (50 mL). Stir 2 h, then remove cold bath and stir 40 h at room temperature. Cool in ice bath and add saturated sodium bicarbonate solution. Warm to room temperature, dry (magnesium sulfate), concentrate (350 mbar, 25° C.) and purify (silica gel chromatography, eluting with diethyl ether and dichloromethane) to give the title compound as an oil (4.01 g, 97%).

MS (ES): m/z=148.1 [M+H, Product-Boc].

4-(S)-Fluoro-2-(R)-hydroxymethylpyrrolidine-1-carboxylic acid tert-butyl ester Add lithium borohydride (0.43 g, 19.6 mmol) to an ice cold solution of 4-(S)-fluoropyrrolidine-N1,2-(R)-dicarboxylic acid 1-tert-butyl ester 2-methyl ester (3.9 g, 13.08 mmol) in THF (50 mL). Warm to room temperature over 18 h. Cool in ice bath. Slowly add acetic acid (3 mL) and water and extract with ethyl acetate. Wash extract with water, saturated aqueous sodium bicarbonate solution, saturated aqueous sodium chloride, dry (magnesium sulfate), concentrate and purify (silica gel chromatography, eluting with hexanes and ethyl acetate) to give the title compound as a thick oil (2.90 g, 100%).

MS (ES): m/z=218.2 [M+H].

4-(S)-Fluoro-2-(R)-formylpyrrolidine-1-carboxylic acid tert-butyl ester

Add triethylamine (1.1 mL, 7.79 mmol) and sulfurtrioxide-pyridine complex (0.63 g, 3.89 mmol) to an ice-cold solution of 4-(S)-fluoro-2-(R)-hydroxymethylpyrrolidine-1-carboxylic acid tert-butyl ester (0.426 g, 1.95 mmol) in DMSO (2 mL). Stir 30 min, warm to room temperature and stir 30 min. Dilute with diethyl ether and wash with 5% aqueous citric acid (3×120 mL), saturated aqueous sodium chloride, dry (magnesium sulfate) and concentrate to give the title compound as an oil that was used in the next step without further purification.

4-(S)-Fluoro-2-(R)-(1-(S)-hydroxy-2-(S)-nitro-3-phenylpropyl)-pyrrolidine-1-carboxylic acid tert-butyl ester and 4-(S)-Fluoro-2-(R)-(1-(R)-hydroxy-2-(S)-nitro-3-phenylpropyl)-pyrrolidine-1-carboxylic acid tert-butyl ester Add tetrabutylammonium fluoride (2.0 mL of 1.0 M solution in THF) to an ice-cold solution of 1-phenyl-2-nitroethane (0.51 mL, 3.79 mmol) in THF (2 mL). Stir 5 min and add 4-(S)-fluoro-2-(R)-formylpyrrolidine-1-carboxylic acid tert-butyl ester (0.58 g, 1.95 mmol) in THF (6 mL). Stir 90 min, dilute with ethyl acetate, wash with water (3×50 mL), saturated aqueous sodium chloride, dry (magnesium sulfate) and purify (silica gel chromatography, eluting with hexanes and ethyl acetate) to give the title compounds as foams, 4-(S)-fluoro-2-(R)-(1-(S)-hydroxy-2-(S)-nitro-3-phenylpropyl)-pyrrolidine-1-carboxylic acid tert-butyl ester (0.21 g, 29%) and 4-(S)-fluoro-2-(R)-(1-(R)-hydroxy-2-(S)-nitro-3-phenylpropyl)-pyrrolidine-1-carboxylic acid tert-butyl ester (0.33 g, 46%).

MS (ES): m/z=367.3 [M–H].

2-(R)-(2-(S)-Amino-1-(S)-hydroxy-3-phenylpropyl)-4-(S)-fluoropyrrolidine-1-carboxylic acid tert-butyl ester Dissolve nickel chloride hexahydrate (0.021 g, 0.09 mmol) and 4-(S)-fluoro-2-(R)-(1-(R)-hydroxy-2-(S)-nitro-3-phenylpropyl)-pyrrolidine-1-carboxylic acid tert-butyl ester (0.33 g, 0.897 mmol) in methanol (5 mL). Cool in an ice bath and add sodium borohydride (0.17 g, 4.485 mmol) portionwise over 1 min. Stir 10 min, then concentrate. Partition in water and ethyl acetate and filter through filter agent. Separate layers and wash organic layer with saturated aqueous sodium chloride, dry (magnesium sulfate), and concentrate to give the title compound as a white foam.

MS (ES): m/z=339.2 [M+H].

The compound of Preparation 5 may be prepared essentially as described in Preparation 4 except 4-(R)-hydroxypyrrolidine-N1,2-(R)-dicarboxylic acid 1-tert-butyl ester 2-methyl ester is oxidized to the ketone and then converted to the geminal difluoride. The compound of Preparation 6 may be prepared essentially as described in Preparation 4 using nitroethane.

| Prep | Compound | MS [M + H] |
|---|---|---|
| 5 | 2-(R)-[(2-(S)-Amino-1-(S)-hydroxy-3-phenylpropyl)]-4,4-difluoropyrrolidine-1-carboxylic acid tert-butyl ester | 357.2 |
| 6 | 2-(R)-[(2-(S)-Amino-1-(S)-hydroxypentyl)]-pyrrolidine-1-carboxylic acid tert-butyl ester | |

Preparation 7

2-(R)-(2-(S)-Amino-1-(S)-hydroxy-3-phenylpropyl)-4-(R)-fluoropyrrolidine-1-carboxylic acid tert-butyl ester

4-(S)-Isopropyl-3-(3-phenylpropionyl)-oxazolidin-2-one

Add n-butyllithium (2.5 M solution in hexanes, 32 mL of, 80 mmol) to a solution of 4-(S)-isopropyloxazolidin-2-one (10.26 g, 79.4 mmol) in THF (250 mL) at –78° C. Stir 30 min. Add 3-phenylpropionyl chloride (13.2 mL, 89 mmol) over 4 min. Stir 2.5 h at –78° C., then warm to –55° C. and stir 2 h. Add saturated aqueous ammonium chloride (75 mL) and warm to room temperature. Extract with dichloromethane and wash extract with 1 N NaOH (200 mL), saturated aqueous sodium chloride, dry (magnesium sulfate) and concentrate. Add hexanes (50 mL), filter solids and dry under vacuum to give a white solid (18.94 g, 91%).

4-(S)-Hydroxypyrrolidine-2-(R)-carboxylic acid methyl ester

Add thionyl chloride (5.8 mL, 79.4 mmol) to an ice-cold suspension of 4-(S)-hydroxypyrrolidine-2-(R)-carboxylic acid (4.97 g, 31.9 mmol) in methanol (70 mL). Stir 10 min, then warm to room temperature and stir 3.5 h. Concentrate, add methanol and concentrate again to give the title compound as a white solid (7.18 g, 99%).

MS (ES): m/z=146.1 [M+H].

4-(S)-Hydroxypyrrolidine-N1,2-(R)-dicarboxylic acid 1-tert-butyl ester 2-methyl ester Add di-tert-butyl dicarbonate (11.2 g, 51.35 mmol) to a solution of 4-(S)-hydroxypyrrolidine-2-(R)-carboxylic acid methyl ester hydrochloride (7.17 g, 39.5 mmol) in 1,4-dioxane (80 mL). Cool in an ice bath and add N,N-diisopropylethylamine (11.7 mL, 67.2 mmol). Remove ice bath and stir 1 h at room temperature. Concentrate and dissolve in ethyl acetate, wash with 5% aqueous citric acid solution (2×100 mL), water, saturated aqueous sodium bicarbonate, saturated aqueous sodium chloride, dry (magnesium sulfate), concentrate and purify (silica gel chromatography, eluting with hexanes and ethyl acetate) to give the title compound as a white solid (9.83 g, 100%).

MS (ES): m/z=246.1 [M+H].

4-(R)-Fluoropyrrolidine-N1,2-(R)-dicarboxylic acid 1-tert-butyl ester 2-methyl ester Add (diethylamino)sulfur trifluoride (10.5 mL, 80 mmol) to a –78° C. cooled solution of 4-(S)-hydroxypyrrolidine-N1,2-(R)-dicarboxylic acid 1-tert-butyl ester 2-methyl ester (9.83 g, 40 mmol) in dichloromethane (60 mL). Stir 2 h, then remove cooling bath and stir 18 h at room temperature. Heat to reflux for 30 min, then cool in ice bath and add saturated aqueous sodium bicarbonate solution. Warm to room temperature, dry (magnesium sulfate), concentrate (350 mbar, 25° C.) and purify (silica gel chromatography, eluting with diethyl ether and dichloromethane) and then concentrate at 120 mbar at 25° C. to give the title compound as an oil (9.09 g, 92%).

MS (ES): m/z=148.1 [M+H, Product-Boc]

4-(R)-Fluoro-2-(R)-hydroxymethylpyrrolidine-1-carboxylic acid tert-butyl ester Add lithium borohydride (1.03 g, 47.4 mmol) to an ice cold solution of 4-(R)-fluoropyrrolidine-N1,2-(R)-dicarboxylic acid 1-tert-butyl ester 2-methyl ester (7.8 g, 31.5 mmol) in THF (100 mL). Let warm to room temperature over 18 h. Cool in ice bath. Slowly add acetic acid (5 mL) and water and extract with ethyl acetate. Wash extract with water, saturated aqueous sodium bicarbonate solution, saturated aqueous sodium chloride, dry (magnesium sulfate), concentrate and purify (silica gel chromatography, eluting with hexanes and ethyl acetate) to give the title compound as a thick oil (5.56 g, 80%).

MS (ES): m/z=218.2 [M−H].

4-(R)-Fluoro-2-(R)-formylpyrrolidine-1-carboxylic acid tert-butyl ester

Add triethylamine (6.6 mL, 47.7 mmol) and sulfurtrioxide-pyridine complex (3.8 g, 23.9 mmol) to an ice cold solution of 4-(R)-fluoro-2-(R)-hydroxymethylpyrrolidine-1-carboxylic acid tert-butyl ester (2.62 g, 11.9 mmol) in DMSO (12 mL). Stir 30 min, then warm to room temperature and stir 30 min. Dilute with diethyl ether and wash with 5% aqueous citric acid (3×120 mL), saturated aqueous sodium chloride, dry (magnesium sulfate) and concentrate to give the title compound as an oil that is used in the next step without further purification.

2-(R)-[2-(S)-Benzyl-1-(S)-hydroxy-3-(4-(S)-isopropyl-2-oxo-oxazolidin-3-yl)-3-oxopropyl]-4-(R)-fluoropyrrolidine-1-carboxylic acid tert-butyl ester Add dibutylboron triflate (1 M in dichloromethane, 11.8 mL, 11.8 mmol) to a solution of 4-(S)-isopropyl-3-(3-phenyl-propionyl)-oxazolidin-2-one (2.8 g, 10.7 mmol) in dichloromethane (40 mL) at 0° C. Stir 5 min. Add N,N-diisopropylethylamine (2.25 mL, 12.87 mmol) and stir 90 min. Cool to −78° C. and add 4-(R)-fluoro-2-(R)-formylpyrrolidine-1-carboxylic acid tert-butyl ester (2.53 g, 11.6 mmol) in dichloromethane (15 mL) over 15 min. Stir 90 min and then warm to room temperature over 18 h. Cool in ice bath and add 0.05 M pH 7 phosphate buffer (15 mL). Extract with dichloromethane and concentrate. Dissolve in methanol (50 mL) and cool in ice bath. Add aqueous hydrogen peroxide (15 mL, 30% solution) and remove ice bath. Stir 5 min and concentrate. Extract with ethyl acetate and wash extract with 1 N HCl, saturated aqueous sodium bicarbonate, saturated aqueous sodium chloride, dry (magnesium sulfate), concentrate and purify (silica gel chromatography, eluting with hexanes and ethyl acetate) to give the title compound as a foam (2.68 g, 52%).

MS (ES): m/z=479.1 [M−H].

2-(R)-[2-(S)-Benzyl-1-(S)-(tert-butyl-dimethylsilanyloxy)-3-(4-(S)-isopropyl-2-oxo-oxazolidin-3-yl)-3-oxopropyl]-4-(R)-fluoropyrrolidine-1-carboxylic acid tert-butyl ester Add 2,6-lutidine (5.3 mL, 54 mmol) and tert-butyl-dimethylsilyl-trifluoromethylsulfonate (1.62 mL, 7.08 mL) to a solution of 2-(R)-[2-(S)-benzyl-1-(S)-hydroxy-3-(4-(S)-isopropyl-2-oxo-oxazolidin-3-yl)-3-oxopropyl]-4-(R)-fluoro-pyrrolidine-1-carboxylic acid tert-butyl ester (2.585 g, 5.4 mmol) in dichloromethane (40 mL) at −78° C. Stir 3 h, warm to room temperature, stir 5 min and cool in an ice bath. Add 1 N HCl (100 mL), wash with 1 N HCl (2×100 mL), saturated aqueous sodium bicarbonate, saturated aqueous sodium chloride, dry (magnesium sulfate), concentrate and purify (silica gel chromatography, eluting with hexanes and ethyl acetate) to give the title compound as a white foam (2.779 g, 87%).

MS (ES): m/z=593.5 [+H].

2-(R)-[2-(S)-Azidocarbonyl-1-(S)-(tert-butyl-dimethylsilanyloxy)-3-phenylpropyl]-4-(R)-fluoropyrrolidine-1-carboxylic acid tert-butyl ester Add an aqueous solution of hydrogen peroxide (30% solution, 2.7 mL, 28.1 mmol) dropwise to a solution of 2-(R)-[2-(S)-benzyl-1-(S)-(tert-butyl-dimethylsilanyloxy)-3-(4-(S)-isopropyl-2-oxo-oxazolidin-3-yl)-3-oxopropyl]-4-(R)-fluoropyrrolidine-1-carboxylic acid tert-butyl ester (2.779 g, 4.69 mmol) in THF (15 mL) at 0° C. Add 2 N lithium hydroxide (4.7 mL, 9.38 mmol) dropwise, stir 60 min and warm to room temperature. Add methanol (5 mL) and stir 18 h. Dilute with ethyl acetate and wash with 1 N HCl, saturated aqueous sodium chloride, dry (magnesium sulfate) and concentrate. Dissolve residue in dichloromethane (30 mL) and add diisopropylethylamine (1.2 mL, 7.03 mmol) followed by diphenylphosphoryl azide (1.1 mL, 5.16 mmol). Stir 1 h and add diisopropylethylamine (1.2 mL, 7.03 mmol) followed by diphenylphosphoryl azide (1.1 mL, 5.16 mmol). Stir 3.5 h, concentrate and purify (silica gel chromatography, eluting with hexanes and ethyl acetate) to give the title compound as a residue (0.79 g, 32%).

2-(R)-(2-(S)-Amino-1-(S)-hydroxy-3-phenylpropyl)-4-(R)-fluoropyrrolidine-1-carboxylic acid tert-butyl ester Heat a solution of benzyl alcohol (1.5 mL, 15 mmol) and 2-(R)-[2-(S)-azidocarbonyl-1-(S)-(tert-butyl-dimethylsilanyloxy)-3-phenylpropyl]-4-(R)-fluoropyrrolidine-1-carboxylic acid tert-butyl ester (0.78 mmol, 1.5 mmol) in toluene (9 mL) to reflux for 18 h. Concentrate and purify (silica gel chromatography, eluting with hexanes and ethyl acetate) to give an oil. Dissolve in methanol (15 mL) and add 10% palladium on carbon (0.1 g) and stir under an atmosphere of hydrogen gas for 1 h. Filter through filter agent, concentrate and purify (silica gel chromatography, eluting with dichloromethane and 2M ammonia in methanol) to give the title compound (0.54 g, 80%).

MS (ES): m/z=453.5 [M+H].

Preparation 8

2-(R)-(2-(R)-Amino-1-(S)-hydroxy-3-phenylpropyl)-pyrrolidine-1-carboxylic acid tert-butyl ester

2-(R)-(2-(R)-Dibenzylamino-1-hydroxy-3-phenylpropyl)-pyrrole-1-carboxylic acid tert-butyl ester Add n-butyllithium (1.6 M in hexanes, 1.06 mL, 1.7 mmol) to a solution of tetramethylpiperidine (0.29 mL, 1.7 mmol) in THF (12 mL) at −78° C. Stir at −78° C. for 5 min, at −10° C. for 5 min and at −78° C. for 5 min. Add N-Boc-pyrrole and stir the solution for 20 min. Add 2-(S)-dibenzylamino-3-phenyl-propionaldehyde (*Org. Process Research and Development*, 1, 45-54, (1997)) dissolved in THF (4 mL) and stir at −78° C. for 45 min. Quench with saturated aqueous ammonium chloride solution and separate the two layers. Extract the aqueous layer with ethyl acetate (2×20 mL) and wash the combined organic layers with 1 N HCl, 5% aqueous sodium bicarbonate and saturated aqueous sodium chloride, dry (magnesium sulfate), concentrate and purify (silica gel chromatography, eluting with 4:1 hexanes:diethyl ether) to give the title compound (240 mg, 32%).

MS (ES): m/z=497 [M+H].

2-(R)-(2-(R)-Dibenzylamino-1-(S)-hydroxy-3-phenylpropyl)-pyrrolidine-1-carboxylic acid tert-butyl ester Dissolve 2-(R)-(2-(R)-dibenzylamino-1-hydroxy-3-phenylpropyl)-pyrrole-1-carboxylic acid tert-butyl ester (160 mg, 0.32 mmol) in methanol (2 mL) and add 10% platinum on carbon (63 mg, 0.032 mmol). Bubble hydrogen gas through the mixture and stir under 1 atmosphere of hydrogen gas overnight. Bubble nitrogen through the mixture for 2 min, filter through a filtering agent, wash with methanol and concentrate. Separate isomers using silica gel chromatography, eluting with 3:1 hexanes:ethyl acetate to give the title compounds as a mixture of 2 isomers, (S) (84 mg, 52%), and isomer (R) (74 mg, 46%).

MS (ES): m/z=501 [M+H].

2-(R)-(2-(R)-Amino-1-(S)-hydroxy-3-phenylpropyl)-pyrrolidine-1-carboxylic acid tert-butyl ester Dissolve 2-(R)-(2-(R)-dibenzylamino-1-(S)-hydroxy-3-phenylpropyl)-pyrrolidine-1-carboxylic acid tert-butyl ester (610 mg, 1.2 mmol) in methanol (13 mL). Add 20% palladium hydroxide on carbon (157 mg, 0.19 mmol). Bubble hydrogen gas through the mixture and stir under 1 atmosphere of hydrogen gas overnight. Bubble nitrogen through the mixture for 2 min, filter through a filtering agent, wash with methanol and concentrate to give the title compound.

Preparation 9

2-(S)-(2-(S)-Amino-1-(S)-hydroxy-3-phenylpropyl)-3-(S)-fluoropyrrolidine-1-carboxylic acid tert-butyl ester and 2-(S)-(2-(S)-Amino-1-(S)-hydroxy-3-phenylpropyl)-3,3-difluoro-pyrrolidine-1-carboxylic acid tert-butyl ester 3,3-Difluoropyrrolidine-1-carboxylic acid tert-butyl ester Dissolve 1-N-tert-butoxycarbonyl)-3-pyrrolidinone (1.70 g, 9.18 mmol) in anhydrous dichloromethane (20 mL) and cool to 0° C. Add bis(2-methoxyethyl)-aminosulfur trifluoride (5.0 mL, 27.5 mmol) and stir overnight at room temperature. Pour the solution carefully into saturated aqueous sodium bicarbonate (30 mL) and stir 15 min at room temperature. Collect the organic layer and wash with water (30 mL), saturated aqueous sodium chloride (30 mL), dry (sodium sulfate), concentrate and purify (silica gel chromatography, eluting with 5:95 acetone:hexanes) to give the title compound as a colorless oil (1.33 g, 70%).

5-(2-(S)-Dibenzylamino-1-(S)-hydroxy-3-phenylpropyl)-4-fluoro-2,3-dihydropyrrole-1-carboxylic acid tert-butyl ester and 2-(S)-(2-(S)-Dibenzylamino-1-(S)-hydroxy-3-phenyl-propyl)-3,3-difluoropyrrolidine-1-carboxylic acid tert-butyl ester Dilute (−)-sparteine (2.0 mL, 8.78 mmol) in diethyl ether (10 mL) and cool to −78° C. Add a solution of sec-butyllithium (1.4 M in cyclohexanes, 6.3 mL, 8.78 mmol) slowly and stir 10 min. Dilute 3,3-difluoropyrrolidine-1-carboxylic acid tert-butyl ester (0.91 g, 4.39 mmol) in diethyl ether (5 mL) and add dropwise. Stir this solution 3 h at −78° C. Dilute 2-(S)-dibenzylamino-3-phenylpropionaldehyde (2.2 g, 6.59 mmol) in diethyl ether (2 mL) and add slowly. After stirring 45 min quench with of glacial acetic acid (0.2 mL) and allow to warm to room temperature. Wash the organic layer with saturated aqueous sodium chloride (30 mL), dry (magnesium sulfate), concentrate and purify (silica gel chromatography, eluting with 15:85 ethyl acetate:hexanes) to give a mixture of the title compounds as a yellow oil (1.44 g, 63%)

MS (ES): m/z=517.3 [M+H], MS (ES): m/z=537.3 [M+H].

2-(S)-(2-(S)-Amino-1-(S)-hydroxy-3-phenylpropyl)-3-(S)-fluoropyrrolidine-1-carboxylic acid tert-butyl ester and 2-(S)-(2-(S)-Amino-1-(S)-hydroxy-3-phenylpropyl)-3,3-difluoro-pyrrolidine-1-carboxylic acid tert-butyl ester Add 5-(2-(S)-dibenzylamino-1-(S)-hydroxy-3-phenylpropyl)-4-fluoro-2,3-dihydropyrrole-1-carboxylic acid tert-butyl ester and 2-(S)-(2-(S)-dibenzylamino-1-(S)-hydroxy-3-phenylpropyl)-3,3-difluoropyrrolidine-1-carboxylic acid tert-butyl ester (1.43 g, 2.77 mmol), 20% palladium hydroxide on carbon (500 mg) and methanol (15 mL) and stir under 1 atmosphere of hydrogen gas for 18 h. Filter over a pad of filtering agent and concentrate to give a mixture of the title compounds (822 mg, 88%) as an off-white solid. Some dehalogenation is observed.

MS (ES): m/z=339.2 [M+H], MS (ES): m/z=357.2 [M+H].

Preparation 10

2-(R)-[(1S,2S)-2-Acetylamino-3-(3,5-difluorophenyl)-1-hydroxypropyl]-piperidine-1-carboxylic acid tert-butyl ester (2-(R)-[(1S,2S)-2-Acetylamino-3-(3,5-difluorophenyl)-1-hydroxypropyl]-piperidine-1-carboxylic acid tert-butyl ester Add 1-acetylimidazole (0.035 g, 0.315 mmol) and triethylamine (0.04 mL, 0.286 mmol) to solution of 2-(R)-[2-(S)-amino-3-(3,5-difluorophenyl)-1-(S)-hydroxypropyl]-piperidine-1-carboxylic acid tert-butyl ester (0.106 mg, 0.286 mmol) in dichloromethane (10 mL) and stir 18 h at room temperature. Dilute with ethyl acetate and wash with 1 N hydrochloric acid (3×), saturated aqueous sodium bicarbonate, saturated aqueous sodium chloride, dry (magnesium sulfate), concentrate and purify (silica gel chromatography, eluting with dichloromethane and ethyl acetate) to give the title compound as a white solid (0.089 g, 76%).

MS (ES): m/z=411.2 [M−H].

The compounds of Preparations 11-13 may be prepared essentially as described in Preparation 10 using the appropriate amines.

| Prep | Compound | MS [M + H] |
| --- | --- | --- |
| 11 | 2-(R)-[(1S,2S)-2-Acetylamino-3-(3,5-difluorophenyl)-1-hydroxypropyl]-pyrrolidine-1-carboxylic acid tert-butyl ester | 397.2 |
| 12 | 2-(R)-((1S,2R)-2-Acetylamino-1-hydroxy-3-phenylpropyl)-4-(S)-(toluene-4-sulfonyloxy)-pyrrolidine-1-carboxylic acid tert-butyl ester | |

-continued

| Prep | Compound | MS [M + H] |
|---|---|---|
| 13 | 2-(R)-[(1S,2R)-2-Acetylamino-3-(3,5-difluorophenyl)-1-hydroxypropyl]-4-(S)-fluoropyrrolidine-1-carboxylic acid tert-butyl ester | |

Preparation 14

2-(S)-sec-butylamino-6-(methanesulfonyl-methylamino)-isonicotinic acid potassium salt 2-(S)-sec-Butylamino-6-chloro-isonicotinic acid methyl ester Add to a 300 mL autoclave reactor 2,6-dichloroisonicotinic acid methyl ester (20 g, 0.09707 mol), palladium acetate (2.18 g, 0.009707 mol, 0), rac-2,2'-bis(diphenylphosphino)-1,1'-binaphthyl (6.04 g, 0.009707 mol), cesium carbonate (37.95 g, 0.1165 mol) and (S)-(+)-2-sec-butylamine (8.52 g, 0.1165 mol) in toluene (200 mL). Flush with nitrogen 3 times and heat to 90° C. for 23 h. Cool to room temperature, filter, concentrate the filtrate and purify (silica gel chromatography) to give the title compound as a yellow solid (11.3 g, 48%).
m.p. 62.3-63.0° C., $^1$H NMR (500 MHz, DMSO) δ 7.07 (s, 1H), 6.84 (s, 1H), 4.72 (br s, 1H), 3.95 (s, 3H), 3.74 (m, 1H), 1.59 (m, 2H) 1.24 (d, J=6.5 Hz, 3H), 0.99 (t, J=7 Hz, 3H).

(S)-(+)-2-sec-Butylamino-6-methanesulfonylamino-isonicotinic acid methyl ester

Add to a 300 mL of autoclave reactor (s)-(+)-2-sec-butylamino-6-chloro-isonicotinic acid methyl ester (12.46 g, 0.05134 mol), bis(dibenzylideneacetone)-palladium (0) (2.35 g, 0.002567 mol), 2-di-tert-butylphosphino biphenyl (1.53 g, 0.005134 mol) and sodium methanesulfonamide (12.02 g, 0.1027 mol) in toluene (250 mL). Flush with nitrogen 3 times and heat to 99° C. for 24 h. Filter and dissolve the filter cake in water (400 mL). Extract the aqueous layer with chloroform (3×200 mL), dry (magnesium sulfate) and concentrate. Dissolve the crude product in dichloromethane (20 mL) and precipitate out by adding hexanes (400 mL) to give a solid (7.18 g, 46%). m.p. 118.6-123.0° C., $^1$H NMR (500 MHz, DMSO) δ 6.87 (s, 1H), 6.69 (s, 1H), 4.83 (br, 1H), 3.94 (s, 3H), 3.74 (m, 1H), 3.27 (s, 1H), 1.60 (m, 2H) 1.25 (d, J=7 Hz, 3H), 0.99 (t, J=7 Hz, 3H).

(S)-(+)-2-sec-Butylamino-6-(methanesulfonyl-methylamino)-isonicotinic acid methyl ester Treat a mixture of (s)-(+)-2-sec-butylamino-6-methanesulfonylamino-isonicotinic acid methyl ester (13.63 g, 0.04523 mol) and potassium carbonate (12.50 g, 0.09046 mol) in DMF (42 mL) with iodomethane (7.90 g, 0.05563 mol). Stir at room temperature for 18 h, and add water (200 mL). The aqueous layer was extracted with methyl tert-butyl ether (5×150 mL). Wash the combined organic layers with 1 N lithium chloride (5×100 mL), dry (magnesium sulfate) and concentrate to give the title compound as a solid (13.19 g, 92%).
$^1$H NMR (500 MHz, DMSO) δ 7.00 (d, J=7.5 Hz, 1H) 6.84 (s, 1H), 6.77 (s, 1H), 3.85 (s, 3H), 3.80 (m, 1H), 3.26 (s, 3H), 3.21 (s, 3H), 1.54 (m, 2H), 1.13 (m, 3H), 0.99 (t, J=5.5 Hz, 3H).

(S)-(+)-2-sec-butylamino-6-(methanesulfonyl-methylamino)-isonicotinate potassium salt Heat a mixture of (S)-(+)-2-sec-butylamino-6-(methanesulfonyl-methylamino)-isonicotinic acid methyl ester (12.66 g, 0.04014 mol) and potassium hydroxide (2.7 g, 0.04817 mol, 1.2 eq) until dissolved. Dilute with water (62 mL) and was heat to reflux for 3 h. Cool to room temperature and add 1 N HCl (8 mL). Concentrate and add dichloromethane (300 mL) and stir well. Filter and concentrate filtrate to give the title compound as a yellow solid (13.62 g, 100%).
m.p. 78-83° C. $^1$H NMR (500 MHz, DMSO) δ 6.72 (s, 1H), 6.67 (s, 1H), 6.30 (d, J=7 Hz, 1H) 3.73 (m, 1H), 3.18 (s, 3H), 3.17 (s, 3H), 1.55 (q, 1H) 1.45 (q, 1H), 1.12 (d, J=5 Hz, 3H), 0.89 (t, J=7.5 Hz, 3H).

Preparation 15

(2R,4R)-2-[(1S,2S)-2-Amino-3-(3,5-difluorophenyl)-1-hydroxypropyl]-4-(3-methoxy-phenoxy)-pyrrolidine-1-carboxylic acid tert-butyl ester (2R,4R)-4-(3-Methoxy-phenoxy)-pyrrolidine-1,2-dicarboxylic acid 1-tert-butyl ester 2-methyl ester To an ice cold solution of (2R,4S)-4-hydroxypyrrolidine-1,2-dicarboxylic acid 1-tert-butyl ester 2-methyl ester (1.15 g, 4.69 mmol) and 3-methoxyphenol (0.56 mL, 5.158 mmol) in THF (10 mL) is added triphenylphosphine (1.84 g, 7.03 mmol) followed by the dropwise addition of diisopropylazodicarboxylate (1.40 mL, 7.03 mmol). Warm to room temperature and stir for 18 h. Dilute the reaction with ethyl acetate and wash with 1 N HCl, saturated aqueous sodium bicarbonate, saturated aqueous sodium chloride, dry (magnesium sulfate) and purify (silica gel chromatography, eluting with dichloromethane/ethyl acetate mixtures) to give the title compound (0.57 g, 34%).
MS (ES): m/z=252.1 [M+H, Product-Boc insitu].

(2R,4R)-2-Hydroxymethyl-4-(3-methoxy-phenoxy)-pyrrolidine-1-carboxylic acid tert-butyl ester (2R,4R)-2-Hydroxymethyl-4-(3-methoxy-phenoxy)-pyrrolidine-1-carboxylic acid tert-butyl ester is prepared using lithium borohydride essentially as described in Preparation 4.
MS (ES): m/z=224.2 [M+H, Product-Boc in situ].

(2R,4R)-2-Formyl-4-(3-methoxy-phenoxy)-pyrrolidine-1-carboxylic acid tert-butyl ester (2R,4R)-2-Formyl-4-(3-methoxy-phenoxy)-pyrrolidine-1-carboxylic acid tert-butyl ester is prepared using sulfur trioxide-pyridine essentially as described in Preparation 4.

(2R,4R)-2-[(1R,2S)-3-(3,5-Difluorophenyl)-1-hydroxy-2-nitropropyl]-4-(3-methoxy-phenoxy)-pyrrolidine-1-carboxylic acid tert-butyl ester (2R,4R)-2-[(1R,2S)-3-(3,5-Difluorophenyl)-1-hydroxy-2-nitropropyl]-4-(3-methoxy-phenoxy)-pyrrolidine-1-carboxylic acid tert-butyl ester is prepared essentially as described in Preparation 4.
MS (ES): m/z=507.3 [M−H].

(2R,4R)-2-[(1S,2S)-2-Amino-3-(3,5-difluorophenyl)-1-hydroxypropyl]-4-(3-methoxy-phenoxy)-pyrrolidine-1-carboxylic acid tert-butyl ester Add to a solution of (2R,4R)-2-[(1R,2S)-3-(3,5-difluorophenyl)-1-hydroxy-2-nitropropyl]-4-(3-methoxy-phenoxy)-pyrrolidine-1-carboxylic acid tert-butyl ester (276 mg, 0.54 mmol) in methanol (9 mL) nickel (II) chloride followed by sodium borohydride (0.082 g, 2.17 mmol). Stir reaction for 15 min, add water (1 mL) and concentrate. Partition with ethyl acetate and water and filter through a filtering agent. Rinse cake with ethyl acetate. Separate layers, dry (magnesium sulfate) and concentrate to give the title compound as a white solid (0.244 g, 94%).

MS (ES): m/z=479.2 [M+H].

Preparation 16

(2R,5S)-2-[(1S,2S)-2-Amino-3-(3,5-difluorophenyl)-1-hydroxypropyl]-5-phenyl-pyrrolidine-1-carboxylic acid tert-butyl ester

(2R,5S)-2-Hydroxymethyl-5-phenylpyrrolidine-1-carboxylic acid tert-butyl ester To an ice cold solution of commercially available (2R,5S)-5-phenyl-pyrrolidine-1,2-dicarboxylic acid 1-tert-butyl ester (1.00 g, 3.45 mmol) in 1,2-dimethoxyethane (5 mL) is added 4-methylmorpholine (0.4 mL, 3.795 mmol) and isobutyl chloroformate (0.50 mL, 3.795 mmol). Stir 15 min and filter into cold flask. Add sodium borohydride (0.196 g, 5.17 mmol) in water (3 mL), followed by addition of water (50 mL). Extract product with ethyl acetate (3×50 mL) and wash with saturated aqueous sodium chloride, dry (magnesium sulfate) and purify on silica gel to give the title compound (0.886 g, 93%).

MS (ES): m/z=278.3 [M+H].

(2R,5S)-2-[(1S,2S)-2-Amino-3-(3,5-difluorophenyl)-1-hydroxy-propyl]-5-phenyl-pyrrolidine-1-carboxylic acid tert-butyl ester The title compound may be prepared from (2R,5S)-2-hydroxymethyl-5-phenyl-pyrrolidine-1-carboxylic acid tert-butyl ester essentially as described in Preparation 4.

MS (ES): m/z=433.3 [M+H].

Preparation 17

(2R,4R)-2-[(1S,2S)-2-Amino-3-(3,5-difluorophenyl)-1-hydroxypropyl]-4-(4-methoxy-benzyloxy)-pyrrolidine-1-carboxylic acid tert-butyl ester

2,2,2-Trichloro-acetimidic acid 4-methoxy-benzyl ester

Add a solution of 4-methoxybenzyl alcohol (31 mL, 250 mmol) in diethyl ether (250 ml) to sodium hydride (1.0 g, 25 mmol, 60% suspension in mineral oil) in diethyl ether (250 ml). Stir 30 min. Cool in ice bath and add trichloroacetonitrile (25 mL, 250 mmol) and let slowly warm to room temperature. Concentrate and dissolve in petroleum ether containing 0.3% methanol (330 mL) and filter through a filtering agent and concentrate to give the title compound (67 g, 95%).

MS (ES): m/z=280.2 [M+H].

(2R,4R)-4-(4-Methoxy-benzyloxy)-pyrrolidine-1,2-dicarboxylic acid 1-tert-butyl ester 2-methyl ester (B)

Add lanthanum triflate (3.6 g, 6.16 mmol) to a solution of 2,2,2-trichloro-acetimidic acid 4-methoxybenzyl ester (52.2 g, 185 mmol) and (2R,4R)-4-hydroxypyrrolidine-1,2-dicarboxylic acid 1-tert-butyl ester 2-methyl ester (30.2 g, 123 mmol) in toluene (200 mL). Stir 2.5 h, add methanol and concentrate. Dissolve in 25:75 dichloromethane:hexanes, filter away the insolubles and purify filtrate (silica gel chromatography, eluting with dichloromethane/ethyl acetate mixtures) to give the title compound (37.85 g, 84%).

MS (ES): m/z=366 [M+H].

(2R,4R)-2-[(1S,2S)-2-Amino-3-(3,5-difluorophenyl)-1-hydroxypropyl]-4-(4-methoxy-benzyloxy)-pyrrolidine-1-carboxylic acid tert-butyl ester The title compound may be prepared from (2R,4R)-4-(4-methoxybenzyloxy)-pyrrolidine-1,2-dicarboxylic acid 1-tert-butyl ester 2-methyl ester essentially as described in Preparation 15.

MS (ES): m/z=493.2 [M+H].

Preparation 18

2-(S)-[(2-(R)-amino-1-(S)-hydroxy-3-phenylpropyl)]-pyrrolidine-1-carboxylic acid tert-butyl ester

2-(S)-[(1-(S)-(2-dibenzylamino-1-hydroxy-3-phenylpropyl)]-pyrrole-1-carboxylic acid tert-butyl ester (1)

Add n-butyl lithium (1.6 M in hexanes, 1.06 mL, 1.7 mmol) to a solution of tetramethylpiperidine (0.29 mL, 1.7 mmol) in dry THF (12 mL) under nitrogen at −78° C. Stir the reaction at −78° C. for 5 min, at −10° C. for 5 min and at −78° C. for 5 min. Add commercially available tert-butyl 1-pyrrolecarboxylate and stir for 20 min. Add 2-dibenzylamino-3-phenyl-propionaldehyde dissolved in dry THF (4 mL) and stir at −78° C. for 45 min. Quench with saturated aqueous ammonium chloride solution and separate the two layers. Extract the aqueous layer with ethyl acetate (2×20 mL) and wash the combined organic layers with 1 N HCl, 5% aqueous sodium bicarbonate, saturated aqueous sodium chloride, dry (magnesium sulfate), concentrate and purify (silica gel chromatography, eluting with 4:1 hexanes:diethyl ether) to give the title compound (240 mg, 32%)

MS (ES): m/z=497 [M+H].

2-(S)-[(2-(R)-dibenzylamino-1-(S)-hydroxy-3-phenylpropyl)]-pyrrolidine-1-carboxylic acid tert-butyl ester (2)

Dissolve 2-(S)-[1-(S)-(2-dibenzylamino-1-hydroxy-3-phenylpropyl)-pyrrole-1-carboxylic acid tert-butyl ester (160 mg, 0.32 mmol) in methanol (2 mL) and add 10% platinum on carbon (63 mg). Bubble hydrogen gas through the mixture and stir under 1 atmosphere of hydrogen overnight. Bubble nitrogen through the mixture for 2 min, filter through a filtering agent, wash with methanol, concentrate and separate the isomers silica gel chromatography, eluting with 3:1 hexanes:ethyl acetate, to obtain the 2-S Isomer (84 mg, 52%), and the 2-R Isomer (74 mg, 46%).

MS (ES): m/z=501=[M+H].

2-(S)-[(2-(R)-amino-1-(S)-hydroxy-3-phenylpropyl)]-pyrrolidine-1-carboxylic acid tert-butyl ester Dissolve 2-(S)-[(2-(R)-dibenzylamino-1-(S)-hydroxy-3-phenylpropyl)]-pyrrolidine-1-carboxylic acid tert-butyl ester (610 mg, 1.2 mmol) in methanol (13 mL). Add 20% palladium hydroxide on carbon (157 mg). Bubble hydrogen gas through the mixture and stir under 1 atmosphere of hydrogen gas overnight. Bubble nitrogen through the mixture for 2 min, filter through a filtering agent, wash with methanol and concentrate to give the title compound (390 mg, 99%)

Preparation 19

2-(R)-[(2-(S)-Amino-1-(S)-hydroxy-3-phenylpropyl)]-5,5-dimethylpyrrolidine-1-carboxylic acid tert-butyl ester

2,2-Dimethylpyrrolidine-1-carboxylic acid tert-butyl ester

Charge a two-neck flask provided with a reflux condenser with lithium aluminum hydride (1 M solution in THF, 32 mL, 32 mmol) under an argon atmosphere and heat at 60° C. Add dropwise a solution of 5,5-dimethylpyrrolidin-2-one 8 (*Tet. Lett.*, 26(52), 6413-6416, (1985)) (2.9 g, 25.7 mmol) in dry THF (10 mL). React at 60° C. overnight. Allow to cool to room temperature and add dropwise water (1.5 mL), NaOH (1.5 mL, 15% v/v aqueous solution) and water (4.5 mL). Filter and wash the salts with diethyl ether. Concentrate by fractional distillation to remove the solvents until the external bath reaches 90° C. Let cool to room temperature and dilute with dichloromethane (50 mL). Add di-tert-butyl dicarbonate (6.7 g, 31 mmol), triethylamine (7 mL, 51 mmol) and dimethylamino pyridine (350 mg, 2.6 mmol). Stir at room temperature overnight, concentrate and purify (silica gel chromatography, eluting with 4:1 pentane:diethyl ether) and concentrate at 0° C. to give the title compound as a colorless oil (1.15 g, 43%).

2-(R)-(2-(S)-Dibenzylamino-1-(S)-hydroxy-3-phenylpropyl)-5,5-dimethylpyrrolidine-1-carboxylic acid tert-butyl ester Add sec-butyllithium (2.9 mL, 2.1 mmol) dropwise to a solution of freshly distilled (–)-sparteine (1 mL, 4.3 mmol) in diethyl ether (25 mL) over 3 min at –78° C. Add 2,2-dimethylpyrrolidine-1-carboxylic acid tert-butyl ester (645 mg, 3.2 mmol) in diethyl ether (2 mL) dropwise over 10 min. Stir 2 h, add 2-(S)-dibenzylamino-3-phenylpropionaldehyde (967 mg, 2.9 mmol) in diethyl ether (2 mL) over 5 min and stir 20 min. Add saturated aqueous ammonium chloride solution and ethyl acetate and let warm to room temperature, separate the layers, extract the aqueous layer with ethyl acetate, wash the organic layer with saturated aqueous sodium chloride solution, dry (magnesium sulfate), concentrate and purify (silica gel chromatography, eluting with 4:1 hexanes:ethyl acetate) to give the title compound as a colorless oil (182 mg, 12%).

2-(R)-(2-(S)-Amino-1-(S)-hydroxy-3-phenylpropyl)-5,5-dimethylpyrrolidine-1-carboxylic acid tert-butyl ester Dissolve 2-(R)-(2-(S)-dibenzylamino-1-(S)-hydroxy-3-phenylpropyl)-5,5-dimethylpyrrolidine-1-carboxylic acid tert-butyl ester (182 mg, 0.34 mmol) in methanol (4 mL) and add 10% palladium hydroxide on carbon (43 mg). Stir under 1 atmosphere of hydrogen gas overnight and filter through a filtering agent, wash with methanol and concentrate to give the title compound as a colorless oil (103 mg, 87% yield).

Preparation 20

(2R,4R)-2-[(1S,2S)-2-Amino-3-(3,5-difluorophenyl)-1-hydroxypropyl]-4-benzyloxypyrrolidine-1-carboxylic acid tert-butyl ester

(2R,4R)-4-Benzyloxypyrrolidine-1,2-dicarboxylic acid 1-tert-butyl ester 2-methyl ester Add silver oxide (2.8 g, 12.3 mmol) to a mixture of 4-(R)-hydroxypyrrolidine-N-1,2-(R)-dicarboxylic acid 1-tert-butyl ester 2-methyl ester (3 g, 12.3 mmol) and benzyl bromide (4.7 g, 27.6 mmol) in diethyl ether (20 mL). Stir the mixture overnight in a sealed tube at 40° C. Filter the silver oxide, concentrate and purify (silica gel chromatography, eluting with ethyl acetate/hexanes mixtures) to give the title compound as a colorless oil (2.5 g, 60%).

MS (ES): m/z=236.1 [M+H, Product-Boc], MS (ES): m/z=358.1 [M+Na].

(2R,4R)-4-Benzyloxy-2-hydroxymethylpyrrolidine-1-carboxylic acid tert-butyl ester Add lithium borohydride (0.0097 g, 0.44 mmol) to an ice cold solution of (2R,4R)-4-benzyloxypyrrolidine-1,2-dicarboxylic acid 1-tert-butyl ester 2-methyl ester (0.1 g, 0.29 mmol) in tetrahydrofuran (1 mL). Warm slowly to room temperature over 18 hours. Cool in ice bath. Slowly add acetone (1 mL), concentrate and purify (silica gel chromatography, eluting with ethyl acetate/hexanes mixtures) to give the title compound as a colorless oil (0.071 g, 80%).

MS (ES): m/z=330.1 [M+Na].

(2R,4R)-4-Benzyloxy-2-formylpyrrolidine-1-carboxylic acid tert-butyl ester

Add triethylamine (1.1 mL, 7.79 mmol) and sulfurtrioxide-pyridine complex (0.63 g, 3.89 mmol) to an ice cold solution of (2R,4R)-4-benzyloxy-2-hydroxymethyl-pyrrolidine-1-carboxylic acid tert-butyl ester (0.6 g, 1.95 mmol) in dimethyl sulfoxide (2 mL). Stir 30 minutes, warm to room temperature and stir 30 minutes. Dilute with ethyl ether and wash with 5% aqueous citric acid (3×120 mL), saturated aqueous sodium chloride, dry (magnesium sulfate) and concentrate to give the title compound as an oil (0.59 g, 100%).

(2R,4R)-4-Benzyloxy-2-[(1R,2S)-3-(3,5-difluorophenyl)-1-hydroxy-2-nitropropyl]pyrrolidine-1-carboxylic acid tert-butyl ester Add tetrabutylammonium fluoride (1.6 mL of 1.0 M solution in tetrahydrofuran, 1.6 mmol) to an ice cold solution of 1-phenyl-2-nitroethane (0.88 mL, 6.55 mmol) in tetrahydrofuran (4 mL). Stir 5 minutes and add (2R,4R)-4-benzyloxy-2-formylpyrrolidine-1-carboxylic acid tert-butyl ester (1.0 g, 3.27 mmol) in tetrahydrofuran (10 mL). Stir 15 minutes, dilute with ethyl acetate, wash with water (3×50 mL), saturated aqueous sodium chloride, dry (magnesium sulfate) and concentrate to give a mixture that contains 3 isomers (ratio: 2.5:1:0.7). Purify (silica gel chromatography, eluting with hexanes/acetone mixtures) to give the major isomer and title compound as a colorless foam (0.696 g, 43%).

MS (ES): m/z=515.3 [M+Na].

(2R,4R)-2-[(1S,2S)-2-Amino-3-(3,5-difluorophenyl)-1-hydroxypropyl]-4-benzyloxypyrrolidine-1-carboxylic acid tert-butyl ester Add sodium borohydride (0.242 mg, 6.42 mmol) over 1 minute to a solution of (2R,4R)-4-benzyloxy-2-[(1R,2S)-3-(3,5-difluorophenyl)-1-hydroxy-2-nitropropyl]pyrrolidine-1-carboxylic acid tert-butyl ester (0.696 g, 1.41 mmol) and nickel (II) chloride (0.29 g, 2.25 mmol) in methanol (30 mL) at room temperature. Stir 20 minutes, add water (3 mL) and evaporate the methanol. Partition the residue with ethyl acetate and water. Filter through a filtering agent, wash with ethyl acetate (300 mL), separate away the aqueous layer, wash with saturated aqueous sodium chloride, dry (magnesium sulfate), filter and concentrate to give the title compound as a colorless oil (619 mg, 95%).

MS (ES): m/z=463.3 [M+H].

Preparation 21

(R)-2-[(4S,5S)-3-Acetyl-4-(3,5-difluoro-benzyl)-2,2-dimethyl-oxazolidin-5-yl]-4-carboxymethyl-pyrrolidine-1-carboxylic acid tert-butyl ester

(2R,4R)-2-[(4S,5S)-3-Acetyl-4-(3,5-difluoro-benzyl)-2,2-dimethyl-oxazolidin-5-yl]-4-benzyloxy-pyrrolidine-1-carboxylic acid tert-butyl ester Dissolve (2R,4R)-2-[(1S,2S)-2-Acetylamino-3-(3,5-difluoro-phenyl)-1-hydroxy-propyl]-4-benzyloxy-pyrrolidine-1-carboxylic acid tert-butyl ester (0.150 g, 0.3 mmol) in 1:1 dichloromethane/acetone (5 mL). Add PPTS (pyridine/p-toluene sulfonic acid) (0.03 mmol) and 2-methoxypropane (1.5 mmol). When the reaction is complete by TLC (15 minutes), concentrate the reaction mixture under reduced pressure. Dissolve the residue in ethyl acetate and wash with saturated aqueous sodium bicarbonate followed by saturated aqueous sodium chloride. Dry over magnesium sulfate, concentrate under reduced pressure, and subject the residue to silica gel chromatography, eluting with ethyl acetate/hexane to provide the desired compound (0.120 g, 75%).

MS(ESI): m/z=545.3 (M+H).

(2R,4R)-2-[(4S,5S)-3-Acetyl-4-(3,5-difluoro-benzyl)-2,2-dimethyl-oxazolidin-5-yl]-4-hydroxy-pyrrolidine-1-carboxylic acid tert-butyl ester Combine (2R,4R)-2-[(4S,5S)-3-Acetyl-4-(3,5-difluoro-benzyl)-2,2-dimethyl-oxazolidin-5-yl]-4-benzyloxy-pyrrolidine-1-carboxylic acid tert-butyl ester (0.12 g, 0.22 mmol), 10% palladium on carbon (12 mg) and methanol (10 mL) and stir overnight under 1 atmosphere of hydrogen. Add filter agent, filter, and concentrate under reduced pressure to provide the desired compound (0.100 g, 98%) as a foam.

MS(ESI): m/z=455.3 (M+H)

(R)-2-[(4S,5S)-3-Acetyl-4-(3,5-difluoro-benzyl)-2,2-dimethyl-oxazolidin-5-yl]-4-oxo-pyrrolidine-1-carboxylic acid tert-butyl ester Cool to 0° C. a solution of (2R,4R)-2-[(4S,5S)-3-Acetyl-4-(3,5-difluoro-benzyl)-2,2-dimethyl-oxazolidin-5-yl]-4-hydroxy-pyrrolidine-1-carboxylic acid tert-butyl ester (0.01 gr, 0.022 mmol) in dichloromethane (0.5 mL). Add trichloroisocyanuric acid (0.023 g, 0.110 mmol). Stir 5 minutes and then add TEMPO (2,2,6,6-tetramethyl-1-piperidinyl-oxy, free radical, 0.0007 g, 0.0044 mmol). After one hour add dichloromethane to the mixture and wash with saturated aqueous sodium bicarbonate followed by saturated aqueous sodium chloride. Dry over magnesium sulfate and concentrate under reduced pressure to provide the desired compound (0.010 g, 95%).

MS(ESI): m/z=453.3 (M+H)

(R)-2-[(4S,5S)-3-Acetyl-4-(3,5-difluoro-benzyl)-2,2-dimethyl-oxazolidin-5-yl]-4-[1-methoxycarbonyl-methylidene]-pyrrolidine-1-carboxylic acid tert-butyl ester Add NaH (60% dispersion in mineral oil, 0.04 g, 1.0 mmol) to a solution of ethyldiethylphosphonacetate (1.0 mmol) in 2 mL of dry THF. Add (R)-2-[(4S,5S)-3-Acetyl-4-(3,5-difluoro-benzyl)-2,2-dimethyl-oxazolidin-5-yl]-4-oxo-pyrrolidine-1-carboxylic acid tert-butyl ester (0.05 g, 0.1 mmol) in 5 mL of THF. Stir the reaction for two days. Add water, extract with ethyl acetate, dry over MgSO$_4$, and concentrate under reduced pressure to provide the desired compound as a 1:1 mixture of Z and E isomers (0.04 g, 95%).

MS(ESI): m/z=509.4 (M+H)

(R)-2-[(4S,5S)-3-Acetyl-4-(3,5-difluoro-benzyl)-2,2-dimethyl-oxazolidin-5-yl]-4-methoxycarbonylmethyl-pyrrolidine-1-carboxylic acid tert-butyl ester Combine (R)-2-[(4S,5S)-3-Acetyl-4-(3,5-difluoro-benzyl)-2,2-dimethyl-oxazolidin-5-yl]-4-[1-methoxycarbonyl-methylidene]-pyrrolidine-1-carboxylic acid tert-butyl ester (as mixture of isomers Z/E) (0.010 g, 0.02 mmol), 10% palladium on carbon (4 mg) and methanol (2 mL) and stir for 3 hours under 1 atmosphere of hydrogen. Add filter agent, filter and concentrate under reduced pressure to provide the desired compound as a mixture of cis and trans isomers, (0.01 g, 98%).

MS(ESI): m/z=511.3 (M+H)

(R)-2-[(4S,5S)-3-Acetyl-4-(3,5-difluoro-benzyl)-2,2-dimethyl-oxazolidin-5-yl]-4-carboxymethyl-pyrrolidine-1-carboxylic acid tert-butyl ester Add LiOH (0.32 mL, 3M solution in water) to a solution of (R)-2-[(4S,5S)-3-Acetyl-4-(3,5-difluoro-benzyl)-2,2-dimethyl-oxazolidin-5-yl]-4-methoxycarbonylmethyl-pyrrolidine-1-carboxylic acid tert-butyl ester (0.1 g, 0.19 mmol) in 0.32 mL of THF and stir overnight. Remove THF under reduced pressure. Add ethyl acetate and separate the layers. Acidify the aqueous layer with citric acid pH: 3) and extract with ethyl acetate. Dry over MgSO$_4$ and concentrate under reduced pressure to provide the title compound (0.087 g, 90%).

MS(ESI): m/z=495.2 (M−H)

Preparation 22

3,5-Difluorophenylnitroethane

1-(3,5-Difluorophenyl)-2-nitroethanol

Add nitromethane (200 mL, 2.5 eq) to a suspension of potassium carbonate (30 g) and 3,5-difluorobenzaldehyde (200 g) in tetrahydrofuran (600 mL) at room temperature. Stir at room temperature overnight, filter, wash with ethyl acetate and concentrate to give the title compound as a crude oil (330 g) which is used in the next step without further purification.

1,3-Difluoro-5-(2-nitrovinyl)-benzene

Add acetic anhydride (160 mL) to a solution of 1-(3,5-difluorophenyl)-2-nitroethanol (330 g) and 4-dimethylaminopyridine (18 g) in dichloromethane (1000 mL), at room temperature using a water bath to keep the temperature below 35° C. Add acetic acid over 30 min and stir the reaction mixture overnight. Dilute with dichloromethane (600 mL) and wash with 2% aqueous HCl, saturated aqueous sodium chloride, saturated aqueous sodium bicarbonate, dry (magnesium sulfate) and concentrate. Wash the crude with hexanes to give the title compound (220 g).

3,5-Difluorophenyl nitroethane

Add portionwise sodium borohydride (12 g) over 1.5 h to a solution of 1,3-difluoro-5-(2-nitrovinyl)-benzene (100 g) in a mixture of dimethylsulfoxide (400 mL) and acetic acid (80 mL) at room temperature using a water bath to keep the temperature below 30° C. Dilute with ethyl acetate (1000 mL) and wash with water (600 mL), saturated aqueous sodium bicarbonate (2×600 mL), saturated aqueous sodium chloride (600 mL), dry (magnesium sulfate) concentrate and purify (silica gel chromatography, eluting with 3:97 ethyl acetate:hexanes) to give the title compound a pale yellow solid (63 g, 62%).

Preparation 23

(S)-2-sec-Butylamino-6-(cyclopropanesulfanyl-methylamino)-isonicotinic acid

Cyclopropanesulfonic Acid Methylamide

Dissolve cyclopropylsulfonyl chloride (1.0 g, 7.1 mmol) in dichloromethane (8 mL). Cool to 0° C. and slowly add methylamine (2.0 M solution in THF, 10.7 mL, 21 mmol). Stir for 5 min and add triethylamine dropwise (1.4 mL, 11 mmol). Stir from 0° C. to room temperature overnight. Filter, concentrate the organic layer and, purify (silica gel chromatography, eluting with 0:100 to 25:75 ethyl acetate:hexanes) to give the title compound.

MS (ES): m/z=134 [M−H].

Sodium Cyclopropanesulfonic Acid Methylamide

Dissolve cyclopropanesulfonic acid methylamide in THF (10 mL) and cool to 0° C. Slowly add sodium hydride (208 mg, 60% suspension in mineral oil) into the solution and stir from 0° C. to room temperature for 3 h. Concentrate and use the solid in the next step without furrer purification.

(S)-2-sec-Butylamino-6-chloro-isonicotinic acid methyl ester

Dissolve 2,6-dichloro-isonicotinic methyl ester (2.0 g, 10 mmol), palladium (II) acetate (224.0 mg, 1.0 mmol), racemic 2,2'-bis(diphenylphosphino)-1,1'-binaphthyl (632 mg, 1.0 mmol) and cesium carbonate (3.96 g, 12 mmol) in toluene (20 mL) in a previously degassed sealed vessel. Flush the mixture with nitrogen gas. Add (S)-(+)-sec-butylamine (1.2 mL, 12 mmol) to the solution and heat the sealed mixture overnight at 100° C. Cool to room temperature and dilute with diethyl ether and filter through a filtering agent. Concentrate the filtrate and purify (silica gel chromatography, eluting with 0:100 to 10:90 ethyl acetate:hexanes) to give the title compound (73%).

MS (ES): m/z=243 [M+H].

(S)-2-sec-Butylamino-6-(cyclopropanesulfonyl-methylamino)-isonicotinic acid methyl ester Dissolve (S)-2-sec-butylamino-6-chloro-isonicotinic acid methyl ester (880 mg, 3.6 mmol), tris(dibenzylideneacetone)dipalladium (0) (164 mg, 0.18 mmol), 2-(di-tert-butylphosphino)biphenyl (107 mg, 0.36 mmol) in toluene (18 mL) and THF (2 mL) in a previously nitrogen-filled sealed vessel. Add sodium cyclopropanesulfonic acid methylamide (700 mg, 4.42 mmol) into the mixture under nitrogen and flush the reactants again with nitrogen before sealing and heating overnight at 100° C. Cool the reaction to room temperature and dilute with ethyl acetate and diethyl ether and filter through a filtering agent. Concentrate and purify (silica gel chromatography, eluting with 0:100 to 08:92 ethyl acetate:hexanes) to give the title compound.

MS (ES): m/z=342 [M+H].

(S)-2-sec-Butylamino-6-(cyclopropanesulfonyl-methylamino)-isonicotinic acid

Dissolve (S)-2-sec-butylamino-6-(cyclopropanesulfonyl-methylamino)-isonicotinic acid methyl ester (600 mg, 1.97 mmol) in methanol (18 mL). Slowly add 2 N NaOH (3 mL) and stir overnight at room temperature. Acidify the mixture to about pH=6 with 5 N HCl and concentrate. Dilute with ethyl acetate (30 mL) and wash the organic layer with saturated aqueous sodium chloride solution, dry (magnesium sulfate) and concentrate to give the title compound.

MS (ES): m/z=328 [M+H].

The compounds of Preparation 24-30 may be prepared essentially as described in Preparation 23 starting with the corresponding sulfonyl chlorides and amines.

| Prep | Compound | MS (ES) [M + H] |
|---|---|---|
| 24 | (S)-2-sec-Butylamino-6-(cyclopropyl-methanesulfonylamino)-isonicotinic acid | 328 |
| 25 | (S)-2-sec-Butylamino-6-(propane-2-sulfonylamino)-isonicotinic acid | 316 |
| 26 | (S)-2-sec-Butylamino-6-[methyl-(propane-2-sulfonyl)-amino]-isonicotinic acid | 330 |
| 27 | (S)-2-sec-Butylamino-6-(ethyl-methanesulfonylamino)-isonicotinic acid | 316 |
| 28 | (S)-2-sec-Butylamino-6-[(2-fluoroethyl)-methanesulfonylamino]-isonicotinic acid | 334 |
| 29 | (S)-2-sec-Butylamino-6-[(2,2-difluoroethyl)-methanesulfonylamino]-isonicotinic acid | 352 |
| 30 | (S)-2-sec-Butylamino-6-[(2,2,2-trifluoroethyl)-methanesulfonylamino]-isonicotinic acid | 370 |

Preparation 31

(S)-2-sec-Butylamino-6-[1,3]dioxan-2-yl-isonicotinic acid

2-Chloro-6-vinyl-isonicotinic acid methyl ester

Add methyl 2,6-dichloro-isonicotinate (3.8 g, 18.4 mmol), tetrakis(triphenylphosphine)palladium (0) (1.15 g, 0.99 mmol), triphenylphosphine (524 mg, 2 mmol) in toluene (40 mL) to a previously nitrogen-filled sealed vessel. Flush the reactants with nitrogen again. Add tributyl(vinyl)tin (6.98 mL, 24.0 mmol) and heat the sealed mixture at 95° C. overnight. Cool to room temperature, dilute with diethyl ether and filter through a filtering agent. Wash the organic filtrate with saturated ammonium chloride, saturated sodium bicarbonate and saturated aqueous sodium chloride. Dry (magnesium sulfate), concentrate and purify (silica gel chromatography, eluting with 5:95 to 10:90 ethyl acetate:hexanes) to give the title compound (70%).

2-Chloro-6-formyl-isonicotinic acid methyl ester

Dissolve 2-chloro-6-vinyl-isonicotinic acid methyl ester (1.6 g, 8 mmol) in dichloromethane (10 mL) and flush the reaction vessel with oxygen gas. Cool to −78° C. and pass positive pressure of ozone through the solution for 15 min until blue color appears. Quench with excess dimethylsulfide (1.5 mL) and warm to room temperature overnight. Concentrate and purify (silica gel chromatography, eluting with 0:100 to 10:90 ethyl acetate:hexanes) to give the title compound.

2-Chloro-6-[1,3]dioxan-2-yl-isonicotinic acid methyl ester

Dissolve 2-chloro-6-formyl-isonicotinic acid methyl ester (200 mg, 1.0 mmol) in THF (8 mL). Add Amberlyst® 15 ion exchange resin (0.3 g) and dropwise 1,3-propanediol (0.1 mL, 1.5 mmol). Stir at room temperature for two days. Filter, concentrate and purify (silica gel chromatography, eluting with 0:100 to 10:90 ethyl acetate:hexanes) to give the title compound (88%).

(S)-2-sec-Butylamino-6-[1,3]dioxan-2-yl-isonicotinic acid methyl ester

Dissolve 2-chloro-6-[1,3]dioxan-2-yl-isonicotinic acid methyl ester (150 mg, 0.6 mmol), palladium (II) acetate (7.0 mg, 0.03 mmol), racemic 2,2'-bis(diphenylphosphino)-1,1'-binaphthyl (20 mg, 0.03 mmol) and cesium carbonate (482 mg, 1.3 mmol) in toluene (2 mL) in a previously degassed sealed vessel. Flush the mixture with nitrogen gas. Add (S)-(+)-sc-butylamine (0.074 mL, 0.74 mmol) and heat the sealed mixture overnight at 100° C. Cool to room temperature, dilute with diethyl ether and filter through filtering agent. Concentrate the filtrate and purify (silica gel chromatography, eluting with 0:100 to 20:80 ethyl acetate:hexanes) to give the title compound (68%).

(S)-2-sec-Butylamino-6-[1,3]dioxan-2-yl-isonicotinic acid

Dissolve (S)-2-sec-butylamino-6-[1,3]dioxan-2-yl-isonicotinic acid methyl ester (100 mg, 0.35 mmol) in methanol (4 mL). Slowly add 1 N lithium hydroxide (0.46 mL) and stir overnight at room temperature. Acidify the mixture to about pH=6 with 5 N HCl and concentrate. Dilute with ethyl acetate (15 mL), wash the organic layer with saturated aqueous sodium chloride, dry (magnesium sulfate) and concentrate to give the title compound.

MS (ES): m/z=281 [M+H].

The compound of Preparation 32 may be prepared essentially as described in Preparation 31.

| Prep | Compound | MS (ES) [M + H] |
|---|---|---|
| 32 | (S)-2-sec-Butylamino-6-[1,3]dioxolan-2-yl-isonicotinic acid | 267 |

Preparation 33

(S)-2-sec-Butylamino-6-difluoromethyl-isonicotinic acid

2-Chloro-6-vinyl-isonicotinic acid methyl ester

Add methyl 2,6-dichloroisonicotinate (3.8 g, 18.4 mmol), tetrakis(triphenylphosphine)palladium (0) (1.15 g, 0.99 mmol), triphenyhlphosphine (524 mg, 2 mmol) and toluene (40 mL) in a previously nitrogen-filled sealed vessel. Flush the reactants with nitrogen again. Add tributyl(vinyl)tin (6.98 mL, 24.0 mmol) under nitrogen and heat the sealed mixture at 95° C. overnight with vigorous stirring. Cool the reaction to room temperature, dilute with diethyl ether and filter through a filtering agent. Wash the organic filtrate with saturated aqueous ammonium chloride, saturated aqueous sodium bicarbonate, saturated aqueous sodium chloride, dry (magnesium sulfate), concentrate and purify (silica gel chromatography, eluting with 5:95 to 10:90 ethyl acetate:hexanes) to give the title compound (70%).

2-Chloro-6-formyl-isonicotinic acid methyl ester

Dissolve 2-chloro-6-vinyl-isonicotinic acid methyl ester (1.6 g, 8 mmol) in dichloromethane (10 mL) and flush the reaction vessel with oxygen gas. Cool to −78° C. and pass positive pressure of ozone through the solution for 15 min until sky blue color appears. At the same temperature quench the reaction with excess dimethylsulfide (1.5 mL) and warm up to room temperature overnight. Concentrate and purify (silica gel chromatography, eluting with 0:100 to 10:90 ethyl acetate:hexanes) to give the title compound.

2-Chloro-6-difluoromethyl-isonicotinic acid methyl ester

Dissolve 2-chloro-6-formyl-isonicotinic acid methyl ester (386 mg, 1.93 mmol) in dichloromethane (2 mL) and cool to 0° C. Add (diethylamino)sulfur trifluoride (0.625 mL, 4.8 mmol) dropwise and stir overnight while warming up to room temperature. Quench the reaction by water and dilute further with dichloromethane (10 mL). Extract the organic layer and dry (magnesium sulfate). Concentrate and purify (silica gel chromatography, eluting with 5:95 ethyl acetate:hexanes) to give the title compound as an oil (47%).

(S)-2-sec-Butylamino-6-difluoromethyl-isonicotinic acid methyl ester

Dissolve 2-chloro-6-difluoromethyl-isonicotinic acid methyl ester (200 mg, 0.9 mmol), palladium (II) acetate (20.0 mg, 0.09 mmol), racemic 2,2'-bis(diphenylphosphino)-1,1'-binaphthyl (56 mg, 0.09 mmol) and cesium carbonate (438 mg, 1.35 mmol) in toluene (3 mL) in a previously degassed sealed vessel. Flush the mixture with nitrogen gas. Add (S)-(+)-sec-butylamine (0.108 mL, 1.08 mmol) to the solution under nitrogen and heat the sealed mixture overnight at 100°

C. Cool the reaction to room temperature. Dilute with diethyl ether and filter through a filtering agent. Concentrate the filtrate and purify (silica gel chromatography, eluting with 10:90 acetate:hexanes) to give the title compound as an oil (60%).

(S)-2-sec-Butylamino-6-difluoromethyl-isonicotinic acid

Dissolve 2-sec-butylamino-6-difluoromethyl-isonicotinic acid methyl ester (140 mg, 0.54 mmol) in methanol (2 mL) and THF (10 mL). Slowly add 1 N aqueous lithium hydroxide (0.7 mL) and stir overnight at room temperature. Acidify the mixture to about pH=6 by 5 N HCl and concentrate to near dryness. Dilute with ethyl acetate (20 mL) and wash the organic layer with saturated aqueous sodium chloride. Dry (magnesium sulfate) and concentrate to give the title compound as a solid.

Preparation 34

(S)-2-sec-Butylamino-6-(1,1-difluoroethyl)-isonicotinic acid

2-Acetyl-6-chloro-isonicotinic acid methyl ester

Add methyl 2,6-dichloroisonicotinate (3.0 g, 15.0 mmol), trans-dichlorobis(triphenylphosphine)palladium (II) (105 mg, 0.15 mmol) and toluene (10 mL) in a previously nitrogen filled sealed vessel. Flush the reactants with nitrogen again. Add tributyl(1-ethoxyvinyl)tin (5.57 mL, 16.5 mmol) under nitrogen and heat the sealed mixture at 100° C. overnight with vigorous stirring. Cool the reaction to room temperature, dilute with diethyl ether and filter through a filtering agent. Concentrate to near dryness and dilute the residue with THF (10 mL). Add dropwise 5 N HCl (5 mL) and stir the mixture overnight. Concentrate to near dryness and extract the organic material by diethyl ether, partitioning with water. Dry (magnesium sulfate), concentrate and purify (silica gel chromatography, eluting with 0:100 to 10:90 ethyl acetate:hexanes) to give the title compound as a solid over two steps (47%).

2-Chloro-6-(1,1-difluoroethyl)-isonicotinic acid methyl ester

Dissolve 2-acetyl-6-chloro-isonicotinic acid methyl ester (410 mg, 1.9 mmol) in dichloromethane (4 mL) and cool to 0° C. Add (diethylamino)sulfur trifluoride (0.55 mL, 4.2 mmol) dropwise and stir over night while warming up to room temperature. Quench the reaction using water and dilute further with dichloromethane (10 mL). Extract the organic layer and dry (magnesium sulfate). Concentrate and purify (silica gel chromatography, eluting with 5:95 ethyl acetate:hexanes) to give the title compound as an oil (45%).

(S)-2-sec-Butylamino-6-(1,1-difluoroethyl)-isonicotinic acid methyl ester

Dissolve 2-chloro-6-(1,1-difluoroethyl)-isonicotinic acid methyl ester (200 mg, 0.85 mmol), palladium (II) acetate (20.0 mg, 0.09 mmol), racemic 2,2'-bis(diphenylphosphino)-1,1'-binaphthyl (56 mg, 0.09 mmol) and cesium carbonate (414 mg, 1.27 mmol) in toluene (3 mL) in a previously degassed sealed vessel. Flush the mixture with nitrogen gas. Add (S)-(+)-sec-butylamine (0.10 mL, 1.02 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, eluting with 0:100 to 5:95 ethyl acetate:hexanes) to give the title compound as an oil (86%).

(S)-2-sec-Butylamino-6-(1,1-difluoroethyl)-isonicotinic acid

Dissolve (S)-2-sec-butylamino-6-(1,1-difluoroethyl)-isonicotinic acid methyl ester (200 mg, 0.73 mmol) in methanol (3 mL). Slowly add 1 N lithium hydroxide (1.0 mL) and stir overnight at room temperature. Acidify the mixture to about pH=6 by 5 N HCl and concentrate to near dryness. Dilute with ethyl acetate (20 mL) and wash the organic layer with saturated aqueous sodium chloride. Dry (magnesium sulfate) and concentrate to give the title compound as a solid (95%).

MS (ES): m/z=259 [M+H].

Preparation 35

(S)-2-sec-Butylamino-6-(2-oxopropyl)-isonicotinic acid

2-Chloro-6-(2-oxopropyl)-isonicotinic acid methyl ester

Add methyl 2,6-dichloroisonicotinate (3.0 g, 15.0 mmol), trans-dichlorobis(tri-o-tolylphosphine)palladium (II) (196 mg, 0.25 mmol), tributyltin methoxide (2.4 g, 7.5 mmol) and toluene (20 mL) in a previously nitrogen filled sealed vessel. Flush the reactants with nitrogen again. Add isopropenyl acetate (0.85 mL, 7.75 mmol) under nitrogen and heat the sealed mixture at 100° C. overnight with vigorous stirring. Cool the reaction to room temperature, dilute with diethyl ether and filter through a filtering agent. Concentrate and purify (silica gel chromatography, eluting with 0:100 to 20:80 ethyl acetate:hexanes) to give the title compound (29%).

(S)-2-sec-Butylamino-6-(2-oxopropyl)-isonicotinic acid methyl ester

Dissolve 2-chloro-6-(2-oxopropyl)-isonicotinic acid methyl ester (200 mg, 0.88 mmol), palladium (II) acetate (2.0 mg, 0.009 mmol), racemic 2,2'-bis(diphenylphosphino)-1,1'-binaphthyl (8.2 mg, 0.014 mmol) and cesium carbonate (458 mg, 1.23 mmol) in toluene (2 mL) in a previously degassed sealed vessel. Flush the mixture with nitrogen gas. Add (S)-(+)-sec-butylamine (0.105 mL, 1.0 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, 0:100 to 20:80 ethyl acetate:hexanes) to give the title compound (22%).

MS (ES): m/z=265 [M+H].

(S)-2-sec-Butylamino-6-(2-oxopropyl)-isonicotinic acid

Dissolve (S)-2-sec-butylamino-6-(2-oxopropyl)-isonicotinic acid methyl ester (50 mg, 0.19 mmol) in THF (2 mL). Slowly add 1 N lithium hydroxide (0.28 mL) and stir overnight at room temperature. Acidify the mixture to about pH=6 by 5 N HCl and concentrate to near dryness. Dilute with ethyl acetate (10 mL) and wash the organic layer with saturated aqueous sodium chloride. Dry (magnesium sulfate) and concentrate to give the title compound as a solid.

MS (ES): m/z=251 [M+H].

Preparation 36

(S)-2-sec-Butylamino-6-(2,2-difluoropropyl)-isonicotinic acid

2-Chloro-6-(2,2-difluoropropyl)-isonicotinic acid methyl ester

Dissolve 2-chloro-6-(2-oxopropyl)-isonicotinic acid methyl ester (760 mg, 3.3 mmol in dichloromethane (5 mL) and cool to 0° C. Add (diethylamino)sulfur trifluoride (1.1 mL, 8.3 mmol) dropwise and stir over night while warming up to room temperature. Quench with water and dilute further with dichloromethane (20 mL). Extract the organic layer and dry (magnesium sulfate), concentrate and purify (silica gel chromatography, eluting with 0:100 to 5:95 ethyl acetate: hexanes) to give the title compound as an oil (18%).

(S)-2-sec-Butylamino-6-(2,2-difluoropropyl)-isonicotinic acid methyl ester

Dissolve 2-chloro-6-(2,2-difluoropropyl)-isonicotinic acid methyl ester-(150 mg, 0.6 mmol), palladium (II) acetate (224.0 mg, 1.0 mmol), racemic 2,2'-bis(diphenylphosphino)-1,1'-binaphthyl (37 mg, 0.06 mmol) and cesium carbonate (293 mg, 0.9 mmol) in toluene (2 mL) in a previously degassed sealed vessel. Flush the mixture with nitrogen gas. Add (S)-(+)-sec-butylamine (0.07 mL, 0.72 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, eluting with 0:100 to 5:95 ethyl acetate:hexanes) to give the title compound as an oil (58%).

(S)-2-sec-Butylamino-6-(2,2-difluoropropyl)-isonicotinic acid

Dissolve (S)-2-sec-butylamino-6-(2,2-difluoropropyl)-isonicotinic acid methyl ester (100 mg, 0.34 mmol) in THF (3 mL). Slowly add 1 N lithium hydroxide (0.52 mL) and stir overnight at room temperature. Acidify the mixture to about pH=6 by 5 N HCl and concentrate to near dryness. Dilute with ethyl acetate (20 mL) and wash the organic layer with saturated aqueous sodium chloride, dry (magnesium sulfate) and concentrate to give the title compound as a solid.

Preparation 37

2-Acetyl-(S)-6-sec-butylamino-isonicotinic acid

2-Acetyl-(S)-6-sec-butylamino-isonicotinic acid methyl ester

Dissolve 2-acetyl-6-chloro-isonicotinic acid methyl ester (300 mg, 1.4 mmol), palladium (II) acetate (16 mg, 0.07 mmol), racemic 2,2'-bis(diphenylphosphino)-1,1'-binaphthyl (46 mg, 0.07 mmol) and cesium carbonate (781 mg, 2.1 mmol) in anhydrous toluene (3 mL) in a previously degassed sealed vessel. Flush the mixture with nitrogen gas. Add (S)-(+)-sec-butylamine (0.16 mL, 1.68 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, eluting with 0:100 to 5:95 ethyl acetate:hexanes) to give the title compound as a solid (17%).

2-Acetyl-(S)-6-sec-butylamino-isonicotinic acid

Dissolve 2-acetyl-(S)-6-sec-butylamino-isonicotinic acid methyl ester (60 mg, 0.24 mmol) in THF (3 mL). Slowly add 1 N lithium hydroxide (0.3 mL) and stir overnight at room temperature. Acidify the mixture to about pH=6 by 5 N HCl and concentrate to near dryness. Dilute with ethyl acetate (15 mL) and wash the organic layer with saturated aqueous sodium chloride, dry (magnesium sulfate) and concentrate to give the title compound as a solid (96%).

MS (ES): m/z=237 [M+H].

Preparation 38

(S)-6-sec-Butylaminopyridine-2,4-dicarboxylic acid 2-ethyl ester

2-Chloro-6-(1-ethoxyvinyl)-isonicotinic acid methyl ester

Add methyl 2,6-dichloroisonicotinate (2.06 g, 10 mmol), tetrakis(triphenylphosphine)palladium (0) (578 mg, 0.5 mmol), triphenyhlphosphine (263 mg, 1 mmol) and toluene (25 mL) in a previously nitrogen filled sealed vessel. Flush the reactants with nitrogen again. Add tributyl(1-ethoxyvinyl)tin (4.05 mL, 12.0 mmol) under nitrogen and heat the sealed mixture at 100° C. overnight with vigorous stirring. Cool the reaction to room temperature, dilute with diethyl ether and filter through a filtering agent. Wash the organic filtrate with saturated aqueous ammonium chloride, saturated aqueous sodium bicarbonate and saturated aqueous sodium chloride respectively. Dry (magnesium sulfate), concentrate and purify (silica gel chromatography, eluting with 5:95 to 10:90 ethyl acetate:hexanes) to give the title compound.

6-Chloropyridine-2,4-dicarboxylic acid 2-ethyl ester 4-methyl ester

Dissolve 2-chloro-6-(1-ethoxyvinyl)-isonicotinic acid methyl ester (4.8 g, 20 mmol) in dichloromethane (40 mL) and flush the reaction vessel with oxygen gas. Cool to −78° C. and pass positive pressure of ozone through the solution for 10 min until sky blue color appears. At the same temperature quench the reaction with excess dimethylsulfide (6 mL) and warm up to room temperature overnight. Concentrate and purify (silica gel chromatography, eluting with 0:100 to 10:90 ethyl acetate:hexanes) to give the title compound.

(S)-6-sec-Butylaminopyridine-2,4-dicarboxylic acid 2-ethyl ester 4-methyl ester Dissolve 6-chloropyridine-2,4-dicarboxylic acid 2-ethyl ester 4-methyl ester (2.8 g, 11.5 mmol), palladium (II) acetate (258.0 mg, 1.15 mmol), racemic 2,2'-bis(diphenylphosphino)-1,1'-binaphthyl (716 mg, 1.15 mmol) and cesium carbonate (5.6 g, 17.2 mmol) in toluene (25 mL) in a previously degassed sealed vessel. Flush the mixture with nitrogen gas. Add (S)-(+)-sec-butylamine (1.38 mL, 13.8 mmol) to the solution under nitrogen and heat the sealed mixture overnight at 100° C. Cool the reaction to room temperature. Dilute with diethyl ether and filter through a filtering agent. Concentrate the filtrate and purify (silica gel chromatography, eluting with 0:100 to 10:90 ethyl acetate:hexanes) to give the title compound as an oil (72%).

(S)-6-sec-Butylamino-pyridine-2,4-dicarboxylic acid 2-ethyl ester 4-methyl ester alternatively may be prepared by the following procedure.

2-Chloro-6-methoxy-isonicotinic acid methyl ester

Mix commercially available 2-chloro-6-methoxy-isonicotinic acid (17 g, 90.6 mmol), concentrated sulfuric acid (0.85 mL) in methanol (150 mL) and reflux overnight. Cool the mixture to room temperature, filter and dry the solid under vacuum to give the title compound (15.5 g). Concentrate filtrate and dilute with ethyl acetate (150 mL). Wash with sodium bicarbonate solution, water, dry (sodium sulfate) and concentrate to give additional title compound (1.7 g) (17.2 g, 93% combined yield).
MS (ES): m/z=202 [M+H].

6-Methoxypyridine-2,4-dicarboxylic acid 2-ethyl ester 4-methyl ester

Add 2-chloro-6-methoxy-isonicotinic acid methyl ester (5 g, 24.8 mmol), palladium acetate (4.157 g, 18.5 mmol), 1,4-bis(diphenylphosphino)butane (1.038 g, 2.43 mmol), ethanol (127 mL), triethylamine (18 mL, 129 mmol) with DMSO (150 mL) to a pressure vessel. Seal the pressure vessel and purge with nitrogen. Pressurize the reaction mixture with carbon monoxide (690 KPa), seal the vessel, agitate the reaction and heat to 80° C. for 19 h. Cool to room temperature, filter the reaction mixture through a filtering agent and concentrate. Dissolve the residue in water (200 mL) and extract with hexanes (3×150 mL) and concentrate to give 6-methoxypyridine-2,4-dicarboxylic acid 2-ethyl ester 4-methyl ester (3.5 g). Extract the aqueous layer with ethyl acetate (3×150 mL) and wash the combined ethyl acetate layers with water, aqueous sodium bicarbonate solution, saturated aqueous sodium chloride, dry (sodium sulfate), concentrate, and purify (silica gel chromatography, eluting with ethyl acetate and hexanes) to give additional title compound (2.1 g) (5.6 g, 95% combined yield).
MS (ES): m/z=240 [M+H].

6-Chloropyridine-2,4-dicarboxylic acid 2-ethyl ester 4-methyl ester

Mix 6-methoxypyridine-2,4-dicarboxylic acid 2-ethyl ester 4-methyl ester (239 mg, 1.0 mmol), phosphorous oxychloride (0.46 mL, 4.93 mmol) in DMF (1.9 mL) and heat to 85° C. for 24 h. Cool to room temperature and quench with saturated aqueous sodium acetate solution (5 mL). Extract with ethyl acetate, wash with water, dry (sodium sulfate), concentrate and purify (silica gel chromatography, eluting with ethyl acetate and hexanes) to give the title compound (190 mg, 78%).
MS (ES): m/z=244 [M+H].

(S)-6-sec-Butylaminopyridine-2,4-dicarboxylic acid 2-ethyl ester 4-methyl ester Add 6-chloropyridine-2,4-dicarboxylic acid 2-ethyl ester 4-methyl ester (2.44 g, 10 mmol), palladium acetate (224 mg, 1.0 mmol), racemic-2,2'-bis(diphenylphosphino)-1,1'-binaphthyl (623 mg, 1.0 mmol), cesium carbonate (4.95 g, 15.2 mmol) in toluene (70 mL) in a sealed tube. Degas the tube for 5 min with nitrogen, add (S)-sec-butylamine (1.2 mL, 11.8 mmol) and seal the tube. Heat to 80° C. overnight. Cool to room temperature and filter the mixture through a filtering agent. Wash with ethyl acetate. Dissolve the solid in water and extract with ethyl acetate. Combine all organic solutions, concentrate and purify (silica gel chromatography, eluting with ethyl acetate and hexanes) to give the title compound (2.5 g, 90%).
MS (ES): m/z=281 [M+H].

(S)-6-sec-Butylaminopyridine-2,4-dicarboxylic acid 2-ethyl ester

Dissolve (S)-6-sec-butylaminopyridine-2,4-dicarboxylic acid 2-ethyl ester 4-methyl ester (990 mg, 3.5 mmol) in THF (35 mL) and dropwise add 1 N lithium hydroxide solution (3.5 mL). Stir at room temperature for 2 h and acidify the mixture to about pH=4 by 5 N HCl and concentrate to near dryness. Dilute with ethyl acetate (20 mL) and wash the organic layer with saturated sodium chloride solution, dry (magnesium sulfate) and concentrate to give a 2:1 ratio of crude title compound to starting material which is used in the next step without further purification.

Preparation 39

(S)-2-sec-Butylamino-6-cyano-isonicotinic acid

(S)-2-sec-Butylamino-6-cyano-isonicotinic acid methyl ester

Dissolve (S)-2-sec-butylamino-6-chloro-isonicotinic acid methyl ester (800 mg, 0.34 mmol), tris(dibenzylideneacetone)dipalladium (0) (120 mg, 0.13 mmol), 1,1'-bis(diphenylphosphino)ferrocene (146 mg, 0.26 mmol), zinc dust (52 mg) and zinc (II) cyamide (387 mg, 3.3 mmol) in N,N-dimethylacetamide (6.6 mL)) in a previously nitrogen-filled sealed vessel. Flush the reactants with nitrogen before sealing and heat for 6 h at 130° C. Cool to room temperature, dilute with ethyl acetate and wash with 2 N ammonium hydroxide. Wash the organic layer with saturated aqueous sodium chloride, dry (magnesium sulfate), concentrate and purify (silica gel chromatography, eluting with 0:100 to 05:95 ethyl acetate:hexanes) to give the title compound.

(S)-2-sec-Butylamino-6-cyano-isonicotinic acid

Dissolve (S)-2-sec-butylamino-6-cyano-isonicotinic acid methyl ester (250 mg, 0.93 mmol) in methanol (3 mL). Slowly add 2 N NaOH (1.5 mL) and stir overnight at room temperature. Acidify to about pH=6 with 5 N HCl and concentrate. Dilute with ethyl acetate (20 mL) and wash the organic layer with saturated aqueous sodium chloride, dry (magnesium sulfate) and concentrate to give the title compound.
MS (ES): m/z=220 [M+H].

Preparation 40

(S)-2-sec-Butylamino-6-methanesulfonyl-isonicotinic acid

(S)-2-sec-Butylamino-6-methylsulfanyl-isonicotinic acid methyl ester

Add toluene (20 mL), (S)-2-sec-butylamino-6-chloro-isonicotinic acid methyl ester (2.01 g, 8.29 mmol), palladium acetate (186 mg, 0.83 mmol), racemic 2,2'-bis(diphenylphosphino)-1,1'-binaphthyl (516 mg, 0.83 mmol), cesium carbonate (5.40 g, 16.6 mmol), and sodium thiomethoxide (1.16 g, 16.6 mmol) to a sealed vessel flushed with nitrogen. Heat the sealed vessel at 90° C. overnight. Cool to room temperature and filter the solution through a filtering agent and concentrate the filtrate. Purify the residue (silica gel chromatography, eluting with ethyl acetate:hexanes 90:10) to give the title compound (1.4 g, 66%).
MS (ES): m/z=255 [M+H].

(S)-2-sec-Butylamino-6-methanesulfonyl-isonicotinic acid methyl ester

Chill a solution of (S)-2-sec-butylamino-6-methylsulfanyl-isonicotinic acid methyl ester (1.22 g, 4.80 mmol) in dichloromethane (20 mL) in an ice bath and add 3-chloroperbenzoic acid (2.74 g, 15.9 mmol). Stir at room temperature for 3 h and partition the solution between dichloromethane and saturated sodium bicarbonate. Extract the aqueous layer with dichloromethane (2×30 mL). Combine the organic extract, wash with water, saturated aqueous sodium chloride, dry (magnesium sulfate), concentrate and purify (silica gel, eluting with ethyl acetate:hexanes 25:75) to give the title compound (1.02 g, 74%).
MS (ES): m/z=287 [M+H].

(S)-2-sec-Butylamino-6-methanesulfonyl-isonicotinic acid

Chill a solution of (S)-2-sec-butylamino-6-methanesulfonyl-isonicotinic acid methyl ester (1.02 g, 3.57 mmol) in THF (10 mL) in an ice bath. Add 1 N lithium hydroxide (5.4 mL, 5.4 mmol) and stir the solution at room temperature for 3 h. Add 1 N HCl until about pH=2. Concentrate and partition the residue between ethyl acetate and water. Separate the layers and extract the aqueous layer with ethyl acetate (2×30 mL). Wash the combined extract with saturated aqueous sodium chloride, dry (magnesium sulfate) and concentrate to give the title compound.
MS (ES): m/z=273 [M+H].

Preparation 41

(S)-2-sec-Butylamino-6-propanesulfonyl-isonicotinic acid

2-Chloro-6-propylsulfanyl-isonicotinic acid methyl ester

Add 2,6-dichloroisonicotinic acid methyl ester (4.12 g, 20.0 mmol), toluene (40 mL), palladium acetate (448 mg, 2.0 mmol), racemic 2,2'-bis(diphenylphosphino)-1,1'-binaphthyl (1.25 g, 2.0 mmol) and cesium carbonate (7.82 g, 24.0 mmol) into a sealed vessel flushed with nitrogen. Slowly add propanethiol (2.2 mL, 24 mmol). Heat and stir the reaction mixture at 80° C. for 18 h. Cool to room temperature, dilute with diethyl ether and filter through a filtering agent. Concentrate the filtrate and purify (silica gel chromatography, 2:98 to 5:95 ethyl acetate:hexane) to give the title compound (55%).

2-Chloro-6-propanesulfonyl-isonicotinic acid methyl ester

Add a suspension of potassium peroxymonosulfate (35.6 g, 57.7 mmol) in water (80 mL) to a cooled solution of 2-chloro-6-propylsulfanyl-isonicotinic acid methyl ester (4.71 g, 19.2 mmol) in methanol (40 mL) and THF (40 mL). Stir the mixture at room temperature for 3 days. Dilute the mixture with water and extract with dichloromethane (3×100 mL). Wash the combined extracts with water, dry (magnesium sulfate), concentrate and purify (silica gel chromatography, eluting with 20:80 ethyl acetate:hexanes) to give the title product (2.75 g, 52%).

(S)-2-sec-Butylamino-6-propanesulfonyl-isonicotinic acid methyl ester

Add 2-chloro-6-propanesulfonyl-isonicotinic acid methyl ester (2.70 g, 9.71 mmol), toluene (40 mL), palladium acetate (218 mg, 0.97 mmol), racemic 2,2'-bis(diphenylphosphino)-1,1'-binaphthyl (605 mg, 0.97 mmol), cesium carbonate (4.75 g, 14.6 mmol), and (S)-sec-butylamine (1.46 mL, 14.6 mmol) to a sealed vessel flushed with nitrogen. Heat and stir the sealed vessel at 90° C. overnight. Cool to room temperature, filter through a pad of filtering agent, concentrate and purify (silica gel chromatography, eluting with 20:80 to 30:70 ethyl acetate:hexanes) to give the title compound (2.47 g, 81%).
MS (ES): m/z=315 [M+H].

(S)-2-sec-Butylamino-6-propanesulfonyl-isonicotinic acid

Add 2 N NaOH (6.0 mL, 12.0 mmol) to a solution of (S)-2-sec-butylamino-6-propanesulfonyl-isonicotinic acid methyl ester (2.47 g, 7.87 mmol) in methanol (10 mL) at 0° C. Stir the mixture at room temperature for 3 h, acidify the solution to about pH=2 and concentrate to one half of the solvent. Partition the residue between ethyl acetate and water. Extract the aqueous layer with ethyl acetate (2×50 mL). Wash the combined extracts with saturated aqueous sodium chloride, dry (magnesium sulfate) and concentrate to give the title compound (90%).
MS (ES): m/z=301 [M+H].

Preparation 42

(S)-2-sec-Butylamino-6-isopropanesulfonyl-isonicotinic acid

2-Chloro-6-isopropylsulfonyl-isonicotinic acid methyl ester

Add sodium isopropylthiolate (0.89 g, 10.0 mmol, (prepared from treatment of isopropanethiol with 0.95 equivalent of sodium hydride) slowly to a solution of methyl 2,6-dichloroisonicotinate (2.06 g, 10.0 mmol) in DMF (10 mL) at 0° C. Stir the mixture at room temperature overnight. Partition the mixture between diethyl ether (30 mL) and water (30 mL) and extract the aqueous layer with diethyl ether (2×30 mL). Wash the combined extracts with 5% aqueous lithium hydroxide solution, dry (magnesium sulfate) and concentrate. The crude material is used directly in the next step reaction without further purification.

2-Chloro-6-isopropanesulfonyl-isonicotinic acid methyl ester

Add 3-chloroperbenzoic acid (5.32 g, 30.8 mmol) to a solution of 2-chloro-6-isopropylsulfanyl-isonicotinic acid methyl ester (2.37 g, 9.63 mmol) in dichloromethane (50 mL) at 0° C. Stir the mixture at room temperature for 4 h and partition the mixture between dichloromethane and aqueous saturated sodium bicarbonate. Extract the aqueous layer with dichloromethane (2×50 mL) and wash the combined organic extracts with water, saturated aqueous sodium chloride, dry (magnesium sulfate), concentrate and purify (silica gel chromatography, eluting with 25:75 ethyl acetate:hexanes) to give the title compound (1.26 g, 47%).

(S)-2-sec-Butylamino-6-isopropanesulfonyl-isonicotinic acid methyl ester

Add 2-chloro-6-isopropanesulfonyl-isonicotinic acid methyl ester (1.26 g, 4.53 mmol), toluene (20 mL), palladium acetate (102 mg, 0.453 mmol), racemic 2,2'-bis(diphenylphosphino)-1,1'-binaphthyl (282 mg, 0.453 mmol) and cesium carbonate (2.21 g, 6.80 mmol) to a sealed vessel flushed with nitrogen. Slowly add (S)-sec-butylamine (0.68 mL, 6.80 mmol) to the mixture. Heat and stir the sealed vessel at 90° C. overnight. Cool to room temperature, concentrate and purify (silica gel chromatography, eluting with 20:80 to 70:30 ethyl acetate:hexanes) to give the title compound.

(S)-2-sec-Butylamino-6-isopropanesulfonyl-isonicotinic acid

Add 2 N NaOH (7.0 mL, 14.0 mmol) to a solution of 2-sec-butylamino-6-isopropanesulfonyl-isonicotinic acid methyl ester (1.46 g, 4.65 mmol) in methanol (10 mL) at 0° C. Stir the mixture at room temperature for 3 h and acidify the solution to about pH=2 and concentrate the solvent to one half volume. Partition the residue between ethyl acetate and water, and extract the aqueous layer with ethyl acetate (2×50 mL). Wash the combined organic extracts with saturated aqueous sodium chloride, dry (magnesium sulfate) and concentrate to give the title compound in 90% yield.

MS (ES): m/z=301 [M+H].

The compounds of Preparation 43-44 may be prepared essentially as described in Preparation 42.

| Prep | Compound | MS (ES) [M + H] |
|---|---|---|
| 43* | (S)-2-sec-Butylamino-6-cyclopropanesulfonyl-isonicotinic acid | 299 |
| 44** | (S)-2-sec-Butylamino-6-cyclopentanesulfonyl-isonicotinic acid | 327 |

*Sodium cyclopropylthiolate Add solid sulfur (0.47 g, 15.0 mmol) to a solution of cyclopropylmagnesium bromide (0.8M, 20.0 mL, 16.0 mmol) in THF (20 mL) at 0° C. according to the reference J. Am. Chem. Soc., 114(9), 3499, (1992). Heat at 50° C. for 3 h and cool to 0° C. Add lithium aluminum hydride (0.49 g, 13.0 mmol) slowly and reflux for 30 min. Cool the reaction mixture in an ice bath and quench with water (1 mL), 5% aqueous sulfuric acid (5 mL), and then dilute with diethyl ether (10 mL). Separate the layers and extract the aqueous layer with diethyl ether (2 × 20 mL). Wash the combined extract with 5% aqueous sulfuric acid, aqueous saturated sodium bicarbonate, aqueous saturated ammonium chloride, saturated aqueous sodium chloride, dry (magnesium sulfate), and concentrate the filtrate to one half volume. Add sodium hydride (0.44 g, 11.0 mmol, 60% dispersion in mineral oil) to the solution with cooling and stir at room temperature overnight. Concentrate and dry the residue in vacuum to give the title product
**Sodium cyclopentylthiolate is prepared from cyclopentyl mercaptan by reaction with 0.95 equivalent of sodium hydride in THF.

Preparation 45

2-(Propane-2-sulfonyl)-6-prop-2-ynylamino-isonicotinic acid

2-Chloro-6-isopropanesulfonyl-isonicotinic acid methyl ester

Add 3-chloroperbenzoic acid (5.32 g, 30.8 mmol) to a solution of 2-chloro-6-isopropylsulfonyl-isonicotinic acid methyl ester (2.37 g, 9.63 mmol) in dichloromethane (50 mL) at 0° C. Stir the mixture at room temperature for 4 h. Partition the mixture between dichloromethane and aqueous saturated sodium bicarbonate. Extract the aqueous layer with dichloromethane (2×50 mL) and wash the combined extracts with water, saturated aqueous sodium chloride, dry (magnesium sulfate), concentrate and purify (silica gel chromatography, eluting with 25:75 ethyl acetate:hexanes) to give the title product as a white solid (1.26 g, 47%).

2-(Propane-2-sulfonyl)-6-prop-2-ynylamino-isonicotinic acid methyl ester

Add THF (10 mL), 2-chloro-6-iso-propanesulfonyl-isonicotinic acid methyl ester (0.50 g, 1.80 mmol), N,N-diisopropylethylamine (0.470 mL, 2.70 mmol), and propargylamine (0.740 mL, 10.8 mmol) to a sealed vessel flushed with nitrogen. Heat and stir the reaction at 80° C. overnight. Cool to room temperature, concentrate and purify (silica gel chromatography, eluting with 20:80 to 30:70 ethyl acetate:hexanes) to give the title product (0.102 g, 19%).

MS (ES): m/z=297 [M+H].

2-(Propane-2-sulfonyl-6-prop-2-2-ynylamino-isonicotinic acid

Add 1 N lithium hydroxide (0.52 mL, 0.52 mmol) to a solution of 2-(propane-2-sulfonyl)-6-prop-2-ynylamino-isonicotinic acid methyl ester (0.102 g, 0.344 mmol) in THF (2 mL) at 0° C. Stir the mixture at room temperature for 3 h and acidify the solution to about pH=2 and concentrate the solvent to one half volume. Partition the residue between ethyl acetate and water, and extract the aqueous layer with ethyl acetate (2×10 mL). Wash the combined organic extract with saturated aqueous sodium chloride, dry (magnesium sulfate) and concentrate to give the title compound (85%).

MS (ES): m/z=283 [M+H].

The compounds of Preparation 46-48 may be prepared essentially as described in Preparation 45.

| Prep | Compound | MS (ES) [M + H] |
|---|---|---|
| 46 | 2-Cyclopropylamino-6-isopropanelsulfonyl-isonicotinic acid | 283 |
| 47 | 2-Cyclopropyl-methylamino-6-isopropanelsulfony-isonicotinic acid | 299 |
| 48 | 2-Cyclobutylamino-6-isopropanelsulfonyl-isonicotinic acid | 299 |

Preparation 49

2-Cyclopropylamino-6-cyclopropanesulfonyl-isonicotinic acid tert-Butyl-2,6-dichloroisonicotinate Add 2,6-dichloro-isonicotinic acid (2.00 g, 10.4 mmol) in dichloromethane (25 mL) and THF (5 mL) to a flask equipped with a gas condenser. Cool to 0° C. and slowly add concentrated sulfuric acid. Condense isobutylene gas via a condenser filled with dry ice in acetone until total volume of the solution increases by about 20 mL. Stir the mixture at room temperature overnight and pour into a cold solution of sodium carbonate. Separate the layers and extract the aqueous layer with dichloromethane (2×50 mL). Wash the combined organic extract with water, dry (magnesium sulfate) and concentrate to give the title compound (1.02 g, 40%).

2-Chloro-6-cyclopropylsulfonyl-isonicotinic acid tert-butyl ester

Add sodium cyclopropylthiolate (0.554 g, 5.76 mmol (prepared from treatment of isopropanethiol with 0.95 equivalent of sodium hydride) slowly to a solution of tert-butyl 2,6-dichloroisonicotinate (1.30 g, 5.24 mmol) in DMF (5 mL) at 0° C. Stir at room temperature and partition the mixture between diethyl ether (20 mL) and water (20 mL) and extract the aqueous layer with diethyl ether (2×20 mL). Wash the combined extract with 5% aqueous lithium hydroxide solution, dry (magnesium sulfate) and concentrate to give the title compound as a crude residue which is used directly in the next reaction without further purification.

2-Chloro-6-cyclopropanesulfonyl-isonicotinic acid tert-butyl ester

Add 3-chloroperbenzoic acid (1.66 g, 9.6 mmol) to a solution of 2-chloro-6-cyclopropylsulfonyl-isonicotinic acid tert-butyl ester (0.785 g, 2.74 mmol) in dichloromethane (20 mL) at 0° C. Stir at room temperature overnight and partition the mixture between dichloromethane and saturated aqueous sodium bicarbonate and extract the aqueous layer with dichloromethane (2×20 mL). Wash the combined extract with water, saturated aqueous sodium chloride, dry (magnesium sulfate) and purify (silica gel chromatography, eluting with 15:85 ethyl acetate:hexanes) to give the title compound (0.193 g, 22%).

2-Cyclopropylamino-6-cyclopropanesulfonyl-isonicotinic acid tert-butyl ester Add 2-chloro-6-cyclopropanesulfonyl-isonicotinic acid tert-butyl ester (0.190 g, 0.607 mmol), palladium acetate (0.020 g, 0.091 mmol), racemic 2,2'-bis(diphenylphosphino)-1,1'-binaphthyl (0.057 g, 0.091 mmol), cesium carbonate (0.297 g, 0.911 mmol), and (S)-sec-butylamine (0.063 mL, 0.911 mmol) in toluene (5 mL) to a sealed tube flushed with nitrogen. Heat and stir the reaction mixture at 90° C. for 18 h. Cool and filter the mixture through a pad of filtering agent, concentrate and purify (silica gel chromatography, eluting with 20:80 ethyl acetate:hexanes) to give the title compound (0.120 g, 59%).

MS (ES): m/z=339 [M+H].

2-Cyclopropylamino-6-cyclopropanesulfonyl-isonicotinic acid

Add trifluoroacetic acid (2 mL) to a solution of 2-cyclopropylamino-6-cyclopropanesulfonyl-isonicotinic acid tert-butyl ester (0.120 g, 0.355 mmol) in dichloromethane (2 mL) at 0° C. Stir the solution at room temperature for 3 h, concentrate and dry the title compound (0.076 g, 54%).

MS (ES): m/z=283 [M+H].

Preparation 50

(S)-2-sec-Butylamino-6-(methanesulfonyl-methylamino)-isonicotinic acid

(S)-2-sec-Butylamino-6-methane-sulfonylamino-isonicotinic acid methyl ester

Add 2-sec-butylamino-6-chloro-isonicotinic acid methyl ester (500 mg, 2.07 mmol), toluene (10 mL), tris(dibenzylideneacetone)dipalladium(0) (95 mg, 0.104 mmol), 2-(di-tert-butylphosphino)biphenyl (62 mg, 0.207 mmol), and methanesulfonamide sodium salt (363 mg, 3.11 mmol) to a sealed flask flushed with nitrogen. (Prepare methanesulfonamide sodium salt by adding sodium hydride (2.0 g, 50.0 mmol, 60% dispersion in mineral oil) slowly to a solution of methanesulfonamide (5.0 g, 52.6 mmol) and THF (80 mL) at 0° C.) Stir the mixture at room temperature overnight. Concentrate and dry the residue under vacuum. Heat and stir the sealed flask at 100° C. for 18 h. Cool to room temperature, filter through a pad of filtering agent, wash with dichloromethane, concentrate the filtrate and purify (silica gel chromatography, eluting with 20:80 to 25:75 ethyl acetate:hexanes) to give the title compound (475 mg, 76%).

MS (ES): m/z=302 [M+H].

(S)-2-sec-Butylamino-6-(methanesulfonyl-methylamino)-isonicotinic acid methyl ester Add sodium hydride (47 mg, 1.18 mmol, 60% dispersion in mineral oil) to a solution of (S)-2-sec-butylamino-6-methanesulfonylamino-isonicotinic acid methyl ester (356 mg, 1.18 mmol) in DMF (5 mL) at 0° C. Stir for 10 min, add iodomethane (0.11 mL, 1.77 mmol) dropwise. Stir the mixture at room temperature for 2 h, cool and quench the reaction with an ammonium chloride solution. Extract the mixture with ethyl acetate (3×30 mL) and wash the combined extract with water, saturated aqueous sodium chloride, dry (magnesium sulfate), concentrate and purify (silica gel chromatography, eluting with 20:80 ethyl acetate:hexanes) to give the title compound (320 mg, 86%).

MS (ES): m/z=316 [M+H].

(S)-2-sec-Butylamino-6-(methanesulfonyl-methylamino)-isonicotinic acid

Add 1 N lithium hydroxide (19.5 mL, 19.5 mmol) to a solution of (S)-2-sec-butylamino-6-(methanesulfonyl-methylamino)-isonicotinic acid methyl ester (2.45 g, 7.77 mmol) in THF (10 mL) at 0° C. After 2 h at room temperature, acidify the mixture to about pH=2 and concentrate. Extract the residue with ethyl acetate (3×40 mL), wash the combined extracts with saturated aqueous sodium chloride, dry (magnesium sulfate) and concentrate to give the title compound as a yellow solid (2.23 g, 95%).

MS (ES): m/z=302 [M+H].

The compound of Preparation 51 may be prepared essentially as described in Preparation 50.

| Prep | Compound | MS (ES) [M + H] |
|---|---|---|
| 51 | (S)-2-sec-Butylamino-6-methane-sulfonylamino-isonicotinic acid | 288 |

Preparation 52

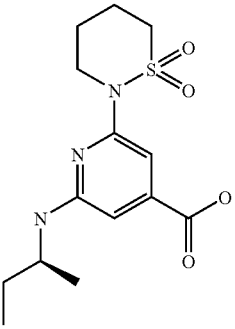

(S)-2-sec-Butylamino-6-(1,1-dioxo-1λ⁶-[1,2]thiazinan-2-yl)-isonicotinic acid

4-Chlorobutanesulfonyl chloride

Add anhydrous sodium sulfite (16.8 g, 130 mmol) to a solution of 4-chlorobutyl acetate (20.0 g, 133 mmol) in water (50 mL) and reflux the mixture for 20 h. Cool to room temperature and add concentrated HCl (19.0 mL) and reflux for 1 h. Cool the mixture to room temperature, neutralize to about pH=7. Concentrate to about one half the volume, filter away the sodium chloride. Concentrate and dry to give the title compound.

4-Chlorobutanesulfonamide

Chill a suspension of 4-chlorobutanesulfonyl chloride (5.0 g, 26.2 mmol) in dichloromethane (50 mL) and add phosphorous pentachloride (12.0 g, 55.0 mmol) portionwise. Stir the mixture at room temperature for 4 h and filter away the precipitate. Bubble ammonia gas into the filtrate at 0° C. for 1 h. Stir the mixture for 1 h, filter away the ammonium chloride, concentrate and purify (silica gel chromatography, eluting with 30:70 to 40:60 ethyl acetate:hexanes) to give the title compound (1.18 g, 26%).

[1,2]thiazinane 1,1-dioxide, sodium salt

Add sodium (0.157 g, 6.84 mmol) to 50 mL of degassed anhydrous ethanol. After dissolution of sodium, add 4-chlorobutanesulfonamide (1.18 g, 6.84 mmol) into the solution and reflux for 2 h. Cool and filter through a filtering agent, concentrate the filtrate and add ethyl acetate. Filter the mixture through a pad of silica gel and wash with ethyl acetate. Concentrate the filtrate and dry. Convert [1,2]thiazinane 1,1-dioxide to the title compound by treatment with 0.95 equivalent of sodium hydride in THF, concentrate and dry.

2-sec-Butylamino-6-(1,1-dioxo-1$\lambda^6$-[1,2]thiazinan-2-yl)-isonicotinic acid methyl ester Add 2-sec-butylamino-6-chloro-isonicotinic acid methyl ester (1.0 g, 4.13 mmol), tris(dibenzylideneacetone)dipalladium(0) (0.189 g, 0.207 mmol), 2-(di-tert-butylphosphino) biphenyl (0.123 g, 0.413 mmol) and the sodium salt of [1,2]thiazinane 1,1-dioxide (0.844 g, 5.37 mmol) in toluene (10 mL) to a sealed flask flushed with nitrogen. Heat and stir the sealed flask at 100° C. for 18 h. Cool to room temperature and filter through a bed of filtering agent, and wash with dichloromethane. Concentrate the filtrate and purify (silica gel chromatography, eluting with 20:80 to 30:70 ethyl acetate:hexanes) to give the title compound (0.533 g, 38%).

MS (ES): m/z=342 [M+H].

2-sec-Butylamino-6-(1,1-dioxo-1$\lambda^6$-[1,2]thiazinan-2-yl)-isonicotinic acid Add 1 N lithium hydroxide (4.0 mL, 3.88 mmol) to a solution of 2-sec-butyl-amino-6-(1,1-dioxo-1$\lambda^6$-[1,2]thiazinan-2-yl)-isonicotinic acid methyl ester (0.590 g, 1.80 mmol) in THF (5 mL) at 0° C. Stir for 2 h at room temperature and acidify the mixture to about pH=2 and concentrate. Extract the residue with ethyl acetate (3×40 mL) and wash the combined extract with saturated aqueous sodium chloride, dry (magnesium sulfate) and concentrate to give the title compound (0.377 g, 74%).

MS (ES): m/z=328 [M+H].

The compound of Preparation 53 may be prepared essentially as described in Preparation 52.

| Prep | Compound | MS (ES) [M + H] |
|---|---|---|
| 53 | (S)-2-sec-Butylamino-6-(1,1-dioxo-1$\lambda^6$-isothiazolidin-2-yl)-isonicotinic acid | 314 |

Preparation 54

(S)-2-sec-Butylamino-6-dimethylsulfamoyl-isonicotinic acid

2-Benzylsulfanyl-6-chloro-isonicotinic acid methyl ester

Add sodium hydride (0.80 g, 20.0 mmol, 60% dispersion in mineral oil) slowly to a solution of methyl 2,6-dichloroisonicotinate (4.12 g, 20.0 mmol) in DMF at 0° C. Stir the mixture at room temperature overnight and partition between diethyl ether (50 mL) and water (50 mL). Extract the aqueous layer with diethyl ether (2×30 mL) and wash the combined extract with 5% aqueous lithium hydroxide. Dry (magnesium sulfate), concentrate and purify (silica gel chromatography, eluting with 3:97 ethyl acetate:hexanes) to give the title compound (5.03 g, 86%).

2-Chloro-6-dimethylsulfamoyl-isonicotinic acid methyl ester

Bubble chlorine gas for 30 min into a solution of 2-benzylsulfanyl-6-chloro-isonicotinic acid methyl ester (2.50 g, 8.50 mmol) in water (5 mL) and glacial acetic acid (30 mL) at 0° C. Concentrate and suspend the residue in THF and add dimethylamine in methanol (2.0 M in methanol, 10.6 mL, 21.2 mmol) with cooling. After stirring at room temperature overnight, filter through a filtering agent and partition the filtrate between ethyl acetate (50 mL) and water (50 mL). Extract aqueous layer with ethyl acetate (2×50 mL) and wash the combined extract with water, saturated aqueous sodium chloride, dry (magnesium sulfate) and filter the filtrate through a pad of silica gel and concentrate to give the title product that is used directly in the next reaction without further purification.

(S)-2-sec-Butylamino-6-dimethylsulfamoyl-isonicotinic acid methyl ester

Add toluene (20 mL), 2-chloro-6-dimethylsulfamoyl-isonicotinic acid methyl ester (2.49 g, 8.93 mmol), palladium acetate (0.201 g, 0.893 mmol), racemic 2,2'-bis(diphenylphosphino)-1,1'-binaphthyl (0.556 g, 0.893 mmol) and cesium carbonate (4.36 g, 13.4 mmol) to a sealed vessel flushed with nitrogen. Slowly add (S)-sec-butylamine (1.36 mL, 13.4 mmol) to the mixture. Heat and stir the sealed vessel at 90° C. overnight. Cool to room temperature, filter through a pad of filtering agent, concentrate and purify (silica gel chromatography, eluting with 20:80 to 30:70 ethyl acetate:hexanes) to give the title compound (1.43 g, 51%).

MS (ES): m/z=326 [M+H].

(S)-2-sec-Butylamino-6-dimethylsulfamoyl-isonicotinic acid

Add 1 N lithium hydroxide (11.4 mL, 11.4 mmol) to a solution of (S)-2-sec-butylamino-6-dimethylsulfamoylisonicotinic acid methyl ester (1.43 g, 4.54 mmol) and THF (10 mL) at 0° C. Stir the mixture overnight, acidify the solution to about pH=2 and concentrate solvent to one half volume. Partition the residue between ethyl acetate and water, and extract the aqueous layer with ethyl acetate (2×30 mL). Wash the combined organic extract with saturated aqueous sodium chloride, dry (magnesium sulfate) and concentrate to give the title compound.

MS (ES): m/z=302 [M+H].

The compounds of Preparation 55-56 may be prepared essentially as described in Preparation 54.

| Prep | Compound | MS (ES) [M + H] |
|---|---|---|
| 55 | (S)-2-sec-Butylamino-6-methylsulfamoyl-isonicotinic acid | 288 |
| 56 | (S)-2-sec-Butylamino-6-(pyrrolidine-1-sulfonyl)-isonicotinic acid | 328 |

Preparation 57

6-Cyclobutylaminopyridine-2,4-dicarboxylic acid 2-ethyl ester

2-Chloro-6-(1-ethoxyvinyl)-isonicotinic acid methyl ester

Add 2,6-dichloro-isonicotinic acid methyl ester, tetrakis(triphenylphosphine)palladium(0) (0.763 g, 0.66 mmol), triphenylphosphine (0.346 g, 1.32 mmol), tributyl(1-ethoxyvinyl)tin (5.0 g, 13.9 mmol) and toluene (30 mL), to a sealed flask flushed with nitrogen. Heat at 100° C. overnight and cool to room temperature. Filter the mixture through a filtering agent, concentrate and purify (silica gel chromatography eluting with 25:75 ethyl acetate:hexanes) to give the title compound (84%).

6-Chloropyridine-2,4-dicarboxylic acid 2-ethyl ester 4-methyl ester

Chill a solution of 2-chloro-6-(1-ethoxyvinyl)-isonicotinic acid methyl ester (2.47 g, 10.2 mmol) in dichloromethane (20 mL) at −78° C. and bubble ozone into it for 15 min until light blue in color. Quench with dimethylsulfide and stir at room temperature for 3 h. Concentrate and purify (silica gel chromatography, eluting with 15:85 ethyl acetate:hexanes) to give the title compound (1.44 g, 58%).

MS (ES): m/z=244 [M+H].

6-Cyclobutylaminopyridine-2,4-dicarboxylic acid 2-ethyl ester 4-methyl ester

Add 6-chloropyridine-2,4-dicarboxylic acid 2-ethyl ester 4-methyl ester (0.500 g, 2.05 mmol), palladium acetate (0.0461 g, 0.205 mmol), racemic 2,2'-bis(diphenylphosphino)-1,1'-binaphthyl (0.128 g, 0.205 mmol), cesium carbonate (0.801 g, 2.46 mmol) and toluene (5 mL), to a sealed vessel flushed with nitrogen. Slowly add cyclobutylamine (0.210 mL, 2.46 mmol) and heat and stir the sealed vessel at 90° C. overnight. Cool to room temperature, filter through a pad of filtering agent, concentrate and purify (silica gel chromatography, eluting with 10:90 to 20:80 ethyl acetate:hexanes) to give the title compound (0.223 g, 39%).

MS (ES): m/z=279 [M+H].

6-Cyclobutylaminopyridine-2,4-dicarboxylic acid 2-ethyl ester

Add 1 N lithium hydroxide (0.80 mL, 0.802 mmol) to a solution of 6-cyclobutylaminopyridine-2,4-dicarboxylic acid 2-ethyl ester 4-methyl ester (0.223 g, 0.802 mmol) in THF (2 mL) at 0° C. Stir for 1 h, acidify the solution to about pH=2, concentrate the solvent to one half volume. Partition the residue between ethyl acetate and water, and extract the aqueous layer with ethyl acetate (2×15 mL). Wash the combined organic extracts with saturated aqueous sodium chloride, dry (magnesium sulfate) and concentrate to give the title compound.

MS (ES): m/z=279 [M+H].

Preparation 58

2-sec-Butylamino-6-(propane-1-sulfinyl)-isonicotinic acid 2-sec-Butylamino-6-propylsulfanyl-isonicotinic acid methyl ester Add 2-chloro-6-propylsulfanyl-isonicotinic acid methyl ester (1.35 g, 5.49 mmol) palladium acetate (0.123 g, 0.549 mmol, 0.1 eq.), racemic 2,2'-bis(diphenylphosphino)-1,1'-binaphthyl (0.342 g, 0.549 mmol, 0.1 eq.), cesium carbonate (2.68 g, 8.24 mmol, 1.5 eq.) and toluene (20 mL) into a sealed vessel flushed with nitrogen. Slowly add (S)-sec-butylamine (0.824 mL, 8.24 mmol) and heat and stir the reaction mixture at 90° C. for 18 h. Cool the reaction mixture to room temperature, dilute with ether and filter through a filtering agent. Concentrate the filtrate and purify (silica gel chromatography, eluting with the 5:95 to 10:90 ethyl acetate:hexanes) to give the title compound (55%).

MS (ES): m/z=284 [M+H].

(S)-2-sec-Butylamino-6-(propane-1-sulfinyl)-isonicotinic acid methyl ester

Add sodium perborate monohydrate (0.133 g, 1.33 mmol) to a cooled solution of (S)-2-sec-butylamino-6-propylsulfanyl-isonicotinic acid methyl ester (0.396 g, 1.40 mmol) in acetic acid (4 mL). Stir at room temperature overnight and concentrate. Dissolve the residue in ethyl acetate and wash the solution with aqueous sodium bicarbonate, saturated aqueous sodium chloride, dry (magnesium sulfate), concentrate and purify (silica gel chromatography, eluting with 30:70 ethyl acetate:hexanes) to give the title compound (0.230 g, 55%).

(S)-2-sec-Butylamino-6-(propane-1-sulfinyl)-isonicotinic acid

Add 1 N lithium hydroxide (1.15 mL, 1.15 mmol) to a solution of (S)-2-sec-butylamino-6-(propane-1-sulfinyl)-isonicotinic acid methyl ester (0.229 g, 0.767 mmol) in THF (2 mL) at 0° C. Stir at room temperature for 3 h, acidify the solution to about pH=2 and concentrate to one half of the solvent. Partition the residue between ethyl acetate and water. Extract the aqueous layer with ethyl acetate (2×10 mL). Wash the combine organic extract with saturated aqueous sodium chloride, dry (magnesium sulfate) and concentrate to give the title compound (95%).

MS (ES): m/z=283 [M−H].

The compound of Preparation 59 may be prepared essentially as described in Preparation 58 using sodium thiomethoxide with 3-chloroperbenzoic acid as the oxidant.

| Prep | Compound | MS (ES) [M + H] |
|---|---|---|
| 59 | (S)-2-sec-Butylamino-6-(methane-1-sulfinyl)-isonicotinic acid | 257 |

Preparation 60

(S)-2-sec-Butylamino-6-(2-fluorophenyl)-isonicotinic acid (S)-2-sec-Butylamino-6-(2-fluorophenyl)-isonicotinic acid methyl ester Add (S)-2-sec-butylamino-6-chloroisonicotinic acid methyl ester (1.40 g, 5.75 mmol), 2-fluorophenylboronic acid (1.0 g, 7.15 mmol), tetrakis(triphenylphosphine)palladium (0) (0.664 g, 0.575 mmol), potassium carbonate (2.38 g, 17.3 mmol) and 1,4-dioxane (25 mL) to a sealed flask flushed with nitrogen. Heat and stir the mixture overnight and cool to room temperature. Filter the mixture through a filtering agent, concentrate and purify (silica gel chromatography, eluting with 4:96 ethyl acetate:hexanes) to give the title compound (1.31 g, 75%).

MS (ES): m/z=303 [M+H].

(S)-2-sec-Butylamino-6-(2-fluorophenyl)-isonicotinic acid

Chill a solution of (S)-2-sec-butylamino-6-(2-fluorophenyl)-isonicotinic acid methyl ester (1.31 g, 4.32 mmol) in methanol (5 mL) and THF (5 mL). Add 2 N NaOH (6.50 mL, 13.0 mmol) stir at room temperature for 3 h, and acidify the solution to about pH=2 and concentrate to one half of the solvent. Partition the residue between ethyl acetate and water. Extract the aqueous layer with ethyl acetate (2×30 mL). Wash the combined organic extracts with saturated aqueous sodium chloride, dry (magnesium sulfate) and concentrate to give the title compound (80%).

MS (ES): m/z=289 [M+H].

Preparation 61

2-Cyclopropylamino-6-(methanesulfonyl-methylamino)-isonicotinic acid

2-Chloro-6-methane-sulfonylamino-isonicotinic acid methyl ester

Add methyl 2,6-dichloro-isonicotinate (2.06 g, 10.0 mmol), toluene (10 mL), tris(dibenzylideneacetone)dipalladium(0) (0.458 g, 0.50 mmol), 2-(di-tert-butylphosphino)biphenyl (0.298 g, 1.00 mmol), and methanesulfonamide sodium salt (1.17 g, 10.0 mmol) to a sealed flask flushed with nitrogen. Heat and stir the sealed flask at 100° C. for 18 h. Cool the mixture to room temperature and filter through a pad of filtering agent, and wash the solid with dichloromethane. Concentrate and purify (silica gel chromatography, eluting with 20:80 to 30:70 ethyl acetate:hexanes) to give the title compound (1.31 g, 50%).

2-Chloro-6-(methanesulfonyl-methylamino)-isonicotinic acid methyl ester

Add sodium hydride (257 mg, 6.43 mmol, 60% dispersion in mineral oil) at 0° C. to a solution of 2-chloro-6-methanesulfonylamino-isonicotinic acid methyl ester (1.31 g, 4.95 mmol) in DMF (10 mL). After stirring at 0° C. for 15 min, add iodomethane (0.4 mL, 6.43 mmol). Stir the reaction at 0° C. for 1 h and at room temperature for 2 h. Quench the reaction with ice and extract the reaction mixture with ethyl acetate. Wash the organic layer with saturated aqueous sodium chloride, dry (sodium sulfate), concentrate and purify (silica gel chromatography, eluting with 30:70 ethyl acetate:hexanes) to give the title compound (1.0 g, 72%).

2-Cyclopropylamino-6-(methanesulfonyl-methylamino)-isonicotinic acid methylester Add palladium acetate (29 mg, 0.13 mmol), racemic 2,2'-bis(diphenylphosphino)-1,1'-binaphthyl (81 mg, 0.13 mmol), cesium carbonate (531 mg, 1.63 mmol), toluene (10 mL), and 2-chloro-6-(methanesulfonyl-methylamino)-isonicotinic acid methyl ester (347 mg, 1.25 mmol) to a sealed tube. After degassing the reaction vessel with nitrogen, add cyclopropylamine (0.114 mL, 1.63 mmol) to the reaction mixture. Heat the reaction vessel at 90° C. overnight. Cool to room temperature and filter the solids through a filtering agent. Wash with ethyl acetate. Concentrate the combined filtrates and purify (silica gel chromatography, eluting with 30:70 ethyl acetate:hexanes) to give the title compound (261 mg 70%).

2-Cyclopropylamino-6-(methanesulfonyl-methylamino)-isonicotinic acid

Treat a solution of 2-cyclopropylamino-6-(methanesulfonyl-methylamino)-isonicotinic acid methyl ester (261 mg, 0.87 mmol) in methanol (8 mL) with 1 N NaOH (1.3 mL, 1.31 mmol) at room temperature. Stir for 5 h, acidify with 1 N HCl to about pH=3. Extract the reaction mixture with ethyl acetate, dry (sodium sulfate) and concentrate to give the title compound (226 mg, 91%).

MS (ES): m/z=286 [M+H].

Preparation 62

(S)-2-sec-Butylamino-6-(2H-tetrazol-5-yl)-isonicotinic acid (S)-2-sec-Butylamino-6-cyano-isonicotinic acid methyl ester Add 2-sec-butylamino-6-chloro-isonicotinic acid methyl ester (1.22 g, 5.0 mmol), tris(dibenzylideneacetone)dipalladium (183 mg, 0.2 mmol), 1,1'-bis(diphenylphosphino)ferrocene (222 mg, 0.4 mmol), zinc cyamide (587 mg, 5.0 mmol), and zinc dust (78 mg, 1.2 mmol) in N,N-dimethylacetamide (10 mL) and heat in a sealed tube at 120° C. overnight. Cool to room temperature, filter through a filtering agent, concentrate and purify (silica gel chromatography, eluting with 10:90 to 15:85 ethyl acetate:hexanes) to give the title compound (703 mg, 59%).

MS (ES): m/z=234 [M+H].

(S)-2-sec-Butylamino-6-(2H-tetrazol-5-yl)-isonicotinic acid methyl ester

Heat a suspension of (S)-2-sec-butylamino-6-cyano-isonicotinic acid methyl ester (932 mg, 4.0 mmol), sodium azide (780 mg, 12 mmol), and triethylamine hydrochloride (1.65 g, 12 mmol) in toluene (13 mL) at 90° C. for 2 days. Cool to room temperature and extract with water (3×30 mL), acidify the combined aqueous layers to about pH=2 using 1 N HCl, extract the desired product with ethyl acetate (4×50 mL), dry (sodium sulfate) and concentrate to give the title compound (720 mg, 65%).

MS (ES): m/z=277 [M+H].

(S)-2-sec-Butylamino-6-(2H-tetrazol-5-yl)-isonicotinic acid

Treat a solution of (S)-2-sec-butylamino-6-(2H-tetrazol-5-yl)-isonicotinic acid methyl ester (250 mg, 0.91 mmol) in methanol (4 mL) at room temperature with 2 N NaOH (1.36 mL, 2.72 mmol). Stir overnight, acidify with 1 N HCl to about pH=3, concentrate and lyophilize to give the title compound.

MS (ES): m/z=261 [M−H].

Preparation 63

(S)-2-sec-Butylamino-6-(2-ethyl-2H-tetrazol-5-yl)-isonicotinic acid

(S)-2-sec-Butylamino-6-(1-ethyl-1H-tetrazol-5-yl)-isonicotinic acid

(S)-2-sec-Butylamino-6-(2-ethyl-2H-tetrazol-5-yl)-isonicotinic acid methyl ester

(S)-2-sec-Butylamino-6-(1-ethyl-1H-tetrazol-5-yl)-isonicotinic acid methyl ester Treat a solution of (S)-2-sec-butylamino-6-(2H-tetrazol-5-yl)-isonicotinic acid methyl ester (720 mg, 2.61 mmol) in DMF (10 mL) with potassium carbonate (541 mg, 3.92 mmol) and iodoethane (0.364 mL, 3.92 mL) at room temperature. Dilute with ethyl acetate (100 mL), wash with water (twice), saturated aqueous sodium chloride, dry (sodium sulfate) and concentrate to give approximately a 1:1 mixture of the two title compounds which are used directly in the next step without further purification.

MS (ES): m/z=303 [M−H].

(S)-2-sec-Butylamino-6-(2-ethyl-2H-tetrazol-5-yl)-isonicotinic acid

(S)-2-sec-Butylamino-6-(1-ethyl-1H-tetrazol-5-yl)-isonicotinic acid

Dissolve the crude product mixture of (S)-2-sec-butylamino-6-(2-ethyl-2H-tetrazol-5-yl)-isonicotinic acid methyl ester and (S)-2-sec-butylamino-6-(1-ethyl-1H-tetrazol-5-yl)-isonicotinic acid methyl ester (approximately 2.61 mmol) in methanol (10 mL) and treat with 2 N NaOH (1.95 mL, 3.9 mmol) overnight. Acidify the reaction mixture to about pH=3 and extract with ethyl acetate (3×50 mL). Dry (sodium sulfate), and concentrate to give the title compounds as a crude mixture.

MS(ES): m/z=289[M−H].

Preparation 64

(S)-2-sec-Butylamino-6-(2-methyl-2H-tetrazol-5-yl)-isonicotinic acid

(S)-2-sec-Butylamino-6-(2-methyl-2H-tetrazol-5-yl)-isonicotinic acid methyl ester Treat a solution of (S)-2-sec-butylamino-6-(2H-tetrazol-5-yl)-isonicotinic acid methyl ester (350 mg, 1.26 mmol) in ethyl acetate (8 mL) with trimethyloxonium tetrafluoroborate at room temperature for 3 h. Dilute with ethyl acetate (50 mL) and wash with saturated sodium bicarbonate and saturated aqueous sodium chloride. Dry (sodium sulfate) and concentrate to give the title compound which is used directly in the next step without further purification.

MS (ES): m/z=291 [M+H].

(S)-2-sec-Butylamino-6-(2-methyl-2H-tetrazol-5-yl)-isonicotinic acid

Treat a solution of (S)-2-sec-butylamino-6-(2-methyl-2H-tetrazol-5-yl)-isonicotinic acid methyl ester (250 mg, 0.86 mmol) in methanol (5 mL) with 2 N NaOH (0.64 mL, 1.29 mmol). Stir at room temperature overnight, acidify the reaction to about pH=3 using 1 N HCl. Extract the reaction mixture with ethyl acetate (3×25 mL). Wash the combined organic layers with saturated aqueous sodium chloride, dry (sodium sulfate) and concentrate to give the title compound.

MS (ES): m/z=277 [M+H].

Preparation 65

(S)-2-sec-Butylamino-isonicotinic acid

(S)-2-sec-Butylamino-isonicotinic acid methyl ester

Degas with nitrogen a suspension containing 2-chloro-isonicotinic acid methyl ester (2.15 g, 12.5 mmol), palladium acetate (281 mg, 1.25 mmol), racemic 2,2'-bis(diphenylphosphino)-1,1'-binapthyl (780 mg, 1.25 mmol), cesium carbonate (4.95 g, 15 mmol), and (S)-sec-butylamine (1.5 mL, 15 mmol) in toluene (30 mL) and heat in a sealed tube at 90° C. overnight. Cool to room temperature and filter the solids through a filtering agent. Wash with ethyl acetate (30 mL), concentrate and purify (silica gel chromatography, eluting with 15:85 to 30:70 ethyl acetate:hexanes) to give the title compound.

(S)-2-sec-Butylamino-isonicotinic acid

Treat a solution of (S)-2-sec-butylamino-isonicotinic acid methyl ester (2.69 g, 12.5 mmol) in methanol (35 mL) with 1 N NaOH (15 mL, 15 mmol) at room temperature for 5 hr. Acidify to about pH=3 with 1 N HCl. Concentrate and redissolve the residue in a 1:1 $CH_3CN$:water solution and lyophilize to give the title compound.

MS (ES): m/z=193 [M−H].

Preparation 66

(S)-2-sec-Butylamino-6-difluoromethoxy-isonicotinic acid

2-Chloro-6-methoxy-isonicotinic acid ethyl ester

Treat an ethanol suspension of 2-chloro-6-methoxy-isonicotinic acid (3.75 g, 20 mmol) at 0° C. with thionyl chloride for 30 min. Heat at 70° C. overnight. Cool to room temperature, concentrate, dissolve the residue in ethyl acetate (200 mL), wash the organic layer with saturated aqueous sodium

(S)-2-sec-Butylamino-6-methoxy-isonicotinic acid ethyl ester

Add (S)-sec-butyl amine (1.18 mL, 11.8 mmol) to a suspension of 2-chloro-6-methoxy-isonicotinic acid ethyl ester (1.69 g, 7.86 mmol), palladium acetate (0.088 g, 0.4 mmol), racemic 2,2'-bis(diphenylphosphino)-1,1'-binaphthyl (0.250 g, 0.4 mmol), and cesium carbonate (3.8 g, 11.8 mmol) in toluene (20 mL) at room temperature and stir 15 h at 80° C. Cool to room temperature, filter through a filtering agent, concentrate and purify (silica gel chromatography, eluting with 5:95 ethyl acetate:hexanes to give the title compound (1.85 g, 93%).

MS (ES): m/z=253 [M+H].

(S)-2-sec-Butylamino-6-hydroxy-isonicotinic acid ethyl ester

Treat sodium iodide (5.58 g, 36.7 mmol) and (S)-2-sec-butylamino-6-methoxy-isonicotinic acid ethyl ester (1.85 g, 7.3 mmol) in acetonitrile (30 mL) with chlorotrimethylsilane (4.66 mL, 36.7 mmol) and stir at reflux for 38 h. Quench with methanol (10 mL), stir for 24 h, and concentrate. Dissolve residue in ethyl acetate, wash with water, saturated aqueous sodium chloride, dry (magnesium sulfate), concentrate and purify (silica gel chromatography, eluting with 70:30 to 100:0 ethyl acetate:hexanes) to give the title compound (0.98 g, 56%).

MS (ES): m/z=239 [M+H].

(S)-2-sec-Butylamino-6-difluoromethoxy-isonicotinic acid ethyl ester

Add cesium carbonate (0.352 g, 1.08 mmol) to (S)-2-sec-butylamino-6-hydroxy-isonicotinic acid ethyl ester (0.172 g, 0.72 mmol) in butan-2-one (10 mL) ((Bioorg. Med. Chem. Lett., 12, 2149-2152 (2002)). Heat at 70° C. for 30 min and add chlorodifluoroacetic acid methyl ester (0.24 mL, 2.16 mmol) in three equal portions over 3 h. Heat for 3 days at 70° C. Add again chlorodifluoroacetic acid methyl ester (0.24 mL, 2.16 mmol) in three equal portions over 3 h and stir at room temperature for 24 h. Concentrate and dissolve the crude mixture in ethyl acetate and filter. Purify (silica gel chromatography, eluting with 2:98 to 6:92 ethyl acetate:hexanes) to give the title compound (0.135 g, 65%). MS (ES): m/z=289 [M+H].

(S)-2-sec-Butylamino-6-difluoromethoxy-isonicotinic acid

Add 2 N NaOH (0.67 mL) to (S)-2-sec-butylamino-6-difluoromethoxy-isonicotinic acid ethyl ester in ethanol (5 mL). Stir 3 h and acidify to about pH=4 with 1 N HCl and extract with ethyl acetate. Wash organic layer with saturated aqueous sodium chloride, dry (magnesium sulfate) and concentrate to give the title compound (0.1 g, 85%).

MS (ES): m/z=261 [M+H].

Preparation 67

2-Methanesulfonyl-6-(methylpropylamino)-isonicotinic acid

2-Chloro-6-methanesulfonyl-isonicotinic acid methyl ester

Stir a mixture of 2,6-dichloro-isonicotinic acid methyl ester (20 g, 90.0 mmol) and sodium methyl thiolate (6.4 g, 90.9 mmol) in DMF (90 mL overnight at room temperature. Partition the reaction between of diethyl ether (50 mL) and water (100 mL). Extract the organics with diethyl ether (2×25 mL). Wash the combined organic layers with 5% aqueous lithium chloride solution, dry (magnesium sulfate) and concentrate to give an oil (19.12 g). Dissolve in dichloromethane (100 mL) and cool the solution in a wet ice/acetone bath. Add peracetic acid (15 mL) dropwise. Remove the ice bath and stir overnight. Quench the reaction with water (100 mL) and solid sodium bisulfite to a negative starch iodide endpoint. Separate the organic layer, dry (magnesium sulfate) and concentrate. Crystallize by the addition of hexanes to give a white solid. Filter the slurry, wash with hexanes, and dry under vacuum to give the title compound (13.7 g) as a white crystalline solid. Recover a second crop of the title compound (6 g) from the filtrate (19.7 g, 83% total yield).

2-Methanesulfonyl-6-(methylpropylamino)-isonicotinic acid methyl ester

Add methylpropylamine (0.21 mL, 2.0 mmol) to a suspension of 2-chloro-6-methanesulfonyl-isonicotinic acid methyl ester (0.25 g, 1.0 mmol), palladium acetate (0.022 g, 0.1 mmol), racemic 2,2'-bis(diphenylphosphino)-1,1'-binaphthyl (0.062 g, 0.1 mmol), and cesium carbonate (0.325 g, 1.0 mmol) in toluene (5 mL) at room temperature and stir 18 h at 80° C. Cool, filter through a filtering agent and purify (silica gel chromatography, eluting with 20:80 to 40:60 ethyl acetate:hexanes) to give the title compound (0.181 g, 63%).

2-Methanesulfonyl-6-(methylpropylamino)-isonicotinic acid

Add 2 N NaOH (0.95 mL) to 2-methanesulfonyl-6-(methylpropylamino)-isonicotinic acid methyl ester (0.181 g, 0.63 mmol) in methanol (5 mL). Stir 3 h, acidify to about pH=3 using 1 N HCl, extract into ethyl acetate, wash organic layer with saturated aqueous sodium chloride, dry (magnesium sulfate) and concentrate to give the title compound (0.14 g, 85%).

MS (ES): m/z=273 [M+H].

Preparation 68

2-Cyclobutylamino-6-methanesulfonyl-isonicotinic acid

2-Cyclobutylamino-6-methanesulfonyl-isonicotinic acid methyl ester

Add cyclobutylamine (0.13 mL, 1.5 mmol) to a suspension of 2-chloro-6-methanesulfonyl-isonicotinic acid methyl ester (0.25 g, 1.0 mmol), palladium acetate (0.022 g, 0.1 mmol), racemic 2,2'-bis(diphenylphosphino)-1,1'-binaphthyl (0.062 g, 0.1 mmol), and cesium carbonate (0.325 g, 1.0 mmol) in toluene (5 mL) at room temperature and heat for 16 h at 80° C. Cool, filter through a filtering agent, concentrate and purify (silica gel chromatography, eluting with 15:85 to 40:60 ethyl acetate:hexanes) to give the title compound (0.255 g, 90%).

2-Cyclobutylamino-6-methanesulfonyl-isonicotinic acid

Add 2 N NaOH (1.26 mL) to 2-cyclobutylamino-6-methanesulfonyl-isonicotinic acid methyl ester (0.24 g 0.85 mmol) in methanol (5 mL). Stir 3 h, acidify to about pH=3 with 1 N HCl, extract into ethyl acetate, wash organic layer with saturated aqueous sodium chloride, dry (magnesium sulfate) and concentrate to give the title compound (0.19 g, 86%).

MS (ES): m/z=271 [M+H].

The compounds of Preparation 69-70 may be prepared essentially as described in Preparation 68 using the appropriate amine.

| Prep | Compound | MS (ES) [M + H] |
|---|---|---|
| 69 | 2-Pyrrolidin-1-yl-6-methanesulfonyl-isonicotinic acid | 271 |
| 70 | 2-Cyclopropylamino-6-methanesulfonyl-isonicotinic acid | |

Preparation 71

2-(Methanesulfonyl-methylamino)-6-(methylpropylamino)-isonicotinic acid

2-Chloro-6-(methylpropylamino)-isonicotinic acid methyl ester

Mix 2,6-dichloro-isonicotinic acid methyl ester (5 g, 24.2 mmol), methylpropyl-amine (3.2 g, 23.06 mmol), cesium carbonate (10 g, 31.2 mmol), racemic-2,2'-bis(diphenylphosphino)-1,1'-binaphthyl (1.5 g, 2.43 mmol), and palladium acetate (0.27 g, 1.21 mmol) in toluene (50 mL). Degas with argon, seal the vessel and heat at 80° C. for 16 h. Cool to room temperature and dilute with diethyl ether (50 mL). Filter through a filtering agent, concentrate, and purify (silica gel chromatography, eluting with 0:100 to 20:80 ethyl acetate:hexanes to give the title compound as an oil (795 mg, 13.5%).

$^1$H NMR (CDCl$_3$) δ 7.00 (s, 1H), 6.93 (s, 1H), 3.92 (s, 3H), 3.49 (t, J=7.2 Hz, 2H), 3.09 (s, 3H), 1.69-1.59 (m, 2H), 0.94 (t, J=7.6 Hz, 3H).

2-Methanesulfonylamino-6-(methylpropylamino)-isonicotinic acid methyl ester

Dissolve methane sulfonamide (951 mg, 10 mmol) in THF (30 mL). Add sodium hydride (380 mg, 9.5 mmol, 60% dispersion in mineral oil) and reflux for 3 h, cool to room temperature and concentrate. Charge a sealed flask with sodium methansulfonamide (478 mg, 4.09 mmol), 2-chloro-6-(methylpropylamino)-isonicotinic acid methyl ester (79 mg, 3.27 mmol), biphenyl-2-yl-di-tert-butylphosphane (98 mg, 0.33 mmol), and tris(dibenzylideneacetone)dipalladium (0) (150 mg, 0.16 mmol) in toluene (7 mL). Degas with argon, seal the vessel and heat at 100° C. for 16 h. Cool to room temperature, dilute with ethyl acetate, wash with water, aqueous sodium chloride, concentrate and purify (silica gel chromatography, eluting with 0:100 to 50:50 ethyl acetate:hexanes) to give the title compound as an oil (870 mg, 88%).

MS (ES): m/z=302 [M+H].

2-(methanesulfonyl-methylamino)-6-(methylpropylamino)-isonicotinic acid methyl ester Dissolve 2-methanesulfonylamino-6-(methylpropylamino)-isonicotinic acid methyl ester (87 mg, 2.89 mmol) and iodomethane (0.27 mL, 4.33 mmoles) in DMF (10 mL). Add potassium carbonate (639 mg, 4.62 mmol) and tetrabutylammonium bromide (93 mg, 0.98 mmol) and stir at room temperature 1 h. Dilute with ethyl acetate (80 mL), wash with 10% aqueous potassium carbonate (2×15 mL), 0.1 N citric acid (2×15 mL), 1 N lithium chloride (2×15 mL) and saturated aqueous sodium chloride (15 mL). Concentrate organic layer and purify (silica gel chromatography, eluting with 10:90 to 40:60 ethyl acetate:hexanes to give the title compound (796 mg, 87%).

MS(ES): m/z=316[M+H].

2-(methanesulfonyl-methylamino)-6-(methylpropylamino)-isonicotinic acid

Dissolve 2-(methanesulfonyl-methylamino)-6-(methylpropylamino)-isonicotinic acid methyl ester (796 mg, 2.52 mmoles) in THF (35 mL) and add 1 N lithium hydroxide (12.6 mL). Stir at room temperature for 16 h, acidify with 5 N HCl (2.6 mL), and partition between diethyl ether and water. Wash the diethyl ether layer with saturated aqueous sodium chloride, dry (magnesium sulfate) and concentrate to give the title compound as a yellow solid (650 mg, 85%).

MS (ES): m/z=302 [M+H].

Preparation 72

2-Benzenesulfonyl-6-(S)-sec-butylamino)-isonicotinic acid

2-benzenesulfonyl-6-chloro-isonicotinic acid methyl ester

Mix 2,6-dichloro-isonicotinic acid methyl ester (1 g, 4.85 mmol) and sodium thiophenoxide (0.64 g, 4.85 mmol) in DMF (10 mL) at room temperature for 4 h. Quench with water and extract with dichloromethane. Dry the dichloromethane layer over magnesium sulfate and concentrate. Dissolve the residue in chloroform (30 mL) and add neutral alumina (6 g) and potassium peroxymonosulfate (11.92 g, 19.39 mmol). Reflux for 16 h, concentrate and purify (silica gel chromatography, eluting with 0:100 to 20:80 ethyl acetate:hexanes) to give the title compound as a white solid (1.4 g, 93%).

MS (ES): m/z=312 [M+H].

2-Benzenesulfonyl-6-(S)-sec-butylamino)-isonicotinic acid

In a sealed tube mix 2-benzenesulfonyl-6-chloro-isonicotinic acid methyl ester (1.4 g, 4.49 mmol), palladium acetate (0.1 g, 0.45 mmol), cesium carbonate (2.19 g, 6.74 mmol), (S)-sec-butylamine (0.36 g, 4.94 mmoles) and racemic 2,2'-bis(diphenylphosphino)-1,1'-binaphthyl (0.28 g. 0.45 mmol) in toluene (50 mL). Degas with argon, seal the flask and heat at 80° C. for 16 h. Cool to room temperature and partition between diethyl ether and water. Dry the organic layer over magnesium sulfate, concentrate and purify (silica gel chromatography, eluting with 0:100 to 20:80 ethyl acetate:hexanes) to give the methyl ester (490 mg, 31%) as an oil. Dissolve the oil in THF (14 mL) and add 1 N lithium hydroxide (7 mL). Stir vigorously at room temperature for 4 h and concentrate. Partition the residue between diethyl ether and 1

N HCl, dry the organic layer (magnesium sulfate) and concentrate to give the title compound as a white solid (430 mg, 91%).

MS (ES): m/z=335 [M+H].

Preparation 73

2-sec-Butylamino-6-methanesulfonyloxy-isonicotinic acid

2-Benzyloxy-6-chloro-isonicotinic acid methyl ester

Add sodium hydride (1.15 g, 28.75 mmol 60% in mineral oil) to a suspension of 2,6-dichloroisonicotinic acid (2 g, 10.42 mmol) at 0° C. in DMF (40 mL). Warm to room temperature and stir for 10 min. Add benzyl alcohol (1.35 mL, 13.045 mmol) dropwise and heat to 80° C. for 1 h. Cool to room temperature, add diiodomethane (2 mL) and stir for 30 min. Pour into saturated aqueous sodium chloride and partition between ethyl acetate and water. Dry (magnesium sulfate), concentrate and purify (silica gel chromatography, eluting with 5:95 ethyl acetate:hexanes) to give the title compound as a colorless oil (2.3 g, 79%).

MS (ES): m/z=278 [M+H].

2-Benzyloxy-6-sec-butylamino-isonicotinic acid methyl ester

Degas a sealed tube for 5 min and add a suspension 2-benzyloxy-6-chloro-isonicotinic acid methyl ester (1 g, 3.604 mmol), palladium acetate (100 mg, 0.445 mmol), racemic 2,2'-bis-diphenylphosphanyl-[1,1']binaphthalenyl (307 mg, 0.493 mmol), cesium carbonate (1.2 g, 3.683 mmol) and (R)-sec-butylamine (0.5 mL, 1.387 mmol) in toluene (14 mL). Heat to 105° C. and stir for 20 h. Cool to room temperature, concentrate and purify (silica gel chromatography, eluting with 3:97 ethyl acetate:hexanes) to give the title compound.

MS (ES): m/z=315 [M+H].

2-sec-Butylamino-6-hydroxy-isonicotinic acid

Treat a solution of 2-benzyloxy-6-sec-butylamino-isonicotinic acid methyl ester (340 mg, 1.036 mmol) in methanol (15 mL) and ethyl acetate (5 mL) with 10% Pd/C (150 mg). Stir the mixture under a balloon containing hydrogen gas for 2.5 h. Filter through a filtering agent, wash with ethyl acetate and concentrate to give the title compound which is used directly in the next step without further purification.

MS (ES): m/z=225 [M+H].

2-sec-Butylamino-6-methanesulfonyloxy-isonicotinic acid methyl ester

Add methanesulfonyl chloride (0.1 mL, 1.292 mmol) to a solution of 2-sec-butylamino-6-hydroxy-isonicotinic acid (242 mg, 1.016 mmol) and triethyl amine (0.25 mL, 1.793 mmol) in dichloromethane (15 mL) at 0° C. Stir at room temperature for 15 min, dilute with dichloromethane, wash with saturated aqueous sodium chloride, dry (magnesium sulfate), concentrate and purify (silica gel chromatography, eluting with 15:85 ethyl acetate:hexanes) to give the title compound as a white solid (240 mg, 75%).

MS (ES): m/z=303 [M+H].

2-sec-Butylamino-6-methanesulfonyloxy-isonicotinic acid

Add 1 N lithium hydroxide (2 mL) to a solution of 2-sec-butylamino-6-methanesulfonyloxy-isonicotinic acid methyl ester (235 mg, 0.743 mmol) in THF (15 mL) at 0° C. Warm to room temperature and stir for 12 h. Acidify with 5% aqueous HCl to about pH=3, extract with ethyl acetate, dry (magnesium sulfate), and concentrate to give the title compound.

MS(ES): m/z=289[M+H].

Preparation 74

6-Fluoro-N,N-dipropyl-isophthalamic acid

3-Bromo-4-fluoro-N,N-dipropylbenzamide

Combine 3-bromo-4-fluorobenzoic acid (5.0 g, 22.8 mmol) with 1-(3-dimethylaminopropyl)-3-ethylcarbodiimide (4.4 g, 22.8 mmol) and N-hydroxy-succinimide (2.6 g, 22.8 mmol) in dichloromethane (75 mL) and stir at room temperature for 30 min. Add N,N-dipropylamine (4.7 mL, 34.3 mmol) and triethylamine (8.0 mL, 57.1 mol) and stir at room temperature overnight. Dilute with ethyl acetate and wash with 1 N HCl, saturated aqueous potassium carbonate, saturated aqueous sodium chloride, dry (magnesium sulfate), concentrate and purify (silica gel chromatography, eluting with 30:70 ethyl acetate:hexanes) to give the title compound.

$^1$HNMR (CDCl$_3$) δ 0.79-0.99 (m, 6H), 1.56-1.68 (m, 4H), 3.17-3.44 (m, 4H), 7.14 (t, 1H)), 7.26-7.31 (m, 1H)), 7.56-7.58 (m, 1H).

3-Cyano-4-fluoro-N,N-dipropylbenzamide

Combine 3-bromo-4-fluoro-N,N-dipropylbenzamide (1.0 g, 3.3 mmol) with copper cyamide (0.45 g, 5.0 mmol) in DMF (5 mL) and heat at reflux until all starting material is consumed. Cool to room temperature and partition between ethyl acetate and saturated aqueous sodium bicarbonate. Separate the organic layer and wash with saturated aqueous sodium bicarbonate, saturated sodium chloride solution, dry (magnesium sulfate), concentrate and purify (silica gel chromatography, eluting with 20:80 ethyl acetate:hexanes) to give the title compound.

$^1$HNMR (CDCl$_3$) δ 0.79-0.99 (m, 6H), 1.66-1.69 (m, 4H)), 3.15-3.45 (m, 4H)), 7.27 (t, 1H), 7.60-7.65 (m, 2H).

6-Fluoro-N,N-dipropyl-isophthalamic acid

Dissolve 3-cyano-4-fluoro-N,N-dipropylbenzamide (0.52 g, 2.1 mmol) in a 3:1 solution of concentrated sulfuric acid:water (5 mL). Heat at 150° C. until no starting material remains. Cool to room temperature, pour into water and extract with ethyl acetate. Wash the organic layer with saturated aqueous sodium chloride solution, dry (magnesium sulfate) and concentrate to give the title compound that is used without further purification.

MS (ES): m/z=268.0=[M+H].

Preparation 75

5-(Methyl-propylcarbamoyl)-isophthalic acid monoethyl ester

5-(Methyl-propylcarbamoyl)-isophthalic acid diethyl ester

Stir a solution of diethyl 1,3,5-benzene tricarboxylate (2.47 g, 9.28 mmol), 1-hydroxybenzotriazole (1.38 g, 10.2 mmol), 1-(3-dimethylaminopropyl)-3-ethylcarbodiimide hydrochloride (EDCl) (1.96 g, 10.2 mmol), N-methylpropylamine (1.04 mL, 10.2 mmol) in dichloromethane (50 mL) at room temperature overnight. Dilute with dichloromethane (300 mL) and extract the solution with 0.1 N citric acid (2×50 mL), saturated aqueous sodium bicarbonate (50 mL), and saturated aqueous sodium chloride (50 mL). Dry (magnesium sulfate), concentrate and purify (silica gel chromatography, eluting with 50:50 ethyl acetate:hexanes) to give the title compound (2.02 g, 68%).
MS (ES): m/z=322 [M+H].

5-(Methyl-propylcarbamoyl)-isophthalic acid monoethyl ester

Stir a solution of 5-(methyl-propylcarbamoyl)-isophthalic acid diethyl ester (2.02 g, 6.3 mmol), NaOH (0.25 g, 6.3 mmol) and ethanol (32 mL) at room temperature overnight. Add 0.2 N HCl (60 mL) and extract with ethyl acetate (2×50 mL). Dry (magnesium sulfate), concentrate and purify (silica gel chromatography, eluting with 50:50 ethyl acetate:hexanes with 1% acetic acid then 100% ethyl acetate with 1% acetic acid) to give the title compound as an oil (1.4 g, 75%).
MS (ES): m/z=294 [M+H].

Preparation 76

3-Ethylcarbamoyl-5-(methyl-propylcarbamoyl)-benzoic acid

3-Ethylcarbamoyl-5-(methyl-propylcarbamoyl)-benzoic acid ethyl ester

Stir a solution of 5-(methyl-propylcarbamoyl)-isophthalic acid monoethyl ester (146 mg, 0.5 mmol), 1-hydroxybenzotriazole (74 mg, 0.55 mmol), 1-(3-dimethylaminopropyl)-3-ethylcarbodiimide hydrochloride (110 mg, 0.55 mmol), ethylamine (2 N in THF, 0.275 mL, 0.55 mmol) in 0.75 mL DMF at room temperature overnight. Dilute with dichloromethane (15 mL) and wash with water (5 mL), 0.1 N aqueous citric acid (5 mL), saturated aqueous sodium bicarbonate (5 mL), and saturated aqueous sodium chloride (5 mL). Dry (magnesium sulfate) and concentrate to give the title compound (157 mg, 100%).
MS (ES): m/z=321 [M+H].

3-Ethylcarbamoyl-5-(methyl-propylcarbamoyl)-benzoic acid

Stir a solution of 3-ethylcarbamoyl-5-(methyl-propylcarbamoyl)-benzoic acid ethyl ester (157 mg, 0.5 mmol), 1 N aqueous lithium hydroxide (2.45 mL, 2.45 mmol) and THF (2.45 mL) at room temperature overnight. Dilute the reaction with water and extract with dichloromethane. Acidify the aqueous with 5 N HCl, extract the aqueous with dichloromethane and dry (magnesium sulfate) and concentrate to give the title compound (106 mg, 74%).
MS (ES): m/z=293 [M+H].

Preparation 77

3,5-Bis(methyl-propylcarbamoyl)-benzoic acid

3,5-Bis(methyl-propylcarbamoyl)-benzoic acid ethyl ester

Stir a solution of 5-(methyl-propylcarbamoyl)-isophthalic acid monoethyl ester (146 mg, 0.5 mmol), 1-hydroxybenzotriazole (68 mg, 0.5 mmol), 1-(3-dimethylaminopropyl)-3-ethylcarbodiimide hydrochloride (96 mg, 0.5 mmol), N-methylpropylamine (51 µL, 0.5 mmol) in dichloromethane (2.5 mL) at room temperature overnight. Dilute with dichloromethane (15 mL) and wash with water (5 mL), 0.1 N citric acid (5 mL), saturated aqueous sodium bicarbonate (5 mL), and saturated aqueous sodium chloride (5 mL). Dry (magnesium sulfate) and concentrate to give the title compound (157 mg, 90%)
MS (ES): m/z=349 [M+H].

3,5-Bis(methyl-propylcarbamoyl)-benzoic acid

Stir a solution of 3,5-bis(methyl-propylcarbamoyl)-benzoic acid ethyl ester (157 mg, 0.45 mmol), 1 N lithium hydroxide (2.25 mL, 2.25 mmol) and THF (2.25 mL) for 2 h at room temperature. Dilute the reaction with water (10 mL) and extract with dichloromethane (10 mL). Acidify the aqueous with 5 N HCl, extract the aqueous with dichloromethane, dry (magnesium sulfate) and concentrate to give the title compound (119 mg, 82%).
MS (ES): m/z=321 [M+H].

Preparation 78

5-(Methyl-propylcarbamoyl)-isophthalic acid monoisopropyl ester

5-(Methyl-propylcarbamoyl)-isophthalic acid 1-ethyl ester 3-isopropyl ester Sonicate a mixture of 5-(methyl-propyl-carbamoyl)-isophthalic acid monoethyl ester (146 mg, 0.5 mmol), isopropanol (0.75 mL) and concentrated sulfuric acid (25 µL) then stir the resulting solution at room temperature for one month. Add 1-hydroxybenzotriazole (68 mg, 0.5 mmol), 1-(3-dimethylaminopropyl)-3-ethylcarbodiimide hydrochloride (96 mg, 0.5 mmol), and triethylamine (100 µL). Stir overnight at room temperature. Add dichloromethane (25 mL) and wash with 0.1 N citric acid (5 mL), saturated aqueous sodium bicarbonate (10 mL), saturated aqueous sodium chloride (10 mL), dry (magnesium sulfate) and concentrate (149 mg, 89%).
MS (ES): m/z=336 [M+H].

5-(Methyl-propylcarbamoyl)-isophthalic acid monoisopropyl ester

Stir a solution of 5-(methyl-propylcarbamoyl)-isophthalic acid 1-ethyl ester 3-isopropyl ester (149 mg, 0.4 mmol) in 0.2 N NaOH in 1:10 water:isopropanol (2.2 mL) overnight. Add 1 N lithium hydroxide (0.44 mL) and stir for 1 h at room temperature. Dilute with water and extract with dichloromethane. Acidify the aqueous with 5 N HCl, extract the aqueous with dichloromethane, dry (magnesium sulfate) and concentrate to give the title compound (79 mg, 56%).
MS(ES): m/z=308[M+H].

Preparation 79

5-Difluoromethyl-N-methyl-N-propyl-isophthalamic acid

5-Hydroxymethyl-isophthalic acid monoethyl ester

Add a solution of diethyl-5-(hydroxymethyl)-isophthalate (5 g, 19.8 mmol) in acetone (88 mL) to a solution of NaOH (792 mg, 19.8 mmol) in ethanol (12 mL). After 4 h collect precipitate. Dissolve the precipitate in water (200 mL), add 5 N HCl to about pH=1 and collect the precipitate. Extract the aqueous with dichloromethane, combine the extracts with the precipitate and concentrate to give to give the title compound (1.9 g, 43%)

MS (ES): m/z=225 [M+H].

5-Hydroxymethyl-N-methyl-isophthalamic acid ethyl ester

Stir a solution of 5-hydroxymethyl-isophthalic acid monoethyl ester (1.9 g, 8.4 mmol), N-methylpropylamine (947 µl, 9.2 mmol), 1-hydroxybenzotriazole (1.24 g, 9.2 mmol), and 1-(3-dimethylaminopropyl)-3-ethylcarbodiimide hydrochloride (1.77 g, 9.2 mmol) in a mixture of dichloromethane (12 mL) and DMF (12 mL) at room temperature for 1.5 h. Concentrate and purify (silica gel chromatography, eluting with 50:50 ethyl acetate:hexanes) to give the title compound (950 mg, 40% yield).

MS (ES): m/z=280 [M+H].

5-Formyl-N-methyl-N-propyl-isophthalamic acid ethyl ester

Add a solution of 5-hydroxymethyl-N-methyl-N-propyl-isophthalamic acid ethyl ester (600 mg, 2.15 mmol) dropwise to a mixture of Dess-Martin periodinane (1.06 g, 2.5 mmol) in dichloromethane (6.5 mL). Stir the exothermic reaction mixture (32° C.) for 20 min without additional heat. To the reaction mixture add diethyl ether (12 mL) and saturated aqueous sodium bicarbonate (12 mL). Separate the layers and wash the aqueous layer with diethyl ether (2×12 mL). Combine the organics and wash with saturated aqueous sodium bicarbonate (12 mL), saturated aqueous sodium chloride (12 mL), dry (magnesium sulfate), concentrate, and purify (silica gel chromatography, eluting with 50:50 ethyl acetate:hexanes) to give the title compound as an oil (0.54 g, 91%).

MS (ES): m/z=278 [M+H].

5-Difluoromethyl-N-methyl-N-propyl-isophthalamic acid ethyl ester

Add a solution of bis(2-methoxyethyl)aminosulfur trifluoride (161 mg, 0.73 mmol) in dichloromethane (88 µL) to a solution of 5-formyl-N-methyl-N-propyl-isophthalamic acid ethyl ester (120 mg, 0.43 mmol) in dichloromethane (130 µL). Place the reaction under nitrogen, add ethanol (3.5 µL) and stir the reaction at room temperature for 48 h. Pour the reaction into saturated aqueous sodium bicarbonate and extract with dichloromethane. Dry (magnesium sulfate), concentrate and purify (silica gel chromatography, eluting with 50:50 ethyl acetate:hexanes) to give the title compound (68 mg, 53%).

MS (ES): m/z=300 [M+H].

5-Difluoromethyl-N-methyl-N-propyl-isophthalamic acid

Stir a solution of 5-difluoromethyl-N-methyl-N-propyl-isophthalamic acid ethyl ester (68 mg, 0.23 mmol), 1 N lithium hydroxide (1.15 mL) and THF (1.15 mL) at room temperature over the weekend. Add water and extract with dichloromethane. Acidify the aqueous with 5 N HCl (240 µL), extract with dichloromethane, dry (magnesium sulfate) and concentrate to give the title compound (61 mg, 100%).

Preparation 80

5-Fluoromethyl-N-methyl-N-propyl-isophthalamic acid

5-Fluoromethyl-N-methyl-N-propyl-isophthalamic acid ethyl ester

Add bis(2-methoxyethyl)aminosulfur trifluoride (220 mg, 1.0 mmol) to a polypropylene tube (5 mL), seal, cool to −78° C., add a solution of 5-hydroxymethyl-N-methyl-N-propyl-isophthalamic acid ethyl ester (250 mg, 0.9 mmol) in dichloromethane 1.0 (1 mL) in 0.2 mL increments. Stir at −78° C. for 3 h then at room temperature overnight. Pour the reaction into saturated aqueous sodium bicarbonate. Extract with dichloromethane, dry (magnesium sulfate), concentrate and purify (silica gel chromatography, eluting with 50:50 ethyl acetate:hexanes) to give the title compound (73 mg, 29%).

MS (ES): m/z=282 [M+H].

5-Fluoromethyl-N-methyl-N-propyl-isophthalamic acid

Stir a solution of 5-fluoromethyl-N-methyl-N-propyl-isophthalamic acid ethyl ester-(73 mg, 0.26 mmol), 1 N lithium hydroxide (1.3 mL, 1.3 mmol) and THF (1.3 mL) at room temperature overnight. Add water (10 mL) and extract with dichloromethane (3×10 mL). Acidify the aqueous with 5 N HCl (260 µL), extract with dichloromethane (3×10 mL), dry (magnesium sulfate) and concentrate to give the title compound (56 mg, 85%).

Preparation 81

N-Methyl-N-propyl-5-vinyl-isophthalamic acid

5-Bromo-isophthalic acid monomethyl ester

Add a solution of NaOH pellets (3.66 g, 91.5 mmol) in methanol (200 mL) to dimethyl-5-bromoisophthalate (25 g) and stir the resulting solution overnight at room temperature. Add water (300 mL) and extract with dichloromethane (3×200 mL). Acidify the aqueous with 5 N HCl (20 mL), filter the precipitate and dry to give a mixture of the title compound and 5-bromo-isophthalic acid in about a 6:4 ratio by LCMS (18.2 g crude).

5-Bromo-N-methyl-N-propyl-isophthalamic acid methyl ester

Add N-methylpropylamine (5.14 g, 70.4 mmol) to a mixture of 5-bromo-isophthalic acid monomethyl ester and 5-bromo-isophthalic acid (18.2 g), 1-hydroxybenzotriazole (9.5 g, 70.4 mmol), and 1-(3-dimethylaminopropyl)-3-ethylcarbodiimide hydrochloride (13.5 g, 70.4 mmol) in dichloromethane (200 mL). Stir the solution for 2 h at room temperature. Add saturated aqueous ammonium chloride (100 mL) and acidify the mixture with 1 N HCl. Filter away the precipitate, extract the filtrate with dichloromethane, wash the organic extracts with 1 N HCl, saturated aqueous sodium bicarbonate, saturated aqueous sodium chloride, dry (magnesium sulfate), concentrate and purify (silica gel chromatography, eluting with 30:70 ethyl acetate:hexanes) to give the title compound as an oil (10.1 g, 46%).

MS (ES): m/z=315 [M+H].

N-Methyl-N-propyl-5-vinyl-isophthalamic acid methyl ester

Dissolve 5-bromo-N-methyl-N-propyl-isophthalamic acid methyl ester (2.7 g, 8.6 mmol) in toluene (16 mL) and place the solution under nitrogen. Add in sequence 2,6-di-tert-butyl-4-methylphenol (a few crystals), tetrakis(triphenylphosphine)palladium (0) (185 mg, 0.16 mmol), and tributylvinyl tin (3 g, 9.5 mmol) and reflux for 4 h. Filter though a filtering agent and concentrate. Add diethyl ether (70 mL) and 20% aqueous potassium fluoride (70 mL) and stir vigorously. Collect the diethyl ether layer and extract with diethyl ether two additional times. Concentrate and purify (silica gel chromatography, eluting with 0:100 to 50:50 ethyl acetate:hexanes) to give the title compound (1.58 g, 70%).

N-Methyl-N-propyl-5-vinyl-isophthalamic acid

Stir a solution of N-methyl-N-propyl-5-vinyl-isophthalamic acid methyl ester (78 mg, 0.3 mmol), 1 N lithium hydroxide (1.5 mL, 1.5 mmol), and THF (1.5 mL) at room temperature overnight. Add water and extract with ethyl acetate. Acidify the aqueous with 5 N HCl, extract with ethyl acetate, dry (magnesium sulfate) and concentrate to give the title compound (52 mg, 70%).

Preparation 82

N-Methyl-5-oxazol-2-yl-N-propyl-isophthalamic acid

N-Methyl-5-oxazol-2-yl-N-propyl-isophthalamic acid methyl ester

Add n-butyllithium (1.6 M in hexanes, 1.25 mL, 2.01 mmol) dropwise to a solution of oxazole (126 mg, 1.83 mmol) in THF (12.6 mL) at −78° C. Stir for 30 min at −78° C. and add a solution of zinc chloride (747 mg, 5.49 mmol) in diethyl ether (5.5 mL) and stir at 0° C. for 1 h. Add a solution of 5-iodo-N-methyl-N-propyl-isophthalamic acid methyl ester (330 mg, 0.91 mmol) in THF (5.1 mL) followed by tetrakis(triphenylphosphine)palladium (0) (105 mg, 0.091 mmol) and heat to reflux for 30 min. Add ethyl acetate (40 mL), wash with water (2×20 mL), dry (magnesium sulfate), concentrate and purify (silica gel chromatography, eluting with 50:50 ethyl acetate:hexane) to give the title compound (225 mg, 82%).

MS (ES): m/z=303 [M+H].

N-Methyl-5-oxazol-2-yl-N-propyl-isophthalamic acid

Stir a solution of N-methyl-5-oxazol-2-yl-N-propyl-isophthalamic acid methyl ester (225 mg, 0.74 mmol) in 1 N lithium hydroxide (3.0 mL, 3.0 mmol) and THF (3.0 mL) at room temperature for 3 h. Add water (40 mL) and extract with ethyl acetate (40 mL). Acidify the aqueous with 5 N HCl, extract with ethyl acetate (2×40 mL), dry (magnesium sulfate) and concentrate to give the title compound (213 mg, 100%).

Preparation 83

N-Methyl-5-(3-methyl-[1,2,4]oxadiazol-5-yl)-N-propyl-isophthalamic acid

N-Methyl-5-(3-methyl-[1,2,4]oxadiazol-5-yl)-N-propyl-isophthalamic acid ethyl ester Stir a solution of 5-(methyl-propyl-carbamoyl)-isophthalic acid monoethyl ester (330 mg, 1.13 mmol), acetamideoxime (117 mg, 1.58 mmol), and 1-(3-dimethylaminopropyl)-3-ethylcarbodiimide hydrochloride (303 mg, 1.58 mmol) in dichloromethane (20 mL) at room temperature overnight. Concentrate and purify (silica gel chromatography, eluting with 2:98 methanol:dichloromethane). Concentrate and add THF (30 mL) and 1 N tetrabutylammonium fluoride in THF (43 µL, 0.043 mmol). Reflux the solution for 30 min and concentrate. Add ethyl acetate, extract with saturated aqueous sodium chloride, dry (magnesium sulfate) concentrate and purify (silica gel chromatography, eluting with 50:50 ethyl acetate:hexanes) to give the title compound (135 mg, 36%).

MS (ES): m/z=332 [M+H].

N-Methyl-5-(3-methyl-[1,2,4]oxadiazol-5-yl)-N-propyl-isophthalamic acid

Stir a solution of N-methyl-5-(3-methyl-[1,2,4]oxadiazol-5-yl)-N-propyl-isophthalamic acid ethyl ester (135 mg, 0.4 mmol), 1 N lithium hydroxide (1.6 mL, 1.6 mmol) and THF (1.6 mL) at room temperature overnight. Add 1 N HCl (20 mL) and extract with ethyl acetate (3×20 mL). Dry (magnesium sulfate) and concentrate to give the title compound.

Preparation 84

N-Methyl-5-oxazol-5-yl-N-propyl-isophthalamic acid

N-Methyl-5-oxazol-5-yl-N-propyl-isophthalamic acid

Heat a solution of 5-formyl-N-methyl-N-propyl-isophthalamic acid ethyl ester (300 mg, 1.08 mmol), tosylmethyl isocyanide (254 mg, 1.3 mmol), and sodium methoxide (193 mg, 3.57 mmol) in methanol (3.1 mL) at 40° C. for 1 h. Add water to the hot solution and extract with dichloromethane and ethyl acetate. Acidify the aqueous with 5 N HCl, extract with dichloromethane, dry (magnesium sulfate), concentrate and purify (silica gel chromatography, eluting with 0:100 to 4:96 methanol:dichloromethane) to give the title compound (203 mg, 65%).

MS (ES): m/z=289 [M+H].

Preparation 85

5-(2,2-Difluorovinyl)-N-methyl-N-propyl-isophthalamic acid

Toluene-4-sulfonic acid 2,2-difluorovinyl ester

Add n-butyllithium (1.6 M in hexanes, 4.9 mL, 7.8 mmol) dropwise over 5 min to a solution of 2,2,2-trifluoroethyl-p- toluene sulfonate (1.0 g, 3.9 mmol) in THF (20 mL) at −78° C. Stir for 30 min, add acetic acid (225 µL, 3.9 mmol) and stir for 30 min. Warm to room temperature, add ethyl acetate and extract with saturated aqueous ammonium chloride, and saturated aqueous sodium bicarbonate. Dry (magnesium sulfate), concentrate and purify (silica gel chromatography, eluting with 0:100 to 15:85 ethyl acetate:hexanes) to give the title compound as an oil (430 mg, 47%).

5-(2,2-Difluorovinyl)-N-methyl-N-propyl-isophthalamic acid ethyl ester

Add n-butyllithium (1.6 M in hexanes, 4.5 mL, 7.4 mmol) dropwise to a mixture of zirconocene dichloride (1.05 g, 3.6 mmol) in dry THF (15 mL) at −78° C. and stir for 1 h. Add a solution of toluene-4-sulfonic acid 2,2-difluorovinyl ester (420 mg, 1.8 mmol) in THF (3.6 mL) dropwise. Stir at −78° C. for 5 min and at room temperature for 3 h. Add triphenyl phosphine (79 mg, 0.3 mmol) and tris(dibenzylidineacetone) dipalladium(0) (34 mg, 0.036 mmol), stir for 10 min, add 5-iodo-N-methyl-N-propyl-isophthalamic acid methyl ester (722 mg, 2.0 mmol) and zinc iodide (1.35 g, 4.3 mmol). Reflux the reaction for 1 h and stir at room temperature overnight. Add pH=7 phosphate buffer (400 mL) and ethyl acetate (250 mL). Separate the layers and wash with saturated aqueous ammonium chloride (2×100 mL), saturated aqueous sodium bicarbonate (2×100 mL), dry (magnesium sulfate), concentrate and purify (silica gel chromatography, eluting with 25:75 ethyl acetate:hexanes) to give the title compound (187 mg, 35%).

MS (ES): m/z=298 [M+H].

5-(2,2-Difluorovinyl)-N-methyl-N-propyl-isophthalamic acid

Stir a solution of 5-(2,2-difluorovinyl)-N-methyl-N-propyl-isophthalamic acid ethyl ester (187 mg, 0.63 mmol), 1 N lithium hydroxide (2.5 mL, 2.5 mmol) and THF (2.5 mL) at room temperature overnight. Partition the reaction between ethyl acetate and water. Acidify the aqueous with 5 N HCl and extract with ethyl acetate. Dry (magnesium sulfate), concentrate and purify (silica gel chromatography, eluting with 2:98 to 6:94 methanol:dichloromethane with 1% acetic acid) to give the title compound (78 mg, 44%).

MS (ES): m/z=284 [M+H].

Preparation 86

N-Methyl-5-(2-methylpyrrolidine-1-carbonyl)-N-propyl-isophthalamic acid

N-Methyl-5-(2-methylpyrrolidine-1-carbonyl)-N-propyl-isophthalamic acid ethyl ester Add 2-methylpyrrolidine (204 mg, 2.4 mmol) to a solution of 5-(methyl-propylcarbamoyl)-isophthalic acid monoethyl ester (640 mg, 2.18 mmol) in dichloromethane (8 mL) followed by 1-hydroxybenzotriazole (20 mg, 0.15 mmol) and diisopropyl carbodiimide (375 µL, 2.4 mmol). Stir the solution at room temperature over the weekend. Add ethyl acetate (25 mL) and wash with saturated aqueous ammonium chloride (2×10 mL), saturated aqueous sodium bicarbonate (10 mL), saturated aqueous sodium chloride (10 mL), dry (sodium sulfate), concentrate and purify (silica gel chromatography, eluting with 50:50 ethyl acetate:hexanes) to give the title compound as an oil (218 mg, 28%).

MS (ES): m/z=361 [M+H].

N-Methyl-5-(2-methylpyrrolidine-1-carbonyl)-N-propyl-isophthalamic acid

Stir a solution of N-methyl-5-(2-methylpyrrolidine-1-carbonyl)-N-propyl-isophthalamic acid ethyl ester (218 mg, 0.6 mmol), 1 N lithium hydroxide (2.4 mL, 2.4 mmol) and THF (2.4 mL) at room temperature overnight. Add 50 mL water and extract with dichloromethane (3×10 mL). Acidify the aqueous with 1 N HCl (3 mL) and extract with dichloromethane (3×10 mL). Dry (sodium sulfate) and concentrate to give the title compound (216 mg, 100%).

MS (ES): m/z=333 [M+H].

Preparation 87

5-(3,3-Difluoropyrrolidine-1-carbonyl)-N-methyl-N-propyl-isophthalamic acid 3,3-Difluoropyrrolidine-1-carboxylic acid tert-butyl ester Add ethanol (270 µL) to a solution of 3-oxopyrrolidine-1-carboxylic acid tert-butyl ester (3.36 g, 18.2 mmol), and bis(2-methoxyethyl)aminosulfur trifluoride (6.85 g, 31 mmol) in dichloromethane in a polypropylene tube. Stir the exothermic reaction at room temperature overnight. Add dichloromethane (100 mL) and wash with saturated aqueous sodium bicarbonate (2×20 mL), saturated aqueous sodium chloride (20 mL), dry (sodium sulfate), concentrate and purify (silica gel chromatography, eluting with 5:95 acetone:hexanes to give the title compound as an oil (2.18 g, 58%).

MS (ES): m/z=347 [M+H].

3,3-Difluoropyrrolidine hydrochloride

Stir a solution of 3,3-difluoropyrrolidine-1-carboxylic acid tert-butyl ester (2.18 g, 10.5 mmol) in hydrogen chloride (4 N in 1,4-dioxane, 65 mL) at room temperature. Concentrate to give the title compound (1.5 g, 97%).

5-(3,3-Difluoropyrrolidine-1-carbonyl)-N-methyl-N-propyl-isophthalamic acid ethyl ester Dissolve 5-(methyl-propylcarbamoyl)-isophthalic acid monoethyl ester (667 mg, 2.3 mmol) in a 0.1 N 1-hydroxybenzotriazole solution of 1:1:5 tert-butanol:acetonitrile:dichloromethane (23 mL, 2.3 mmol). Stir the solution at room temperature for 5 min, add 3,3-difluoropyrrolidine hydrochloride (331 mg, 2.3 mmol) and triethylamine (640 µL, 4.6 mmol); Stir the reaction at room temperature for 2 h, add ethyl acetate (100 mL) and wash with saturated aqueous ammonium chloride (2×30 mL), saturated aqueous sodium chloride (30 mL), dry (sodium sulfate), concentrate and purify (silica gel chromatography, eluting with 50:50 ethyl acetate:hexanes) to give the title compound (270 mg, 31%).

MS (ES): m/z=283 [M+H].

5-(3,3-Difluoropyrrolidine-1-carbonyl-N-methyl-N-propyl-isophthalamic acid

Stir a solution of 5-(3,3-difluoropyrrolidine-1-carbonyl)-N-methyl-N-propyl-isophthalamic acid ethyl ester (270 mg, 0.71 mmol), 1 N lithium hydroxide (1.1 mL, 1.1 mmol) and THF (2.0 mL) at room temperature for 4 h. Add 10 mL water, acidify with 1 N HCl (2 mL), extract with dichloromethane (3×10 mL), dry (sodium sulfate) and concentrate to give the title compound (262 mg, 100%).

Preparation 88

5-Chloro-N-methyl-N-propyl-isophthalamic acid

5-Chloro-N-methyl-N-propyl-isophthalamic acid

Dissolve commercially available 5-chloroisophthalic acid dimethyl ester (1.0 g, 4.37 mmol) in acetone (10 mL) and add a solution of NaOH (192 mg, 4.81 mmol) in methanol (2 mL). Stir 3 h and concentrate. Partition the residue between diethyl ether and water. Acidify the water layer to about pH=1 and collect the precipitate, 5-chloro-isophthalic acid monomethyl ester (675 mg, 72%). Dissolve 5-chloro-isophthalic acid monomethyl ester (459 mg, 2.13 mmol) in DMF (20 mL), add 1-(3-dimethylamino-propyl)-3-ethyl-carbodiimide hydrochloride (513 mg, 2.67 mmol) and 1-hydroxybenzotriazole (360 mg, 2.67 mmol). Stir at room temperature 1 h and add methyl propylamine (584 mg, 8.0 mmol). Stir at room temperature 3 h, dilute with ethyl acetate, wash with 10% aqueous potassium carbonate, 0.1 N citric acid, 1 N lithium chloride and saturated aqueous sodium chloride and concentrate. Dissolve the residue in THF (30 mL) and add 1 N lithium hydroxide (10 mL, 10 mmol). Stir at room temperature 3 h and acidify to about pH=1 by addition of 1 N HCl. Extract with diethyl ether, dry (magnesium sulfate) and concentrate to give the title compound.
MS (ES): m/z=256.1 [M+H].

Preparation 89

N,N-Dipropyl-isophthalamic acid

Dissolve isophthalic acid monomethyl ester (2.25 g, 12.5 mmol), 1-(3-dimethylamino-propyl)-3-ethyl-carbodiimide hydrochloride (2.88 g, 15 mmol), 1-hydroxybenzotriazole (2.02 g, 15 mmol) and triethylamine (3.03 g, 30 mmol) in THF (50 mL) and DMF (20 mL). Stir at room temperature 15 min and add dipropylamine (1.52 g, 15 mmol). Stir at room temperature 16 h and dilute with ethyl acetate. Wash with 10% aqueous potassium carbonate, 0.1 N citric acid, 1 N lithium chloride and saturated aqueous sodium chloride and concentrate. Dissolve the residue in THF (60 mL), methanol (18 mL) and water (9 mL). Add lithium hydroxide (2.1 g, 50 mmol), stir at room temperature 16 h and concentrate. Partition the residue between diethyl ether and 1 N HCl. Dry (magnesium sulfate) and concentrate to give the title compound as a solid.
MS (ES): m/z=250.2 [M+H].

Preparation 90

N-Methyl-5-propoxy-N-propyl-isophthalamic acid

5-Propoxy-isophthalic acid monomethyl ester

Heat commercially available 5-hydroxy-isophthalic acid dimethyl ester (1.0 g, 4.8 mmol), potassium carbonate (5.25 g, 38 mmol) and iodopropane (1.36 g, 8.0 mmol) in DMF (20 mL) at 70° C. for 8 h. Cool to room temperature, partition between ethyl acetate and 10% aqueous potassium carbonate. Wash the ethyl acetate layer with 1 N lithium chloride, saturated aqueous sodium chloride, dry (magnesium sulfate) and concentrate. Dissolve the residue in acetone (10 mL) and add a solution of NaOH (192 mg, 4.80 mmol) in methanol (2 mL). Stir at room temperature 16 h and concentrate. Partition between diethyl ether and 0.1 N citric acid, dry (magnesium sulfate) and concentrate to give the title compound.
MS (ES): m/z=239.0 [M+H].

N-Methyl-5-propoxy-N-propyl-isophthalamic acid

Mix 5-propoxy-isophthalic acid monomethyl ester (500 mg, 2.10 mmol), 1-(3-dimethylamino-propyl)-3-ethylcarbodiimide hydrochloride (403 mg, 2.10 mmol) and 1-hydroxybenzotriazole (283 mg, 2.10 mmol) in DMF (15 mL) at room temperature 1 h. Add methyl-propylamine (438 mg, 6.0 mmol) and stir at room temperature 16 h. Dilute with ethyl acetate, wash with 10% aqueous potassium carbonate, 0.1 N citric acid, 1 N lithium chloride and saturated aqueous sodium chloride. Dry (magnesium sulfate), concentrate and purify (silica gel chromatography, eluting with 20:80 to 30:70 ethyl acetate:hexanes) to give the carboxamide. Dissolve the residue (265 mg, 0.90 mmol) in THF (10 mL) and add 1 N lithium hydroxide (5 mL, 5 mmol) and stir at room temperature 16 h. Acidify the solution to about pH=1 with 1 N HCl, extract with ethyl acetate, dry (magnesium sulfate) and concentrate to give the title compound as a solid.
MS (ES): m/z=280.0 [M+H].

Preparation 91

5-Methanesulfonyl-N-methyl-N-propyl-isophthalamic acid

5-Methanesulfonyl-isophthalic acid dimethyl ester

Dissolve sodium sulfite (1.7 g, 13.51 mmol) and sodium bicarbonate (1.2 g, 14.19 mmol) in water (10 mL). Add 5-chlorosulfonyl-isophthalic acid dimethyl ester (2.0 g, 6.76 mmol) and ethanol (2 mL). Heat to 50° C. for 2 h, concentrate and dry the solid. Add DMF (40 mL) and iodomethane (4.56 g, 32 mmol) and stir at room temperature for 3 h. Dilute with ethyl acetate, wash with 10% aqueous potassium carbonate, 1 N lithium chloride and saturated aqueous sodium chloride. Dry (magnesium sulfate) and concentrate to give the title compound as a solid.
$^1$H NMR (CDCl$_3$) δ 8.93 (s, 1H), 8.76 (s, 2H), 4.00 (s, 6H), 3.13 (s, 3H).

5-Methanesulfonyl-N-methyl-N-propyl-isophthalamic acid

Dissolve 5-methanesulfonyl-isophthalic acid dimethyl ester (1.45 g, 5.33 mmol) in acetone (16 mL) and add a solution of NaOH (210 mg, 5.33 mmol) in methanol (2.5 mL). Stir at room temperature 1 h and concentrate. Partition between diethyl ether and water. Acidify the water layer to about pH=1 with 1 N HCl. Collect and dry the white precipitate. Dissolve the precipitate (500 mg, 1.95 mmol) in DMF (20 mL), add 1-(3-dimethylamino-propyl)-3-ethyl-carbodiimide hydrochloride (374 mg, 1.95 mmol) and 1-hydroxybenzotriazole (263 mg, 1.95 mmol) and stir at room temperature 40 min. Add methyl-propylamine (568 mg, 7.78 mmol) and stir at room temperature 14 h. Dilute with ethyl acetate, wash with 10% aqueous potassium carbonate, 0.1 N citric acid, 1 N lithium chloride and saturated aqueous sodium chloride. Dry (magnesium sulfate), concentrate and purify (silica gel chromatography, eluting with 50:50 to 0:100 ethyl acetate:hexanes) to give the amide ester intermediate (340 mg). Dissolve in THF (10 mL) and add 1 N lithium hydroxide (5 mL, 5 mmol). Stir at room temperature 3 h and pour into 1

N HCl (20 mL). Extract with ethyl acetate, wash with saturated aqueous sodium chloride, dry (magnesium sulfate), filter and concentrate to give the title compound as a solid.

MS (ES): m/z=300.1 [M+H].

Preparation 92

5-Dimethylsulfamoyl-isophthalic acid monomethyl ester

Dissolve commercially available 5-chlorosulfonyl-isophthalic acid dimethyl ester (422 mg, 1.43 mmol) in THF (10 mL) and add dimethylamine (2.0 M in THF, 2.5 mL, 5 mmol). Stir at room temperature 3 h, dilute with ethyl acetate, wash with 10% aqueous potassium carbonate, 0.1 N citric acid and saturated aqueous sodium chloride. Dry (magnesium sulfate), filter and concentrate. Dissolve the residue in acetone (10 mL) and methanol (5 mL). Add a solution of NaOH (60 mg, 1.43 mmol) in methanol (0.7 mL). Stir at room temperature 16 h and acidify with 1 N HCl to about pH=1. Partition between ethyl acetate and water, dry (magnesium sulfate) and concentrate to give the title compound.

MS (ES): m/z=288.0 [M+H].

Preparation 93

N-methyl-5-(2-methylpropenyl)-N-propyl-isophthalamic acid 5-(2-Methylprgopenyl)-isophthalic acid diethyl ester Dissolve commercially available 5-hydroxymethyl-isophthalic acid diethyl ester (2.0 g, 7.91 mmol) in dichloromethane (30 mL) and add this solution to Dess-Martin periodinane (3.69 g, 8.71 mmol) in dichloromethane (30 mL). Stir 30 min at room temperature and pour into saturated aqueous sodium bicarbonate (100 mL) containing sodium thiosulfate (25 g). Extract with diethyl ether (200 mL), dry (magnesium sulfate), concentrate and purify (silica gel plug, washing with 20:80 ethyl acetate:hexanes) to give the aldehyde. Suspend isopropyltriphenylphosphonium iodide (4.76 g, 11 mmol) in THF (40 mL). Add potassium tert-butoxide (1.23 g, 11 mmol), then a solution of the aldehyde prepared above in THF (40 mL). Stir at room temperature for 30 min, dilute with water and ethyl acetate. Wash the organic layer with saturated aqueous sodium chloride, dry (magnesium sulfate), concentrate and purify (silica gel chromatography, eluting with 0:100 to 5:95 ethyl acetate:hexanes) to give the title compound as an oil (535 mg, 25%).

$^1$H NMR (CDCl$_3$) δ 8.49 (s, 1H), 8.07 (s, 2H), 6.31 (s, 1H), 4.40 (q, J=6.8 Hz, 4H), 1.93 (s, 3H), 1.87 (s, 3H), 1.41 (t, J=6.8 Hz, 6H).

N-Methyl-5-(2-methylpropenyl)-N-propyl-isophthalamic acid

Dissolve 5-(2-methylpropenyl)-isophthalic acid diethyl ester (535 mg, 1.94 mmol) in acetone (10 mL) and add a solution of NaOH (77 mg, 1.94 mmol) in methanol (2 mL). Stir at room temperature 2 days and concentrate. Dissolve in water and wash with diethyl ether. Acidify the water layer to about pH=1 with 1 N HCl and extract with dichloromethane. Dry the dichloromethane layer over magnesium sulfate, filter and concentrate. Dissolve the residue in DMF (10 mL) and add 1-(3-dimethylamino-propyl)-3-ethyl-carbodiimide hydrochloride (409 mg, 2.13 mmol) and 1-hydroxybenzotriazole (288 mg, 2.13 mmol). After 30 min, add methyl-propyl-amine (283 mg, 3.87 mmol) and triethylamine (665 mg, 6.58 mmol) in DMF (2 mL). Stir at room temperature 1 h and dilute with ethyl acetate. Wash with 10% aqueous potassium carbonate, 0.1 N citric acid, 1 N lithium chloride and saturated aqueous sodium chloride and concentrate. Dissolve the residue in THF (20 mL) and add 1 N lithium hydroxide (10 mL, 10 mmol). Stir at room temperature for 4 h and acidify to about pH=1 with 1 N HCl. Extract with dichloromethane, dry (magnesium sulfate), filter and concentrate to give the title compound as a solid (220 mg, 41%).

MS (ES): m/z=276.1=[M+H].

Preparation 94

6-Fluoro-5-methanesulfonyl-N-methyl-N-propyl-isophthalamic acid

3-Bromo-5-chlorosulfonyl-4-fluorobenzoic acid

Heat 3-bromo-4-fluorobenzoic acid (6.25 g, 26.2 mmol) in chlorosulfonic acid (15 mL) at 125° C. for 120 h. Cool to room temperature and add dropwise to about 125 mL ice water. Collect the filtered solid as the title compound.

MS (ES): m/z=317.1 [M+H].

3-Bromo-4-fluoro-5-methanesulfonylbenzoic acid

To sodium thiosulfite (2.6 g, 20.7 mmol) and sodium bicarbonate (1.74 g, 20.7 mmol) in water (20 mL) at 75° C. add 3-bromo-5-chlorosulfonyl-4-fluorobenzoic acid (6.25 g, 19.7 mmol) in portions over 5 min. After 1 h, cool to room temperature and add chloroacetic acid (5.29 g, 56 mmol) and NaOH (1.18 g, 29.5 mmol) and reflux 16 h. Cool to room temperature and collect the title compound as a solid MS (ES): m/z=297.1 [M+H].

3-Bromo-4-fluoro-5-methanesulfonyl-N-methyl-N-propyl-benzamide

Mix 3-bromo-4-fluoro-5-methanesulfonylbenzoic acid (1.6 g, 5.04 mmol), 1-(3-dimethylamino-propyl)-3-ethyl-carbodiimide hydrochloride (968 mg, 5.04 mmol) and 1-hydroxybenzotriazole (680 mg, 5.04 mmol) in DMF (20 mL) at room temperature for 20 min. Add methyl-propylamine (368 mg, 5.04 mmol) and triethylamine (520 mg, 15.1 mmol) and stir at room temperature for 1 h. Dilute with ethyl acetate, wash with 10% aqueous potassium carbonate, 0.1 N citric acid, 1 N lithium chloride and saturated aqueous sodium chloride, concentrate and purify (silica gel chromatography, eluting with 10:90 to 50:50 ethyl acetate:hexanes) to give the title compound as an oil.

MS(ES): m/z=352.0, 354.0[M+E].

6-Fluoro-5-methanesulfonyl-N-methyl-N-propyl-isophthalamic acid

Mix 3-bromo-4-fluoro-5-methanesulfonyl-N-methyl-N-propyl-benzamide (1.36 g, 3.86 mmol), palladium acetate (337 mg, 1.5 mmol) and 1,4-bis(diphenylphosphino)-butane (1.35 g, 3.17 mmol) in DMSO (60 mL), tert-butanol (40 mL), triethylamine (3.88 mL) and water (0.22 mL) under an atmosphere of carbon monoxide (100 psi) at 90° C. for 18 h. Cool to room temperature and filter. Pour the mixture into water and wash thoroughly with ethyl acetate. Extract the organic layer with 10% aqueous potassium carbonate. Acidify the aqueous layer and extract with ethyl acetate. Dry (magnesium sulfate) and concentrate to give the title compound.

MS (ES): m/z=318.0 [M+H].

Preparation 95

5-(Methanesulfonyl-methylamino)-N-methyl-N-propyl-isophthalamic acid

5-Amino-N-methyl-N-propyl-isophthalamic acid methyl ester

Mix 5-nitro-isophthalic acid monomethylester (3.0 g, 13.32 mmol), 1-(3-dimethylaminopropyl)-3-ethylcarbodiimide hydrochloride (3.20 g, 16.65 mmol), and 1-hydroxybenzotriazole (2.25 g, 16.65 mmol) in dichloromethane (100 mL) at room temperature for 20 min. Add propylmethylamine (1.46 g, 16.65 mmol) and triethylamine (3.36 g, 33.3 mmol). Stir at room temperature for 1 h, dilute with ethyl acetate, wash with 10% aqueous potassium carbonate, 1 N citric acid, saturated aqueous sodium chloride and concentrate. Dissolve in ethanol (100 mL), add a slurry of 10% Pd/C (300 mg) in ethanol (10 mL) and place under a hydrogen atmosphere using a balloon and stir overnight. Flush with nitrogen, filter and concentrate to give the title compound as an oil.

MS (ES): m/z=251.1 [M+H].

5-Methanesulfonylamino-N-methyl-N-propyl-isophthalamic acid methyl ester

Dissolve 5-amino-N-methyl-N-propyl-isophthalamic acid methyl ester (1.64 g, 6.55 mmol) in dichloromethane (20 mL) and add pyridine (620 mg, 6.88 mmol) and methanesulfonyl chloride (788 mg, 6.88 mmol). Stir at room temperature for 72 h, dilute with dichloromethane, wash with 0.1 N citric acid and saturated aqueous sodium chloride. Dry (magnesium sulfate) and concentrate to give the title compound as an oil.

MS (ES): m/z=329.1 [M+H].

5-(Methanesulfonyl-methylamino)-N-methyl-N-propyl-isophthalamic acid methyl ester Mix 5-methanesulfonylamino-N-methyl-N-propyl-isophthalamic acid methyl ester (2.09 g, 6.36 mmol), iodomethane (1.35 g, 9.55 mmol), potassium carbonate (1.38 g, 10 mmol), and tetrabutylammonium bromide (206 mg, 0.64 mmol) in DMF (10 mL) at room temperature for 30 min. Dilute with ethyl acetate and wash with 10% aqueous potassium carbonate, 1 N lithium chloride and saturated aqueous sodium chloride. Dry (magnesium sulfate), concentrate and purify (silica gel chromatography, eluting with 0:100 to 40:60 ethyl acetate:dichloromethane) to give the title compound as an oil.

MS (ES): m/z=343.1 [M+H].

5-(Methanesulfonyl-methylamino)-N-methyl-N-propyl-isophthalamic acid

Dissolve 5-(methanesulfonyl-methylamino)-N-methyl-N-propyl-isophthalamic acid methyl ester (1.09 g, 3.18 mmol) in THF (80 mL) and add 1 N NaOH (16 mL, 16 mmol). Stir at room temperature for 16 h and add 5 N HCl (5 mL). Dilute with ethyl acetate, wash with saturated aqueous sodium chloride, dry (magnesium sulfate) and concentrate to give the title compound.

MS (ES): m/z=329.1 [M+H].

Preparation 96

5-Acetylamino-N-methyl-N-propyl-isophthalamic acid methyl ester

5-Acetylamino-N-methyl-N-propyl-isophthalamic acid methyl ester

Dissolve 5-amino-N-methyl-N-propyl-isophthalamic acid methyl ester (1.64 g, 6.55 mmol) in dichloromethane (20 mL) and add triethylamine (0.993 g, 9.83 mmol), then acetyl chloride (772 mg, 9.83 mmol). Stir at room temperature for 1 h, add N,N-dimethylamino propylamine (0.5 mL), stir 10 min, dilute with dichloromethane, wash with 1 N HCl and saturated aqueous sodium chloride. Dry (magnesium sulfate), filter and concentrate to give the title compound as a solid.

MS (ES): m/z=293.1 [M+H].

5-Acetylamino-N-methyl-N-propyl-isophthalamic acid methyl ester

Dissolve 5-acetylamino-N-methyl-N-propyl-isophthalamic acid methyl ester (1.35 g, 4.62 mmol) in THF (20 mL) and add sodium hydride (0.222 g, 5.54 mmol, 60% dispersion in mineral oil) Add iodomethane (977 mg, 6.93 mmol) and stir at room temperature overnight. Partition between ethyl acetate and 10% aqueous potassium carbonate, wash with saturated aqueous sodium chloride, dry (magnesium sulfate), concentrate and purify (silica gel chromatography, eluting with 0:100 to 5:95 methanol:dichloromethane) to give the N-methyl amide. Dissolve the residue in THF (60 mL) and add 1 N lithium hydroxide (20 mL). Stir at room temperature over the weekend. Acidify to about pH=1 with 1 N HCl and extract with diethyl ether. Dry (magnesium sulfate) and concentrate. Dissolve the residue in dichloromethane (20 mL) and add acetyl chloride (1 mL). Stir 1 h and wash with 0.1 N HCl and saturated aqueous sodium chloride. Dry (magnesium sulfate), and concentrate to give the title compound as a solid.

MS (ES): m/z=293.1 [M+H].

Preparation 97

5-Hydroxymethyl-N-methyl-N-propyl-isophthalamic acid

5-Hydroxymethyl-isophthalic acid monoethyl ester

Add commercially available 5-hydroxymethyl-isophthalic acid diethyl ester (5 g, 19.8 mmol) and NaOH (0.79 g, 19.8 mmol) to ethanol (100 mL). Stir for 4 h at room temperature. Concentrate and pour the residue into water (100 mL) and diethyl ether (100 mL). Separate the aqueous layer and wash it with diethyl ether (40 mL). Acidify the aqueous layer with 5 N HCl to about pH=1. Extract the acidic solution with ethyl acetate (3×40 mL). Wash the combined organic layers with water, saturated aqueous sodium chloride, dry (sodium sulfate) and concentrate to give the title compound as a solid (3.3 g, 74%).

MS (ES): m/z=225 [M+H].

5-Hydroxymethyl-N-methyl-N-propyl-isophthalamic acid ethyl ester

Mix 5-hydroxymethyl-isophthalic acid monoethyl ester (3.3 g, 14.7 mmol), N-methyl propylamine (1.5 mL, 14.7 mmol), 1-[3-(dimethylamino)propyl]-3-ethylcarbodiimide hydrochloride (2.8 g, 14.7 mmol), and 1-hydroxybenzotriazole hydrate (2.0 g, 14.7 mmol) in dichloromethane (40 mL) and DMF (4 mL). Stir at room temperature for 3 h. Concentrate and redissolve in ethyl acetate (150 mL). Wash with aqueous sodium bicarbonate solution, aqueous ammonium chloride solution, water, saturated aqueous sodium chloride, dry (sodium sulfate), concentrate and purify (silica gel chromatography, eluting with ethyl acetate and hexanes) to give the title compound (2.5 g, 61%).

MS (ES): m/z=280 [M+H].

5-Hydroxymethyl-N-methyl-N-propyl-isophthalamic acid

Mix 5-hydroxymethyl-N-methyl-N-propyl-isophthalamic acid ethyl ester (1.0 g, 3.6 mmol), 1 N NaOH (25 mL) in THF (5 mL). Stir at room temperature overnight. Wash with diethyl ether (2×20 mL). Acidify the aqueous layer with 5 N HCl to about pH=2. Extract with ethyl acetate (2×20 mL), concentrate and purify (silica gel chromatography eluting with 1% acetic acid in ethyl acetate and hexanes) to give the title compound (0.80 g, 89%).

MS (ES): m/z=252 [M+H].

Preparation 98

5-Isopropoxymethyl-N-methyl-N-propyl-isophthalamic acid

5-Isopropoxymethyl-N-methyl-N-propyl-isophthalamic acid ethyl ester

Mix dichloromethane (1.8 mL), pyridine (56 mL, 0.7 mmol), and trifluomethanesulfonic anhydride (97 µL, 0.58 mmol) to a flask at −35 to 45° C. Add premixed 5-hydroxymethyl-N-methyl-N-propyl-isophthalamic acid ethyl ester (65 mg, 0.23 mmol) in dichloromethane (4 mL) dropwise at 40° C. Stir for 5 min and quench with isopropyl alcohol (2 mL). Dilute the reaction mixture with dichloromethane (10 mL), wash with water (2×10 mL), and concentrate to give the title compound and used directly in the next step without further purification.

MS (ES): m/z=322 [M+H].

5-Isopropoxymethyl-N-methyl-N-propyl-isophthalamic acid

Dissolve the crude 5-isopropoxymethyl-N-methyl-N-propyl-isophthalamic acid ethyl ester (0.23 mmol) in 5 N NaOH (1 mL) and methanol (2 mL). Stir at room temperature for 15 min, concentrate methanol and redissolve the residue in water (20 mL). Wash with diethyl ether (2×10 mL), acidify the aqueous layer with 5 N HCl to about pH=1. Extract with dichloromethane to give the title compound.

MS (ES): m/z=294 [M+H].

Preparation 99

5-Isopropoxy-N-methyl-N-propyl-isophthalamic acid

5-Isopropoxy-isophthalic acid dimethyl ester

Stir 5-hydroxy-isophthalic acid dimethyl ester (4 g, 19.0 mmol), 2-iodopropane (10.2 mL, 101 mmol), and potassium carbonate (4 g, 28.9 mmol) in acetone (20 mL) at 60° C.

overnight. Cool to room temperature and pour into ethyl acetate (100 mL) and 5% aqueous ammonium chloride solution (100 mL). Separate the organic layer and wash it with water, saturated aqueous sodium chloride, dry (sodium sulfate), and concentrate to give the title compound and which is used directly in the next step without further purification.

$^1$HNMR (CDCl$_3$) δ 8.24 (d, J=0.8 Hz, 1H), 7.72 (s, 2H), 4.68-4.62 (m, 1H), 3.93 (s, 6H), 1.35 (d, J=6 Hz, 6H).

5-Isopropoxy-isophthalic acid monomethyl ester

Stir 5-isopropoxy-isophthalic acid dimethyl ester (3.7 g, 14.7 mmol) and NaOH (0.56 g, 14 mmol) in methanol (100 mL) and water (2 mL) overnight at room temperature. Concentrate methanol and redissolve the residue in diethyl ether (100 mL) and water (100 mL). Separate the layers and wash with diethyl ether. Concentrate the diethyl ether layer and recover 5-isopropoxy-isophthalic acid dimethyl ester (0.45 g). Acidify the aqueous layer with 5 N HCl to about pH=2, extract with ethyl acetate (3×50 mL). Wash the combined organic layers with saturated aqueous sodium chloride, dry (sodium sulfate) and concentrate to give the title compound (3.0 g, 86%).

MS (ES): m/z=237 [M+H].

5-Isopropoxy-N-methyl-N-propyl-isophthalamic acid methyl ester

Mix 5-isopropoxy-isophthalic acid monomethyl ester (3 g, 12.7 mmol), methyl propyl amine (1.3 mL, 12.7 mmol), 1-[3-(dimethylamino)propyl]-3-ethylcarbodiimide hydrochloride (2.4 g, 12.7 mmol), and 1-hydroxybenzotriazole hydrate (1.7 g, 12.7 mmol) in dichloromethane (50 mL) and stir overnight at room temperature. Dilute with dichloromethane (50 mL), wash with water, 5% aqueous ammonium chloride solution, 5% aqueous sodium bicarbonate solution, dry (sodium sulfate) and concentrate to give the title product which is used directly without further purification.

MS (ES): m/z=294 [M+H].

5-Isopropoxy-N-methyl-N-propyl-isophthalamic acid

Dissolve crude 5-isopropoxy-N-methyl-N-propyl-isophthalamic acid ethyl ester (12.7 mmol) in 1 N lithium hydroxide (50 mL) and THF (50 mL). Stir at room temperature for 4 h. Dilute with water (100 mL). Wash with diethyl ether (3×30 mL), and acidify the aqueous layer with 5 N HCl to about pH=1. Extract with ethyl acetate to give the title compound (3.1 g, 87% over 2 steps).

MS (ES): m/z=280 [M+H].

The compounds of Preparation 100-101 may be prepared essentially as described in Preparation 99 using pyrrolidine or piperidine as the amine.

| Prep | Compound | MS (ES) [M + H] |
|---|---|---|
| 100 | N-Methyl-N-propyl-5-(pyrrolidine-1-carbonyl)-isophthalamic acid | 319 |
| 101 | N-Methyl-5-(piperidine-1-carbonyl)-N-propyl-isophthalamic acid | 333 |

Preparation 102

5-Methoxymethyl-N-methyl-N-propyl-isophthalamic acid

5-Methoxymethyl-N-methyl-N-propyl-isophthalamic acid ethyl ester

Stir 5-hydroxymethyl-N-methyl-N-propyl-isophthalamic acid ethyl ester (1.1 g, 3.9 mmol) in THF (20 mL). Add sodium hydride (0.78 g, 60% in mineral oil) and iodomethane (729 μL, 11.7 mmol). Stir at room temperature for 3 h. Concentrate to give the title product which is used directly in the next step without further purification.
MS (ES): m/z=294 [M+H].

5-Methoxymethyl-N-methyl-N-propyl-isophthalamic acid

Dissolve the crude 5-methoxymethyl-N-methyl-N-propyl-isophthalamic acid ethyl ester (3.9 mmol) in 5 N NaOH (2 mL) and water (10 mL). Stir at room temperature for 30 min. Dilute with water (20 mL). Wash with dichloromethane, and acidify the aqueous layer with 5 N HCl to about pH=2. Extract with dichloromethane and concentrate to give the title compound (0.96 g, 93%). MS (ES): m/z=266 [M+H].

Preparation 103

5-[1,3]Dioxolan-2-yl-N-methyl-N-propyl-isophthalamic acid

5-Formyl-N-methyl-N-propyl-isophthalamic acid ethyl ester

Mix 5-hydroxymethyl-N-methyl-N-propyl-isophthalamic acid ethyl ester (2.8 g, 10 mmol) and Dess-Martin periodinane (5.1 g, 12 mmol) in dichloromethane (50 mL) in an ice-bath. Stir the mixture overnight at room temperature. Dilute with dichloromethane (50 mL) and quench it with premixed sodium thiosulfate (1.5 g) in 5% aqueous sodium bicarbonate solution (50 mL). Filter the slurry through a filtering agent and separate the organic layer. Dry (sodium sulfate), concentrate and purify (silica gel chromatography, eluting with 50:50 ethyl acetate:hexanes) to give the title compound (2.2 g, 79%).
MS (ES): m/z=278 [M+H].

5-[1,3]Dioxolan-2-yl-N-methyl-N-propyl-isophthalamic acid

Mix 5-formyl-N-methyl-N-propyl-isophthalamic acid ethyl ester (580 mg, 2.1 mmol), ethane-1,2-diol (0.35 mL, 6.3 mmol), and boron trifluoride diethyl etherate (0.2 mL, 1.6 mmol) in THF (5 mL) and stir for 1.5 h. Add additional ethane-1,2-diol (0.35 mL, 6.3 mmol) and stir for 20 min. Add 1 N NaOH (10 mL) and stir for 1 h. Add additional 5 N NaOH (1 mL) and stir for 30 min. Dilute the reaction mixture with water (10 mL) and wash with diethyl ether (2×10 mL). Acidify the aqueous layer with 0.5 N HCl to about pH=5. Extract with dichloromethane (3×20 mL), dry (sodium sulfate) and concentrate to give the title compound as a crude residue that is used in the next step without further purification.
MS (ES): m/z=294 [M+H].

The compounds of Preparation 104-107 may be prepared essentially as described in Preparation 103 using the appropriate diols or thiols.

| Prep | Compound | MS (ES) [M + H] |
| --- | --- | --- |
| 104 | 5-[1,3]Dioxan-2-yl-N-methyl-N-propyl-isophthalamic acid | |
| 105 | 5-[1,3]Dithiolan-2-yl-N-methyl-N-propyl-isophthalamic acid | |
| 106 | 5-[1,3]Dithian-2-yl-N-methyl-N-propyl-isophthalamic acid | |
| 107 | N-Methyl-5-[1,3]oxathiolan-2-yl-N-propyl-isophthalamic acid | 310 |

Preparation 108

5-Cyclopropanecarbonyl-N-methyl-N-propyl-isophthalamic acid

5-(Cyclopropyl-hydroxymethyl)-N-methyl-N-propyl-isophthalamic acid ethyl ester Add cyclopropyl magnesium bromide (0.8 M in THF, 1.3 mL, 1.02 mmol) dropwise to a solution of 5-formyl-N-methyl-N-propyl-isophthalamic acid ethyl ester (283 mg, 1.02 mmol) in THF (5 mL) at −10° C. After stirring at 0° C. for 1.5 h, quench the mixture with 5% aqueous ammonium chloride solution while maintaining the temperature below 5° C. Extract with ethyl acetate (3×30 mL), dry (sodium sulfate) concentrate and purify (silica gel chromatography, eluting with ethyl acetate and hexanes) to give the title compound (122 mg, 38%).
MS (ES): m/z=320 [M+H].

5-Cyclopropanecarbonyl-N-methyl-N-propyl-isophthalamic acid ethyl ester

Mix 5-(cyclopropyl-hydroxymethyl)-N-methyl-N-propyl-isophthalamic acid ethyl ester (122 mg, 0.38 mmol) and Dess-Martin periodinane (245 mg, 0.57) in CDCl$_3$ (5 mL) and stir at room temperature for 2 h. Quench the reaction mixture with premixed sodium thiosulfate (500 mg) in 5% aqueous sodium carbonate solution (5 mL). Separate the organic layer and extract the aqueous layer with dichloromethane (2×5 mL). Combine organic layers and concentrate to give the title compound as a crude residue which is used in the next step without further purification.
MS (ES): m/z=318 [M+H].

5-Cyclopropanecarbonyl-N-methyl-N-propyl-isophthalamic acid

Stir the crude 5-cyclopropanecarbonyl-N-methyl-N-propyl-isophthalamic acid ethyl ester (0.38 mmol) in 1 N NaOH (1 mL) and ethanol (1 mL) for 3 h at room temperature. Dilute the mixture with water (5 mL) and wash the aqueous solution with diethyl ether (2×3 mL). Acidify with 1 N HCl (1 mL) and extract with ethyl acetate (3×5 mL). Wash the combined organic layer with saturated aqueous sodium chloride, dry (sodium sulfate) and concentrate to give the title compound as a crude residue which is used in the next step without further purification.
MS (ES): m/z=290 [M+H].

Preparation 109

N-Methyl-5-(2-oxo-pyrrolidin-1-yl)-N-propyl-isophthalamic acid

5-Iodo-isophthalic acid monomethyl ester

Dissolve 5-iodo-isophthalic acid (5 g, 15.6 mmol), NaOH (600 mg, 14.8 mmol) in a mixture of methanol (100 mL), acetone (20 mL) and water (2 mL). Stir at room temperature overnight. Concentrate and redissolve the residue in diethyl ether (100 mL) and water (100 mL). Separate the aqueous layer and wash with diethyl ether (50 mL). Acidify the washed solution with 5 N HCl to about pH=1. Stir for 30 min at room temperature and filter off solid. Wash the solid with water and dry to give the title compound (3.7 g, 77%).

5-Iodo-N-methyl-N-propyl-isophthalamic acid methyl ester

Mix 5-iodo-isophthalic acid monomethyl ester (3.6 g), N-methyl propyl amine (1.2 mL, 11.8 mmol), 1-[3-(dimethylamino)propyl]-3-ethylcarbodiimide hydrochloride (2.3 g, 11.8 mmol), and 1-hydroxybenzotriazole hydrate (1.6 g, 11.8 mmol) in dichloromethane (40 mL) and stir at room temperature for 4 h. Dilute with dichloromethane (20 mL), wash with water, 5% aqueous ammonium chloride solution, 5% aqueous sodium bicarbonate solution. Dry (sodium sulfate), concentrate and purify (silica gel chromatography, eluting with ethyl acetate and hexanes) to give the title compound (3.2 g, 74%).

MS (ES): m/z=362 [M+H].

N-Methyl-5-(2-oxopyrrolidin-1-yl)-N-propyl-isophthalamic acid methyl ester

Mix 5-iodo-N-methyl-N-propyl-isophthalamic acid methyl ester (220 mg, 0.61 mmol), 2-pyrrolidone (56 µL, 0.73 mmol), ethane-1,2-diamine (4 µL, 0.061 mmol), cesium carbonate (398 mg, 1.22) and copper (I) iodide (12 mg, 0.061 mmol) in 1,4-dioxane (4 mL). Heat the mixture to 110° C. for 1 h then stir at room temperature overnight. Dilute with dichloromethane and filter through a filtering agent. Concentrate and purify (silica gel chromatography, eluting with ethyl acetate and hexanes) to give the title compound (100 mg, 52%).

MS (ES): m/z=319 [M+H].

N-Methyl-5-(2-oxopyrrolidin-1-yl)-N-propyl-isophthalamic acid

Stir N-methyl-5-(2-oxopyrrolidin-1-yl)-N-propyl-isophthalamic acid methyl ester (100 mg, 0.314 mmol) in 1 N NaOH (0.5 mL) and methanol (0.5 mL) at room temperature for 3 days. Dilute the mixture with water (1 mL) and wash the aqueous solution with diethyl ether. Acidify with 1 N HCl (0.55 mL) and extract with ethyl acetate (3×2 mL). Concentrate the organic layers to give the title compound as a crude residue which is used in the next step without further purification.

MS (ES): m/z=305 [M+H].

Preparation 110

2'-Fluoro-5-(methyl-propylcarbamoyl)-biphenyl-3-carboxylic acid

2'-Fluoro-5-(methyl-propylcarbamoyl)-biphenyl-3-carboxylic acid methyl ester Add 1,4-dioxane (10 mL), 5-iodo-N-methyl-N-propyl-isophthalamic acid methyl ester (0.720 g, 2.00 mmol), 2-fluorophenylboronic acid (0.364 g, 2.60 mmol), tetrakis(triphenylphosphine)palladium (0) (0.347 g, 0.300 mmol), and potassium carbonate (0.829 g, 6.00 mmol) to a sealed flask flushed with nitrogen. Heat the mixture overnight and cool to room temperature. Filter the mixture though a filtering agent, concentrate and purify (silica gel chromatography, eluting with 4:96 ethyl acetate:hexanes) to give the title compound (0.297 g, 45%).

MS (ES): m/z=329.9 [M+H].

2'-Fluoro-5-(methyl-propylcarbamoyl)-biphenyl-3-carboxylic acid

Chill a solution of 2'-fluoro-5-(methyl-propylcarbamoyl)-biphenyl-3-carboxylic acid methyl ester (0.297 g, 0.903 mmol) in MeOH (2 mL) and THF (2 mL) in an ice bath. Add 2 N NaOH (1.35 mL, 2.70 mmol) to the mixture and stir at room temperature for 3 h. Acidify the solution to about pH=2 and concentrate to one half of the solvent. Partition the residue between ethyl acetate and $H_2O$ and extract the aqueous layer with ethyl acetate (2×15 mL). Wash the combined organic extract with saturated aqueous sodium chloride, dry (magnesium sulfate) and concentrate to give the title compound.

MS (ES): m/z=314.2 [M−H].

The compounds of Preparation 111-112 are prepared essentially as described in Preparation 110 using the appropriate difluorophenylboronic acid.

| Prep | Compound | MS (ES) [M − H] |
|---|---|---|
| 111 | 2',6'-Difluoro-5-(methyl-propylcarbamoyl)-biphenyl-3-carboxylic acid | 333.2 |
| 112 | 2',4'-Difluoro-5-(methyl-propylcarbamoyl)-biphenyl-3-carboxylic acid | 332.1 |

Preparation 113

N-Methyl-N-propyl-5-(pyridine-3-carbonyl)-isophthalamic acid

N-Methyl-N-propyl-5-tributylstannanyl-isophthalamic acid methyl ester

Add toluene (40 mL), 5-iodo-N-methyl-N-propyl-isophthalamic acid methyl ester (5.0 g, 13.8 mmol), bis(tributyltin) (8.3 mL, 16.6 mmol), and trans-dichlorobis(triphenylphosphine)palladium (II) (0.968 mg, 1.38 mmol) to a sealed flask flushed with nitrogen. Heat the mixture at 100° C. for 24 h and cool to room temperature. Filter the mixture though a filtering agent, concentrate and purify (silica gel chromatography, eluting with 10:90 to 20:80 ethyl acetate:hexanes) to give the title compound (4.58 g, 63%).

N-Methyl-N-propyl-5-(pyridine-3-carbonyl)-isophthalamic acid methyl ester

Add THF (3 mL), N-methyl-N-propyl-5-tributylstannanyl-isophthalamic acid methyl ester (0.524 g, 1.00 mmol), nicotinoyl chloride hydrochloride (0.232 g, 1.30 mmol), 2-(di-tert-butylphosphino)biphenyl (0.045 g, 0.151 mmol), bis(dibenzylidene-acetone)palladium (0) (029 g, 0.05 mmol) to a sealed tube flushed with nitrogen. Heat the mixture at 50° C. for 16 h and cool to room temperature. Filter the mixture though a filtering agent, concentrate and purify (silica gel chromatography, eluting with 50:50 to 100:0 ethyl acetate:hexanes) to give the title compound (0.070 g, 21%).
MS (ES): m/z=340.9 [M+H].

N-Methyl-N-propyl-5-(pyridine-3-carbonyl)-isophthalamic acid

Chill a solution of N-methyl-N-propyl-5-(pyridine-3-carbonyl)-isophthalamic acid methyl ester (0.070 g, 0.206 mmol) in MeOH (1 mL) and THF (1 mL) in an ice bath. Add 1 N NaOH (0.62 mL, 0.62 mmol) and stir at room temperature for 2 h. Acidify the solution to about pH=2 and concentrate to one half of the solvent. Partition the residue between ethyl acetate and H$_2$O. Extract the aqueous layer with ethyl acetate (2×15 mL). Wash the combined organic extract with saturated aqueous sodium chloride, dry (magnesium sulfate) and concentrate to give the title compound (72%).
MS (ES): m/z=326.9 [+H].

The compound of Preparation 114 is prepared essentially as described in Preparation 113 using the appropriate nicotinoyl chloride hydrochloride.

| Prep | Compound | MS (ES) [M − H] |
|---|---|---|
| 114 | N-Methyl-N-propyl-5-(pyridine-2-carbonyl)-isophthalamic acid | 333.2 |

Preparation 115

5-(Difluorophenyl-methyl)-N-methyl-N-propyl-isophthalamic acid

N-Methyl-5-(2-phenyl-[1,3]dithian-2-yl)-N-propyl-isophthalamic acid methyl ester Add boron trifluoride diethyl etherate (0.358 mL, 2.83 mmol) to a solution of 5-benzoyl-N-methyl-N-propyl-isophthalamic acid methyl ester (0.192 g, 0.566 mmol) in dichloromethane (3 mL) at 0° C. Add 1,3-propanedithiol (0.114 mL, 1.12 mmol). Stir at room temperature overnight. Partition between water (20 mL) and dichloromethane (20 mL) and extract the aqueous layer with dichloromethane (20 mL). Dry (magnesium sulfate), concentrate and purify (silica gel chromatography, eluting with 30:70 ethyl acetate:hexanes) to give the title compound (51%).
MS (ES): m/z=430.0 [M+H].

5-(Difluorophenyl-methyl)-N-methyl-N-propyl-isophthalamic acid methyl ester

Chill a solution of nitrosonium tetrafluoroborate (0.074 g, 0.63 mmol), hydrogen fluoride-pyridine (0.250 mL) in dichloromethane (2 mL) in a plastic bottle. Add a solution of N-methyl-5-(2-phenyl-[1,3]dithian-2-yl)-N-propyl-isophthalamic acid methyl ester (0.123 g, 0.286 mmol) in dichloromethane (1 mL) to the bottle and stir at room temperature for 2 h. Dilute the solution with dichloromethane (5 mL) and filter though a pad of magnesium sulfate and aluminum oxide. Wash solid with ethyl acetate (50 mL), concentrate and purify (silica gel chromatography, eluting with 20:80 to 30:70 ethyl acetate:hexanes) to give the title compound (42%).
MS (ES): m/z=361.9 [M+H].

5-(Difluorophenyl-methyl)-N-methyl-N-propyl-isophthalamic acid

Chill a solution of 5-(difluorophenyl-methyl)-N-methyl-N-propyl-isophthalamic acid methyl ester (0.043 g, 0.119 mmol) in THF (1 mL) in an ice bath. Add 1 N lithium hydroxide (0.18 mL, 0.18 mmol) and stir at room temperature for 3 h. Acidify the solution to about pH=2 and concentrate to one half of the solvent. Partition the residue between ethyl acetate and H$_2$O. Extract the aqueous layer with ethyl acetate (2×10 mL). Wash the combined organic extract with saturated aqueous sodium chloride, dry (magnesium sulfate) and concentrate to give the title compound (95%).
MS (ES): m/z=346.2 [M+H].

Preparation 116

N-Methyl-N-propyl-5-thiazol-2-yl-isophthalamic acid

5-Iodo-isophthalic acid monomethyl ester

Dissolve 5-iodo-isophthalic acid dimethyl ester (10 g, 31.2 mmol) in methanol (90 mL) and cool to 0° C. Add 2 N NaOH (15.6 mL) dropwise and slowly warm up to room temperature. Stir overnight and acidify to about pH=3 with 5 N HCl. Extract with ethyl acetate (2×50 mL). Wash the combined organic layers by water, saturated aqueous sodium chloride, dry (magnesium sulfate) and concentrate to give the title compound as a crude residue which is used in the next step without further purification.
MS (ES): m/z=305.0 [M−H].

5-Iodo-N-methyl-N-propyl-isophthalamic acid methyl ester

Dissolve 5-iodo-isophthalic acid monomethyl ester (9.34 g, 30.5 mmol), 1-hydroxybenzotriazole hydrate (4.86 g, 36 mmol) and a solution of 1,3-dicyclohexylcarbodiimide (1 M in dichloromethane; 36 mL) in THF (70 mL). Cool to 0° C. for 15 min. Add methylpropylamine (3.69 mL, 36 mmol) and stir at room temperature for 12 h. Filter the solution though a filtering agent and wash with ethyl acetate, concentrate and purify (silica gel chromatography, eluting with 20:80 ethyl acetate:hexanes) to give the title compound.

N-Methyl-N-propyl-5-thiazol-2-yl-isophthalamic acid methyl ester

To a previously nitrogen-flushed vessel, add zinc dust (<10 microns, 0.196 g, 3 mmol) and 1,2-dibromoethane (0.023 mL, 0.27 mmol) to THF (0.5 mL). Heat the solution until bubbles appear. Repeat the heating twice and cool to room temperature. Add chlorotrimethylsilane (15 µL) and 2-bromothiazole (90 µL, 1 mmol) in THF (0.4 mL). Stir at room temperature for 15 min. Add 5-iodo-N-methyl-N-propyl-isophthalamic acid methyl ester (541 mg, 1.5 mmol), tetrakis(triphenylphosphine)palladium (0) (15 mg) and flush the mixture with nitrogen again before heating to reflux for 10 h. Cool to room temperature, concentrate and purify (silica gel chromatography, eluting with 0:100 to 40:60 ethyl acetate:hexanes) to give the title compound (95%).
MS (ES): m/z=319.2 [M+H].

N-Methyl-N-propyl-5-thiazol-2-yl-isophthalamic acid

Dissolve N-Methyl-N-propyl-5-thiazol-2-yl-isophthalamic acid methyl ester (150 mg, 0.47 mmol) in methanol (6

Preparation 117

N-Methyl-5-(1-methyl-1H-imidazol-2-yl)-N-propyl-isophthalamic acid

N-Methyl-5-(1-methyl-1H-imidazol-2-yl)-N-propyl-isophthalamic acid methyl ester Add n-butyl lithium (2.0 M in pentane, 0.78 mL, 1.55 mmol) dropwise over 30 min to a previously nitrogen-flushed, flame-dried vessel containing 1-methyl-1H-imidazole (0.12 mL, 1.5 mmol) in THF (10 mL) at −78° C., and stir for 30 min at the same temperature. Warm the solution to 0° C. and add dropwise zinc (II) chloride (1.0 M in diethyl ether, 4.5 mL, 4.5 mmol) over 10 min. Stir the mixture at the same temperature for 1 h and at room temperature for 30 min. Add 5-iodo-N-methyl-N-propyl-isophthalamic acid methyl ester (361 mg, 1.0 mmol) and tetrakis(triphenylphosphine)palladium (0) (12 mg) under nitrogen before heating the reaction to reflux for 20 min. Cool to room temperature, concentrate and purify (silica gel chromatography, eluting with 0:100 to 8:92 methanol:dichloromethane) to give the title compound.

N-Methyl-5-(1-methyl-1H-imidazol-2-yl)-N-propyl-isophthalamic acid

Dissolve N-methyl-5-(1-methyl-1H-imidazol-2-yl)-N-propyl-isophthalamic acid methyl ester (100 mg, 0.32 mmol) in methanol (10 mL). Dropwise add 1 N lithium hydroxide (0.38 mL) and stir overnight at room temperature. Add 2 N NaOH (0.1 mL) and stir for 48 h at room temperature. Acidify the mixture to about pH=6 by DOWEX® 50WX2-100 ion exchange resin and filter. Concentrate filtrate and lyophilize (1:1 acetonitrile:water) to give the title compound.

MS (ES): m/z=300 [M−H].

Preparation 118

5-Benzoyl-N-methyl-N-propyl-isophthalamic acid

N-Methyl-N-propyl-5-tributylstannanyl-isophthalamic acid methyl ester

Dissolve 5-iodo-N-methyl-N-propyl-isophthalamic acid methyl ester (3.0 g, 8.3 mmol), bis(tributyltin) (4.99 mL, 9.97 mmol) and trans-dichlorobis(triphenylphosphine)palladium (II) (582 mg, 0.83 mmol) in toluene (20 mL) in a previously degassed sealed vessel. Flush the mixture with nitrogen and heat the sealed mixture for 24 h at 90° C. Cool the reaction to room temperature and filter though a filtering agent. Concentrate the filtrate and purify (silica gel chromatography, eluting with 0:100 to 20:80 ethyl acetate:hexanes) to give the title compound (66%).

5-Benzoyl-N-methyl-N-propyl-isophthalamic acid methyl ester

Dissolve N-methyl-N-propyl-5-tributylstannanyl-isophthalamic acid methyl ester (480 mg, 0.8 mmol), benzoyl chloride (117 mg), tris(dibenzylideneacetone)dipalladium (0) (19.3 mg) and 2-(di-tert-butylphosphino)biphenyl (34.5 mg) in chloroform (8 mL) in a previously degassed sealed vessel. Flush the mixture with nitrogen and heat the sealed mixture overnight at 60° C. Cool the reaction to room temperature and filter though a filtering agent. Concentrate the filtrate and purify (silica gel chromatography, eluting with 0:100 to 30:70 ethyl acetate:hexanes) to give the title compound (66%).

5-Benzoyl-N-methyl-N-propyl-isophthalamic acid

Dissolve 5-benzoyl-N-methyl-N-propyl-isophthalamic acid methyl ester (60 mg, 0.17 mmol) in methanol (4 mL). Add dropwise 1 N lithium hydroxide (0.23 mL) and stir overnight at room temperature. Acidify the mixture to about pH=6 by 5 N HCl and concentrate to near dryness. Dilute the residue with ethyl acetate and wash with saturated aqueous sodium chloride solution, dry (magnesium sulfate) and concentrate to give the title compound (83%).

MS (ES): m/z=324 [M−H].

Preparation 119

5-(Furan-2-carbonyl)-N-methyl-N-propyl-isophthalamic acid

5-(Furan-2-carbonyl)-N-methyl-N-propyl-isophthalamic acid methyl ester

Dissolve N-methyl-N-propyl-5-tributylstannanyl-isophthalamic acid methyl ester (500 mg, 1 mmol), furan-2-carbonyl chloride (0.12 mL), tris(dibenzylideneacetone)-dipalladium (0) (19 mg) and 2-(di-tert-butylphosphino)biphenyl (35 mg) in THF (6 mL) in a previously degassed, sealed vessel. Flush the mixture with nitrogen and heat the sealed mixture overnight at 50° C. Cool the reaction to room temperature and filter though a filtering agent. Concentrate the filtrate and purify (silica gel chromatography, 0:100 to 38:62 ethyl acetate:hexanes) to give the title compound (50%).

5-(Furan-2-carbonyl)-N-methyl-N-propyl-isophthalamic acid

Dissolve 5-(furan-2-carbonyl)-N-methyl-N-propyl-isophthalamic acid methyl ester (100 mg, 0.3 mmol) in methanol (10 mL). Add dropwise 2 N NaOH (0.225 mL) and stir overnight at room temperature. Acidify the mixture to about pH=6 by 5 N HCl and concentrate to near dryness. Dilute the residue with ethyl acetate and wash by saturated aqueous sodium chloride solution, dry (magnesium sulfate) and concentrate.

MS (ES): m/z=314.2 [M−H].

Preparation 120

5-(Difluorofuran-2-ylmethyl)-N-methyl-N-propyl-isophthalamic acid

5-(2-Furan-2-yl-[1,3]dithiolan-2-yl)-N-methyl-N-propyl-isophthalamic acid methyl ester Dissolve 5-(furan-2-carbonyl)-N-methyl-N-propyl-isophthalamic acid methyl ester (290 mg, 0.88 mmol) in dichloromethane (2 mL). Cool to 0° C., add a solution of ethane-1,2-dithiol (0.22 mL, 2.2 mmol) and then add a solution of boron trifluoride dibutyl etherate (0.66 mL, 5.2 mmol) in dichloromethane (5 mL). Warm the mixture to room temperature and stir overnight. Quench with water and dilute with dichloromethane. Wash the organic layer by saturated aqueous sodium chloride, dry (magnesium sulfate), concentrate and purify (silica gel chromatography, eluting with 0:100 to 30:70 ethyl acetate:hexanes) to give the title compound (38%).

5-(Difluorofuran-2-yl-methyl)-N-methyl-N-propyl-isophthalamic acid methyl ester

Under nitrogen and in a plastic vessel, dissolve nitrosonium tetrafluoroborate (84.8 μg, 0.72 mmol) and pyridinium poly(hydrogen fluoride) (70% hydrogen fluoride, 30% pyridine, 300 μL) in dichloromethane (2 mL) and cool to 0° C. Add dropwise 5-(2-furan-2-yl-[1,3]dithiolan-2-yl)-N-methyl-N-propyl-isophthalamic acid methyl ester in dichloromethane (1.5 mL) to the mixture, warm up to room temperature and stir for 2 h. Dilute the mixture with dichloromethane (20 mL) and filter the organic liquid though a pad of aluminum oxide and magnesium sulfate mixture. Concentrate the filtrate and purify (silica gel chromatography, 1:99 to 30:70 ethyl acetate:hexanes) to give the title compound (30%).

MS (ES): m/z=352 [M+H].

5-(Difluorofuran-2-yl-methyl)-N-methyl-N-propyl-isophthalamic acid

Dissolve 5-(difluorofuran-2-yl-methyl)-N-methyl-N-propyl-isophthalamic acid methyl ester (30 mg, 0.08 mmol) in methanol (2 mL). Add dropwise 2 N NaOH (0.06 mL) and stir overnight at room temperature. Acidify the mixture to about pH=6 with 5 N HCl and concentrate to near dryness. Dilute the residue with ethyl acetate, wash with saturated aqueous sodium chloride solution, dry (magnesium sulfate) and concentrate to give the title compound (66%).

MS (ES): m/z=335 [M−H].

Preparation 121

N-Methyl-5-(2-methylacryloyl)-N-propyl-isophthalamic acid

N-Methyl-5-(2-methylacryloyl)-N-propyl-isophthalamic acid methyl ester

Dissolve N-methyl-N-propyl-5-tributylstannanyl-isophthalamic acid methyl ester (885 mg, 168 mmol), 2-methylacryloyl chloride (172 mg, 1.64 mmol), tris(dibenzylideneacetone)dipalladium (46 mg, 0.05 mmol) and tricyclohexylphosphine (46 mg, 0.16 mmol)) in chloroform (15.5 mL) in a previously degassed vessel. Flush the mixture with nitrogen gas and heat the sealed mixture overnight at 60° C. Cool to room temperature and filter though a filtering agent. Concentrate the filtrate and purify (silica gel chromatography, eluting with 0:100 to 20:80 ethyl acetate:hexanes) to give the title compound.

N-Methyl-5-(2-methylacryloyl)-N-propyl-isophthalamic acid

Dissolve N-methyl-5-(2-methylacryloyl)-N-propyl-isophthalamic acid methyl ester (50 mg, 0.16 mmol) in methanol (3 mL). Add 2 N NaOH (0.12 mL) and stir overnight at room temperature. Add 2 N NaOH (0.05 mL) and stir for an additional 3 h. Acidify the mixture to about pH=6 using DOWEX® 50WX2-100 ion exchange resin and filter. Concentrate filtrate to give the title compound which is used in the next step without further purification.

MS (ES): m/z=288 [M−H].

Preparation 122

5-Isobutyryl-N-methyl-N-propyl-isophthalamic acid 5-(1-Hydroxy-2-methyl-propyl)-N-methyl-N-propyl-isophthalamic acid methyl ester Dissolve N-methyl-5-(2-methylacryloyl)-N-propyl-isophthalamic acid methyl ester (80 mg, 0.26 mmol) in ethyl acetate (25 mL) under nitrogen. Add Raney® nickel (100 mg) and hydrogenate the reaction for 2 h at room temperature under an atmosphere of hydrogen gas (40 psi). Filter the reaction and concentrate to give the crude title product.

MS (ES): m/z=308 [M+H].

5-Isobutyryl-N-methyl-N-propyl-isophthalamic acid methyl ester

Dissolve 5-(1-hydroxy-2-methyl-propyl)-N-methyl-N-propyl-isophthalamic acid methyl ester (70 mg, 0.23 mmol) in dichloromethane (3 mL) and add Dess-Martin periodinane (174 mg, 0.41 mmol) at room temperature. Stir the mixture overnight and quench with 10% aqueous sodium bisulfite solution. Extract the organic layer, wash with saturated aqueous sodium chloride solution, dry (magnesium sulfate), concentrate and purify (silica gel chromatography, eluting with 30:70 ethyl acetate:hexanes) to give the title compound.

Isobutyryl-N-methyl-N-propyl-isophthalamic acid

Dissolve 5-isobutyryl-N-methyl-N-propyl-isophthalamic acid methyl ester (50 mg, 0.16 mmol) in methanol (3 mL) and add dropwise 2 N NaOH (0.16 mL). Stir the mixture at room temperature for 6 h, store overnight at 4° C. and acidify to about pH=6 by 5 N HCl. Concentrate to near dryness and dilute the residue with ethyl acetate. Wash with saturated aqueous sodium chloride solution and extract the organic layer, dry (magnesium sulfate) and concentrate to give the title compound.

MS (ES): m/z=289[M−H].

Preparation 123

5-Nitro-N,N-dipropyl-isophthalamic acid

5-Nitro-N,N-dipropyl-isophthalamic acid methyl ester

Dissolve commercially available monomethyl 5-nitroisophthalate (3.000 g, 14.07 mmol), 1-(3-dimethylaminopropyl)-3-ethylcarbodiimide hydrochloride (3.238 g, 16.89 mmol), 1-hydroxybenzotriazole hydrate (2.587 g, 16.89 mmol) and 4-dimethylaminopyridine (0.172 g, 1.407 mmol) and triethylamine (5.885 mL, 42.22 mmol) in dichloromethane (309 mL) and stir the mixture at room temperature for 0.5 h. Add dipropylamine (2.026 mL, 14.78 mmol) and triethylamine (5.885 mL, 42.22 mmol) and stir the mixture overnight. Concentrate and redissolve the residue in ethyl acetate and wash with two portions each of 5% aqueous potassium hydrogen sulfate solution, 5% aqueous sodium bicarbonate solution, saturated aqueous sodium chloride, dry (magnesium sulfate) and concentrate to give the title compound (3.885 g, 90%).

MS (ES): m/z=309.1 [M+H].

5-Nitro-N,N-dipropyl-isophthalamic acid

Dissolve 5-nitro-N,N-dipropyl-isophthalamic acid methyl ester (1.000 g, 3.243 mmol) and lithium hydroxide (0.089 g, 3.730 mmol) in a mixture of THF (3.16 mL), water (1.58 mL) and methanol (1.58 mL). Stir the mixture at room temperature until the starting material is consumed. Concentrate and acidify with 1 N HCl. Extract with ethyl acetate, dry (magnesium sulfate) and concentrate to give the title compound (0.874 g, 92%).

MS (ES): m/z=293.1 [M-H].

Preparation 124

5-Acetyl-N-methyl-N-propyl-isophthalamic acid

5-Formyl-N-methyl-N-propyl-isophthalamic acid ethyl ester

Treat a solution 5-hydroxymethyl-N-methyl-N-propyl-isophthalamic acid ethyl ester (5.79 g, 20.7 mmol) in dichloromethane (50 mL) at −78° C. with oxalyl chloride (1.99 mL, 22.8 mmol), DMSO (3.5 mL, 49.5 mmol), and triethylamine (8.6 mL, 62.1 mmol). Stir at −78° C. for 30 min, warm to room temperature and stir for 1 h. Quench with ice and extract with dichloromethane (100 mL). Wash with saturated aqueous NaHCO$_3$, saturated aqueous sodium chloride, dry (magnesium sulfate) concentrate and purify (silica gel chromatography, eluting with 40:60 to 50:50 ethyl acetate:hexanes) to give the title compound (4.53 g, 78%).

MS (ES): m/z=278.3 [M+H].

5-(1-Hydroxyethyl)-N-methyl-N-propyl-isophthalamic acid ethyl ester

Treat a solution of 5-formyl-N-methyl-N-propyl-isophthalamic acid ethyl ester (400 mg, 1.44 mmol) in THF (10 mL) at 0° C. with methylmagnesium bromide (3.0 M in diethyl ether, 0.58 mL, 1.73 mmol). Stir at 0° C. for 1 h and quench with saturated aqueous ammonium chloride solution. Extract with ethyl acetate (100 mL), dry (magnesium sulfate), concentrate and purify (silica gel chromatography, eluting with 40:60 to 70:30 ethyl acetate:hexanes) to give the title compound (250 mg, 59%).

MS (ES): m/z=293.9 [M+H].

5-Acetyl-N-methyl-N-propyl-isophthalamic acid ethyl ester

Treat a solution of 5-(1-hydroxyethyl)-N-methyl-N-propyl-isophthalamic acid ethyl ester (250 mg, 0.85 mmol) in dichloromethane (10 mL) with Dess-Martin periodinane (470 mg, 1.11 mmol). Stir at room temperature for 2.5 h, quench with 10% aqueous sodium sulfate, extract with ethyl acetate (50 mL). Wash with 10% aqueous sodium sulfate solution, saturated aqueous sodium chloride, dry (magnesium sulfate), concentrate and purify (silica gel chromatography, eluting with 50:50 ethyl acetate:hexanes) to give the title compound (196 mg, 78%).

MS (ES): m/z=291.9 [M+H].

5-Acetyl-N-methyl-N-propyl-isophthalamic acid

Treat a solution of 5-acetyl-N-methyl-N-propyl-isophthalamic acid ethyl ester (196 mg, 0.67 mmol) in ethanol (7 mL) at room temperature with 2 N NaOH (0.5 mL, 1.0 mmol) for 12 h. Acidify to about pH=3 using 1 N HCl. Extract with ethyl acetate (50 mL), dry (magnesium sulfate) and concentrate to give the title compound (179 mg, 95%).

MS (ES): m/z=263.9 [M+H].

Preparation 125

N-Methyl-N-propyl-5-(2,2,2-trifluoro-acetyl)-isophthalamic acid

N-Methyl-N-propyl-5-(2,2,2-trifluoro-1-hydroxyethyl)-isophthalamic acid

N-Methyl-N-propyl-5-(2,2,2-trifluoro-1-hydroxyethyl)-isophthalamic acid ethyl ester Treat a solution of 5-formyl-N-methyl-N-propyl-isophthalamic acid ethyl ester (500 mg, 1.8 mmol) in THF (10 mL) at 0° C. with trimethyl(trifluoromethyl)silane (0.5 M in THF, 5.4 mL, 2.70 mmol) and tetrabutylammonium fluoride (1.0 M in THF, 2.7 mL, 2.70 mmol). Stir at 0° C. for 2 h and quench with saturated aqueous NaHCO$_3$. Extract with ethyl acetate (100 mL), dry (magnesium sulfate) and concentrate to give the crude title product which is used in the next step without further purification.

MS (ES): m/z=347.9 [+H].

N-Methyl-N-propyl-5-(2,2,2-trifluoroacetyl)-isophthalamic acid ethyl ester

Treat a solution of N-methyl-N-propyl-5-(2,2,2-trifluoro-1-hydroxyethyl)-isophthalamic acid ethyl ester (1.8 mmol) in dichloromethane (20 mL) with Dess-Martin reagent at room temperature for 2 h. Quench with 10% aqueous sodium sulfite and extract with ethyl acetate (100 mL). Wash the organic layer with 10% aqueous sodium sulfite, saturated aqueous sodium chloride, dry (magnesium sulfate), concentrate and purify (silica gel chromatography, eluting with 60:40 ethyl acetate:hexanes) to give the title compound (330 mg) which is contaminated with recovered N-methyl-N-propyl-5-(2,2,2-trifluoro-1-hydroxyethyl)-isophthalamic acid ethyl ester in a ratio of about 4:1).

MS (ES): m/z=346.3 [M+H].

N-Methyl-N-propyl-5-(2,2,2-trifluoroacetyl)-isophthalamic acid

N-Methyl-N-propyl-5-(2,2,2-trifluoro-1-hydroxyethyl)-isophthalamic acid

Treat a solution of a mixture of N-methyl-N-propyl-5-(2,2,2-trifluoroacetyl)-isophthalamic acid (330 mg, 0.96 mmol) and N-methyl-N-propyl-5-(2,2,2-trifluoro-1-hydroxyethyl)-isophthalamic acid in a ratio of about 4:1 in ethanol (12 mL) with 2 N NaOH (0.72 mL, 1.43 mmol). Stir at room temperature for 12 h, add more 2 N NaOH (1.5 eq.), and stir overnight at room temperature. Acidify to about pH=3 with 1 N HCl. Extract with ethyl acetate (50 mL), dry (magnesium sulfate) and concentrate to give a mixture of the two title products, N-methyl-N-propyl-5-(2,2,2-trifluoroacetyl)-isophthalamic acid (MS (ES): m/z=316.1 [M−H] and N-methyl-N-propyl- 5-(2,2,2-trifluoro-1-hydroxyethyl)-isophthalamic acid (MS (ES): m/z=318.1 [M−H]) in a ratio of about 4:1 respectively.

Preparation 126

5-Difluoromethoxy-N-methyl-N-propyl-isophthalamic acid

5-Difluoromethoxy-isophthalic acid dimethyl ester

React 5-hydroxy-isophthalic acid dimethyl ester (5.88 g, 28 mmol), methyl 2-chloro-2,2-difluoroacetate (5.9 mL, 56 mmol), cesium carbonate (18.2 g, 56 mmol) in methyl ethyl ketone at reflux for 2 days. Cool to room temperature, filter though a filtering agent, wash with ethyl acetate, concentrate and purify (silica gel chromatography, eluting with 10:90 to 30:70 ethyl acetate:hexanes) to give the title compound (2.7 g, 37%).

MS (ES): m/z=261.2 [M+H].

5-Difluoromethoxy-isophthalic acid monomethyl ester

Treat a solution of 5-difluoromethoxy-isophthalic acid dimethyl ester (2.7 g, 10.4 mmol) in methanol (35 mL) with 2 N NaOH (5.2 mL, 10.4 mmol) at room temperature for 12 h. Acidify to about pH=3 using 5 N HCl. Extract with ethyl acetate, wash the organic layer with water, saturated aqueous sodium chloride, dry (sodium sulfate) and concentrate to give the crude title product which is used in the next step without further purification.

MS (ES): m/z=245.1 [M−H].

5-Difluoromethoxy-N-methyl-N-propyl-isophthalamic acid methyl ester

Treat a solution containing crude 5-difluoromethoxy-isophthalic acid monomethyl ester (2.5 g, 10 mmol) in THF (20 mL) at room temperature with 1-hydroxybenzotriazole hydrate (1.62 g, 12 mmol), 1,3-dicyclohexylcarbodiimide (12 mL, 1 N, 12 mmol), and n-methylpropylamine (1.23 mL, 12 mmol). Stir at room temperature overnight, filter through a filtering agent, wash with 1:1 ethyl acetate:hexanes (50 mL). Concentrate the combined filtrates and purify (silica gel chromatography, eluting with 0:100 to 30:70 ethyl acetate:hexanes) to give the title compound as a solid (1.6 g, 53%).

MS (ES): m/z=302 [M+H].

5-Difluoromethoxy-N-methyl-N-propyl-isophthalamic acid

Treat a solution of 5-difluoromethoxy-N-methyl-N-propyl-isophthalamic acid methyl ester (1.6 g, 5.3 mmol) in methanol (30 mL) with 2 N NaOH (4 mL, 8.0 mmol). Stir at room temperature overnight and acidify to about pH=4 using 1 N HCl. Extract with ethyl acetate (150 mL), wash the organic layer with saturated aqueous sodium chloride, dry (magnesium sulfate) and concentrate to give the title compound which is used in the next step without further purification.

MS (ES): m/z=286.1 [M−H].

Preparation 127

N-Methyl-N-propyl-5-pyridin-4-yl-isophthalamic acid

5-Iodo-N-methyl-N-propyl-isophthalamic acid benzyl ester

Add benzyl chloroformate (5.96 mL, 41.77 mmol) to a solution of 5-iodo-N-methyl-N-propyl-isophthalamic acid (14.5 g, 41.77 mmol), triethylamine (6.4 mL, 45.95 mmol) and 4-dimethylaminopyridine (2.55 g, 20.88 mmol) in dichloromethane (125 mL) at 0° C. and at room temperature for 40 h. Wash the solution twice with a saturated aqueous solution of NaHCO$_3$, 5% aqueous solution of potassium hydrogen sulfate, saturated aqueous sodium chloride, dry (magnesium sulfate), and concentrate. Dissolve the crude in dichloromethane, wash with a 0.5 N NaOH solution, H$_2$O, saturated aqueous sodium chloride, dry (magnesium sulfate) and concentrate to give the title compound (6 g, 33%).

MS (ES): m/z=438.1 [M+H].

N-Methyl-N-propyl-5-pyridin-4-yl-isophthalamic acid benzyl ester

Add pyridine-4-boronic acid (2.361 g, 19.21 mmol) and 2 N sodium carbonate (19.21 mL, 38.42 mmol) to a solution of 5-iodo-N-methyl-N-propyl-isophthalamic acid benzyl ester (6.000 g, 13.72 mmol) in ethylene glycol dimethyl ether (206 mL) under nitrogen at room temperature. Add tetrakis(triphenylphosphine)palladium (0) (0.634 g, 0.549 mmol) and reflux for 20 h. Cool to room temperature and concentrate. Add ethyl acetate, separate the organic layer and extract the aqueous layer with ethyl acetate (4×). Wash the combined organic layers with H$_2$O, saturated aqueous sodium chloride, dry (magnesium sulfate), concentrate and purify (silica gel chromatography, eluting with ethyl acetate) to give the title compound (56%).

MS (ES): m/z=389.2[M+H].

N-Methyl-N-propyl-5-pyridin-4-yl-isophthalamic acid

Stir a mixture of N-methyl-N-propyl-5-pyridin-4-yl-isophthalamic acid benzyl ester (1.900 g, 4.891 mmol), 10% palladium on carbon (0.208 g) in MeOH (50 mL) under an atmosphere of hydrogen gas (1 atm) for 0.5 h. Filter through a filtering agent and concentrate to give the title compound (quantitative yield).

MS (ES): m/z=299.2 [+H].

Preparation 128

6-Fluoro-5-(methanesulfonyl-methylamino)-N-methyl-N-propyl-isophthalamic acid

5-Bromo-2-fluorophenylamine

Dissolve tin (II) chloride hydrate (86.2 g, 455 mmol), 4-bromo-2-fluoro-1-nitro-benzene (20.0 g, 90.9 mmol) and water (16.4 mL, 909 mmol) in ethanol (475 mL). Reflux the mixture for 6 h. Cool to room temperature and concentrate to a minimal volume. Add ethyl acetate (400 mL) and saturated aqueous sodium bicarbonate solution (1.6 L) to the residue and stir vigorously for 1 h. Filter through a filtering agent and wash with ethyl acetate (2 L). Separate the layers and extract the aqueous layer with ethyl acetate (1 L). Combine the organic layers, wash with saturated aqueous sodium chloride (500 mL), dry (magnesium sulfate) and concentrate to give the title compound as a solid (16.8 g, 97%).

MS (ES): m/z=190 [M+].

Dibenzyl-(5-bromo-2-fluorophenyl)-amine

Stir a slurry of 4-bromo-2-fluorophenylamine (15.0 g, 78.9 mmol), potassium carbonate (43.6 g, 316 mmol) and benzyl bromide (28.2 mL, 237 mmol) in DMF (75 mL) at 100° C. for 18 h. Cool to room temperature and dilute with dichloromethane (200 mL). Filter the slurry and wash with dichloromethane. Wash the filtrate with water (500 mL) and 1 N lithium chloride (250 mL). Dry (magnesium sulfate), concentrate and purify (silica gel chromatography, eluting with 5:95 to 35:65 dichloromethane:hexanes) to give the title compound as a solid (26.2 g, 90%).

MS(ES): m/z=372[M+2].

5-Bromo-3-dibenzylamino-2-fluorobenzoic acid

Add dropwise a solution of dibenzyl-(5-bromo-2-fluorophenyl)-amine (4.00 g, 10.8 mmol) in THF (12 mL) to a solution of lithium diisopropylamide, freshly prepared by adding n-butyllithium (1.6 M in hexanes, 7.09 mL, 11.3 mmol) to diisopropylamine (1.74 mL, 12.4 mmol) in THF (25 mL) at −78° C. Stir the resulting yellow solution at −78 C for 45 min. Pour into a dry ice slurry containing about 100 g in dry THF (40 mL). Stir the solution until it reaches room temperature. Concentrate the solution and dissolve the residue in 10% aqueous potassium hydroxide solution (40 mL) and extract with diethyl ether (70 mL). Acidify the aqueous layer to about pH=3 with concentrated HCl. Extract the aqueous layer with diethyl ether (2×200 mL). Combine the organic layers and wash with water (150 mL), dry (magnesium sulfate) and concentrate to give the title compound as a solid (1.81 g, 40%).

MS (ES): m/z=416 [M+2].

5-Bromo-3-dibenzylamino-2-fluorobenzoic acid ethyl ester

Dissolve 5-bromo-3-dibenzylamino-2-fluorobenzoic acid (1.53 g, 3.69 mmol) in ethanol (40 mL). Add concentrated sulfuric acid (0.2 mL) as a catalyst and heat to at reflux for 1 day. Cool to room temperature and concentrate. Dissolve the residue in diethyl ether (30 mL) and wash with 10% aqueous potassium carbonate solution (10 mL) and water (10 mL). Dry (magnesium sulfate) and concentrate to give the title compound as an oil (1.50 g, 92%).

MS (ES): m/z=442 [M].

5-Dibenzylamino-4-fluoro-isophthalic acid 3-ethyl ester

Combine 5-bromo-3-dibenzylamino-2-fluorobenzoic acid ethyl ester (4.74 g, 10.7 mmol), palladium (II) acetate (0.72 g, 3.20 mmol), 1,4-bis(diphenylphosphino)butane (2.84 g, 6.66 mmol), triethylamine (7.90 mL, 56.7 mmol), DMSO (150 mL), tert-butyl alcohol (100 mL), and water (0.50 mL, 27.8 mmol). Place mixture in a container pressurized to 100 psi with carbon monoxide and heat at 80° C. for 24 h. Filter the reaction mixture over a pad of filtering agent. Pour the filtrate into water (500 mL), acidify with 5 N HCl and extract (2×500 mL) with ethyl acetate. Dry (magnesium sulfate), concentrate and purify (silica gel chromatography, eluting with 4:96 methanol:dichloromethane) to give the title compound as a solid (2.40 g, 55%).

MS (ES): m/z=408 [M+H].

5-Dibenzylamino-6-fluoro-N-methyl-N-propyl-isophthalamic acid ethyl ester

Dissolve the 1-hydroxybenzotriazole hydrate (139 mg, 1.03 mmol), 1-[3-(dimethylamino)propyl]-3-ethylcarbodiimide hydrochloride (197 mg, 1.03 mmol) and 5-dibenzylamino-4-fluoro-isophthalic acid 3-ethyl ester (381 mg, 0.934 mmol) in dichloromethane (10.0 mL). Stir for 30 min. Add methylpropyl amine (68.3 mg, 0.93 mmol) to the reaction mixture. Stir the reaction for 4 h. Add 10% aqueous potassium carbonate solution (10 mL). Extract with dichloromethane (2×50 mL). Combine the organic layers, wash with water (20 mL), saturated aqueous sodium chloride (20 mL), dry (magnesium sulfate), concentrate and purify (silica gel chromatography, eluting with 40:60 ethyl acetate:hexanes) to give the title compound (279 mg, 65%).

MS (ES): m/z=463 [M+H].

5-Amino-6-fluoro-N-methyl-N-propyl-isophthalamic acid ethyl ester

Dissolve 5-dibenzylamino-6-fluoro-N-methyl-N-propyl-isophthalamic acid ethyl ester (275 mg, 0.595 mmol) in ethanol (6 mL). Add 10% Pd/C to the solution (50 mg). Stir the black slurry under a balloon containing hydrogen gas for 2.5 days. Filter the slurry through a pad of filtering agent and wash with ethanol. Concentrate the filtrate to give the title compound as a crude product.

MS (ES): m/z=283 [M+H].

6-Fluoro-5-methanesulfonylamino-N-methyl-N-propyl-isophthalamic acid ethyl ester Dissolve 5-amino-6-fluoro-N-methyl-N-propyl-isophthalamic acid ethyl ester (0.162 g, 0.58 mmol) in dichloromethane (1.5 mL). Cool to 0° C. Add pyridine (51.2 µL, 0.63 mmol) and methanesulfonyl chloride (44.5 µL, 0.58 mmol) to the solution. Allow the reaction to warm to room temperature and stir for 2 days. Quench with water (10 mL) and extract with dichloromethane (2×30 mL). Combine the organic layers and wash with saturated aqueous sodium chloride (20 mL), dry (magnesium sulfate), concentrate and purify (silica gel chromatography, eluting with 40:60 ethyl acetate:dichloromethane) to give the title compound as a solid (157 mg, 76%).

MS (ES): m/z=361 [M+H].

6-Fluoro-5-(methanesulfonyl-methylamino)-N-methyl-N-propyl-isophthalamic acid ethyl ester Dissolve 6-fluoro-5-methanesulfonylamino-N-methyl-N-propyl-isophthalamic acid ethyl ester (0.160 g, 0.444 mmol) in DMF (1.0 mL). Add potassium carbonate (44.4 mg, 0.32 mmol), iodomethane (41.5 µL, 0.67 mmol) and tetrabutylammonium bromide (14.3 mg, 0.04 mmol) to the solution. Stir the resulting slurry at room temperature for 16 h. Quench with saturated aqueous sodium sulfate solution (10 mL) and extract with ethyl acetate (3×30 mL). Combine the organic layers and dry (magnesium sulfate). Azeotrope the residue with xylenes to remove residual DMF. Purify (silica gel chromatography, eluting with 40:60 ethyl acetate:dichloromethane) to give the title compound as a solid (111 mg, 67%).

MS (ES): m/z=375 [M+H].

6-Fluoro-5-(methanesulfonyl-methylamino)-N-methyl-N-propyl-isophthalamic acid

Dissolve the 6-fluoro-5-(methanesulfonyl-methylamino)-N-methyl-N-propyl-isophthalamic acid ethyl ester (110 mg, 0.30 mmol) in THF (7.5 mL). Add 1 N sodium hydroxide solution (1.48 mL, 1.48 mmol) and stir the resulting biphasic mixture vigorously for 4 h. Acidify with 1 N HCl (1.55 mL, 1.55 mmol) and concentrate the solution to a volume of about 3 mL. Extract the solution with diethyl ether (2×20 μL). Combine the organic layers, dry (magnesium sulfate) and concentrate to give the title compound as a solid (95.2 mg, 93%).

MS (ES): m/z=347 [M+H].

Preparation 129

5-(Methyl-propylcarbamoyl)-1-oxy-nicotinic acid 5-(Methyl-propylcarbamoyl)-1-oxy-nicotinic acid methyl ester Mix 5-(methyl-propylcarbamoyl)-nicotinic acid methyl ester (396 mg, 1.67 mmol) and 3-chloroperoxybenzoic acid (1.2 g, 50-85%) in dichloromethane (50 mL) and stir over the weekend. Dilute with dichloromethane (50 mL) and wash with 5% aqueous sodium bicarbonate solution (20 mL), dry (sodium sulfate), and concentrate to give the crude title compound which is used in the next step without further purification.

MS (ES): m/z=253 [M+H].

5-(Methyl-propylcarbamoyl)-1-oxy-nicotinic acid

Dissolve crude 5-(methyl-propylcarbamoyl)-1-oxy-nicotinic acid methyl ester (0.72 mmol) in 1 N sodium hydroxide (1.4 mL) and methanol (2 mL). Stir at room temperature overnight. Concentrate organic and redissolve the residue in water (15 mL). Wash with dichloromethane (3×10 mL), acidify with 1 N HCl to about pH=2 and concentrate to give the crude title product which is directly in the next step.

MS (ES): m/z=239 [M+H].

Preparation 130

2-Chloro-5-(methyl-propylcarbamoyl)-nicotinic acid

2-Chloro-5-(methyl-propylcarbamoyl)-nicotinic acid methyl ester

Stir 5-(methyl-propylcarbamoyl)-1-oxy-nicotinic acid methyl ester (353 mg, 1.40 mmol) in phosphorus oxychloride (2 mL) at 100° C. for 1 h. Cool to room temperature and quench with saturated aqueous sodium acetate (50 mL) and ethyl acetate (100 mL). Separate the organic layer, wash with water (50 mL), dry (sodium sulfate), concentrate and purify (silica gel chromatography, eluting with ethyl acetate and hexanes) to give the title compound (208 mg, 55%).

MS (ES): m/z=271 [M+H].

2-Chloro-5-(methyl-propylcarbamoyl)-nicotinic acid

Dissolve 2-chloro-5-(methyl-propylcarbamoyl)-nicotinic acid methyl ester (96 mg, 0.35 mmol) in 1 N sodium hydroxide (0.71 mL, 0.71 mmol) and methanol (2 mL). Stir at room temperature for 2 h. Concentrate organic and redissolve the residue in water (15 mL). Wash with dichloromethane (3×10 mL), acidify the aqueous layer with 1 N HCl to about pH=2. Extract with dichloromethane, dry (sodium sulfate) and concentrate to give the crude title product which is used in the next step without further purification.

MS (ES): m/z=257 [M+H].

Preparation 131

2-Dipropylcarbamoyl-isonicotinic acid

4-Chloropyridine-2-carboxylic acid dipropylamide

Stir a solution of 4-chloro-2-pyridine carboxylic acid (1.0 g, 6.3 mmol), 1-hydroxybenzotriazole (850 mg, 6.3 mmol), 1-(3-dimethylaminopropyl)-3-ethylcarbodiimide hydrochloride (1.21 g, 6.3 mmol), dipropyl amine (862 μL, 6.3 mmol), and triethylamine (1.75 mL, 12.6 mmol) in dichloromethane (63 mL) at room temperature over the weekend. Wash the solution with 0.1 N citric acid (2×50 mL), saturated aqueous sodium bicarbonate (50 mL), saturated aqueous sodium chloride (50 mL), dry (sodium sulfate), concentrate and purify (silica gel chromatography, eluting with 10:90 to 20:80 ethyl acetate:hexanes)to give the title compound (1.02 g, 67%).

2-Dipropylcarbamoyl-isonicotinic acid

Heat a mixture of 4-chloropyridine-2-carboxylic acid dipropylamide (1.02 g, 4.2 mmol), palladium (II) acetate (11.3 mg, 0.05 mmol), triethylamine (1.0 mL, 7.1 mmol), 1,1'-bis(3,5-dimethylphenylphosphino)ferrocene (138 mg, 0.55 mmol), DMF (35 mL) and water (5 mL) at 110° C. under an atmosphere of carbon monoxide (200 psi) overnight. Filter the reaction, concentrate and purify (silica gel chromatography, eluting with 0:100 to 10:90 methanol:chloroform) to give the title compound (75 mg, 7%).

MS (ES): m/z=251 [M+H].

Preparation 132

5-(Methyl-propylcarbamoyl)-nicotinic acid 5-(Methyl-propylcarbamoyl)-nicotinic acid Add a solution of pyridine-3,5-dicarboxylic acid (220 mg, 1.32 mmol), diisopropylethylamine (918 μL, 5.28 mmol), and DMF (1.5 mL) in dichloromethane (10 mL) to 2-chlorotritylchloride resin (11.0 g, 1.1 mmol) in a peptide synthesis vessel and mix for 3 h. Filter and wash the resin with a 17:2:1 mixture of dichloromethane:methanol:diisopropylethylamine, followed by dichloromethane. Add a solution of methylpropylamine (225 μL, 2.2 mmol), and benzotriazole-1-yl-oxy-tris-pyrrolidinophosphonium hexafluorophosphate (1.14 g, 2.2 mmol) in dichloromethane (10 mL) to the resin and mix for 1 h. Filter and wash the resin with dichloromethane (2×10 mL). Add a solution of 5% trifluoroacetic acid in dichloromethane (10 mL) to the resin and let stand for 10 min. Filter the resin and wash with dichloromethane (2×10 mL). Combine the filtrates and concentrate to give the title compound (110 mg, 50%).

MS (ES): m/z=223 [M+H].

Preparation 133

4-Dipropylcarbamoyl-pyridine-2-carboxylic acid 2-chloro-N,N-dipropylisonicotinamide Stir a solution of 2-chloroisonicotinic acid (1.0 g, 6.3 mmol), 1-hydroxybenzotriazole (850 mg, 6.3 mmol), 1-(3-dimethylaminopropyl)-3-ethylcarbodiimide hydrochloride (1.21 g, 6.3 mmol), dipropyl amine (862 µL, 6.3 mmol), and triethylamine (1.75 mL, 12.6 mmol) in dichloromethane (63 mL) at room temperature over the weekend. Wash the solution with 0.1 N citric acid (2×50 mL), saturated aqueous sodium bicarbonate (50 mL), saturated aqueous sodium chloride (50 mL), dry (sodium sulfate), concentrate and purify (silica gel chromatography, eluting with 10:90 to 20:80 ethyl acetate:hexanes) to give the title compound (1.16 g, 76%).

MS (ES): m/z=241 [M+H].

4-Dipropylcarbamoyl-pyridine-2-carboxylic acid

Heat a mixture of 2-chloro-N,N-dipropylisonicotinamide (0.91 g, 3.8 mmol), palladium (II) acetate (13.2 mg), triethylamine (1.0 mL, 7.1 mmol), 1,1'-bis(3,5-dimethylphenylphosphino)ferrocene (161 mg, 0.64 mmol), DMF (35 mL) and water (5 mL) at 110° C. under an atmosphere of carbon monoxide (200 psi) overnight. Filter the reaction, concentrate and purify (silica gel chromatography, eluting with 0:100 to 10:90 methanol:chloroform) to give the title compound (486 mg, 51%).

MS (ES): m/z=251.1 [M+H].

Preparation 134

3-(Methanesulfonyl-methylamino)-benzoic acid

Prepare the title compound starting from ethyl 3-aminobenzoate according to the procedure described in WO 00/55153.

MS (ES): m/z=228.1 [M−H].

Preparation 135

(2R,4S)- and (2R,4R)-2-[(4S,5S)-3-Acetyl-4-(3,5-difluoro-benzyl)-2,2-dimethyl-oxazolidin-5-yl]-4-hexyl-pyrrolidine-1-carboxylic acid tert-butyl ester (R)-2-[(4S,5S)-3-Acetyl-4-(3,5-difluoro-benzyl)-2,2-dimethyl-oxazolidin-5-yl]-4-hex-(Z)-ylidene-pyrrolidine-1-carboxylic acid tert-butyl ester Place under argon a suspension of n-hexyltriphenylphosphonium bromide (0.420 g, 1 mmol) in 10 mL of dry THF. Add potassium tert-butoxide (0.112 g, 1 mmol). Stir the mixture for 1 h. Add a solution of (R)-2-[(4S,5S)-3-Acetyl-4-(3,5-difluoro-benzyl)-2,2-dimethyl-oxazolidin-5-yl]-4-oxo-pyrrolidine-1-carboxylic acid tert-butyl ester (0.045 g, 0.1 mmol) in 5 mL of dry THF. Stir the mixture overnight. Add water, extract with diethyl ether, dry over MgSO$_4$, concentrate under reduced pressure and purify (silica gel chromatography, eluting with ethyl ether:hexane mixtures) to give the title compound (0.04 g, 76%).

MS(ESI): m/z=521.3 (M+H)

(R)-2-[(4S,5S)-3-Acetyl-4-(3,5-difluoro-benzyl)-2,2-dimethyl-oxazolidin-5-yl]-4-hexyl-pyrrolidine-1-carboxylic acid tert-butyl ester Combine (R)-2-[(4S,5S)-3-Acetyl-4-(3,5-difluoro-benzyl)-2,2-dimethyl-oxazolidin-5-yl]-4-hex-(Z)-ylidene-pyrrolidine-1-carboxylic acid tert-butyl ester (0.04 g, 0.076 mmol), 10% palladium on carbon (4 mg) and methanol (2 mL) and stir for 2 days under 1 atmosphere of hydrogen. Add filter agent, filter and concentrate under reduced pressure to provide the desired compound as a mixture of isomers (2:1 4(S):4(R); 0.036 g, 90%). Subject isomer mixture to HPLC chromatography under acidic conditions: TFA 0.05% at pH 2.5; Organic solvent: acetonitrile; Gradient from 90 to 95% acetonitrile.

4(S)-isomer: Retention time=8.12 minutes; (0.011 g, 27.3%); MS(ESI): m/z=523.4 (M+H).

4(R)-isomer: Retention time=8.57 minutes; (0.020 g, 49.6%); MS(ESI): m/z=523.4 (M+H).

Preparation 136

(2R,4R)-2-[(4S,5S)-3-Acetyl-4-(3,5-difluorobenzyl)-2,2-dimethyloxazolidin-5-yl]-4-hydroxypyrrolidine-1-carboxylic acid tert-butyl ester (2R,4R)-2-[(4S,5S)-3-Acetyl-4-(3,5-difluorobenzyl)-2,2-dimethyloxazolidin-5-yl]-4-(4-methoxy-benzyloxy)-pyrrolidine-1-carboxylic acid tert-butyl ester Add p-toluene sulfonic acid pyridine salt (0.245 g, 1 mmol) and 2-methoxypropene (4.6 mL, 49 mmol) to a solution of (2R,4R)-2-[(1S,2S)-2-acetylamino-3-(3,5-difluorophenyl)-1-hydroxypropyl]-4-(4-methoxy-benzyloxy)-pyrrolidine-1-carboxylic acid tert-butyl ester (5.64 g, 10.55 mmol) in dichloromethane (25 mL) and acetone (25 mL). Stir 60 min and concentrate under reduced pressure. Dissolve residue in ethyl acetate and wash with saturated aqueous sodium bicarbonate, saturated aqueous sodium chloride, dry magnesium sulfate and purify on silica gel with hexanes/ethyl acetate mixtures to give the desired compound as a foam (3.49 g, 61%).

MS (ES): m/z=575 [M+H].

(2R,4R)-2-[(4S,5S)-3-Acetyl-4-(3,5-difluorobenzyl)-2,2-dimethyloxazolidin-5-yl]-4-hydroxypyrrolidine-1-carboxylic acid tert-butyl ester To an ice cold solution of (2R,4R)-2-[(4S,5S)-3-acetyl-4-(3,5-difluorobenzyl)-2,2-dimethyloxazolidin-5-yl]-4-(4-methoxy-benzyloxy)-pyrrolidine-1-carboxylic acid tert-butyl ester (7.48 g, 13.0 mmol) in 20:1 dichloromethane:water (130 mL) add 2,3-dichloro-5,6-dicyano-1,4-benzoquinone (4.71 g, 20.74 mmol). Stir 4 h in an ice bath and wash with saturated aqueous sodium bicarbonate (3×300 mL), saturated aqueous sodium chloride, dry magnesium sulfate and purify on silica gel with dichloromethane/ethyl acetate mixtures to give the title compound as a foam (5.288 g, 89%).

MS (ES): m/z=455.3 [M+H].

Preparation 137

(2R,4S)-2-[(4S,5S)-3-Acetyl-4-(3,5-difluoro-benzyl)-2,2-dimethyl-oxazolidin-5-yl]-4-hydroxy-pyrrolidine-1-carboxylic acid tert-butyl ester (2R,4S)-2-[(4S,5S)-3-Acetyl-4-(3,5-difluoro-benzyl)-2,2-dimethyl-oxazolidin-5-yl]-4-hydroxy-pyrrolidine-1-carboxylic acid tert-butyl ester Add dropwise diisopropyl azodicarboxylate (0.20 mL, 1.04 mmol) to a solution of (2R,4R)-2-[(4S,5S)-3-acetyl-4-

(3,5-difluorobenzyl)-2,2-dimethyloxazolidin-5-yl]-4-hydroxypyrrolidine-1-carboxylic acid tert-butyl ester (0.314 g, 0.69 mmol), acetic acid (0.06 mL, 1.04 mmol) and 4-diphenylphosphanyl-benzoic acid 2-trimethylsilanyl-ethyl ester (0.42 g, 1.04 mmol, prepared according to Synlett 2003 (4) p 473-476) in tetrahydrofuran (3 mL). Stir solution 18 hours, then add a 1M solution of tetrabutylammonium fluoride in tetrahydrofuran (3 mL) and stir 90 minutes. Add a 1N aqueous solution of sodium hydroxide (3 mL) and stir 30 minutes. Dilute with ethyl acetate and water. Evaporate the organic layer and dissolve in methanol (30 mL). Add sodium carbonate (0.365 g) and water (1 mL) and stir 18 hours. Evaporate and partition with ethyl acetate and water, wash organic layer with saturated sodium chloride solution, dry with magnesium sulfate and purify on silica gel with hexane/ethyl acetate mixtures to give the title compound as a foam (0.295 g, 95%).

MS (ES): m/z=455 [M+H].

Preparation 138

(2R,4R)-2-[(4S,5S)-3-Acetyl-4-(3,5-difluoro-benzyl)-2,2-dimethyl-oxazolidin-5-yl]-4-(3-methyl-but-2-phenyloxy)-pyrrolidine-1-carboxylic acid tert-butyl ester Add 95% sodium hydride (0.02 g, 0.825 mmol) portionwise over 7 minutes to a solution of (2R,4R)-2-[(4S,5S)-3-acetyl-4-(3,5-difluorobenzyl)-2,2-dimethyloxazolidin-5-yl]-4-hydroxypyrrolidine-1-carboxylic acid tert-butyl ester (0.25 g, 0.55 mmol) and 3,3-dimethylallyl bromide (0.095 mL, 0.825 mmol) in N,N-dimethyl formamide (1 mL). Stir 20 minutes. Dilute with ethyl acetate and wash with water, saturated aqueous sodium chloride, dry with magnesium sulfate and purify on silica gel with ethyl acetate/hexane mixtures to give the title compound as a foam (0.27 g, 95%).

MS (ES): m/z=523 [M+H].

The compound of Preparation 139 may be prepared essentially as described in Preparation 138.

| PREP | Compound | MS [M + H] |
|---|---|---|
| 139 | N-{(1S,2R)-1-(3,5-Difluoro-benzyl)-2-hydroxy-2-[(2R,4R)-4-(3-trifluoromethyl-benzyloxy)-pyrrolidin-2-yl]-ethyl}-acetamide hydrochloride | 495 |

Preparation 140

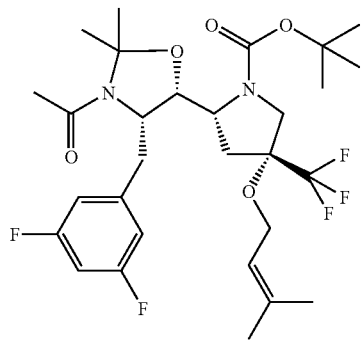

(2R,4R)-2-[(4S,5S)-3-Acetyl-4-(3,5-difluoro-benzyl)-2,2-dimethyl-oxazolidin-5-yl]-4-(3-methyl-but-2-phenyloxy)-4-trifluoromethyl-pyrrolidine-1-carboxylic acid tert-butyl ester (R)-2-[(4S,5S)-3-Acetyl-4-(3,5-difluoro-benzyl)-2,2-dimethyl-oxazolidin-5-yl]-4-oxo-pyrrolidine-1-carboxylic acid tert-butyl ester Add sulfur trioxide pyridine complex (1.99 g, 12.46 mmol) to a solution of (2R,4R)-2-[(4S,5S)-3-acetyl-4-(3,5-difluoro-benzyl)-2,2-dimethyl-oxazolidin-5-yl]-4-(3,3-dimethyl-2-oxo-butoxy)-pyrrolidine-1-carboxylic acid tert-butyl ester (2.83 g, 6.23 mmol) and triethylamine (3.5 mL, 24.9 mmol) in dimethyl sulfoxide (14 mL) at 10° C. Stir 50 minutes, dilute with ethyl acetate and wash with water, saturated aqueous sodium chloride, dry with magnesium sulfate. Purify on silica gel with dichloromethane/ethyl acetate mixtures to give the desired compound as a foam (2.69 g, 95%).

MS (ES): m/z=453 [M+H].

(2R,4R)-2-[(4S,5S)-3-Acetyl-4-(3,5-difluoro-benzyl)-2,2-dimethyl-oxazolidin-5-yl]-4-hydroxy-4-trifluoromethyl-pyrrolidine-1-carboxylic acid tert-butyl ester Add (trifluoromethyl)trimethylsilane (0.28 mL, 1.88 mmol) to an ice cold solution of (R)-2-[(4S,5S)-3-acetyl-4-(3,5-difluoro-benzyl)-2,2-dimethyl-oxazolidin-5-yl]-4-oxo-pyrrolidine-1-carboxylic acid tert-butyl ester (0.50 g, 1.11 mmol) in tetrahydrofuran (10 mL). Add tetrabutylammonium fluoride (0.035 mL of 1M solution in tetrahydrofuran). Stir 2.5 hours and add tetrabutylammonium fluoride (2 mL of 1M solution in tetrahydrofuran) and stir 2 hours. Add saturated aqueous ammonium chloride (3 mL) and dilute with ethyl acetate and water. Wash organic layer with saturated aqueous sodium chloride, dry with magnesium sulfate and purify on silica gel with dichloromethane/ethyl acetate mixtures to give the desired compound and 10% hydroxy diastereomer as a foam (0.48 g, 83%).

MS (ES): m/z=523 [M+H].

(2R,4R)-2-[(4S,5S)-3-Acetyl-4-(3,5-difluoro-benzyl)-2,2-dimethyl-oxazolidin-5-yl]-4-(3-methyl-but-2-phenyloxy)-4-trifluoromethyl-pyrrolidine-1-carboxylic acid tert-butyl ester Add 95% sodium hydride (0.024 g, 1.0 mmol) to a solution of (2R,4R)-2-[(4S,5S)-3-acetyl-4-(3,5-difluoro-benzyl)-2,2-dimethyl-oxazolidin-5-yl]-4-hydroxy-4-trifluoromethyl-pyrrolidine-1-carboxylic acid tert-butyl ester (0.104 g, 0.20 mmol) and 3,3-dimethylallyl bromide (0.047 mL, 0.40 mmol) in N,N-dimethyl formamide (2 mL). Stir 50 minutes and dilute with ethyl acetate and wash with water, saturated aqueous sodium chloride, dry with magnesium sulfate and purify on silica gel with dichloromethane/ethyl acetate mixtures to give the title compound as a foam (0.10 g, 84%).

MS (ES): m/z=591 [M+H].

The compounds of Preparations 141-142 may be prepared essentially as described in Preparation 140.

| PREP | Compound | MS [M + H] |
|------|----------|------------|
| 141 | (2R,4S)-2-[(4S,5S)-3-Acetyl-4-(3,5-difluoro-benzyl)-2,2-dimethyl-oxazolidin-5-yl]-4-(3-methyl-but-2-enyloxy)-4-trifluoromethyl-pyrrolidine-1-carboxylic acid tert-butyl ester | 591 |
| 142 | (2R,4R)-2-[(4S,5S)-3-Acetyl-4-(3,5-difluoro-benzyl)-2,2-dimethyl-oxazolidin-5-yl]-4-(2-cyclohexyl-ethoxy)-4-trifluoromethyl-pyrrolidine-1-carboxylic acid tert-butyl ester | 633 |

Preparation 143

(2R,4R)-2-[(4S,5S)-3-Acetyl-4-(3,5-difluoro-benzyl)-2,2-dimethyl-oxazolidin-5-yl]-4-(3-methyl-butoxy)-4-trifluoromethyl-pyrrolidine-1-carboxylic acid tert-butyl ester Add 20% palladium hydroxide on carbon (0.025 g) and ammonium formate (0.11 g, 1.69 mmol) to a solution of (2R,4R)-2-[(4S,5S)-3-acetyl-4-(3,5-difluoro-benzyl)-2,2-dimethyl-oxazolidin-5-yl]-4-(3-methyl-but-2-phenyloxy)-4-trifluoromethyl-pyrrolidine-1-carboxylic acid tert-butyl ester (0.10 g, 0.17 mmol) in methanol (10 mL) and heat to reflux for 60 minutes. Filter and evaporate and purify on silica gel with dichloromethane/ethyl acetate mixtures to give the title compound as a foam (0.084 g, 84%).

MS (ES): m/z=593 [M+H].

The compound of Preparation 144 may be prepared essentially as described in Preparation 143.

| PREP | Compound | MS [M + H] |
|------|----------|------------|
| 143 | (2R,4S)-2-[(4S,5S)-3-Acetyl-4-(3,5-difluoro-benzyl)-2,2-dimethyl-oxazolidin-5-yl]-4-(3-methyl-butoxy)-4-trifluoromethyl-pyrrolidine-1-carboxylic acid tert-butyl ester | 593 |

EXAMPLE 1

2-(S)-(2-{[2-(S)-sec-Butylamino-6-(methanesulfonyl-methylamino)-pyridine-4-carbonyl]-amino}-1-(S)-hydroxy-3-phenylpropyl)-3-(S)-fluoropyrrolidine-1-carboxylic acid hydrochloride and 2-(S)-(2-{[2-(S)-sec-Butylamino-6-(methanesulfonyl-methylamino)-pyridine-4-carbonyl]-amino}-1-(S)-hydroxy-3-phenylpropyl)-3,3-difluoropyrrolidine-1-carboxylic acid hydrochloride

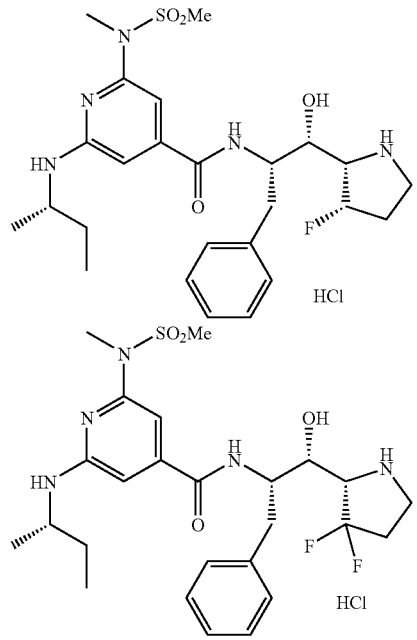

Dissolve a mixture of 2-(S)-(2-(S)-amino-1-(S)-hydroxy-3-phenylpropyl)-3-(S)-fluoropyrrolidine-1-carboxylic acid tert-butyl ester and 2-(S)-(2-(S)-amino-1-(S)-hydroxy-3-phenylpropyl)-3,3-difluoropyrrolidine-1-carboxylic acid tert-butyl ester (822 mg, 2.43 mmol) in dichloromethane (10 mL). Add 2-(S)-sec-butylamino-6-(methanesulfonyl-methylamino)-isonicotinic acid potassium salt (822 mg, 2.43 mmol), 1-(3-dimethylaminopropyl)-3-ethylcarbodiimide hydrochloride (EDCI) (512 mg, 2.67 mmol), 1-hydroxybenzotriazole hydrate (HOBt) (361 mg, 2.67 mmol) and diisopropylethylamine (0.93 mL, 5.34 mmol). Stir the reaction for 18 h at room temperature. Dilute the reaction with dichloromethane, wash with 5% aqueous potassium carbonate, dry (sodium sulfate), concentrate and purify (silica gel chromatography, eluting with 2:98 methanol:dichloromethane) to give the 2 separate title compounds (97 mg and 32 mg respectively).

MS (ES): m/z=622.3 [M+H], MS (ES): m/z=640.4 [M+H].

N-[1-Benzyl-2-(S)-(3-(S)-fluoropyrrolidin-2-yl)-2-(S)-hydroxyethyl]-2-(S)-sec-butylamino-6-(methanesulfonyl-methylamino)-isonicotinamide hydrochloride Add 4 M HCl in 1,4-dioxane (6 mL) to 2-(S)-(2-{[2-(S)-sec-butylamino-6-(methanesulfonyl-methylamino)-pyridine-4-carbonyl]-amino}-1-(S)-hydroxy-3-phenylpropyl)-3-(S)-fluoropyrrolidine-1-carboxylic acid tert-butyl ester (97 mg, 0.16 mmol) and stir at room temperature for 20 min. Concentrate the reaction to give the title compound. MS (ES): m/z=522.2 [M+H].

N-[1-Benzyl-2-(S)-(3,3-difluoropyrrolidin-2-yl)-2-(S)-hydroxyethyl]-2-(S)-sec-butylamino-6-(methanesulfonyl-methylamino)-isonicotinamide hydrochloride Add 4 M HCl in 1,4-dioxane (5 mL) to 2-(S)-(2-{[2-(S)-sec-butylamino-6-(methanesulfonyl-methylamino)-pyridine-4-carbonyl]-amino}-1-(S)-hydroxy-3-phenylpropyl)-3-difluoropyrrolidine-1-carboxylic acid tert-butyl ester (32 mg, 0.05 mmol) and stir at room temperature for 15 min. Concentrate the reaction to a residue and purify (silica gel chromatography, eluting with 4:96 methanol:dichloromethane) to give the title compound (18 mg, 62%).

MS (ES): m/z=540.3 [M+H].

The compounds of EXAMPLE 2-4 may be prepared by reacting the corresponding pyrrolidine-1-carboxylic acid tert-butyl esters with 4M HCl essentially as described in EXAMPLE 1.

| EX | Compound | MS [M + H] |
|---|---|---|
| 2 | N-[(1S,2R)-1-(3,5-Difluorobenzyl)-2-hydroxy-2-(R)-pyrrolidin-2-yl-ethyl]-acetamide hydrochloride | 299.3 |
| 3 | Toluene-4-sulfonic acid (3R,5R)-5-((1R,2S)-2-acetylamino-1-hydroxy-3-phenylpropyl)-pyrrolidin-3-yl ester hydrochloride | 433.3 |
| 4 | N-[(1S,2R)-1-(3,5-Difluorobenzyl)-2-((S)-4-fluoropyrrolidin-2-yl)-2-hydroxyethyl]-acetamide hydrochloride | 317.3 |

EXAMPLE 5

2-(S)-sec-Butylamino-N-[1-(S)-(3,5-difluorobenzyl)-2-(R)-hydroxy-2-(R)-piperidin-2-yl-ethyl]-6-(methanesulfonyl-methylamino)-isonicotinamide hydrochloride

2-(R)-[2-(S)-{[2-(S)-sec-Butylamino-6-(methanesulfonyl-methylamino)-pyridine-4-carbonyl]-amino}-3-(3,5-difluorophenyl)-1-(S)-hydroxypropyl]-piperidine-1-carboxylic acid tert-butyl ester Cool a solution of 2-(R)-[2-(S)-amino-3-(3,5-difluorophenyl)-1-(S)-hydroxypropyl]-piperidine-1-carboxylic acid tert-butyl ester (0.096 g, 0.258 mmol) and 2-(S)-sec-butylamino-6-(methanesulfonyl-methylamino)-isonicotinic acid (0.0856 g, 0.284 mmol) in dichloromethane (2 mL) in an ice bath. Add 4-methylmorpholine (0.17 mL, 1.55 mmol) and n-propylphosphonic anhydride (0.227 mL, 0.387 mmol, 50 wt % in ethyl acetate). Stir 30 min, warm to room temperature and stir 30 min. Add water (3 mL) and ethyl acetate (20 mL). Wash with 5% aqueous citric acid, water, saturated aqueous sodium bicarbonate, saturated aqueous sodium chloride, dry (magnesium sulfate), concentrate and purify (silica gel chromatography, eluting with dichloromethane and ethyl acetate) to give the title compound as a solid (0.13 g, 78%).

MS (ES): m/z=654.4 [M+H].

2-(S)-sec-Butylamino-N-[1-(S)-(3,5-difluorobenzyl)-2-(R)-hydroxy-2-(R)-piperidin-2-yl-ethyl]-6-(methanesulfonyl-methylamino)-isonicotinamide hydrochloride Cool a solution of 2-(R)-[2-(S)-{[2-(S)-sec-butylamino-6-(methanesulfonyl-methylamino)-pyridine-4-carbonyl]-amino}-3-(3,5-difluorophenyl)-1-(S)-hydroxypropyl]-piperidine-1-carboxylic acid tert-butyl ester (0.082 g, 0.125 mmol) in dichloromethane (3 mL) in an ice bath. Add 4 M hydrogen chloride in 1,4-dioxane (6 mL), warm to room temperature, stir 1 h and concentrate to give the title compound as a foam (0.08 g, 100%).

MS (ES): m/z=554.2 [M+H].

The compounds of EXAMPLES 6-9 may be prepared essentially as described in EXAMPLE 5.

| EX | Compound | MS [M + H] |
|---|---|---|
| 6 | 2-(S)-sec-Butylamino-N-[1-(S)-(3,5-difluorobenzyl)-2-(S)-hydroxy-2-pyrrolidin-2-(R)-ylethyl]-6-(methanesulfonyl-methylamino)-isonicotinamide hydrochloride | 540.4 |
| 7 | N-[1-(S)-Benzyl-2-(R)-(4-(S)-fluoropyrrolidin-2-yl)-2-(R)-hydroxyethyl]-2-(S)-sec-butylamino-6-(methanesulfonyl-methylamino)-isonicotinamide bishydrochloride | 522.2 |
| 8 | N-[1-(S)-Benzyl-2-(R)-(4-(R)-fluoropyrrolidin-2-yl)-2-(R)-hydroxyethyl]-2-(S)-sec-butylamino-6-(methanesulfonyl-methylamino)-isonicotinamide bishydrochloride | 522.2 |
| 9 | N-[(1S,2R)-1-Benzyl-2-((R)-4,4-difluoropyrrolidin-2-yl)-2-hydroxyethyl]-2-((S)-sec-butylamino)-6-(methanesulfonyl-methylamino)-isonicotinamide bishydrochloride | 540.3 |

EXAMPLE 10

N-[1-(S)-Benzyl-2-hydroxy-2-(4-methyl-3-oxopiperazin-2-yl)-ethyl]-2-(S)-sec-butylamino-6-(methylsulfonyl-methylamino)-isonicotinamide hydrochloride Stir overnight at room temperature a solution of 2-sec-butylamino-6-(methylsulfonyl-methylamino)-pyridine-4-carboxylic acid (115 mg, 0.38 mmol), 3-(2-amino-1-hydroxy-3-phenylpropyl)-1-methylpiperazin-2-one (101 mg, 0.38 mmol), 1-(3-dimethylaminopropyl)-3-ethylcarbodiimide hydrochloride (EDCI) (87.4 mg, 0.45 mmol), triethylamine (0.16 mL, 1.14 mmol) and 4-(dimethylamino)pyridine (4.6 mg, 0.04 mmol) in dichloromethane (10 mL). Dilute with more dichloromethane and wash with 5% aqueous sodium bicarbonate. Separate organic layer and wash with saturated aqueous sodium chloride, dry (magnesium sulfate concentrate and purify (silica gel chromatography, eluting with 9:1 dichloromethane:methanol) to give a white solid. Suspend the solid in 4 M HCl in 1,4-dioxane and stir for 10 min. Concentrate the solution to give the title compound as a yellow solid (Isomer 2, 47 mg, 21%).

MS (ES): m/z=547 [M+H].

The compounds of EXAMPLE 11-19 may be prepared essentially as described in EXAMPLE 10 using the appropriate acids.

| EX | Compound | MS [M + H] |
|---|---|---|
| 11 | N-((1S,2R)-1-Benzyl-2-hydroxy-2-(R)-pyrrolidin-2-ylethyl)-2-(S)-sec-butylamino-6-methanesulfonyl-isonicotinamide hydrochloride | 475 |
| 12 | N-((1S,2R)-1-Benzyl-2-hydroxy-2-(R)-pyrrolidin-2-ylethyl)-2-(S)-sec-butylamino-6-(methanesulfonyl-methylamino)-isonicotinamide hydrochloride | 504 |
| 13 | N-((1S,2R)-1-Benzyl-2-hydroxy-2-(R)-pyrrolidin-2-ylethyl)-2-(methanesulfonyl-methylamino)-6-(methyl-propyl-amino)-isonicotinamide hydrochloride | 504.3 |
| 14 | N-[(1S,2R)-1-Benzyl-2-hydroxy-2-(R)-(2-pyrrolidinyl)-ethyl]-N',N'-dipropyl-isophthalamide hydrochloride | 452 |
| 15 | N-[(1S,2R)-1-Benzyl-2-hydroxy-2-(R)-(2-pyrrolidinyl)ehtyl]-2-(2'-fluorophenyl)isonicotinamide bishydrochloride | 420 |
| 16 | (2'-Fluorobiphenyl-3-carboxylic acid (1-(S)-benzyl-2-(R)-hydroxy-2-(R)-pyrrolidin-2-yl-ethyl)-amide hydrochloride | 418 |
| 17 | (2'-Fluorobiphenyl-3,5-dicarboxylic acid 3-[(1-(S)-benzyl-2-(R)-hydroxy-2-(R)-pyrrolidin-2-yl-ethyl]-amide] 5-dipropylamide hydrochloride | 546 |
| 18 | N-[(1S,2R)-1-Benzyl-2-hydroxy-2-(R)-pyrrolidin-2-yl-ethyl)]-2-dipropylamino-isonicotinamide hydrochloride | 425 |
| 19 | N-[(1S,2R)-1-Benzyl-2-(R)-(5,5-dimethylpyrrolidin-2-yl)-2-hydroxyethyl]-2-(S)-sec-butylamino-6-(methanesulfonyl-methylamino)-isonicotinamide hydrochloride | 532 |

EXAMPLE 20

$N^3$-((1S,2R)-1-Benzyl-2-hydroxy-2-(R)-pyrrolidin-2-ylethyl)-4-fluoro-5-methanesulfonyl-methylamino)-$N^1$-methyl-$N^1$-propyl-isophthalamide hydrochloride Dissolve 6-fluoro-5-(methanesulfonyl-methylamino)-N-methyl-N-propylisothalamic acid (102 mg, 0.294 mmol), O-benzotriazol-1-yl-tetramethyluronium hexafluorophosphate (123 mg, 0.324 mmol), 1-hydroxybenzotriazole hydrate (HOBt) (49.6 mg, 324 mmol) and diisopropylethylamine (102.76 μL, 0.589 mmol) in dimethylformamide (DMF) (3.00 mL). Stir for 30 min. Add (R)-2-((1S,2S)-2-amino-1-hydroxy-3-phenylpropyl)-pyrrolidine-1-carboxylic acid tert-butyl ester and stir at room temperature for 4 h. Add 10% aqueous potassium carbonate solution (10 mL) and extract with ethyl acetate (2×50 mL). Combine the organic layers, wash with 1 N lithium chloride solution (25 mL), saturated aqueous sodium chloride solution (25 mL), dry (magnesium sulfate) concentrate and purify (silica gel chromatography, eluting with 2.5:97.5 methanol:ethyl acetate) to give the desired tert-butyl carbamate intermediate as a white foam. Dissolve the purified material in a 20:1 diethyl ether: methanol mixture (2.1 mL) and add 1 N HCl in diethyl ether solution (4.1 mL) and stir overnight. Concentrate the reaction mixture to dryness to give the title compound as a white solid (120 mg, 70%).

MS (ES): m/z=549.2 [M+H].

EXAMPLE 21

N-[1(S)-Benzyl-2-hydroxy-2-(4-methyl-3-oxopiperazin-2-yl)-ethyl]-acetamide hydrochloride Stir overnight at room temperature under a nitrogen atmosphere a solution of acetic acid (25 μl, 0.45), 3-(2-(S)-amino-1-hydroxy-3-phenylpropyl)-1-methylpiperazin-2-one (120 mg, 0.45 mmol), 1-(3-dimethylaminopropyl)-3-ethylcarbodiimide hydrochloride (EDCI) (112 mg, 0.58 mmol), triethylamine (0.12 mL, 0.9 mmol), dimethylaminopyridine (5.5 mg, 0.04 mmol) and 1-hydroxybenzotriazole hydrate (HOBt) (79 mg, 0.58 mmol) in dichloromethane (10 mL/mmol). Dilute with more dichloromethane and wash with, 5% aqueous sodium bicarbonate solution, saturated aqueous sodium chloride. Dry (magnesium sulfate), concentrate and purify (silica gel chromatography, eluting with 9:1 dichloromethane:methanol) to provide a white solid. Suspend the solid in 4 M HCl in 1,4-dioxane and stir for 10 min and concentrate the solution to give the title compound as a white solid (15 mg, 10%).

The compounds of EXAMPLES 22-23 may be prepared essentially as described in EXAMPLE 21.

| EX | Compound | MS [M + H] |
|---|---|---|
| 22 | N-[(1S,2R)-1-Benzyl-2-hydroxy-2-(R)-pyrrolidin-2-ylethyl)]-acetamide hydrochloride | 263 |
| 23 | N-[(1S,2R)-1-Benzyl-2-(R)-(5,5-dimethylpyrrolidin-2-yl)-2-hydroxyethyl]-acetamide hydrochloride | 291 |

EXAMPLE 24

N-{(1S,2R)-1-(3,5-Difluorobenzyl)-2-hydroxy-2-[(2R,4R)-4-(3-methoxy-phenoxy)-pyrrolidin-2-yl]-ethyl}-acetamide hydrochloride (2R,4R)-2-[(1S,2S)-2-Acetylamino-3-(3,5-difluorophenyl)-1-hydroxypropyl]-4-(3-methoxy-phenoxy)-pyrrolidine-1-carboxylic acid tert-butyl ester Add to an ice cold solution of (2R,4R)-2-[(1S,2S)-2-amino-3-(3,5-difluorophenyl)-1-hydroxypropyl]-4-(3-methoxy-phenoxy)-pyrrolidine-1-carboxylic acid tert-butyl ester (0.24 g, 0.51 mmol) and 4-methylmorpholine (0.061 mL, 0.556 mmol) in dichloromethane (15 mL) 1-acetylimidazole (0.061 g, 0.556 mmol). Warm to room temperature and stir 18 h. Concentrate and dissolve in ethyl acetate and wash with 1N HCl, saturated aqueous sodium bicarbonate, saturated aqueous sodium chloride, dry (magnesium sulfate) and purify (silica gel chromatography, eluting with dichloromethane/ethyl acetate mixtures) to give the title compound as a foam (0.18 g, 69%).

MS (ES): m/z=521.3 [M+H].

N-{(1S,2R)-1-(3,5-Difluorobenzyl)-2-hydroxy-2-[(2R,4R)-4-(3-methoxy-phenoxy)-pyrrolidin-2-yl]-ethyl}-acetamide hydrochloride React (2R,4R)-2-[(1S,2S)-2-Acetylamino-3-(3,5-difluorophenyl)-1-hydroxypropyl]-4-(3-methoxy-phenoxy)-pyrrolidine-1-carboxylic acid tert-butyl ester With 4M HCl in dioxane essentially as described in EXAMPLE 1 to provide the title compound.

MS (ES): m/z=421.3 [M+H].

The compound of EXAMPLE 25 may be prepared essentially as described in EXAMPLE 24.

| EX | Compound | MS [M + H] |
|---|---|---|
| 25 | N-[(1S,2R)-1-(3,5-Difluorobenzyl)-2-hydroxy-2-((2R,5S)-5-phenyl-pyrrolidin-2-yl)-ethyl]-acetamide hydrochloride | 375.3 |

EXAMPLE 26

N-[(1S,2R)-1-(3,5-Difluorobenzyl)-2-hydroxy-2-((2R,4R)-4-hydroxypyrrolidin-2-yl)-ethyl]-acetamide hydrochloride (2R,4R)-2-[(4S,5S)-3-Acetyl-4-(3,5-difluorobenzyl)-2,2-dimethyloxazolidin-5-yl]-4-(4-methoxy-benzyloxy)-pyrrolidine-1-carboxylic acid tert-butyl ester Add to a solution of (2R,4R)-2-[(1S,2S)-2-acetylamino-3-(3,5-difluorophenyl)-1-hydroxypropyl]-4-(4-methoxy-benzyloxy)-pyrrolidine-1-carboxylic acid tert-butyl ester (5.64 g, 10.55 mmol) in dichloromethane (25 mL) and acetone (25 mL) p-toluene sulfonic acid pyridine salt (0.245 g, 1 mmol) and 2-methoxy propene (4.6 mL, 49 mmol). Stir 60 min and concentrate. Dissolve in ethyl acetate and wash with saturated aqueous sodium bicarbonate, saturated aqueous sodium chloride, dry (magnesium sulfate) and purify (silica gel chromatography, eluting with hexanes/ethyl acetate mixtures) to give the title compound as a foam (3.49 g, 61%).

MS (ES): m/z=575 [M+H].

(2R,4R)-2-[(4S,5S)-3-Acetyl-4-(3,5-difluorobenzyl)-2,2-dimethyloxazolidin-5-yl]-4-hydroxypyrrolidine-1-carboxylic acid tert-butyl ester To an ice cold solution of (2R,4R)-2-[(4S,5S)-3-acetyl-4-(3,5-difluorobenzyl)-2,2-dimethyloxazolidin-5-yl]-4-(4-methoxy-benzyloxy)-pyrrolidine-1-carboxylic acid tert-butyl ester (7.48 g, 13.0 mmol) in 20:1 dichloromethane:water (130 mL) add 2,3-dichloro-5,6-dicyano-1,4-benzoquinone (4.71 g, 20.74 mmol). Stir 4 h in an ice bath and wash with saturated aqueous sodium bicarbonate (3×300 mL), saturated aqueous sodium chloride, dry (magnesium sulfate) and purify (silica gel chromatography, eluting with dichloromethane/ethyl acetate mixtures) to give the title compound as a foam (5.288 g, 89%).

MS (ES): m/z=455.3 [M+H].

N-[(1S,2R)-1-(3,5-Difluorobenzyl)-2-hydroxy-2-((2R,4R)-4-hydroxy-pyrrolidin-2-yl)-ethyl]-acetamide hydrochloride The title compound is prepared essentially as described in EXAMPLE 24 to give a solid (0.072 g, 100%).

MS (ES): m/z=315.2 [M+H].

EXAMPLE 27

N-[1-Benzyl-2-hydroxy-2-(7-methoxymethyl-2-azabicyclo[2,2,1]hept-3-yl)-ethyl]-acetamide hydrochloride (Isomer 1)

3-(2-Acetylamino-1-hydroxy-3-phenylpropyl)-7-methoxymethyl-2-azabicyclo[2.2.1]heptane-2-carboxylic acid tert-butyl ester (Isomer 1 and Isomer 2)

Dissolve 3-(2-amino-1-hydroxy-3-phenylpropyl)-7-methoxymethyl-2-azabicyclo[2.2.1]heptane-2-carboxylic acid tert-butyl ester (0.243 mg, 0.622 mmol) in tetrahydrofuran (3 mL) and cool the mixture in an ice bath. Add triethylamine (0.091 mL, 0.653 mmol) and acetic anhydride (0.059 mL, 0.622 mmol) in tetrahydrofuran (2 mL). Stir the mixture at room temperature for 1 h. Add dichloromethane (30 mL) and water (10 mL). Separate layers and wash the organic layer with 0.5 N HCl, saturated aqueous sodium bicarbonate, dry (magnesium sulfate), concentrate and purify (silica gel chromatography, eluting with 3-5% isopropyl alcohol/47-45% dichlormethane in 50% hexanes) to give the title compound Isomer-1 (0.044 g, 16%) and Isomer-2 (0.077 mg, 29%).

MS (ES): m/z=433.3 [+H].

N-[1-Benzyl-2-hydroxy-2-(7-methoxymethyl-2-azabicyclo[2,2,1]hept-3-yl)-ethyl]-acetamide hydrochloride (Isomer-1)

Cool a solution of 3-(2-acetylamino-1-hydroxy-3-phenylpropyl)-7-methoxymethyl-2-azabicyclo[2.2.1]heptane-2-carboxylic acid tert-butyl ester (Isomer 1) (0.044 g, 0.102 mmol) in tetrahydrofuran (1 mL) and add a solution of hydrochloric acid (2.0 mL, 4 M in 1,4-dioxane). Stir the mixture for 5 h at room temperature, concentrate and purify (silica gel chromatography, eluting with 2 M ammonia in 5:95 to 10:90 methanol:dichloromethane) to give the title compound after treatment with the same equivalent of hydrochloric acid in diethyl ether (16 mg, 43%).

MS (ES): m/z=333.3 [M+H].

The compound of EXAMPLE 28 may be prepared essentially as described in EXAMPLE 27.

| EX | Compound | MS [M + H] |
|---|---|---|
| 28 | N-{(1S,2R)-1-(3,5-Difluorobenzyl-2-[(2R,4R)-4-(benzyloxy)-pyrrolidin-2-yl]-2-hydroxyethyl}-acetamide hydrochloride | 405.5 |

EXAMPLE 29

{(R)-5-[(1R,2S)-2-Acetylamino-3-(3,5-difluoro-phenyl)-1-hydroxy-propyl]-pyrrolidin-3-yl}-acetic acid hydrochloride Combine (R)-2-[(4S,5S)-3-Acetyl-4-(3,5-difluoro-benzyl)-2,2-dimethyl-oxazolidin-5-yl]-4-carboxymethyl-pyrrolidine-1-carboxylic acid tert-butyl ester (0.05 g, 0.101 mmol) and HCl (4M in dioxane, 1.88 mL, 7.55 mmol). Stir overnight. Concentrate under reduced pressure to provide the title compound (0.042 g, 92%).
MS(ESI): m/z=357.2 (M+H)

The compounds of EXAMPLES 30-31 may be prepared essentially as described in EXAMPLE 29

| EX | Compound | MS [M + H] |
|---|---|---|
| 30 | N-{(1S,2R)-1-(3,5-Difluorobenzyl-2-[(2R,4S)-4-(hexyl)-pyrrolidin-2-yl]-2-hydroxyethyl}-acetamide hydrochloride | 383.4 |
| 31 | N-{(1S,2R)-1-(3,5-Difluorobenzyl-2-[(2R,4R)-4-(hexyl)-pyrrolidin-2-yl]-2-hydroxyethyl}-acetamide hydrochloride | 383.4 |

EXAMPLE 32

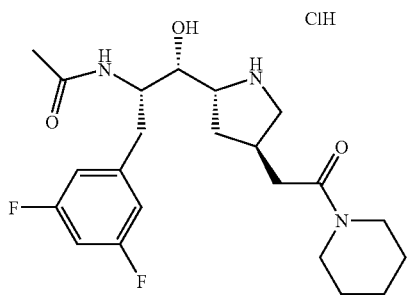

N-{(1S,2R)-1-(3,5-Difluoro-benzyl)-2-hydroxy-2-[(2R,4R)-4-(2-oxo-2-piperidin-1-yl-ethyl)-pyrrolidin-2-yl]-ethyl}-acetamide hydrochloride (R)-2-[(4S,5S)-3-Acetyl-4-(3,5-difluoro-benzyl)-2,2-dimethyl-oxazolidin-5-yl]-4-(2-oxo-2-piperidin-1-yl-ethyl)-pyrrolidine-1-carboxylic acid tert-butyl ester Add piperidine (0.013 g, 0.151 mmol) to a solution of (R)-2-[(4S,5S)-3-Acetyl-4-(3,5-difluoro-benzyl)-2,2-dimethyl-oxazolidin-5-yl]-4-carboxymethyl-pyrrolidine-1-carboxylic acid tert-butyl ester (mixture of isomers) (0.05 g, 0.101 mmol), bromo tris-pyrrolidinophosphonium hexafluorophosphate (0.094 g, 0.201 mmol), dimethylamino-pyridine (0.001 g, 0.01 mmol) and triethylamine (0.021 mL, 0.151 mmol) in 2.2 mL of dichloromethane. Stir the reaction overnight. Concentrate under reduced pressure and subject the residue to silica gel chromatography, eluting with hexane/ethyl acetate (70% gradient to 100%) to provide both isomers of the desired compound. The 4(R) isomer is the slower eluting (0.033 g, 60%).
MS(ESI): m/z=564.4 (M+H)

Deprotection

Add HCl (4M in dioxane, 0.729 mL, 2.9 mmol) to (R)-2-[(4S,5S)-3-Acetyl-4-(3,5-difluoro-benzyl)-2,2-dimethyl-oxazolidin-5-yl]-4-(2-oxo-2-piperidin-1-yl-ethyl)-pyrrolidine-1-carboxylic acid tert-butyl ester (0.022 g, 0.039 mmol). Stir overnight. Concentrate the reaction mixture under reduced pressure to provide the title compound (0.020 g, 98%).
MS(ESI): m/z=424.3 (M+H)

The compounds of EXAMPLES 33-43 may be prepared essentially as described in EXAMPLE 32.

| EX | Compound | MS [M + H] |
|---|---|---|
| 33 | N-{(1S,2R)-1-(3,5-Difluoro-benzyl)-2-hydroxy-2-[(2R,4S)-4-(2-oxo-2-piperidin-1-yl-ethyl)-pyrrolidin-2-yl]-ethyl}-acetamide hydrochloride | 424.3 |
| 34 | N-{(1S,2R)-1-(3,5-Difluoro-benzyl)-2-hydroxy-2-[(2R,4R)-4-(2-morph-olin-4-yl-2-oxo-ethyl)-pyrrolidin-2-yl]-ethyl}-acetamide hydrochloride | 426.2 |
| 35 | N-{(1S,2R)-1-(3,5-Difluoro-benzyl)-2-hydroxy-2-[(2R,4S)-4-(2-morph-olin-4-yl-2-oxo-ethyl)-pyrrolidin-2-yl]-ethyl}-acetamide hydrochloride | 426.2 |
| 36 | 2-{(3R,5R)-5-[(1R,2S)-2-Acetylamino-3-(3,5-difluoro-phenyl)-1-hydroxy-propyl]-pyrrolidin-3-yl}-N,N-dimethyl-acetamide hydrochloride | 384.2 |
| 37 | 2-{(3S,5R)-5-[(1R,2S)-2-Acetylamino-3-(3,5-difluoro-phenyl)-1-hydroxy-propyl]-pyrrolidin-3-yl}-N,N-dimethyl-acetamide hydrochloride | 384.2 |
| 38 | 2-{(3R,5R)-5-[(1R,2S)-2-Acetylamino-3-(3,5-difluoro-phenyl)-1-hydroxy-propyl]-pyrrolidin-3-yl}-N,N-diethyl-acetamide hydrochloride | 412.3 |
| 39 | 2-{(3S,5R)-5-[(1R,2S)-2-Acetylamino-3-(3,5-difluoro-phenyl)-1-hydroxy-propyl]-pyrrolidin-3-yl}-N,N-diethyl-acetamide hydrochloride | 412.3 |
| 40 | N-[(1S,2R)-2-[(2R,4R)-4-(2-Azepan-1-yl-2-oxo-ethyl)-pyrrolidin-2-yl]-1-(3,5-difluoro-benzyl)-2-hydroxy-ethyl]-acetamide hydrochloride | 438.3 |
| 41 | N-[(1S,2R)-2-[(2R,4S)-4-(2-Azepan-1-yl-2-oxo-ethyl)-pyrrolidin-2-yl]-1-(3,5-difluoro-benzyl)-2-hydroxy-ethyl]-acetamide hydrochloride | 438.3 |
| 42 | N-{(1S,2R)-1-(3,5-Difluoro-benzyl)-2-hydroxy-2-[(2R,4R)-4-(2-oxo-2-pyrrolidin-1-yl-ethyl)-pyrrolidin-2-yl]-ethyl}-acetamide hydrochloride | 410.2 |
| 43 | N-{(1S,2R)-1-(3,5-Difluoro-benzyl)-2-hydroxy-2-[(2R,4S)-4-(2-oxo-2-pyrrolidin-1-yl-ethyl)-pyrrolidin-2-yl]-ethyl}-acetamide hydrochloride | 410.2 |

EXAMPLE 44

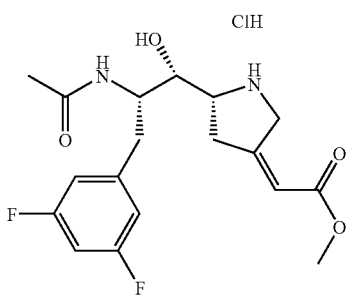

[(R)-5-[(1R,2S)-2-Acetylamino-3-(3,5-difluoro-phenyl)-1-hydroxy-propyl]-pyrrolidin-(3Z)-ylidene]-acetic acid methyl ester hydrochloride

(R)-2-[(4S,5S)-3-Acetyl-4-(3,5-difluoro-benzyl)-2,2-dimethyl-oxazolidin-5-yl]-4-[1-methoxycarbonyl-meth-(Z)-ylidene]-pyrrolidine-1-carboxylic acid tert-butyl ester Subject mixture of Z and E isomers of (R)-2-[(4S,5S)-3-acetyl-4-(3,5-difluoro-benzyl)-2,2-dimethyl-oxazolidin-5-yl]-4-[1-methoxycarbonyl-methylidene]-pyrrolidine-1-carboxylic acid tert-butyl ester to reverse phase HPLC under basic conditions with aqueous ammonium bicarbonate (10 mM) at pH 8, Isocratic mode: 67% CH3CN. Retention time 3.7 (isomer E) and 4.1 min (isomer Z).

[(R)-5-[(1R,2S)-2-Acetylamino-3-(3,5-difluoro-phenyl)-1-hydroxy-propyl]-pyrrolidin-(3Z)-ylidene]-acetic acid methyl ester hydrochloride Add HCl 4M in dioxane (0.861 mL, 3.4 mmol) to (R)-2-[(4S,5S)-3-Acetyl-4-(3,5-difluoro-benzyl)-2,2-dimethyl-oxazolidin-5-yl]-4-[1-methoxycarbonyl-meth-(Z)-ylidene]-pyrrolidine-1-carboxylic acid tert-butyl ester (0.024 g, 0.046 mmol). Stir overnight. Concentrate under reduced pressure to provide the title compound (0.021 g, 93%).

MS(ESI): m/z=369.2 (M+H)

The compound of EXAMPLE 45 may be prepared essentially as described in EXAMPLE 44 beginning with the corresponding E-isomer.

| EX | Compound | MS [M + H] |
|---|---|---|
| 45 | [(R)-5-[(1R,2S)-2-Acetylamino-3-(3,5-difluoro-phenyl)-1-hydroxy-propyl]-pyrrolidin-(3E)-ylidene]-acetic acid methyl ester hydrochloride | 369.2 |

EXAMPLE 46

N-{(1S,2R)-1-(3,5-Difluoro-benzyl)-2-hydroxy-2-[(2R,4R)-4-(2-methoxy-phenoxy)-pyrrolidin-2-yl]-ethyl}-acetamide hydrochloride

(2R,4R)-2-[(4S,5S)-3-Acetyl-4-(3,5-difluoro-benzyl)-2,2-dimethyl-oxazolidin-5-yl]-4-(2-methoxy-phenoxy)-pyrrolidine-1-carboxylic acid tert-butyl ester Add dropwise diisopropyl azodicarboxylate (0.065 mL, 0.327 mmol) to a solution of (2R,4S)-2-[(4S,5S)-3-acetyl-4-(3,5-difluoro-benzyl)-2,2-dimethyl-oxazolidin-5-yl]-4-hydroxy-pyrrolidine-1-carboxylic acid tert-butyl ester (0.099 g, 0.218 mmol), 2-methoxy phenol (0.036 mL, 0.327 mmol) and triphenylphosphine (0.086 g, 0.327 mmol) in tetrahydrofuran (1.5 mL). Stir 18 hours. Purify reaction mixture on silica gel with ethyl acetate/hexane mixtures to give the desired compound as a foam (0.064 g, 53%). MS(ES): m/z=561 [M+H].

N-{(1S,2R)-1-(3,5-Difluoro-benzyl)-2-hydroxy-2-[(2R,4R)-4-(2-methoxy-phenoxy)-pyrrolidin-2-yl]-ethyl}-acetamide hydrochloride Add 4M hydrogen chloride in dioxane (3 mL) to (2R,4R)-2-[(4S,5S)-3-acetyl-4-(3,5-difluoro-benzyl)-2,2-dimethyl-oxazolidin-5-yl]-4-(2-methoxy-phenoxy)-pyrrolidine-1-carboxylic acid tert-butyl ester (0.061 g, 0.21 mmol). Stir 1 h and concentrate to give the title compound as a foam (0.05 g, 100%).

MS (ES): m/z=421 [M+H].

The compounds of EXAMPLES 47-51 may be prepared essentially as described in EXAMPLE 46.

| EX | Compound | MS [M + H] |
|---|---|---|
| 47 | N-{(1S,2R)-1-(3,5-Difluoro-benzyl)-2-hydroxy-2-[(2R,4R)-4-(4-methoxy-phenoxy)-pyrrolidin-2-yl]-ethyl}-acetamide hydrochloride | 421 |
| 48 | N-{(1S,2R)-1-(3,5-Difluoro-benzyl)-2-hydroxy-2-[(2R,4R)-4-(3-butoxy-phenoxy)-pyrrolidin-2-yl]-ethyl}-acetamide hydrochloride | 463 |
| 49 | N-[(1S,2R)-2-[(2R,4S)-4-(3-Butoxy-phenoxy)-pyrrolidin-2-yl]-1-(3,5-difluoro-benzyl)-2-hydroxy-ethyl]-acetamide hydrochloride | 463 |
| 50 | N-{(1S,2R)-1-(3,5-Difluoro-benzyl)-2-hydroxy-2-[(2R,4S)-4-(3-methoxy-phenoxy)-pyrrolidin-2-yl]-ethyl}-acetamide hydrochloride | 421 |
| 51 | N-{(1S,2R)-1-(3,5-Difluoro-benzyl)-2-hydroxy-2-[(2R,4S)-4-(2-methoxy-phenoxy)-pyrrolidin-2-yl]-ethyl}-acetamide hydrochloride | 421 |

EXAMPLE 52

N-{(1S,2R)-1-(3,5-Difluoro-benzyl)-2-hydroxy-2-[(2R,4R)-4-(3-trifluoromethoxy-benzyloxy)-pyrrolidin-2-yl]-ethyl}-acetamide hydrochloride (2R,4R)-2-[(4S,5S)-3-Acetyl-4-(3,5-difluoro-benzyl)-2,2-dimethyl-oxazolidin-5-yl]-4-(3-trifluoromethoxy-benzyloxy)-pyrrolidine-1-carboxylic acid tert-butyl ester Add 95% sodium hydride (0.008 g, 0.33 mmol) over 5 minutes to a solution of (2R,4R)-2-[(4S,5S)-3-acetyl-4-(3,5-difluorobenzyl)-2,2-dimethyloxazolidin-5-yl]-4-hydroxy-pyrrolidine-1-carboxylic acid tert-butyl ester (0.101 g, 0.22 mmol) and 1-bromomethyl-3-trifluoromethoxy-benzene (0.054 mL, 0.333 mmol) in N,N-dimethylformamide (1 mL). Stir 1 hour and partition with ethyl acetate and water, wash with saturated aqueous sodium chloride, dry with magnesium sulfate and purify on silica gel with ethyl acetate/hexane mixtures to give the desired compound as a foam (0.141 g, 100%).

MS (ES): m/z=629 [M+H].

N-{(1S,2R)-1-(3,5-Difluoro-benzyl)-2-hydroxy-2-[(2R,4R)-4-(3-trifluoromethoxy-benzyloxy)-pyrrolidin-2-yl]-ethyl}-acetamide hydrochloride Add 4M hydrogen chloride in dioxane (5 mL) to (2R,4R)-2-[(4S,5S)-3-acetyl-4-(3,5-difluoro-benzyl)-2,2-dimethyl-oxazolidin-5-yl]-4-(3-trifluoromethoxy-benzyloxy)-pyrrolidine-1-carboxylic acid tert-butyl ester (0.138 g, 0.22 mmol). Stir 18 h and concentrate to give the title compound as a foam (0.11 g, 100%).

MS (ES): m/z=489 [M+H].

The compounds of EXAMPLES 53-66 may be prepared essentially as described in EXAMPLE 52.

| EX | Compound | MS [M + H] |
|---|---|---|
| 53 | N-{(1S,2R)-1-(3,5-Difluoro-benzyl)-2-hydroxy-2-[(2R,4R)-4-(3-trifluoromethyl-benzyloxy)-pyrrolidin-2-yl]-ethyl}-acetamide hydrochloride | 473 |
| 54 | N-{(1S,2R)-1-(3,5-Difluoro-benzyl)-2-hydroxy-2-[(2R,4R)-4-(3-methyl-benzyloxy)-pyrrolidin-2-yl]-ethyl}-acetamide hydrochloride | 419 |
| 55 | N-{(1S,2R)-1-(3,5-Difluoro-benzyl)-2-hydroxy-2-[(2R,4R)-4-(3-methoxy-benzyloxy)-pyrrolidin-2-yl]-ethyl}-acetamide hydrochloride | 435 |
| 56 | N-{(1S,2R)-1-(3,5-Difluoro-benzyl)-2-hydroxy-2-[(2R,4R)-4-(4-methyl-benzyloxy)-pyrrolidin-2-yl]-ethyl}-acetamide hydrochloride | 419 |
| 57 | N-[(1S,2R)-2-[(2R,4R)-4-(4-tert-Butyl-benzyloxy)-pyrrolidin-2-yl]-1-(3,5-difluoro-benzyl)-2-hydroxy-ethyl]-acetamide hydrochloride | 461 |
| 58 | N-{(1S,2R)-1-(3,5-Difluoro-benzyl)-2-hydroxy-2-[(2R,4R)-4-(4-methyl-pentyloxy)-pyrrolidin-2-yl]-ethyl}-acetamide hydrochloride | 399 |
| 59 | N-{(1S,2R)-1-(3,5-Difluoro-benzyl)-2-[(2R,4R)-4-(3,3-dimethyl-butoxy)-pyrrolidin-2-yl]-2-hydroxy-ethyl}-acetamide hydrochloride | 399 |
| 60 | N-[(1S,2R)-2-[(2R,4R)-4-(2-Cyclohexyl-ethoxy)-pyrrolidin-2-yl]-1-(3,5-difluoro-benzyl)-2-hydroxy-ethyl]-acetamide hydrochloride | 425 |
| 61 | N-[(1S,2R)-2-((2R,4R)-4-Cyclohexylmethoxy-pyrrolidin-2-yl)-1-(3,5-difluoro-benzyl)-2-hydroxy-ethyl]-acetamide hydrochloride | 411 |
| 62 | N-(((1S,2R)-1-(3,5-Difluoro-benzyl)-2-hydroxy-2-{(2R,4R)-4-[((E/Z)-propenyl)oxy]-pyrrolidin-2-yl}-ethyl)-acetamide hydrochloride | 355 |
| 63 | N-{(1S,2R)-1-(3,5-Difluoro-benzyl)-2-[(2R,4R)-4-(3,3-dimethyl-pentyloxy)-pyrrolidin-2-yl]-2-hydroxy-ethyl}-acetamide hydrochloride | 413 |
| 64 | N-{(1S,2R)-1-(3,5-Difluoro-benzyl)-2-[(2R,4R)-4-(4,4-dimethyl-pentyloxy)-pyrrolidin-2-yl]-2-hydroxy-ethyl}-acetamide hydrochloride | 413 |
| 65 | N-{(1S,2R)-1-(3,5-Difluoro-benzyl)-2-[(2R,4R)-4-(3,3-dimethyl-2-oxo-butoxy)-pyrrolidin-2-yl]-2-hydroxy-ethyl}-acetamide hydrochloride | 413 |
| 66 | N-[(1S,2R)-2-((2R,4R)-4-Cyclopropylmethoxy-pyrrolidin-2-yl)-1-(3,5-difluoro-benzyl)-2-hydroxy-ethyl]-acetamide hydrochloride | 369 |

EXAMPLE 67

N-{(1S,2R)-1-(3,5-Difluoro-benzyl)-2-hydroxy-2-[(2R,4R)-4-(3-methyl-butoxy)-pyrrolidin-2-yl]-ethyl}-acetamide hydrochloride (2R,4R)-2-[(4S,5S)-3-Acetyl-4-(3,5-difluoro-benzyl)-2,2-dimethyl-oxazolidin-5-yl]-4-(3-methyl-butoxy)-pyrrolidine-1-carboxylic acid tert-butyl ester Stir a solution of (2R,4R)-2-[(4S,5S)-3-acetyl-4-(3,5-difluoro-benzyl)-2,2-dimethyl-oxazolidin-5-yl]-4-(3-methylbut-2-enyloxy)-pyrrolidine-1-carboxylic acid tert-butyl ester and 10% palladium on carbon (0.02 g) in methanol (5 mL) under one atmosphere of hydrogen gas for 18 hours. Filter and evaporate to give the desired compound as a foam (0.081 g, 76%).
MS (ES): m/z=525 [M+H].

N-{(1S,2R)-1-(3,5-Difluoro-benzyl)-2-hydroxy-2-[(2R,4R)-4-(3-methyl-butoxy)-pyrrolidin-2-yl]-ethyl}-acetamide hydrochloride Add 4M hydrogen chloride in dioxane (8 mL) to (2R,4R)-2-[(4S,5S)-3-acetyl-4-(3,5-difluoro-benzyl)-2,2-dimethyl-oxazolidin-5-yl]-4-(3-methyl-butoxy)-pyrrolidine-1-carboxylic acid tert-butyl ester (0.079 g, 0.15 mmol). Stir 2 hours and evaporate to give the title compound as a foam (0.089 g, 100%).
MS (ES): m/z=385 [M+H].
The compound of EXAMPLE 68 may be prepared essentially as described in EXAMPLE 67.

| EX | Compound | MS [M + H] |
|---|---|---|
| 68 | N-[(1S,2R)-1-(3,5-Difluoro-benzyl)-2-hydroxy-2-((2R,4R)-4-propoxy-pyrrolidin-2-yl)-ethyl]-acetamide hydrochloride | 357 |

EXAMPLE 69

N-{(1S,2R)-1-(3,5-Difluoro-benzyl)-2-hydroxy-2-[(2R,4R)-4-(2-R/S-hydroxy-3,3-dimethyl-butoxy)-pyrrolidin-2-yl]-ethyl}-acetamide hydrochloride (2R,4R)-2-[(4S,5S)-3-Acetyl-4-(3,5-difluoro-benzyl)-2,2-dimethyl-oxazolidin-5-yl]-4-(2-R/S-hydroxy-3,3-dimethyl-butoxy)-pyrrolidine-1-carboxylic acid tert-butyl ester Add lithium borohydride (0.004 g, 0.194 mmol) to a solution of (2R,4R)-2-[(4S,5S)-3-acetyl-4-(3,5-difluoro-benzyl)-2,2-dimethyl-oxazolidin-5-yl]-4-(3,3-dimethyl-2-oxo-butoxy)-pyrrolidine-1-carboxylic acid tert-butyl ester (0.071 g, 0.129 mmol) in tetrahydrofuran. Stir 90 minutes. Cool in ice bath and add glacial acetic acid (0.06 mL). Stir 2 minutes. Dilute with ethyl acetate and water, wash organic layer with saturated aqueous sodium bicarbonate, saturated aqueous sodium chloride, dry magnesium sulfate. Purify on silica gel with dichloromethane/ethyl acetate mixtures to give the desired compound as a foam (0.062 g, 86%).
MS (ES): m/z=555 [M+H].

N-{(1S,2R)-1-(3,5-Difluoro-benzyl)-2-hydroxy-2-[(2R,4R)-4-(2-R/S-hydroxy-3,3-dimethyl-butoxy)-pyrrolidin-2-yl]-ethyl}-acetamide hydrochloride Add 4M hydrogen chloride in dioxane (5 mL) to (2R,4R)-2-[(4S,5S)-3-acetyl-4-(3,5-difluoro-benzyl)-2,2-dimethyl-oxazolidin-5-yl]-4-(2-R/S-hydroxy-3,3-dimethyl-butoxy)-pyrrolidine-1-carboxylic acid tert-butyl ester (0.06 g, 0.11 mmol). Stir 18 hours and evaporate to give the title compound as a foam (0.05 g, 100%).
MS (ES): m/z=415 [M+H].
The compounds of EXAMPLES 70-71 may be prepared essentially as described in EXAMPLE 69.

| EX | Compound | MS [M + H] |
|---|---|---|
| 70 | N-{(1S,2R)-1-(3,5-Difluoro-benzyl)-2-hydroxy-2-[(2R,4R)-4-(2-R-hydroxy-3,3-dimethyl-butoxy)-pyrrolidin-2-yl]-ethyl}-acetamide hydrochloride | 415 |
| 71 | N-{(1S,2R)-1-(3,5-Difluoro-benzyl)-2-hydroxy-2-[(2R,4R)-4-(2-S-hydroxy-3,3-dimethyl-butoxy)-pyrrolidin-2-yl]-ethyl}-acetamide hydrochloride | 415 |

EXAMPLE 72

N-{(1S,2R)-1-(3,5-Difluoro-benzyl)-2-[(2R,4R)-4-(2,3-dihydroxy-3-methyl-butoxy)-pyrrolidin-2-yl]-2-hydroxy-ethyl}-acetamide hydrochloride (2R,4R)-2-[(4S,5S)-3-Acetyl-4-(3,5-difluoro-benzyl)-2,2-dimethyl-oxazolidin-5-yl]-4-(2,3-dihydroxy-3-methyl-butoxy)-pyrrolidine-1-carboxylic acid tert-butyl ester Add osmium tetroxide (0.0018 g, 0.007 mmol) and N-methyl morpholine oxide (0.033 g, 0.28 mmol) to a solution of (2R,4R)-2-[(4S,5S)-3-acetyl-4-(3,5-difluoro-benzyl)-2,2-dimethyl-oxazolidin-5-yl]-4-(3-methyl-but-2-phenyloxy)-pyrrolidine-1-carboxylic acid tert-butyl ester (0.073 g, 0.14 mmol) in 5:1 acetone/water (5 mL). Stir 30 minutes. Add 30 wt % aqueous sodium sulfite (20 mL) and evaporate organic solvent. Extract with ethyl acetate, wash with saturated aqueous sodium bicarbonate, saturated aqueous sodium chloride, dry with magnesium sulfate and purify on silica gel with dichloromethane/ethyl acetate mixtures to give the desired compound as a foam (0.073 g, 94%).
MS (ES): m/z=557 [M+H].

N-{(1S,2R)-1-(3,5-Difluoro-benzyl)-2-[(2R,4R)-4-(2,3-dihydroxy-3-methyl-butoxy)-pyrrolidin-2-yl]-2-hydroxy-ethyl}-acetamide hydrochloride Add 4M hydrogen chloride in dioxane (5 mL) to (2R,4R)-2-[(4S,5S)-3-acetyl-4-(3,5-difluoro-benzyl)-2,2-dimethyl-oxazolidin-5-yl]-4-(2,3-dihydroxy-3-methyl-butoxy)-pyrrolidine-1-carboxylic acid tert-butyl ester (0.07 g, 0.126 mmol). Stir 4 hours and evaporate to give the title compound as a foam (0.062 g, 100%).
MS (ES): m/z=417 [M+H].

EXAMPLE 73

N-{(1S,2R)-1-(3,5-Difluoro-benzyl)-2-hydroxy-2-[(2R,4R)-4-(3-hydroxy-3-methyl-butoxy)-pyrrolidin-2-yl]-ethyl}-acetamide hydrochloride (2R,4R)-2-[(4S,5S)-3-Acetyl-4-(3,5-difluoro-benzyl)-2,2-dimethyl-oxazolidin-5-yl]-4-(3-hydroxy-3-methyl-butoxy-pyrrolidine-1-carboxylic acid tert-butyl ester Add a solution of (2R,4R)-2-[(4S,5S)-3-acetyl-4-(3,5-difluoro-benzyl)-2,2-dimethyl-oxazolidin-5-yl]-4-(3-methyl-but-2-phenyloxy)-pyrrolidine-1-carboxylic acid tert-butyl ester (0.152 g, 0.29 mmol) in tetrahydrofuran (1.5 mL) dropwise to an ice cold solution of mercuric acetate (0.092 g, 0.29 mmol) in water (0.95 mL) and stir 45 minutes. Remove ice bath and stir 5.5 hours. Add 3M aqueous sodium hydroxide (0.38 mL) and a solution of sodium borohydride (0.145 mmol, 0.0055 g in 0.38 mL 3M aqueous sodium hydroxide). Stir 10 minutes and saturate with solid sodium chloride and filter through filter agent and wash cake with ethyl acetate. Wash organic layer with saturated aqueous sodium chloride, dry with magnesium sulfate and purify on silica gel with dichloromethane/ethyl acetate mixtures to give the desired compound as a foam (0.115 g, 73%).

MS (ES): m/z=541 [M+H].

N-{(1S,2R)-1-(3,5-Difluoro-benzyl)-2-hydroxy-2-[(2R,4R)-4-(3-hydroxy-3-methyl-butoxy)-pyrrolidin-2-yl]-ethyl}-acetamide hydrochloride Add 4M hydrogen chloride in dioxane (5 mL) to (2R,4R)-2-[(4S,5S)-3-acetyl-4-(3,5-difluoro-benzyl)-2,2-dimethyl-oxazolidin-5-yl]-4-(3-hydroxy-3-methyl-butoxy)-pyrrolidine-1-carboxylic acid tert-butyl ester (0.11 g, 0.207 mmol). Stir 4 hours and evaporate to give the title compound as a foam (0.102 g, 100%).

MS (ES): m/z=401 [M+H].

EXAMPLE 74 tert-Butyl-carbamic acid (3R,5R)-5-[(1R,2S)-2-acetylamino-3-(3,5-difluoro-phenyl)-1-hydroxy-propyl]-pyrrolidin-3-yl ester hydrochloride (2R,4R)-2-[(4S,5S)-3-Acetyl-4-(3,5-difluoro-benzyl)-2,2-dimethyl-oxazolidin-5-yl]-4-tert-butylcarbamoyloxy-pyrrolidine-1-carboxylic acid tert-butyl ester Add 95% sodium hydride (0.05 g, 2.1 mmol) portionwise to a solution of tert-butylisocyanate (0.245 mL, 2.1 mmol) and (2R,4R)-2-[(4S,5S)-3-acetyl-4-(3,5-difluorobenzyl)-2,2-dimethyl-oxazolidin-5-yl]-4-(3,3-dimethyl-2-oxo-butoxy)-pyrrolidine-1-carboxylic acid tert-butyl ester (0.318 g, 0.70 mmol) in dichloromethane (4 mL) and stir 45 minutes. Wash with water, saturated aqueous sodium chloride, dry with magnesium sulfate and purify on silica gel with dichloromethane/ethyl acetate mixtures to give the desired compound as a foam (0.341 g, 88%).

MS (ES): m/z=554 [M+H].

tert-Butyl-carbamic acid (3R,5R)-5-[(1R,2S)-2-acetylamino-3-(3,5-difluoro-phenyl)-1-hydroxy-propyl]-pyrrolidin-3-yl ester hydrochloride Add 4M hydrogen chloride in dioxane (5 mL) to (2R,4R)-2-[(4S,5S)-3-acetyl-4-(3,5-difluoro-benzyl)-2,2-dimethyl-oxazolidin-5-yl]-4-tert-butylcarbamoyloxy-pyrrolidine-1-carboxylic acid tert-butyl ester (0.34 g, 0.616 mmol). Stir 4 hours and evaporate to give the title compound as a foam (0.291 g, 100%).

MS (ES): m/z=414 [M+H].

The compound of EXAMPLE 75 may be prepared essentially as described in EXAMPLE 74.

| EX | Compound | MS [M + H] |
|---|---|---|
| 75 | Adamantan-1-yl-carbamic acid (3R,5R)-5-[(1R,2S)-2-acetylamino-3-(3,5-difluoro-phenyl)-1-hydroxy-propyl]-pyrrolidin-3-yl ester hydrochloride | 492 |

EXAMPLE 76

N-{(1S,2R)-1-(3,5-Difluoro-benzyl)-2-hydroxy-2-[(2R,4R)-4-(3-methyl-butoxy)-4-trifluoromethyl-pyrrolidin-2-yl]-ethyl}-acetamide hydrochloride Add 4M hydrogen chloride in dioxane (8 mL) to (2R,4R)-2-[(4S,5S)-3-acetyl-4-(3,5-difluoro-benzyl)-2,2-dimethyl-oxazolidin-5-yl]-4-(3-methyl-butoxy)-4-trifluoromethyl-pyrrolidine-1-carboxylic acid tert-butyl ester (0.084 g, 0.14 mmol). Stir 2 hours and evaporate to give the title compound as a foam (0.073 g, 100%).

MS (ES): m/z=453 [M+H].

The compounds of EXAMPLES 77-78 may be prepared essentially as described in EXAMPLE 76.

| EX | Compound | MS [M + H] |
|---|---|---|
| 77 | N-{(1S,2R)-1-(3,5-Difluoro-benzyl)-2-hydroxy-2-[(2R,4S)-4-(3-methyl-butoxy)-4-trifluoromethyl-pyrrolidin-2-yl]-ethyl}-acetamide hydrochloride | 453 |
| 78 | N-[(1S,2R)-2-[(2R,4R)-4-(2-Cyclohexyl-ethoxy)-4-trifluoromethyl-pyrrolidin-2-yl]-1-(3,5-difluoro-benzyl)-2-hydroxy-ethyl]-acetamide hydrochloride | 493 |

EXAMPLE 79

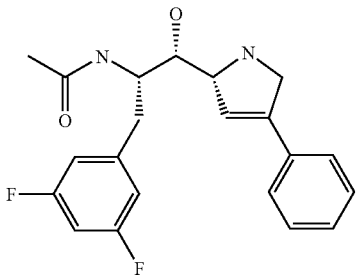

N-[(1S,2S)-1-(3,5-Difluoro-benzyl)-2-hydroxy-2-((R)-4-phenyl-2,5-dihydro-1H-pyrrol-2-yl)-ethyl]-acetamide 1,1,1-trifluoroacetate (2R,4S)-2-[(4S,5S)-3-Acetyl-4-(3,5-difluoro-benzyl)-2,2-dimethyl-oxazolidin-5-yl]-4-hydroxy-4-phenyl-pyrrolidine-1-carboxylic acid tert-butyl ester Add phenyl magnesium bromide (3.0 mL, 9 mmol, 3M in ether) dropwise to an ice cold solution of (R)-2-[(4S,5S)-3-acetyl-4-(3,5-difluoro-benzyl)-2,2-dimethyl-oxazolidin-5-yl]-4-oxo-pyrrolidine-1-carboxylic acid tert-butyl ester (0.40 g, 0.89 mmol) in ether (20 mL). Stir 60 minutes and warm to 23° C. Dilute with ethyl acetate and wash with saturated aqueous ammonium chloride. Purify on silica gel with dichloromethane/ethyl acetate mixtures to give the desired compound as a foam (0.19 g, 41%).

MS (ES): m/z=531 [M+H].

N-[(1S,2S)-1-(3,5-Difluoro-benzyl)-2-hydroxy-2-((R)-4-phenyl-2,5-dihydro-1H-pyrrol-2-yl)-ethyl]-acetamide 1,1,1-trifluoroacetate Add trifluoroacetic acid (5 mL) to (2R,4S)-2-[(4S,5S)-3-acetyl-4-(3,5-difluoro-benzyl)-2,2-dimethyl-oxazolidin-5-yl]-4-hydroxy-4-phenyl-pyrrolidine-1-carboxylic acid tert-butyl ester (0.053 g, 0.1 mmol). Stir 3 hours and evaporate to give the title compound as a foam (0.053 g, 100%).

MS (ES): m/z=373 [M+H].

The compounds of EXAMPLES 80-81 may be prepared essentially as described in EXAMPLE 79, except EXAMPLE 81 was deprotected with 4M HCl in dioxane.

| EX | Compound | MS [M + H] |
|---|---|---|
| 80 | N-{(1S,2S)-1-(3,5-Difluoro-benzyl)-2-hydroxy-2-[(R)-4-(3-isopropoxy-phenyl)-2,5-dihydro-1H-pyrrol-2-yl]-ethyl}-acetamide 1,1,1-trifluoroacetate | 431 |
| 81 | N-[(1S,2R)-1-(3,5-Difluoro-benzyl)-2-hydroxy-2-((2R,4R)-4-hydroxy-4-propyl-pyrrolidin-2-yl)-ethyl]-acetamide hydrochloride | 357 |

EXAMPLE 82

N-[(1S,2R)-1-(3,5-Difluoro-benzyl)-2-hydroxy-2-((2R,4S)-4-phenyl-pyrrolidin-2-yl)-ethyl]-acetamide 1,1,1-trifluoroacetate Stir a solution of N-[(1S,2S)-1-(3,5-difluoro-benzyl)-2-hydroxy-2-((R)-4-phenyl-2,5-dihydro-1H-pyrrol-2-yl)-ethyl]-acetamide 1,1,1-trifluoroacetate (0.05 g, 0.1 mmol) and 10% palladium on carbon (0.018 g) in methanol (5 mL) under an atmosphere of hydrogen gas for 18 hours. Filter and evaporate to give the title compound as a foam (0.042 g, 86%).

MS (ES): m/z=375 [M+H].

The compound of EXAMPLE 83 may be prepared essentially as described in EXAMPLE 82.

| EX | Compound | MS [M + H] |
|---|---|---|
| 83 | N-{(1S,2R)-1-(3,5-Difluoro-benzyl)-2-hydroxy-2-[(2R,4S)-4-(3-isopropoxy-phenyl)-pyrrolidin-2-yl]-ethyl}-acetamide hydrochloride | 433 |

The compounds of Formula I are inhibitors of BACE and thereby inhibit the production of A-β peptide which has been implicated in the pathology and progression of a number of neurodegenerative disorders, including Alzheimer's disease (See: Cumming, et al., *Current Opinion in Drug Discovery and Development*, 7(4), 536-556, (2004); and Varghese, et al., *Journal of Medicinal Chemistry*, 46(22), 4625 (2003)). Methods for determining the BACE inhibitory activity of compounds are well known in the art (See: Sinha, et al., *Science*, 286, 735 (1999); Turner, et al., *Biochemistry*, 40, 10001 (2001); Hom, et al., *Journal of Medicinal Chemistry*, 46, 1799 (2003); U.S. Pat. No. 5,744,346; U.S. Pat. No. 5,942,400; WO00/17369; WO00/03819; WO 03/040096; and WO 04/024081).

In Vitro Assay Procedures:

For in vitro enzymatic and cellular assays, test compounds are prepared in DMSO to make up a 10 millimolar stock solution. The stock solution is serially diluted (in a 1:3, 1:2.5, 1:2, or 1:1 dilution series) in DMSO to obtain a final compound concentration of 10 millimolar to 1 micromolar at the first highest concentration of a ten-point dilution curve in a 96-well round-bottom plate right before conducting the in vitro enzymatic and whole assays.

In Vitro Protease Inhibition Assays:

BACE1 mcaFRET Assay

Serial dilutions of test compounds are prepared as described above. Two microliter of each dilution is added to each well on row A to H of a corresponding low protein binding black plate to which 50 microliter of 50 millimolar ammonium acetate, pH 4.6, 1 mM Triton X-100, 1 mg/ml Bovine Serum Albumin, and 15 micromolar of FRET substrate (sequence: (MCA)-S-E-V-N-L-D-A-E-F-R-K(Dnp)-R-R-R-R-NH$_2$) for BACE1 activity are pre-added. The content is mixed well on a plate shaker for 10 min. Fifty microliter of two hundred picomolar human BACE1 (1-460):Fc (See: Vasser, et al., *Science*, 286, 735-741 (1999)) in the same reaction buffer described above is added to the plate containing substrate and test compounds to initiate the reaction. The relative fluorescence unit (RFU) of the mixture at time 0 is recorded at excitation wavelength 330 nm and emission wavelength 400 nm, after brief mixing on a plate shaker. The reaction plate is covered with aluminum foil and kept in a dark humidified oven at room temperature for 16 to 24 hours. The RFU at the end of incubation is recorded with the same excitation and emission setting. The difference of the RFU at time 0 and the end of incubation represents the activity of BACE1 under the compound treatment. The 10-point inhibition curve was plotted and fitted with the four-parameter logistic equation to obtain the EC$_{50}$ and IC$_{50}$ values. (See: Sinha, et al., *Nature*, 402, 537-540 (2000)). Representative compounds of Formula I were tested essentially as described above and exhibited an IC$_{50}$ for BACE1 of at least 15 µM. Data for selected compounds of the invention tested in this assay are contained in the following table.

| EXAMPLE | IC$_{50}$ (µM) |
|---|---|
| 7 | 0.0039 |
| 12 | 0.0018 |
| 33 | 0.82 |
| 35 | 1.4 |
| 37 | 5.2 |
| 41 | 0.38 |
| 60 | 2.3 |

BACE2 mcaFRET Assay

Serial dilutions of test compounds are prepared as described above. Two microliter of each dilution is added to each well on row A to H of a corresponding low protein binding black plate to which 50 microliter of 50 millimolar ammonium acetate, pH 4.6, 1 mM Triton X-100, 1 mg/ml Bovine Serum Albumin, and 15 micromolar of FRET substrate (sequence: (MCA)-S-E-V-N-L-D-A-E-F-R-K(Dnp)-R-R-R-R-NH$_2$) for BACE2 activity are pre-added. The content is mixed well on a plate shaker for 10 min. Fifty microliter of four hundred picomolar purified recombinant human BACE2(1-460):Fc in the same reaction buffer described above is added to the plate containing substrate and test compounds to initiate the reaction. The relative fluorescence unit (RFU) of the mixture at time 0 is recorded at excitation wavelength 330 nm and emission wavelength 400 nm, after brief mixing on a plate shaker. The reaction plate is covered with aluminum foil and kept in a dark humidified oven at room temperature for 16 to 24 hours. The RFU at the end of incubation is recorded with the same excitation and emission setting. The difference of the RFU at time 0 and the end of incubation represents the activity of BACE2 under the compound treatment. The 10-point inhibition curve was plotted and fitted with the four-parameter logistic equation to obtain the $EC_{50}$ and $IC_{50}$ values. Representative compounds of Formula I were tested essentially as described above and exhibited an $IC_{50}$ for BACE2 of at least 15 µM.

Expression of Human and Murine BACE1.

Both human (accession number: AF190725) and murine (accession number: NM_011792) BACE1 were cloned from total brain cDNA by room temperature-PCR. The nucleotide sequences corresponding to amino acid sequences #1 to 460 were inserted into the cDNA encoding human $IgG_1$ (Fc) polypeptide (Vassar et al. 1999). This fusion protein of BACE1 (1-460) and human Fc, named huBACE1:Fc, was constructed into the pJB02 vector. Human BACE1(1-460):Fc (huBACE1:Fc) and murine BACE1(1-460):Fc (muBACE1:Fc) were transiently expressed in HEK293 cells. 250 µg cDNA of each construct was mixed with Fugene 6 and added to 1 liter HEK293 cells. Four days after the transfection, conditioned media were harvested for purification.

Purification of huBACE1:Fc and muBACE1:Fc.

Conditioned media of HEK293 cell transiently transfected with huBACE1:Fc or muBACE1:Fc cDNA were collected. Cell debris was removed by filtering the conditioned media through 0.22 µm sterile filter. 5 ml Protein A-agarose (bed volume) was added to 4 liter conditioned media. This mixture was gently stirred overnight at 4° C. The Protein A-agarose resin was collected and packed into a low-pressure chromatography column. The column washed with 20× bed volumes of PBS at flow rate 20 ml per hour. Bound huBACE1:Fc or muBACE1:Fc protein was eluted with 50 mM acetic acid, pH 3.6, at flow rate 20 ml per hour. 1 ml fractions of eluate were neutralized immediately with 0.5 ml 200 mM ammonium acetate, pH 6.5. The purity of final product was assessed by electrophoresis in 4-20% Tris-Glycine SDS-PAGE. The enzyme was stored at −80 C in small aliquots.

Whole Cell Assay for Measuring the Inhibition of Beta-Secretase Activity

The routine whole cell assay for the measurement of inhibition of beta-secretase activity utilizes the human embryonic kidney cell line HEK293p (ATCC Accession No. CRL-1573) stably expressing a human APP751 cDNA containing the naturally occurring double mutation Lys651Met52 to Asn651Leu652, commonly called the Swedish mutation (noted HEK293/APP751sw) and shown to overproduce Abeta (Citron et al., 1992, Nature 360:672-674). Human embryonic kidney HEK293p cells stably expressing wild-type human APP751 cDNA (noted HEK293/APP751 wt) are also used to assess the inhibition of beta-secretase activity. In vitro Aβ reduction assays have been described in the literature (See: Dovey, et al., Journal of Neurochemistry, 76, 173-181 (2001); Seubert, et al., Nature, 361, 260 (1993); and Johnson-Wood, et al., Proc. Natl. Acad. Sci. USA, 94, 1550-1555 (1997))

Cells (HEK293/APP751sw or HEK293/APP751wt, at 3×10$^4$ cells/well, containing 200 microliters culture media, DMEM containing 10% FBS) are incubated at 37 C for 4 to 6 hours in the presence/absence of inhibitors (diluted in DMSO) at the desired concentration. At the end of the incubation, conditioned media are analyzed for beta-secretase activity, for example, by analysis of cleavage fragments, Abeta peptide and sAPPbeta. Abeta peptides are measured by a sandwich ELISA, using monoclonal 266 as a capture antibody and biotinylated 3D6 as reporting antibody. The sAPPbeta fragments are analyzed by a sandwich ELISA, using monoclonal 8E5 antibody as a capture antibody and rabbit polyclonal 192sw or 192wt as a reporting antibody. Note that sAPPbeta is the cleavage product of full length APP by BACE1. The concentration of sAPPbeta released in the conditioned media following the compound treatment corresponds to the activity of BACE1 under such conditions. The 10-point inhibition curve was plotted and fitted with the four-parameter logistic equation to obtain the $EC_{50}$ and $IC_{50}$ values for the Abeta, sAPPbeta-lowering effect. Data for selected compounds of the invention tested in this assay are contained in the following table.

| EXAMPLE | $IC_{50}$ (µM) |
|---|---|
| 7 | 0.013 |
| 12 | 0.015 |
| 33 | 14.27 |
| 41 | 6.07 |

In Vivo Inhibition of Beta-Secretase

Several animal models, including mouse, guinea pig, dog, and monkey, may be used to screen for inhibition of beta-secretase activity in vivo following compound treatment. Animals used in this invention can be wild type, transgenic, or gene knockout animals. For example, the PDAPP mouse model, prepared as described in Ganes et al., 1995, Nature 373:523-527, and other non-transgenic or gene knockout animals are useful to analyze in vivo inhibition of Abeta and sAPPbeta production in the presence of inhibitory compounds. Generally, 4 to 12 month old PDAPP mice, gene knockout mice or non-transgenic animals are administered compound formulated in vehicles, such as corn oil, cyclodextran, phosphate buffers, Pharmasolve, or other suitable vehicles. One to twenty-four hours following the administration of compound, animals are sacrificed, and brains as well as plasma are removed for analysis of Abeta and sAPP fragments. (See: Dovey, et al., Journal of Neurochemistry, 76, 173-181 (2001); and Johnson-Wood, et al., Proc. Natl. Acad. Sci. USA, 94, 1550-1555 (1997))

Beginning at time 0, brain tissue, plasma or cerebrospinal fluid is obtained from selected animals and analyzed for the presence of APP cleavage peptides, including Abeta peptides, sAPPbeta and other APP fragments, for example, by specific sandwich ELISA assays. At the end of the test period, animals are sacrificed and brain tissues, plasma or cerebrospinal fluid are analyzed for the presence of Abeta peptide and sAPPbeta. Brain tissues of APP transgenic animals are also analyzed for the amount of beta-amyloid plaques following compound treatment.

Animals (PDAPP or other APP transgenic mice) administered an inhibitory compound may demonstrate the reduction of Abeta or sAPPbeta in brain tissues, plasma or cerebrospinal fluids and decrease of beta amyloid plaques in brain tissue, as compared with vehicle-treated controls. Animals (PDAPP or other APP transgenic mice) administered the inhibitory compounds of the invention may also show improvement in cognitive behavioral assessments for learning and memory tasks.

Oral administration of the compounds of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

In order to achieve or maintain appropriate levels of the compounds of Formula I in the brain of an afflicted mammal, it may be necessary or desirable to co-administer an effective amount of an inhibitor of P-glycoprotein (P-gp). P-gp inhibitors and the use of such compounds are known to those skilled in the art. (See: *Cancer Research,* 53, 4595 (1993); *Clin. Cancer Res.,* 2, 7 (1996); *Cancer Research,* 56, 4171 (1996); WO99/64001; and WO01/10387).

The P-gp inhibitor may be administered in any manner that achieves a sufficient degree of inhibition of P-gp to achieve or maintain sufficient levels of the compounds of Formula I for effective BACE inhibition in the brain of an afflicted mammal. As such, the P-gp inhibitor may be administered separately before, during, or after the administration of a compound of Formula I. Furthermore, if desirable, the P-gp inhibitor may be formulated with a compound of Formula I. These formulations and methods represent further embodiments of the present invention.

Many suitable P-gp inhibitors are known today and undoubtably others will be identified in the future. Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as GF120918, FK506, VX-710, LY355979, PSC-833, GF-102,918 and other steroids.

We claim:

1. A compound of Formula I(*a*):

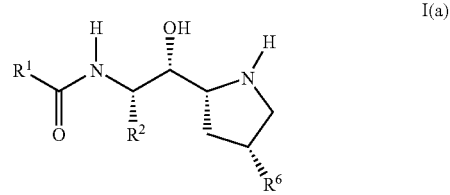

where:
$R^1$ is $(C_3-C_7$ cycloalkyl$)_{0-1}(C_1-C_6$ alkyl$)$
$R^2$ is benzyl optionally mono- or difluorinated in the phenyl ring
$R^6$ is $R^{34}$,-$CH_2C(O)R^{35}$
$R^{32}$ is $C_1-C_{10}$ alkyl optionally substituted with 1-6 fluorine atoms, oxo, or one or two hydroxy groups, $C_2-C_6$ alkenyl, or -$(CH_2)_{0-3}$-$R^{33}$;
$R^{33}$ is $C_3-C_7$ cycloalkyl or phenyl each optionally substituted with one or two substitutents independently selected from the group consisting of halo, $C_1-C_6$ alkyl, $C_1-C_6$ alkoxy, hydroxy, trifluoromethyl, and trifluoromethoxy, or $R^{33}$ is adamantyl;
$R^{34}$ is —$(CH_2)_{0-2}$-$OR^{32}$;
$R^{35}$ is hydroxy, $C_1-C_6$ alkoxy, or $NR^{37}R^{38}$ where $R^{37}$ and $R^{38}$ are independently hydrogen or $C_1-C_6$ alkyl, or $R^{37}$ and $R^{38}$, taken together with the nitrogen to which they are attached, form a piperidine ring optionally substituted with $C_1-C_6$ alkyl, a homopiperidine ring, a morpholine ring, or a pyrrolidine ring optionally substituted with $(C_1-C_6$ alkoxy)methyl;

or a pharmaceutically acceptable salt thereof.

2. A pharmaceutical composition comprising a compound of claim 1, in combination with a pharmaceutically acceptable carrier, diluent, or excipient.

3. A compound of claim 1 where $R^2$ is benzyl.

* * * * *